US011154615B2

(12) United States Patent
Igawa et al.

(10) Patent No.: US 11,154,615 B2
(45) Date of Patent: Oct. 26, 2021

(54) LIBRARY OF ANTIGEN-BINDING MOLECULES INCLUDING MODIFIED ANTIBODY VARIABLE REGION

(71) Applicant: CHUGAI SEIYAKU KABUSHIKI KAISHA, Tokyo (JP)

(72) Inventors: Tomoyuki Igawa, Shizuoka (JP); Shojiro Kadono, Kanagawa (JP); Naoka Hironiwa, Shizuoka (JP); Mika Sakurai, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 636 days.

(21) Appl. No.: 15/525,603

(22) PCT Filed: Nov. 11, 2015

(86) PCT No.: PCT/JP2015/081693
§ 371 (c)(1),
(2) Date: May 10, 2017

(87) PCT Pub. No.: WO2016/076345
PCT Pub. Date: May 19, 2016

(65) Prior Publication Data

US 2018/0296668 A1 Oct. 18, 2018

(30) Foreign Application Priority Data

Nov. 11, 2014 (WO) .................. PCT/JP2014/079785
May 13, 2015 (JP) ............................. JP2015-097884

(51) Int. Cl.
*C40B 40/10* (2006.01)
*A61K 39/395* (2006.01)
(Continued)

(52) U.S. Cl.
CPC ............ *A61K 39/395* (2013.01); *C07K 16/28* (2013.01); *C07K 16/2809* (2013.01);
(Continued)

(58) Field of Classification Search
None
See application file for complete search history.

(56) References Cited

U.S. PATENT DOCUMENTS 6,344,443 B1 2/2002 Liu et al.
8,568,726 B2 10/2013 Beaumont et al.
(Continued)

FOREIGN PATENT DOCUMENTS

CN 1069124 2/1993
CN 101123983 2/2008
(Continued)

OTHER PUBLICATIONS

Chen et al., "Enhancement and destruction of antibody function by somatic mutation: unequal occurrence is controlled by V gene combinatorial associations," The EMBO Journal, Jun. 1995, 14(12):2784-2794.
(Continued)

*Primary Examiner* — Christian C Boesen
(74) *Attorney, Agent, or Firm* — Fish & Richardson P.C.

(57) ABSTRACT

The present inventors have successfully prepared a library consisting essentially of a plurality of antigen-binding molecules differing in sequence from each other, the antigen-binding molecules each comprising an antibody variable region that has binding activity against a first antigen and a second antigen different from the first antigen, but does not bind to the first antigen and the second antigen at the same time. Use of the library of the present invention allows the obtainment of a variable region having enhanced ability to bind to the first antigen and the production of a bispecific
(Continued)

antibody against the first antigen and a cancer antigen. Moreover, the present inventors have also successfully prepared an antigen-binding molecule comprising an antibody variable region that has binding activity against three different antigens, but does not bind to these antigens at the same time.

11 Claims, 25 Drawing Sheets

Specification includes a Sequence Listing.

(51) Int. Cl.
*C40B 30/04* (2006.01)
*C07K 16/42* (2006.01)
*C07K 16/28* (2006.01)
*C40B 40/08* (2006.01)
*C12N 15/09* (2006.01)

(52) U.S. Cl.
CPC ...... *C07K 16/2848* (2013.01); *C07K 16/2866* (2013.01); *C07K 16/2875* (2013.01); *C07K 16/2896* (2013.01); *C07K 16/42* (2013.01); *C12N 15/09* (2013.01); *C40B 30/04* (2013.01); *C40B 40/08* (2013.01); *C40B 40/10* (2013.01); *C07K 2317/31* (2013.01); *C07K 2317/35* (2013.01); *C07K 2317/55* (2013.01); *C07K 2317/92* (2013.01)

(56) References Cited

U.S. PATENT DOCUMENTS

| | | | |
|---|---|---|---|
| 9,890,218 | B2 | 2/2018 | Mimoto et al. |
| 2006/0121042 | A1 | 6/2006 | Dallacqua et al. |
| 2006/0140934 | A1 | 6/2006 | Gegg et al. |
| 2007/0148164 | A1 | 6/2007 | Farrington et al. |
| 2007/0237767 | A1 | 10/2007 | Lazar et al. |
| 2007/0286859 | A1 | 12/2007 | Lazar et al. |
| 2008/0014205 | A1 | 1/2008 | Horowitz et al. |
| 2008/0089892 | A1 | 4/2008 | Allan et al. |
| 2010/0150918 | A1 | 6/2010 | Kufer et al. |
| 2010/0316641 | A1 | 12/2010 | Dimitrov |
| 2010/0322946 | A1 | 12/2010 | Bostrom et al. |
| 2011/0111406 | A1 | 5/2011 | Igawa et al. |
| 2012/0149876 | A1 | 6/2012 | Kreudenstein et al. |
| 2012/0328624 | A1 | 12/2012 | Yoshida et al. |
| 2013/0101581 | A1 | 4/2013 | Kuramochi et al. |
| 2014/0112914 | A1 | 4/2014 | Nezu et al. |
| 2014/0112926 | A1 | 4/2014 | Liu |
| 2014/0199294 | A1 | 7/2014 | Mimoto et al. |
| 2015/0166636 | A1 | 6/2015 | Igawa et al. |
| 2015/0344570 | A1 | 12/2015 | Igawa et al. |
| 2016/0280787 | A1 | 9/2016 | Igawa et al. |
| 2017/0037130 | A1 | 2/2017 | Raum et al. |
| 2017/0274072 | A1 | 9/2017 | Kumagai et al. |
| 2017/0306036 | A1 | 10/2017 | Vu et al. |
| 2020/0332001 | A1 | 10/2020 | Igawa et al. |
| 2020/0377595 | A1 | 12/2020 | Shimizu et al. |

FOREIGN PATENT DOCUMENTS

| | | | |
|---|---|---|---|
| EP | 1 293 514 | | 3/2003 |
| EP | 1752471 | A | 2/2007 |
| EP | 2 241 578 | A | 10/2010 |
| EP | 2647707 | A | 10/2013 |
| EP | 3 070 168 | | 9/2016 |
| EP | 3 130 606 | A | 2/2017 |
| EP | 3219724 | A | 9/2017 |
| JP | 2007-536912 | | 12/2007 |
| JP | 2008-514201 | | 5/2008 |
| JP | 2008-518023 | | 5/2008 |
| JP | 2008-526809 | | 7/2008 |
| JP | 2009-511587 | | 3/2009 |
| JP | 2009-538273 | | 11/2009 |
| JP | 2009-540837 | | 11/2009 |
| JP | 2010-524851 | | 7/2010 |
| JP | 2012-501648 | | 1/2012 |
| JP | 6628966 | | 1/2020 |
| WO | WO 92/19973 | | 11/1992 |
| WO | WO 94/18221 | | 8/1994 |
| WO | WO 95/14714 | | 6/1995 |
| WO | WO 00/42072 | | 7/2000 |
| WO | WO 2005/070966 | | 8/2005 |
| WO | WO 2006/019447 | | 2/2006 |
| WO | WO 2006/036834 | | 4/2006 |
| WO | WO 2006/047639 | | 5/2006 |
| WO | WO 2006/072620 | | 7/2006 |
| WO | WO 2006/083706 | | 8/2006 |
| WO | WO 2006/106905 | | 10/2006 |
| WO | WO 2007/047291 | | 4/2007 |
| WO | WO 2007/121354 | | 10/2007 |
| WO | WO 2008/003103 | | 1/2008 |
| WO | WO 2008/119567 | | 10/2008 |
| WO | WO 2009/087978 | | 7/2009 |
| WO | WO 2009/125825 | | 10/2009 |
| WO | WO 2010/027981 | | 3/2010 |
| WO | WO 2010/035012 | | 4/2010 |
| WO | WO 2010/080538 | | 7/2010 |
| WO | WO 2011/057788 | | 5/2011 |
| WO | WO 2011/093097 | | 8/2011 |
| WO | WO 2011/108714 | | 9/2011 |
| WO | WO 2011/122011 | | 10/2011 |
| WO | WO 2011/133886 | | 10/2011 |
| WO | WO 2012/003956 | | 1/2012 |
| WO | WO 2012/064792 | | 5/2012 |
| WO | WO 2012/073985 | | 6/2012 |
| WO | WO 2012/096994 | | 7/2012 |
| WO | WO 2012/143524 | | 10/2012 |
| WO | WO 2012/156018 | | 11/2012 |
| WO | WO 2012/162067 | | 11/2012 |
| WO | WO 2013/026833 | | 2/2013 |
| WO | WO 2013/059593 | | 4/2013 |
| WO | WO 2013/126746 | | 8/2013 |
| WO | WO 2013/187495 | | 12/2013 |
| WO | WO 2014/075697 | | 5/2014 |
| WO | WO 2014/075788 | | 5/2014 |
| WO | WO 2014/116846 | | 7/2014 |
| WO | WO 2015/068847 | | 5/2015 |
| WO | WO 2015/069794 | | 5/2015 |
| WO | WO 2015/156268 | | 10/2015 |
| WO | WO 2016/076345 | | 5/2016 |
| WO | WO 2017/021349 | | 2/2017 |
| WO | WO 2019/111871 | | 6/2019 |
| WO | WO 2019/131988 | | 7/2019 |
| WO | WO 2019/135404 | | 7/2019 |
| WO | WO 2020/067399 | | 4/2020 |
| WO | WO 2020/067419 | | 4/2020 |

OTHER PUBLICATIONS

De Pascalis et al., "Grafting of 'Abbreviated' Complementarity-Determining Regions Containing Specificity-Determining Residues Essential for Ligand Contact to Engineer a Less Immunogenic Humanized Monoclonal Antibody," J. Immunol., Sep. 15, 2002, 169(6):3076-3084.

Kussie et al., "A Single Engineered Amino Acid Substitution Changes Antibody Fine Specificity," J. Immunol., Jan. 1, 1994, 152(1):146-152.

Lederman et al., "A Single Amino Acid Substitution in a Common African Allele of the CD4 Molecule Ablates Binding of the Monoclonal Antibody, OKT4," Molecular Immunology, Nov. 1991, 28(11):1171-1181.

MacCallum et al., "Antibody-antigen Interactions: Contact Analysis and Binding Site Topography," J. Mol. Biol., Oct. 11, 1996, 262(5):732-745.

Stancovski et al., "Mechanistic Aspects of the Opposing Effects of Monoclonal Antibodies to the ERBB2 Receptor on Tumor Growth," Proc Nat Acad Sci USA, Oct. 1, 1991, 88(19):8691-8695.

(56) References Cited

OTHER PUBLICATIONS

Vajdos et al., "Comprehensive Functional Maps of the Antigen-binding Site of an Anti-ErbB2 Antibody Obtained with Shotgun Scanning Mutagenesis," J. Mol Biol., Jul. 5, 2002, 320(2):415-428.
Witte et al., "Monoclonal antibodies targeting the VEGF receptor-2 (Flk1/KDR) as an anti-angiogenic therapeutic strategy," Cancer and Metastasis Reviews, Jun. 1998, 17(2):155-161.
Wu et al., "Humanization of a Murine Monoclonal Antibody by Simultaneous Optimization of Framework and CDR Residues," J. Mol. Biol., Nov. 19, 1999, 294(1):151-162.
Yu et al., "Interaction between Bevacizumab and Murine VEGF-A: A Reassessment," Investigative Ophthalmology and Visual Science, Feb. 2008, 49(2):522-527.
Dermer et al., "Another Anniversary for the War on Cancer," Bio/Technology, Mar. 12, 1994, 12:320.
Dufner, "Harnessing phage and ribosome display for antibody optimization," Trends Biotechnol, Nov. 2006, 24(11):523-529.
Gura et al., "Systems for Identifying New Drugs Are Often Faulty," Science, Nov. 7, 1997, 278:1041-1042.
Li et al., "β-Endorphin omission analogs: Dissociation of immunoreactivity from other biological activities," Proc Natl Acad Sci USA, Jun. 1980, 77:3211-3214.
Baeuerle et al., "Bispecific T-Cell Engaging Antibodies for Cancer Therapy," Cancer Res, Jun. 15, 2009, 69(12):4941-4. doi:10.1158/0008-5472.CAN-09-0547. Epub Jun. 9, 2009.
Holen et al., "Activation of EphA receptors on $CD4^{+}$CD45RO+ memory cells stimulates migration," J Leukoc Biol, Jun. 2010, 87(6):1059-68, doi: 10.1189/jlb.0709497. Epub Feb. 16, 2010.
Lum et al., "Targeting T Cells with Bispecific Antibodies for Cancer Therapy," BioDrugs, Dec. 1, 2011, 25(6):365-79. doi: 10.2165/11595950-000000000-00000.
U.S. Appl. No. 16/704,464, filed Dec. 5, 2019, Igawa et al.
Berntzen et al., "Identification of a High Affinity FcγRIIA-binding Peptide that Distinguishes FcγRIIA from FcγRIIB and Exploits FcγRIIA-mediated Phagocytosis and Degradation," J Biol Chem, Jan. 2009, 284(2): 1126-1135. doi: 10.1074/jbc.M803584200. Epub Oct. 28, 2008.
Lightfield et al., "Critical function for Naip5 in inflammasome activation by a conserved carboxy-terminal domain of flagellin," Nature Immunology, Oct. 2008, 9(10): 1171-1178. doi: 10.1038/ni.1646, Epub Aug. 24, 2008.
Chen et al., "Characterization of human IgG repertoires in an acute HIV-1 infection," Exp Mol Pathol. Dec. 2012;93(3):399-407. doi: 10.1016/j.yexmp.2012.09.022. Epub Oct. 1, 2012.
Atwell et al., "Stable heterodimers from remodeling the domain interface of a homodimer using a phage display library," J Mol Biol., Jul. 4, 1997;270(1):26-35.
Chan et al., "Therapeutic antibodies for autoimmunity and inflammation," Nat Rev Immunol., May 2010;10(5):301-16. doi: 10.1038/nri2761.
Clark, "IgG effector mechanisms," Chem Immunol., 1997;65:88-110.
Eigenbrot et al., "Two-in-One antibodies with dual action Fabs," Curr Opin Chem Biol. Jun. 2013;17(3):400-5. doi: 10.1016/j.cbpa.2013.04.015. Epub May 14, 2013.
Greenwood et al., "Structural motifs involved in human IgG antibody effector functions," Eur J Immunol., May 1993;23(5):1098-104.
Guilliams et al., "The function of Fcγ receptors in dendritic cells and macrophages," Nat Rev Immunol., Feb. 2014;14(2):94-108. doi: 10.1038/nri3582. Epub Jan. 21, 2014.
Hess et al., "Cancer therapy with trifunctional antibodies: linking innate and adaptive immunity," Future Oncol., Jan. 2012;8(1):73-85. doi: 10.2217/fon.11.138.
Janeway et al., Immunobiology, The Immune System in Health and Disease, 3rd Edition, 1997 Garland Publishing Inc., pp. 3:1-3:11.
Jefferis et al., "Interaction sites on human IgG-Fc for Fc gamma R: current models," Immunol Lett, Jun. 3, 2002;82(1-2):57-65.
Jones et al., "Growth factor receptor interplay and resistance in cancer," Endocr Relat Cancer, Dec. 2006;13 Suppl 1:S45-51.
Lazar et al., "Engineered antibody Fc variants with enhanced effector function," Proc Natl Acad Sci USA, Mar. 2006;103(11):4005-10. Epub Mar. 6, 2006.
Lutterbuese et al., "T cell-engaging BiTE antibodies specific for EGFR potently eliminate KRAS- and BRAF-mutated colorectal cancer cells," Pro Natl Acad Sci U.S.A., 107(28):12605-10 (2010). doi: 10.1073/pnas.1000976107. Epub Jun. 28, 2010.
Marino et al., "Prevention of systemic lupus erythematosus in MRL/lpr mice by administration of an immunoglobulin-binding peptide," Nat Biotechnol., Jul. 2000;18(7):735-9.
Morgan et al., "The N-terminal end of the CH2 domain of chimeric human IgG1 anti-HLA-DR is necessary for C1q, Fc gamma RI and Fc gamma RIII binding," Immunology, Oct. 1995; 86(2):319-24.
Natsume et al., "Engineered antibodies of IgG1/IgG3 mixed isotype with enhanced cytotoxic activities," Cancer Res., May 15, 2008;68(10):3863-72. doi: 10.1158/0008-5472.CAN-07-6297.
Nimmerjahn et al., "Fcgamma receptors as regulators of immune responses," Nat Rev Immunol., Jan. 2008;8(1):34-47.
Pavlou et al., "The therapeutic antibodies market to 2008," Eur J Pharm Biopharm., Apr. 2005;59(3):389-96.
Reichert et al., "Monoclonal antibody successes in the clinic," Nat Biotechnol., Sep. 2005;23(9):1073-8.
Riechelmann et al., "Adoptive therapy of head and neck squamous cell carcinoma with antibody coated immune cells: a pilot clinical trial," Cancer Immunol Immunother., Sep. 2007;56(9):1397-406, Epub Feb. 2, 2007.
Rothe et al., "Recombinant proteins in rheumatology—recent advances," N Biotechnol., Sep. 2011;28(5):502-10. doi: 10.1016/j.nbt.2011.03.019. Epub Apr. 5, 2011.
Rudikoff et al., "Single amino acid substitution altering antigen-binding specificity," Proc Natl Acad Sci U S A., Mar. 1982;79(6):1979-83.
Schaefer et al., "A two-in-one antibody against HER3 and EGFR has superior inhibitory activity compared with monospecific antibodies," Cancer Cell, 20(4):472-86 (2011). doi: 10.1016/j.ccr.2011.09.003.
Seimetz et al., "Development and approval of the trifunctional antibody catumaxomab (anti-EpCAM x anti-CD3) as a targeted cancer immunotherapy," Cancer Treat Rev., Oct. 2010;36(6):458-67. doi: 10.1016/j.ctrv.2010.03.001. Epub Mar. 27, 2010.
Shinkawa et al., "The absence of fucose but not the presence of galactose or bisecting N-acetylglucosamine of human IgG1 complex-type oligosaccharides shows the critical role of enhancing antibody-dependent cellular cytotoxicity," J Biol Chem., Jan. 31, 2003;278(5):3466-73. Epub Nov. 8, 2002.
Unkeless et al., "Structure and function of human and murine receptors for IgG," Annu Rev Immunol., 1988;6:251-81.
Werwitzke et al., "Treatment of lupus-prone NZB/NZW F1 mice with recombinant soluble Fc gamma receptor II (CD32)," Ann Rheum Dis., Feb. 2008;67(2):154-61. Epub Jun. 8, 2007.
Wozniak-Knopp et al., "Introducing antigen-binding sites in structural loops of immunoglobulin constant domains: Fc fragments with engineered HER2/neu-binding sites and antibody properties," Protein Eng Des Sel., Apr. 2010;23(4):289-97. doi: 10.1093/protein/gzq005. Epub Feb. 11, 2010.
Xi et al., "Increased survival and reduced renal injury in MRL/lpr mice treated with a human Fcγ receptor II (CD32) peptide," Immunology, May 2012;136(1):46-53. doi: 10.1111/j.1365-2567.2012.03553.x.
Xie et al., "A new format of bispecific antibody: highly efficient heterodimerization, expression and tumor cell lysis," J Immunol Methods., Jan. 2005;296(1-2):95-101. Epub Nov. 19, 2004.
Zeidler et al., Simultaneous activation of T cells and accessory cells by a new class of intact bispecific antibody results in efficient tumor cell killing, J Immunol., Aug. 1, 1999;163(3):1246-52.
International Search Report for App. Ser. No. PCT/JP2014/079785, dated Feb. 24, 2015, 4 pages.
International Preliminary Report on Patentability for App. Ser. No. PCT/JP2014/079785, dated May 17, 2016, 9 pages.
International Preliminary Report on Patentability in International Application No. PCT/JP2015/081693, dated May 26, 2017, 10 pages.
U.S. Appl. No. 15/525,603, filed May 10, 2017, Igawa et al.

(56) References Cited

OTHER PUBLICATIONS

International Search Report for App. Ser. No. PCT/JP2015/081693, dated Feb. 2, 2016, 2 pages.
Beljaars et al., "The preferential homing of a platelet derived growth factor receptor-recognizing macromolecule to fibroblast-like cells in fibrotic tissue," Biochemical Pharmacology, Oct. 2003, 66(7):1307-17.
Binetruy-Tournaire et al., "Identification of a peptide blocking vascular endothelial growth factor (VEGF)-mediated angiogenesis," EMBO J., Apr. 3, 2000, 19(7):1525-33.
Brennand et al., "A cyclic peptide analogue of loop III of PDGF-BB causes an apoptosis in human fibroblasts," FEBS Lett., Dec. 15, 1997, 419(2-3):166-70.
Chamarthy et al., "Gene delivery to dendritic cells facilitated by a tumor necrosis factor alpha-competing peptide," Mol Immunol, Jul. 2004, 41(8):741-9.
Conrad et al, "TCR and CD3 antibody cross-reactivity in 44 species," Cytometry A, Nov. 2007, 71(11):925-33.
Dall'Acqua et al., "Modulation of the Effector Functions of a Human IgG1 through Engineering of Its Hinge Region," J Immunol., Jul. 15, 2006, 177(2):1129-38.
Deambrosis et al., "Inhibition of CD40-CD154 costimulatory pathway by a cyclic peptide targeting CD154," J Mol Med., Feb. 2009, 87(2):181-97.
Faham et al., "Antigen-Containing Liposomes Engrafted with Flagellin-Related Peptides Are Effective Vaccines That Can Induce Potent Antitumor Immunity and Immunotherapeutic Effect," J Immunol, Jul. 7, 2010, 185:1744-1754.
Hetian et al., "A Novel Peptide Isolated from a Phage Display Library Inhibits Tumor Growth and Metastasis by Blocking the Binding of Vascular Endothelial Growth Factor to Its Kinase Domain Receptor," J Biol Chem., Nov. 8, 2002, 277(45):43137-42.
Hezareh et al., Effector Function Activities of a Panel of Mutants of a Broadly Neutralizing Antibody against Human Immunodeficiency Virus Type 1, J Virol., Dec. 2001, 75(24):12161-8.
Ikuta et al, "Expression of human immunodeficiency virus type 1 (HIV-1) gag antigens on the surface of a cell line persistently infected with HIV-1 that highly expresses HIV-1 antigens," Virology, Jun. 1989, 170(2):408-17.
Kraft et al., "Definition of an Unexpected Ligand Recognition Motif for αvβ6 Integrin," J. Biol. Chem., Jan. 22, 1999, 274:1979-1985.
Kramer et al, "Molecular basis for the binding promiscuity of an anti-p24 (HIV-1) monoclonal antibody" Cell, Dec. 12, 1997, 91(6):799-809.
Li et al., Activation of the Proapoptotic Death Receptor DR5 by Oligomeric Peptide and Antibody Agonists, J. Mol. Biol., Aug. 18, 2006, 361(3): 522-536.
Nakamura et al., "Peptide mimics of epidermal growth factor (EGF) with antagonistic activity," Journal of Biotechnology, Mar. 30, 2005, 116(3): 211-219.
Rao et al., "Novel cyclic and linear oligopeptides that bind to integrin β1 chain and either inhibit or costimulate T lymphocytes," Int. Immunopharmacol., Mar. 2003, 3(3): 435-43.
Richards et al., "A peptide containing a novel FPGN CD40-binding sequence enhances adenoviral infection of murine and human dendritic cells," Eur J Biochem, May 2003, 70(10):2287-94.
Shanmugam et al., "Synthetic Toll Like Receptor-4 (TLR-4) Agonist Peptides as a Novel Class of Adjuvants," PLoS ONE, Feb. 2012, 7(2):e30839.
Wu et al., "Structures of the CXCR4 Chemokine GPCR with Small-Molecule and Cyclic Peptide Antagonists," Science, Nov. 19, 2010, 330:1066-1071.
U.S. Appl. No. 15/035,098, Igawa et al., filed May 6, 2016.
Vidarsson et al., "IgG subclasses and allotypes: from structure to effector functions," Front Immunol., Oct. 20, 2014;5:520. doi: 10.3389/fimmu.2014.00520. eCollection 2014.
Edelman et al., "A Covalent Structure of an Entire KG Immunoglobulin Molecule," Proc Natl Acad Sci USA, May 1969; 63(1): 78-85.
Kontermann, "Dual targeting strategies with bispecific antibodies," Mabs, Mar.-Apr. 2012; 4(2): 182-97, doi: 10.4161/mabs.4.2.19000. Epub Mar. 1, 2012.
Stevenson et al., "A chimeric antibody with dual Fc regions (bisFabFc) prepared by manipulations at the IgG hinge," Anticancer Drug Des. Mar. 1989; 3(4): 219-30.
Traxlmayr et al., "Integrin binding human antibody constant domains—Probing the C-terminal structural loops for grafting the RGD motif," J Biotechnol. Sep. 10, 2011; 155(2): 193-202. doi: 10.1016/j.jbiotec.2011.06.042. Epub Jul. 8, 2011.
U.S. Appl. No. 15/035,098, Igawa et al., filed May 6, 2016 (abandoned).
U.S. Appl. No. 16/704,464, Igawa et al., filed Dec. 5, 2019.
U.S. Appl. No. 16/769,299, Shimizu et al., filed Jun. 3, 2020.
U.S. Appl. No. 14/406,232, Igawa et al., filed Dec. 8, 2014.
U.S. Appl. No. 16/769,299, filed Jun. 3, 2020, Shimizu et al.
Boder et al., "Directed evolution of antibody fragments with monovalent femtomolar antigen binding affinity," Proc Natl Acad Sci USA, Sep. 26, 2000, 97(20):10701-10705.
Bostrom et al., "Variants of the Antibody Herceptin That Interact with HER2 and VEGF at the Antigen Binding Site," Science, Mar. 20, 2009, 323(5921):1610-1614.
Clackson et al., "Making antibody fragments using phage display libraries," Nature, Aug. 15, 1991, 352(6336):624-628.
Dubrot et al., "Treatment with anti-CD137 mAbs causes intense accumulations of liver T cells without selective antitumor immunotherapeutic effects in this organ," Cancer Immunol Immunother, Aug. 2010, 59(8):1223-1233.
Fukuda et al., "In vitro evolution of single-chain antibodies using mRNA display," Nucleic Acids Res, Nov. 2006, 34(19):e127, 8 pages.
Hanes et al., "Picomolar affinity antibodies from a fully synthetic naïve library selected and evolved by ribosome display," Nat Biotechnol, Dec. 2000, 18(12):1287-1292.
Harvey et al., "Anchored periplasmic expression, a versatile technology for the isolation of high-affinity antibodies from *Escherichia coli*-expressed libraries," Proc Natl Acad Sci USA, Jun. 22, 2004, 101(25):9193-9198.
Hawkins et al., "Selection of Phage Antibodies by Binding Affinity—Mimicking Affinity Maturation," J Mol Biol, Aug. 5, 1992, 226(3):889-896.
Houot et al., "Therapeutic effect of CD137 immunomodulation in lymphoma and its enhancement by $T_{reg}$ depletion," Blood, Oct. 15, 2009, 114(16):3431-3438.
Kronqvist et al., "A novel affinity protein selection system based on staphylococcal cell surface display and flow cytometiy," Protein Eng Des Sel, Apr. 2008, 21(4):247-255.
Li et al., "Antitumor activities of agonistic anti-TNFR antibodies require differential FcγRIIB coengagement in vivo," Proc Natl Acad Sci USA, Nov. 26, 2013, 110(48):19501-19506. doi: 10.1073/pnas.1319502110, Epub Nov. 11, 2013.
Marks et al., "By-passing Immunization—Human Antibodies from V-gene Libraries Displayed on Phage," J Mol Biol, Dec. 5, 1991, 222(3):581-597.
Odegrip et al., "CIS display: In vitro selection of peptides from libraries of protein-DNA complexes," Proc Natl Acad Sci USA, Mar. 2, 2004, 101(9):2806-2810.
Porter et al., "Chimeric Antigen Receptor-Modified T Cells in Chronic Lymphoid Leukemia," N Engl J Med, Aug. 25, 2011, 365(8):725-733. doi: 10.1056/NEJMoa1103849, Epub Aug. 10, 2011.
Schabowsky et al., "A Novel Form of 4-1BBL Has Better Immunomodulatory Activity than an Agonistic Anti-4-1BB Ab without Ab Associated Severe Toxicity," Vaccine, Dec. 11, 2009, 28(2):512-522. doi: 10.1016/j.vaccine.2009.09.127. Epub Oct. 29, 2009.
Schraa et al., "RGD-Modified Anti-CD3 Antibodies Redirect Cytolytic Capacity of Cytotoxic T Lymphocytes Toward αvβ3-Expressing Endothelial Cells," Int J Cancer, Nov. 1, 2004, 112(2):279-285.
Sepp et al., "Cell-Free Selection of Domain Antibodies by in vitro Compartmentalization," Methods Mol Biol, Jul. 2012, 911:183-198.

(56) References Cited

OTHER PUBLICATIONS

Tutt et al., "Trispecific F(ab')3 derivatives that use cooperative signaling via the TCR/CD3 complex and CD2 to activate and redirect resting cytotoxic T cells," J Immunol, Jul. 1, 1991, 147(1):60-69.
Vaughan et al., "Human Antibodies with Sub-nanomolar Affinities Isolated from a Large Non-immunized Phage Display Library," Nat Biotechnol, Mar. 1996, 14(3):309-314.
Vinay et al., "4-1BB signaling beyond T Cells," Cell Mol Immunol, Jul. 2011, 8(4):281-284. doi: 10.1038/cmi.2010.82. Epub Jan. 10, 2011.
Xiao et al., "A large library based on a novel (CH2) scaffold: Identification of HIV-1 inhibitors," Biochem Biophys Res Commun, Sep. 18, 2009, 387(2):387-392. doi: 10.1016/j.bbrc.2009.07.044. Epub Jul. 15, 2009.
Zhou et al., "Development of a novel mammalian cell surface antibody display platform," mAbs, Sep.-Oct. 2010, 2(5):508-518.
U.S. Appl. No. 17/272,972, Ho et al., filed Mar. 3, 2021.
U.S. Appl. No. 17/280,239, Igawa et al., filed Mar. 26, 2021.
U.S. Appl. No. 17/272,972, filed Mar. 3, 2021, Ho et al.
U.S. Appl. No. 17/280,239, filed Mar. 26, 2021, Igawa et al.
Abuazza et al., "Claudins 6, 9, and 13 are developmentally expressed renal tight junction proteins," Am J Physiol Renal Physiol, Dec. 2006, 291(6):F1132-1141.
Amann et al., "Therapeutic window of an EpCAM/CD3-specific BiTE antibody in mice is determined by a subpopulation of EpCAM-expressing lymphocytes that is absent in humans," Cancer Immunol Immunother, Jan. 2009, 58(1):95-109, Epub Jul. 2, 2008.
Bulman et al., "Mutations in the human Delta homologue, DLL3, cause axial skeletal defects in spondylocostal dysostosis," Nat Genet, Apr. 2000, 24(4):438-441.
Campoli et al., "Immunotherapy of Malignant Disease with Tumor Antigen-Specific Monoclonal Antibodies," Clin Cancer Res, Jan. 1, 2010, 16(1):11-20. Epub Dec. 22, 2009.
Dreier et al., "Extremely Potent, Rapid and Costimulation-Independent Cytotoxic T-Cell Response Against Lymphoma Cells Catalyzed by a Single-Chain Bispecific Antibody," Int J Cancer, Aug. 20, 2002, 100(6):690-697.
Ferran et al., "Cytokine-related syndrome following injection of anti-CD3 monoclonal antibody: Further evidence for transient in vivo T cell activation," Eur J Immunol, Mar. 1990, 20(3):509-515.
Frey et al., "Cytokine release syndrome with novel therapeutics for acute lymphoblastic leukemia," Hematology Am Soc Hematol Educ Program, Dec. 2, 2016, 2016(1):567-572.
Furuse et al., "Claudins in occluding junctions of humans and flies," Trends Cell Biol, Apr. 2006, 16(4):181-188, Epub Mar. 14, 2006.
Hashizume et al., "Expression Patterns of Claudin Family of Tight Junction Membrane Proteins in Developing Mouse Submandibular Gland," Dev Dyn, Oct. 2004, 231(2):425-431.
Mack et al., "A small bispecific antibody construct expressed as a functional single-chain molecule with high tumor cell cytotoxicity," Proc Natl Acad Sci USA, Jul. 18, 1995, 92(15):7021-7025.
Mezzanzanica et al., "Human Ovarian Carcinoma Lysis by Cytotoxic T Cells Targeted by Bispecific Monoclonal Antibodies: Analysis of the Antibody Components," Int J Cancer, Apr. 15, 1988, 41(4):609-615.
Micke et al., "Aberrantly activated claudin 6 and 18.2 as potential therapy targets in non-small-cell lung cancer," Int J Cancer, Nov. 1, 2014, 135(9):2206-2214.
Morita et al., "Claudin multigene family encoding four-transmembrane domain protein components of tight junction strands," Proc Natl Acad Sci USA, Jan. 19, 1999, 96(2):511-516.
Mullendore et al., "Ligand-dependent Notch Signaling is Involved in Tumor Initiation and Tumor Maintenance in Pancreatic Cancer," Clin Cancer Res, Apr. 1, 2009, 15(7):2291-2301.
Phillips et al., "Molecular subclasses of high-grade glioma predict prognosis, delineate a pattern of disease progression, and resemble stages in neurogenesis," Cancer Cell, Mar. 2006, 9(3):157-173.
Rahner et al., "Heterogeneity in Expression and Subcellular Localization of Claudius 2, 3, 4, and 5 in the Rat Liver, Pancreas, and Gut," Gastroenterology, Feb. 2001, 120(2):411-422.
Rendon-Huerta et al., "Distribution and Expression Pattern of Claudins 6, 7, and 9 in Diffuse- and Intestinal-Type Gastric Adenocarcinomas," J Gastrointest Cancer, Mar. 2010, 41(1):52-59.
Sazinsky et al., "Aglycosylated immunoglobulin G1 variants productively engage activating Fc receptor," Proc Natl Acad Sci USA, Dec. 23, 2008, 105(51):20167-20172. doi: 10.1073/pnas.0809257105. Epub Dec. 12, 2008.
Schlereth et al., "T-cell activation and B-cell depletion in chimpanzees treated with a bispecific anti-CD19/anti-CD3 single-chain antibody construct," Cancer Immunol Immunother, May 2006, 55(5):503-514, Epub Jul. 20, 2005.
Sebastian et al., "Treatment of non-small cell lung cancer patients with the trifunctional monoclonal antibody catumaxomab (anti-EpCAM x anti-CD3): a phase I study," Cancer Immunol Immunother, Oct. 2007, 56(10):1637-1644, Epub Apr. 5, 2007.
Stadler et al., "Characterization of the first-in-class T-cell-engaging bispecific single-chain antibody for targeted immunotherapy of solid tumors expressing the oncofetal protein claudin 6," Oncoimmunology, Oct. 29, 2015, 5(3):e1091555, eCollection Mar. 2016.
Staerz et al., "Hybrid antibodies can target sites for attack by T cells," Nature, Apr. 18-24, 1985, 314(6012):628-631.
Staerz et al., "Hybrid hybridoma producing a bispecific monoclonal antibody that can focus effector T-cell activity," Proc Natl Acad Sci USA, Mar. 1986, 83(5):1453-1457.
Turnpenny et al., "Novel mutations in DLL3, a somitogenesis gene encoding a ligand for the Notch signaling pathway, cause a consistent pattern of abnormal vertebral segmentation in spondylocostal dysostosis," J Med Genet, May 2003, 40(5):333-339.
Ushiku et al., "Distinct expression pattern of claudin-6, a primitive phenotypic tight junction molecule, in germ cell tumours and visceral carcinomas," Histopathology, Dec. 2012, 61(6):1043-1056.
Wilcox et al., "Mutations in the Gene Encoding Tight Junction Claudin-14 Cause Autosomal Recessive Deafness DFNB29," Cell, Jan. 12, 2001, 104(1):165-172.
Wolf et al., "BiTEs: bispecific antibody constructs with unique anti-tumor activity," Drug Discov Today, Sep. 15, 2005, 10(18):1237-1244.

Fig. 20 hIADHB2b-4

| # | Value of ELISA (absorbance at 450 nm) | | | Ratio to NC | |
|---|---|---|---|---|---|
| | **hIgA** | **CD3** | **NC** | S/N of hIgA | S/N of CD3 |
| 1 | 0.069 | 0.049 | 0.065 | 1.1 | 0.8 |
| 2 | 0.064 | 0.053 | 0.061 | 1.0 | 0.9 |
| 3 | 0.058 | 0.057 | 0.056 | 1.0 | 1.0 |
| 4 | 0.066 | 0.053 | 0.064 | 1.0 | 0.8 |
| 5 | 0.067 | 0.061 | 0.065 | 1.0 | 0.9 |
| 6 | 0.102 | 0.545 | 0.056 | 1.8 | **9.7** |
| 7 | 0.110 | 0.624 | 0.054 | **2.0** | **11.6** |
| 8 | 0.077 | 0.075 | 0.077 | 1.0 | 1.0 |
| 9 | 0.123 | 0.806 | 0.052 | **2.4** | **15.5** |
| 10 | 0.051 | 0.372 | 0.051 | 1.0 | **7.3** |
| 11 | 0.056 | 0.055 | 0.053 | 1.1 | 1.0 |
| 12 | 0.054 | 0.053 | 0.052 | 1.0 | 1.0 |
| 13 | 0.056 | 0.052 | 0.056 | 1.0 | 0.9 |
| 14 | 0.063 | 0.059 | 0.062 | 1.0 | 1.0 |
| 15 | 0.069 | 0.060 | 0.062 | 1.1 | 1.0 |
| 16 | 0.066 | 0.062 | 0.063 | 1.0 | 1.0 |
| 17 | 0.067 | 0.057 | 0.061 | 1.1 | 0.9 |
| 18 | 0.061 | 0.055 | 0.057 | 1.1 | 1.0 |
| 19 | 0.067 | 0.060 | 0.067 | 1.0 | 0.9 |
| 20 | 0.058 | 0.526 | 0.057 | 1.0 | **9.2** |
| 21 | 0.059 | 0.051 | 0.054 | 1.1 | 0.9 |
| 22 | 0.064 | 0.059 | 0.061 | 1.0 | 1.0 |
| 23 | 0.067 | 0.063 | 0.069 | 1.0 | 0.9 |
| 24 | 0.065 | 0.062 | 0.062 | 1.0 | 1.0 |
| 25 | 0.068 | 0.056 | 0.062 | 1.1 | 0.9 |
| 26 | 0.055 | 0.051 | 0.053 | 1.0 | 1.0 |
| 27 | 0.061 | 0.061 | 0.060 | 1.0 | 1.0 |
| 28 | 0.065 | 0.063 | 0.063 | 1.0 | 1.0 |
| 29 | 0.065 | 0.061 | 0.063 | 1.0 | 1.0 |
| 30 | 0.067 | 0.060 | 0.062 | 1.1 | 1.0 |
| 31 | 0.066 | 0.060 | 0.064 | 1.0 | 0.9 |
| 32 | 0.071 | 0.070 | 0.067 | 1.1 | 1.0 |
| 33 | 0.071 | 0.061 | 0.063 | 1.1 | 1.0 |
| 34 | 0.053 | 0.063 | 0.052 | 1.0 | 1.2 |
| 35 | 0.051 | 0.049 | 0.048 | 1.1 | 1.0 |
| 36 | 0.121 | 0.794 | 0.049 | **2.5** | **16.2** |
| 37 | 0.050 | 0.346 | 0.049 | 1.0 | **7.1** |
| 38 | 0.071 | 0.061 | 0.060 | 1.2 | 1.0 |
| 39 | 0.063 | 0.059 | 0.061 | 1.0 | 1.0 |
| 40 | 0.069 | 0.067 | 0.067 | 1.0 | 1.0 |
| 41 | 0.075 | 0.067 | 0.071 | 1.1 | 0.9 |
| 42 | 0.051 | 0.391 | 0.048 | 1.1 | **8.1** |
| 43 | 0.121 | 0.820 | 0.048 | **2.5** | **17.1** |
| 44 | 0.126 | 0.816 | 0.053 | **2.4** | **15.4** |
| 45 | 0.054 | 0.050 | 0.052 | 1.0 | 1.0 |
| 46 | 0.067 | 0.063 | 0.063 | 1.1 | 1.0 |
| 47 | 0.054 | 0.051 | 0.053 | 1.0 | 1.0 |
| 48 | 0.083 | 0.081 | 0.092 | 0.9 | 0.9 |

| # | Value of ELISA (absorbance at 450 nm) | | | Ratio to NC | |
|---|---|---|---|---|---|
| | **hIgA** | **CD3** | **NC** | S/N of hIgA | S/N of CD3 |
| 49 | 0.062 | 0.055 | 0.061 | 1.0 | 0.9 |
| 50 | 0.106 | 0.807 | 0.048 | **2.2** | **16.8** |
| 51 | 0.061 | 0.059 | 0.059 | 1.0 | 1.0 |
| 52 | 0.063 | 0.060 | 0.060 | 1.1 | 1.0 |
| 53 | 0.063 | 0.061 | 0.061 | 1.0 | 1.0 |
| 54 | 0.070 | 0.063 | 0.064 | 1.1 | 1.0 |
| 55 | 0.122 | 0.821 | 0.049 | **2.5** | **16.8** |
| 56 | 0.126 | 0.889 | 0.052 | **2.4** | **17.1** |
| 57 | 0.060 | 0.050 | 0.053 | 1.1 | 0.9 |
| 58 | 0.052 | 0.048 | 0.050 | 1.0 | 1.0 |
| 59 | 0.068 | 0.064 | 0.067 | 1.0 | 1.0 |
| 60 | 0.062 | 0.070 | 0.055 | 1.1 | 1.3 |
| 61 | 0.063 | 0.061 | 0.061 | 1.0 | 1.0 |
| 62 | 0.065 | 0.062 | 0.061 | 1.1 | 1.0 |
| 63 | 0.134 | 0.832 | 0.050 | **2.7** | **16.6** |
| 64 | 0.061 | 0.058 | 0.055 | 1.1 | 1.1 |
| 65 | 0.075 | 0.067 | 0.074 | 1.0 | 0.9 |
| 66 | 0.063 | 0.057 | 0.060 | 1.1 | 1.0 |
| 67 | 0.083 | 0.672 | 0.050 | 1.7 | **13.4** |
| 68 | 0.064 | 0.060 | 0.063 | 1.0 | 1.0 |
| 69 | 0.055 | 0.050 | 0.053 | 1.0 | 0.9 |
| 70 | 0.069 | 0.071 | 0.070 | 1.0 | 1.0 |
| 71 | 0.053 | 0.050 | 0.053 | 1.0 | 0.9 |
| 72 | 0.059 | 0.056 | 0.055 | 1.1 | 1.0 |
| 73 | 0.102 | 0.785 | 0.051 | 2.0 | **15.4** |
| 74 | 0.060 | 0.055 | 0.058 | 1.0 | 0.9 |
| 75 | 0.061 | 0.057 | 0.059 | 1.0 | 1.0 |
| 76 | 0.061 | 0.058 | 0.058 | 1.1 | 1.0 |
| 77 | 0.063 | 0.062 | 0.069 | 0.9 | 0.9 |
| 78 | 0.054 | 0.073 | 0.049 | 1.1 | 1.5 |
| 79 | 0.143 | 0.844 | 0.054 | **2.6** | **15.6** |
| 80 | 0.068 | 0.068 | 0.063 | 1.1 | 1.1 |
| 81 | 0.059 | 0.056 | 0.058 | 1.0 | 1.0 |
| 82 | 0.061 | 0.056 | 0.059 | 1.0 | 0.9 |
| 83 | 0.064 | 0.059 | 0.059 | 1.1 | 1.0 |
| 84 | 0.068 | 0.060 | 0.064 | 1.1 | 0.9 |
| 85 | 0.065 | 0.061 | 0.064 | 1.0 | 1.0 |
| 86 | 0.058 | 0.051 | 0.052 | 1.1 | 1.0 |
| 87 | 0.055 | 0.052 | 0.052 | 1.1 | 1.0 |
| 88 | 0.062 | 0.060 | 0.056 | 1.1 | 1.1 |
| 89 | 0.067 | 0.131 | 0.061 | 1.1 | **2.1** |
| 90 | 0.065 | 0.060 | 0.058 | 1.1 | 1.0 |
| 91 | 0.133 | 0.826 | 0.049 | **2.7** | **16.9** |
| 92 | 0.080 | 0.087 | 0.083 | 1.0 | 1.0 |
| 93 | 0.060 | 0.054 | 0.053 | 1.1 | 1.0 |
| 94 | 0.076 | 0.069 | 0.068 | 1.1 | 1.0 |
| 95 | 0.088 | 0.089 | 0.082 | 1.1 | 1.1 |
| 96 | 0.076 | 0.069 | 0.071 | 1.1 | 1.0 |

Fig. 23

154DHB2b-4

| | Value of ELISA (absorbance at 450 nm) | | | Ratio to NC | |
|---|---|---|---|---|---|
| # | CD154 | CD3 | NC | S/N of CD154 | S/N of CD3 |
| 1 | 0.077 | 0.061 | 0.062 | 1.2 | 1.0 |
| 2 | 0.060 | 0.114 | 0.050 | 1.2 | **2.3** |
| 3 | 0.053 | 0.048 | 0.050 | 1.1 | 1.0 |
| 4 | 0.048 | 0.045 | 0.049 | 1.0 | 0.9 |
| 5 | 0.053 | 0.050 | 0.057 | 0.9 | 0.9 |
| 6 | 0.057 | 0.052 | 0.054 | 1.1 | 1.0 |
| 7 | 0.086 | 0.075 | 0.079 | 1.1 | 0.9 |
| 8 | 0.060 | 0.059 | 0.059 | 1.0 | 1.0 |
| 9 | 0.053 | 0.062 | 0.060 | 0.9 | 1.0 |
| 10 | 0.048 | 0.047 | 0.048 | 1.0 | 1.0 |
| 11 | 0.049 | 0.062 | 0.052 | 0.9 | 1.2 |
| 12 | 0.059 | 0.047 | 0.047 | 1.3 | 1.0 |
| 13 | 0.058 | 0.292 | 0.052 | 1.1 | **5.6** |
| 14 | 0.059 | 0.110 | 0.059 | 1.0 | 1.9 |
| 15 | 0.053 | 0.053 | 0.058 | 0.9 | 0.9 |
| 16 | 0.061 | 0.117 | 0.064 | 1.0 | 1.8 |
| 17 | 0.064 | 0.058 | 0.058 | 1.1 | 1.0 |
| 18 | 0.163 | 0.255 | 0.083 | 2.0 | **3.1** |
| 19 | 0.054 | 0.067 | 0.059 | 0.9 | 1.1 |
| 20 | 0.057 | 0.179 | 0.049 | 1.2 | **3.7** |
| 21 | 0.051 | 0.051 | 0.053 | 1.0 | 1.0 |
| 22 | 0.050 | 0.680 | 0.054 | 0.9 | **12.6** |
| 23 | 0.058 | 0.094 | 0.063 | 0.9 | 1.5 |
| 24 | 0.059 | 0.234 | 0.061 | 1.0 | **3.8** |
| 25 | 0.056 | 0.050 | 0.051 | 1.1 | 1.0 |
| 26 | 0.050 | 0.057 | 0.049 | 1.0 | 1.2 |
| 27 | 0.046 | 0.046 | 0.048 | 1.0 | 1.0 |
| 28 | 0.054 | 0.169 | 0.051 | 1.1 | **3.3** |
| 29 | 0.049 | 0.183 | 0.047 | 1.0 | **3.9** |
| 30 | 0.051 | 0.052 | 0.050 | 1.0 | 1.0 |
| 31 | 0.045 | 0.045 | 0.046 | 1.0 | 1.0 |
| 32 | 0.051 | 0.050 | 0.053 | 1.0 | 0.9 |
| 33 | 0.073 | 0.125 | 0.074 | 1.0 | 1.7 |
| 34 | 0.052 | 0.050 | 0.053 | 1.0 | 0.9 |
| 35 | 0.067 | 0.121 | 0.072 | 0.9 | 1.7 |
| 36 | 0.055 | 0.648 | 0.053 | 1.0 | **12.2** |
| 37 | 0.051 | 0.381 | 0.053 | 1.0 | **7.2** |
| 38 | 0.050 | 0.047 | 0.051 | 1.0 | 0.9 |
| 39 | 0.051 | 0.047 | 0.051 | 1.0 | 0.9 |
| 40 | 0.072 | 0.104 | 0.070 | 1.0 | 1.5 |
| 41 | 0.052 | 0.051 | 0.051 | 1.0 | 1.0 |
| 42 | 0.054 | 0.055 | 0.058 | 0.9 | 0.9 |
| 43 | 0.052 | 0.086 | 0.052 | 1.0 | 1.7 |
| 44 | 0.061 | 0.050 | 0.055 | 1.1 | 0.9 |
| 45 | 0.049 | 0.047 | 0.048 | 1.0 | 1.0 |
| 46 | 0.043 | 0.043 | 0.046 | 0.9 | 0.9 |
| 47 | 0.056 | 0.217 | 0.058 | 1.0 | **3.7** |
| 48 | 0.073 | 0.115 | 0.073 | 1.0 | 1.6 |

| | Value of ELISA (absorbance at 450 nm) | | | Ratio to NC | |
|---|---|---|---|---|---|
| # | CD154 | CD3 | NC | S/N of CD154 | S/N of CD3 |
| 49 | 0.069 | 0.210 | 0.066 | 1.0 | **3.2** |
| 50 | 0.110 | 0.751 | 0.049 | **2.2** | **15.3** |
| 51 | 0.046 | 0.044 | 0.049 | 0.9 | 0.9 |
| 52 | 0.050 | 0.178 | 0.052 | 1.0 | **3.4** |
| 53 | 0.050 | 0.048 | 0.059 | 0.8 | 0.8 |
| 54 | 0.063 | 0.057 | 0.064 | 1.0 | 0.9 |
| 55 | 0.053 | 0.975 | 0.054 | 1.0 | **18.1** |
| 56 | 0.056 | 0.057 | 0.061 | 0.9 | 0.9 |
| 57 | 0.050 | 0.052 | 0.049 | 1.0 | 1.1 |
| 58 | 0.050 | 0.045 | 0.049 | 1.0 | 0.9 |
| 59 | 0.062 | 0.067 | 0.059 | 1.1 | 1.1 |
| 60 | 0.060 | 0.067 | 0.052 | 1.2 | 1.3 |
| 61 | 0.057 | 0.065 | 0.058 | 1.0 | 1.1 |
| 62 | 0.109 | 0.749 | 0.052 | **2.1** | **14.4** |
| 63 | 0.062 | 0.068 | 0.069 | 0.9 | 1.0 |
| 64 | 0.049 | 0.052 | 0.051 | 1.0 | 1.0 |
| 65 | 0.065 | 0.059 | 0.059 | 1.1 | 1.0 |
| 66 | 0.054 | 0.055 | 0.058 | 0.9 | 0.9 |
| 67 | 0.049 | 0.045 | 0.048 | 1.0 | 0.9 |
| 68 | 0.065 | 0.175 | 0.064 | 1.0 | **2.7** |
| 69 | 0.055 | 0.052 | 0.057 | 1.0 | 0.9 |
| 70 | 0.047 | 0.046 | 0.048 | 1.0 | 1.0 |
| 71 | 0.059 | 0.058 | 0.061 | 1.0 | 1.0 |
| 72 | 0.057 | 0.090 | 0.059 | 1.0 | 1.5 |
| 73 | 0.059 | 0.077 | 0.057 | 1.0 | 1.4 |
| 74 | 0.052 | 0.192 | 0.057 | 0.9 | **3.4** |
| 75 | 0.059 | 0.130 | 0.071 | 0.8 | 1.8 |
| 76 | 0.055 | 0.046 | 0.048 | 1.1 | 1.0 |
| 77 | 0.049 | 0.054 | 0.050 | 1.0 | 1.1 |
| 78 | 0.054 | 0.052 | 0.054 | 1.0 | 1.0 |
| 79 | 0.054 | 0.056 | 0.054 | 1.0 | 1.0 |
| 80 | 0.125 | 0.816 | 0.057 | **2.2** | **14.3** |
| 81 | 0.048 | 0.046 | 0.049 | 1.0 | 0.9 |
| 82 | 0.052 | 0.056 | 0.051 | 1.0 | 1.1 |
| 83 | 0.053 | 0.410 | 0.054 | 1.0 | **7.6** |
| 84 | 0.065 | 0.057 | 0.064 | 1.0 | 0.9 |
| 85 | 0.054 | 0.048 | 0.053 | 1.0 | 0.9 |
| 86 | 0.053 | 0.102 | 0.056 | 0.9 | 1.8 |
| 87 | 0.051 | 0.050 | 0.054 | 0.9 | 0.9 |
| 88 | 0.054 | 0.054 | 0.053 | 1.0 | 1.0 |
| 89 | 0.065 | 0.087 | 0.070 | 0.9 | 1.2 |
| 90 | 0.047 | 0.072 | 0.051 | 0.9 | 1.4 |
| 91 | 0.062 | 0.047 | 0.052 | 1.2 | 0.9 |
| 92 | 0.052 | 0.052 | 0.052 | 1.0 | 1.0 |
| 93 | 0.048 | 0.047 | 0.048 | 1.0 | 1.0 |
| 94 | 0.056 | 0.803 | 0.058 | 1.0 | **13.8** |
| 95 | 0.059 | 0.183 | 0.058 | 1.0 | **3.2** |
| 96 | 0.074 | 0.069 | 0.067 | 1.1 | 1.0 |

(1)

(2)

```
SEQUENCE LISTING

<160> NUMBER OF SEQ ID NOS: 141

<210> SEQ ID NO 1
<211> LENGTH: 330
<212> TYPE: PRT
<213> ORGANISM: Homo sapiens

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

```
Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 2
<211> LENGTH: 326
<212> TYPE: PRT
<213> ORGANISM: Homo sapiens

<400> SEQUENCE: 2

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320
```

```
Ser Leu Ser Pro Gly Lys
                325


<210> SEQ ID NO 3
<211> LENGTH: 377
<212> TYPE: PRT
<213> ORGANISM: Homo sapiens

<400> SEQUENCE: 3

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
```

```
        355                 360                 365

Lys Ser Leu Ser Leu Ser Pro Gly Lys
    370                 375


<210> SEQ ID NO 4
<211> LENGTH: 327
<212> TYPE: PRT
<213> ORGANISM: Homo sapiens

<400> SEQUENCE: 4

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 5
<211> LENGTH: 4
```

<212> TYPE: PRT
<213> ORGANISM: Artificial sequence
<220> FEATURE:
<223> OTHER INFORMATION: An artificially synthesized peptide sequence

<400> SEQUENCE: 5

Gly Gly Gly Ser
1

<210> SEQ ID NO 6
<211> LENGTH: 4
<212> TYPE: PRT
<213> ORGANISM: Artificial sequence
<220> FEATURE:
<223> OTHER INFORMATION: An artificially synthesized peptide sequence

<400> SEQUENCE: 6

Ser Gly Gly Gly
1

<210> SEQ ID NO 7
<211> LENGTH: 5
<212> TYPE: PRT
<213> ORGANISM: Artificial sequence
<220> FEATURE:
<223> OTHER INFORMATION: An artificially synthesized peptide sequence

<400> SEQUENCE: 7

Gly Gly Gly Gly Ser
1               5

<210> SEQ ID NO 8
<211> LENGTH: 5
<212> TYPE: PRT
<213> ORGANISM: Artificial sequence
<220> FEATURE:
<223> OTHER INFORMATION: An artificially synthesized peptide sequence

<400> SEQUENCE: 8

Ser Gly Gly Gly Gly
1               5

<210> SEQ ID NO 9
<211> LENGTH: 6
<212> TYPE: PRT
<213> ORGANISM: Artificial sequence
<220> FEATURE:
<223> OTHER INFORMATION: An artificially synthesized peptide sequence

<400> SEQUENCE: 9

Gly Gly Gly Gly Gly Ser
1               5

<210> SEQ ID NO 10
<211> LENGTH: 6
<212> TYPE: PRT
<213> ORGANISM: Artificial sequence
<220> FEATURE:
<223> OTHER INFORMATION: An artificially synthesized peptide sequence

<400> SEQUENCE: 10

Ser Gly Gly Gly Gly Gly
1               5

<210> SEQ ID NO 11
<211> LENGTH: 7
<212> TYPE: PRT

<213> ORGANISM: Artificial sequence
<220> FEATURE:
<223> OTHER INFORMATION: An artificially synthesized peptide sequence

<400> SEQUENCE: 11

Gly Gly Gly Gly Gly Gly Ser
1               5

<210> SEQ ID NO 12
<211> LENGTH: 7
<212> TYPE: PRT
<213> ORGANISM: Artificial sequence
<220> FEATURE:
<223> OTHER INFORMATION: An artificially synthesized peptide sequence

<400> SEQUENCE: 12

Ser Gly Gly Gly Gly Gly Gly
1               5

<210> SEQ ID NO 13
<211> LENGTH: 122
<212> TYPE: PRT
<213> ORGANISM: Rattus norvegicus

<400> SEQUENCE: 13

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Lys Ser Asn Asn Tyr Ala Thr Tyr Tyr Ala Glu
    50                  55                  60

Ser Val Lys Gly Arg Phe Thr Ile Ser Arg Asp Asp Ser Lys Ser Asn
65                  70                  75                  80

Ile Tyr Leu Gln Met Asn Ser Leu Lys Glu Glu Asp Thr Ala Val Tyr
                85                  90                  95

Tyr Cys Arg Tyr Val His Tyr Gly Ala Tyr Tyr Gly Val Asp Ala Trp
            100                 105                 110

Gly Gln Gly Thr Ser Val Thr Val Ser Ser
        115                 120

<210> SEQ ID NO 14
<211> LENGTH: 112
<212> TYPE: PRT
<213> ORGANISM: Rattus norvegicus

<400> SEQUENCE: 14

Asp Val Val Met Thr Gln Thr Pro Val Ser Met Ser Val Ser Leu Gly
1               5                   10                  15

Gly Gln Val Ser Ile Ser Cys Arg Ser Ser Gln Ser Leu Val His Asn
            20                  25                  30

Asn Gly Asn Thr Tyr Val Ser Trp Tyr Ile Gln Lys Pro Ser Gln Ser
        35                  40                  45

Pro Gln Leu Leu Ile Tyr Lys Val Ser Asn Arg Phe Ser Gly Ile Ser
    50                  55                  60

Asp Arg Phe Ser Gly Ser Gly Ser Gly Thr Asp Phe Thr Leu Lys Ile
65                  70                  75                  80

Ser Arg Val Glu Pro Asp Asp Leu Gly Val Tyr Tyr Cys Gly Gln Gly
                85                  90                  95

```
Thr Gln Asp Pro Tyr Thr Phe Gly Ala Gly Thr Lys Leu Glu Leu Lys
            100                 105                 110


<210> SEQ ID NO 15
<211> LENGTH: 119
<212> TYPE: PRT
<213> ORGANISM: Mus musculus

<400> SEQUENCE: 15

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115


<210> SEQ ID NO 16
<211> LENGTH: 107
<212> TYPE: PRT
<213> ORGANISM: Mus musculus

<400> SEQUENCE: 16

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys
            100                 105


<210> SEQ ID NO 17
<211> LENGTH: 447
<212> TYPE: PRT
<213> ORGANISM: Artificial sequence
<220> FEATURE:
<223> OTHER INFORMATION: An artificially synthesized peptide sequence

<400> SEQUENCE: 17

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
```

-continued

```
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445
```

<210> SEQ ID NO 18
<211> LENGTH: 447
<212> TYPE: PRT
<213> ORGANISM: Artificial sequence
<220> FEATURE:
<223> OTHER INFORMATION: An artificially synthesized peptide sequence

<400> SEQUENCE: 18

Gln Val Gln Leu Lys Gln Ser Gly Pro Gly Leu Val Gln Pro Ser Gln
1 5 10 15

Ser Leu Ser Ile Thr Cys Thr Val Ser Gly Phe Ser Leu Thr Asn Tyr
20 25 30

Gly Val His Trp Val Arg Gln Ser Pro Gly Lys Gly Leu Glu Trp Leu
35 40 45

Gly Val Ile Trp Ser Gly Gly Asn Thr Asp Tyr Asn Thr Pro Phe Thr
50 55 60

Ser Arg Leu Ser Ile Asn Lys Asp Asn Ser Lys Ser Gln Val Phe Phe
65 70 75 80

Lys Met Asn Ser Leu Gln Ser Asn Asp Thr Ala Ile Tyr Tyr Cys Ala
85 90 95

Arg Ala Leu Thr Tyr Tyr Asp Tyr Glu Phe Ala Tyr Trp Gly Gln Gly
100 105 110

Thr Leu Val Thr Val Ser Ala Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Lys Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn Arg Tyr Thr Gln Lys Ser Leu Ser Leu Ser Pro
435 440 445

<210> SEQ ID NO 19
<211> LENGTH: 447
<212> TYPE: PRT
<213> ORGANISM: Artificial sequence
<220> FEATURE:
<223> OTHER INFORMATION: An artificially synthesized peptide sequence

<400> SEQUENCE: 19

Gln Val Gln Leu Lys Gln Ser Gly Pro Gly Leu Val Gln Pro Ser Gln
1 5 10 15

Ser Leu Ser Ile Thr Cys Thr Val Ser Gly Phe Ser Leu Thr Asn Tyr
20 25 30

Gly Val His Trp Val Arg Gln Ser Pro Gly Lys Gly Leu Glu Trp Leu
35 40 45

Gly Val Ile Trp Ser Gly Gly Asn Thr Asp Tyr Asn Thr Pro Phe Thr
50 55 60

Ser Arg Leu Ser Ile Asn Lys Asp Asn Ser Lys Ser Gln Val Phe Phe
65 70 75 80

Lys Met Asn Ser Leu Gln Ser Asn Asp Thr Ala Ile Tyr Tyr Cys Ala
85 90 95

Arg Ala Leu Thr Tyr Tyr Asp Tyr Glu Phe Ala Tyr Trp Gly Gln Gly
100 105 110

Thr Leu Val Thr Val Ser Ala Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

```
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 20
<211> LENGTH: 445
<212> TYPE: PRT
<213> ORGANISM: Artificial sequence
<220> FEATURE:
<223> OTHER INFORMATION: An artificially synthesized peptide sequence

<400> SEQUENCE: 20

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Ser Ser Ala Ser Thr
            100                 105                 110

Lys Gly Pro Ser Val Phe Pro Leu Ala Pro Ser Ser Lys Ser Thr Ser
        115                 120                 125

Gly Gly Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
        195                 200                 205
```

```
Pro Lys Ser Cys Asp Lys Thr His Thr Cys Pro Pro Cys Pro Ala Pro
    210                 215                 220

Glu Ala Ala Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser His Glu Asp Pro Glu Val Lys Phe Asn Trp Tyr Val Asp
            260                 265                 270

Gly Val Glu Val His Asn Ala Lys Thr Lys Pro Arg Glu Glu Gln Tyr
        275                 280                 285

Ala Ser Thr Tyr Arg Val Val Ser Val Leu Thr Val Leu His Gln Asp
    290                 295                 300

Trp Leu Asn Gly Lys Glu Tyr Lys Cys Lys Val Ser Asn Lys Ala Leu
305                 310                 315                 320

Pro Ala Pro Ile Glu Lys Thr Ile Ser Lys Ala Lys Gly Gln Pro Arg
                325                 330                 335

Glu Pro Gln Val Cys Thr Leu Pro Pro Ser Arg Asp Glu Leu Thr Lys
            340                 345                 350

Asn Gln Val Ser Leu Trp Cys Leu Val Lys Gly Phe Tyr Pro Ser Asp
        355                 360                 365

Ile Ala Val Glu Trp Glu Ser Asn Gly Gln Pro Glu Asn Asn Tyr Lys
    370                 375                 380

Thr Thr Pro Pro Val Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
                405                 410                 415

Cys Ser Val Met His Glu Ala Leu His Asn Arg Tyr Thr Gln Lys Ser
            420                 425                 430

Leu Ser Leu Ser Pro His His His His His His His His
        435                 440                 445


<210> SEQ ID NO 21
<211> LENGTH: 226
<212> TYPE: PRT
<213> ORGANISM: Artificial sequence
<220> FEATURE:
<223> OTHER INFORMATION: An artificially synthesized peptide sequence

<400> SEQUENCE: 21

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Arg Thr Val Ala Ala Pro Ser Val Phe
        115                 120                 125
```

```
Ile Phe Pro Pro Ser Asp Glu Gln Leu Lys Ser Gly Thr Ala Ser Val
    130                 135                 140

Val Cys Leu Leu Asn Asn Phe Tyr Pro Arg Glu Ala Lys Val Gln Trp
145                 150                 155                 160

Lys Val Asp Asn Ala Leu Gln Ser Gly Asn Ser Gln Glu Ser Val Thr
                165                 170                 175

Glu Gln Asp Ser Lys Asp Ser Thr Tyr Ser Leu Ser Ser Thr Leu Thr
            180                 185                 190

Leu Ser Lys Ala Asp Tyr Glu Lys His Lys Val Tyr Ala Cys Glu Val
        195                 200                 205

Thr His Gln Gly Leu Ser Ser Pro Val Thr Lys Ser Phe Asn Arg Gly
    210                 215                 220

Glu Cys
225


<210> SEQ ID NO 22
<211> LENGTH: 458
<212> TYPE: PRT
<213> ORGANISM: Artificial sequence
<220> FEATURE:
<223> OTHER INFORMATION: An artificially synthesized peptide sequence

<400> SEQUENCE: 22

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Lys Ser Asn Asn Tyr Ala Thr Tyr Tyr Ala Glu
    50                  55                  60

Ser Val Lys Gly Arg Phe Thr Ile Ser Arg Asp Asp Ser Lys Ser Asn
65                  70                  75                  80

Ile Tyr Leu Gln Met Asn Ser Leu Lys Glu Glu Asp Thr Ala Val Tyr
                85                  90                  95

Tyr Cys Arg Tyr Val His Tyr Gly Ala Tyr Tyr Gly Val Asp Ala Trp
            100                 105                 110

Gly Gln Gly Thr Ser Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255
```

```
Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Ala Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Cys Glu Leu Thr Lys Asn Gln Val
        355                 360                 365

Ser Leu Ser Cys Ala Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Val Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Asp Tyr Lys Asp Asp Asp Asp Lys
    450                 455

<210> SEQ ID NO 23
<211> LENGTH: 219
<212> TYPE: PRT
<213> ORGANISM: Artificial sequence
<220> FEATURE:
<223> OTHER INFORMATION: An artificially synthesized peptide sequence

<400> SEQUENCE: 23

Asp Val Val Met Thr Gln Thr Pro Val Ser Met Ser Val Ser Leu Gly
1               5                   10                  15

Gly Gln Val Ser Ile Ser Cys Arg Ser Ser Gln Ser Leu Val His Asn
            20                  25                  30

Asn Gly Asn Thr Tyr Val Ser Trp Tyr Ile Gln Lys Pro Ser Gln Ser
        35                  40                  45

Pro Gln Leu Leu Ile Tyr Lys Val Ser Asn Arg Phe Ser Gly Ile Ser
    50                  55                  60

Asp Arg Phe Ser Gly Ser Gly Ser Gly Thr Asp Phe Thr Leu Lys Ile
65                  70                  75                  80

Ser Arg Val Glu Pro Asp Asp Leu Gly Val Tyr Tyr Cys Gly Gln Gly
                85                  90                  95

Thr Gln Asp Pro Tyr Thr Phe Gly Ala Gly Thr Lys Leu Glu Leu Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160
```

```
Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 24
<211> LENGTH: 462
<212> TYPE: PRT
<213> ORGANISM: Artificial sequence
<220> FEATURE:
<223> OTHER INFORMATION: An artificially synthesized peptide sequence

<400> SEQUENCE: 24

```
Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Gly Cys Arg Gly Asp Cys Leu Asn Tyr Ala Thr
    50                  55                  60

Tyr Tyr Ala Glu Ser Val Lys Gly Arg Phe Thr Ile Ser Arg Asp Asp
65                  70                  75                  80

Ser Lys Ser Asn Ile Tyr Leu Gln Met Asn Ser Leu Lys Glu Glu Asp
                85                  90                  95

Thr Ala Val Tyr Tyr Cys Arg Tyr Val His Tyr Gly Ala Tyr Tyr Gly
            100                 105                 110

Val Asp Ala Trp Gly Gln Gly Thr Ser Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Ala Ala Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300
```

```
Tyr Ala Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Cys Glu Leu Thr
        355                 360                 365

Lys Asn Gln Val Ser Leu Ser Cys Ala Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Val
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Asp Tyr Lys Asp Asp Asp Asp Lys
    450                 455                 460


<210> SEQ ID NO 25
<211> LENGTH: 462
<212> TYPE: PRT
<213> ORGANISM: Artificial sequence
<220> FEATURE:
<223> OTHER INFORMATION: An artificially synthesized peptide sequence

<400> SEQUENCE: 25

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Lys Gly Cys Arg Gly Asp Cys Leu Tyr Ala Thr
    50                  55                  60

Tyr Tyr Ala Glu Ser Val Lys Gly Arg Phe Thr Ile Ser Arg Asp Asp
65                  70                  75                  80

Ser Lys Ser Asn Ile Tyr Leu Gln Met Asn Ser Leu Lys Glu Glu Asp
                85                  90                  95

Thr Ala Val Tyr Tyr Cys Arg Tyr Val His Tyr Gly Ala Tyr Tyr Gly
            100                 105                 110

Val Asp Ala Trp Gly Gln Gly Thr Ser Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205
```

```
Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Ala Ala Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Ala Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Cys Glu Leu Thr
        355                 360                 365

Lys Asn Gln Val Ser Leu Ser Cys Ala Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Val
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Asp Tyr Lys Asp Asp Asp Asp Lys
    450                 455                 460


<210> SEQ ID NO 26
<211> LENGTH: 465
<212> TYPE: PRT
<213> ORGANISM: Artificial sequence
<220> FEATURE:
<223> OTHER INFORMATION: An artificially synthesized peptide sequence

<400> SEQUENCE: 26

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Gly Cys Arg Gly Asp Cys Leu Lys Ser Asn Asn
    50                  55                  60

Tyr Ala Thr Tyr Tyr Ala Glu Ser Val Lys Gly Arg Phe Thr Ile Ser
65                  70                  75                  80

Arg Asp Asp Ser Lys Ser Asn Ile Tyr Leu Gln Met Asn Ser Leu Lys
                85                  90                  95

Glu Glu Asp Thr Ala Val Tyr Tyr Cys Arg Tyr Val His Tyr Gly Ala
            100                 105                 110
```

```
Tyr Tyr Gly Val Asp Ala Trp Gly Gln Gly Thr Ser Val Thr Val Ser
        115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Lys Val Glu Pro Lys Ser Cys Asp Lys Thr His Thr Cys Pro Pro
225                 230                 235                 240

Cys Pro Ala Pro Glu Ala Ala Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
    290                 295                 300

Glu Glu Gln Tyr Ala Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Ser Arg Cys
        355                 360                 365

Glu Leu Thr Lys Asn Gln Val Ser Leu Ser Cys Ala Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Val Ser Lys Leu Thr Val Asp Lys Ser Arg Trp Gln Gln Gly
            420                 425                 430

Asn Val Phe Ser Cys Ser Val Met His Glu Ala Leu His Asn His Tyr
        435                 440                 445

Thr Gln Lys Ser Leu Ser Leu Ser Pro Asp Tyr Lys Asp Asp Asp Asp
    450                 455                 460

Lys
465
```

<210> SEQ ID NO 27
<211> LENGTH: 465
<212> TYPE: PRT
<213> ORGANISM: Artificial sequence
<220> FEATURE:
<223> OTHER INFORMATION: An artificially synthesized peptide sequence

<400> SEQUENCE: 27

-continued

```
Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Lys Gly Cys Arg Gly Asp Cys Leu Ser Asn Asn
    50                  55                  60

Tyr Ala Thr Tyr Tyr Ala Glu Ser Val Lys Gly Arg Phe Thr Ile Ser
65                  70                  75                  80

Arg Asp Asp Ser Lys Ser Asn Ile Tyr Leu Gln Met Asn Ser Leu Lys
                85                  90                  95

Glu Glu Asp Thr Ala Val Tyr Tyr Cys Arg Tyr Val His Tyr Gly Ala
            100                 105                 110

Tyr Tyr Gly Val Asp Ala Trp Gly Gln Gly Thr Ser Val Thr Val Ser
        115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Lys Val Glu Pro Lys Ser Cys Asp Lys Thr His Thr Cys Pro Pro
225                 230                 235                 240

Cys Pro Ala Pro Glu Ala Ala Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
    290                 295                 300

Glu Glu Gln Tyr Ala Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Ser Arg Cys
        355                 360                 365

Glu Leu Thr Lys Asn Gln Val Ser Leu Ser Cys Ala Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415
```

```
Phe Leu Val Ser Lys Leu Thr Val Asp Lys Ser Arg Trp Gln Gln Gly
            420                 425                 430

Asn Val Phe Ser Cys Ser Val Met His Glu Ala Leu His Asn His Tyr
        435                 440                 445

Thr Gln Lys Ser Leu Ser Leu Ser Pro Asp Tyr Lys Asp Asp Asp Asp
    450                 455                 460

Lys
465


<210> SEQ ID NO 28
<211> LENGTH: 465
<212> TYPE: PRT
<213> ORGANISM: Artificial sequence
<220> FEATURE:
<223> OTHER INFORMATION: An artificially synthesized peptide sequence

<400> SEQUENCE: 28

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Lys Ser Asn Asn Tyr Ala Thr Tyr Tyr Ala Glu
    50                  55                  60

Ser Val Lys Gly Arg Phe Thr Ile Ser Arg Asp Gly Cys Arg Gly Asp
65                  70                  75                  80

Cys Leu Asp Ser Lys Ser Asn Ile Tyr Leu Gln Met Asn Ser Leu Lys
                85                  90                  95

Glu Glu Asp Thr Ala Val Tyr Tyr Cys Arg Tyr Val His Tyr Gly Ala
            100                 105                 110

Tyr Tyr Gly Val Asp Ala Trp Gly Gln Gly Thr Ser Val Thr Val Ser
        115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Lys Val Glu Pro Lys Ser Cys Asp Lys Thr His Thr Cys Pro Pro
225                 230                 235                 240

Cys Pro Ala Pro Glu Ala Ala Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
    290                 295                 300
```

-continued

Glu Glu Gln Tyr Ala Ser Thr Tyr Arg Val Val Ser Val Leu Thr Val
305 310 315 320

Leu His Gln Asp Trp Leu Asn Gly Lys Glu Tyr Lys Cys Lys Val Ser
325 330 335

Asn Lys Ala Leu Pro Ala Pro Ile Glu Lys Thr Ile Ser Lys Ala Lys
340 345 350

Gly Gln Pro Arg Glu Pro Gln Val Tyr Thr Leu Pro Pro Ser Arg Cys
355 360 365

Glu Leu Thr Lys Asn Gln Val Ser Leu Ser Cys Ala Val Lys Gly Phe
370 375 380

Tyr Pro Ser Asp Ile Ala Val Glu Trp Glu Ser Asn Gly Gln Pro Glu
385 390 395 400

Asn Asn Tyr Lys Thr Thr Pro Pro Val Leu Asp Ser Asp Gly Ser Phe
405 410 415

Phe Leu Val Ser Lys Leu Thr Val Asp Lys Ser Arg Trp Gln Gln Gly
420 425 430

Asn Val Phe Ser Cys Ser Val Met His Glu Ala Leu His Asn His Tyr
435 440 445

Thr Gln Lys Ser Leu Ser Leu Ser Pro Asp Tyr Lys Asp Asp Asp Asp
450 455 460

Lys
465

<210> SEQ ID NO 29
<211> LENGTH: 463
<212> TYPE: PRT
<213> ORGANISM: Artificial sequence
<220> FEATURE:
<223> OTHER INFORMATION: An artificially synthesized peptide sequence

<400> SEQUENCE: 29

Glu Val Gln Leu Val Glu Thr Gly Gly Ser Leu Val Gln Pro Gly Lys
1 5 10 15

Ser Leu Lys Leu Thr Cys Ala Thr Ser Gly Phe Thr Phe Ser Asn Ala
20 25 30

Trp Met His Trp Val Arg Gln Ser Pro Glu Lys Gln Leu Glu Trp Val
35 40 45

Ala Gln Ile Lys Ala Gly Cys Arg Gly Asp Cys Leu Asn Asn Tyr Ala
50 55 60

Thr Tyr Tyr Ala Glu Ser Val Lys Gly Arg Phe Thr Ile Ser Arg Asp
65 70 75 80

Asp Ser Lys Ser Asn Ile Tyr Leu Gln Met Asn Ser Leu Lys Glu Glu
85 90 95

Asp Thr Ala Val Tyr Tyr Cys Arg Tyr Val His Tyr Gly Ala Tyr Tyr
100 105 110

Gly Val Asp Ala Trp Gly Gln Gly Thr Ser Val Thr Val Ser Ser Ala
115 120 125

Ser Thr Lys Gly Pro Ser Val Phe Pro Leu Ala Pro Ser Ser Lys Ser
130 135 140

Thr Ser Gly Gly Thr Ala Ala Leu Gly Cys Leu Val Lys Asp Tyr Phe
145 150 155 160

Pro Glu Pro Val Thr Val Ser Trp Asn Ser Gly Ala Leu Thr Ser Gly
165 170 175

Val His Thr Phe Pro Ala Val Leu Gln Ser Ser Gly Leu Tyr Ser Leu
180 185 190

Ser Ser Val Val Thr Val Pro Ser Ser Ser Leu Gly Thr Gln Thr Tyr
195 200 205

Ile Cys Asn Val Asn His Lys Pro Ser Asn Thr Lys Val Asp Lys Lys
210 215 220

Val Glu Pro Lys Ser Cys Asp Lys Thr His Thr Cys Pro Pro Cys Pro
225 230 235 240

Ala Pro Glu Ala Ala Gly Gly Pro Ser Val Phe Leu Phe Pro Pro Lys
245 250 255

Pro Lys Asp Thr Leu Met Ile Ser Arg Thr Pro Glu Val Thr Cys Val
260 265 270

Val Val Asp Val Ser His Glu Asp Pro Glu Val Lys Phe Asn Trp Tyr
275 280 285

Val Asp Gly Val Glu Val His Asn Ala Lys Thr Lys Pro Arg Glu Glu
290 295 300

Gln Tyr Ala Ser Thr Tyr Arg Val Val Ser Val Leu Thr Val Leu His
305 310 315 320

Gln Asp Trp Leu Asn Gly Lys Glu Tyr Lys Cys Lys Val Ser Asn Lys
325 330 335

Ala Leu Pro Ala Pro Ile Glu Lys Thr Ile Ser Lys Ala Lys Gly Gln
340 345 350

Pro Arg Glu Pro Gln Val Tyr Thr Leu Pro Pro Ser Arg Cys Glu Leu
355 360 365

Thr Lys Asn Gln Val Ser Leu Ser Cys Ala Val Lys Gly Phe Tyr Pro
370 375 380

Ser Asp Ile Ala Val Glu Trp Glu Ser Asn Gly Gln Pro Glu Asn Asn
385 390 395 400

Tyr Lys Thr Thr Pro Pro Val Leu Asp Ser Asp Gly Ser Phe Phe Leu
405 410 415

Val Ser Lys Leu Thr Val Asp Lys Ser Arg Trp Gln Gln Gly Asn Val
420 425 430

Phe Ser Cys Ser Val Met His Glu Ala Leu His Asn His Tyr Thr Gln
435 440 445

Lys Ser Leu Ser Leu Ser Pro Asp Tyr Lys Asp Asp Asp Asp Lys
450 455 460

<210> SEQ ID NO 30
<211> LENGTH: 465
<212> TYPE: PRT
<213> ORGANISM: Artificial sequence
<220> FEATURE:
<223> OTHER INFORMATION: An artificially synthesized peptide sequence

<400> SEQUENCE: 30

Glu Val Gln Leu Val Glu Thr Gly Gly Ser Leu Val Gln Pro Gly Lys
1 5 10 15

Ser Leu Lys Leu Thr Cys Ala Thr Ser Gly Phe Thr Phe Ser Asn Ala
20 25 30

Trp Met His Trp Val Arg Gln Ser Pro Glu Lys Gln Leu Glu Trp Val
35 40 45

Ala Gln Ile Lys Ala Lys Ser Asn Asn Tyr Ala Thr Tyr Tyr Ala Glu
50 55 60

Ser Val Lys Gly Arg Phe Thr Ile Ser Arg Asp Asp Ser Lys Ser Asn
65 70 75 80

Ile Tyr Leu Gln Met Asn Ser Leu Lys Glu Glu Asp Thr Ala Val Tyr
85 90 95

-continued

```
Tyr Cys Arg Tyr Val His Tyr Gly Gly Cys Arg Gly Asp Cys Leu Ala
            100                 105                 110

Tyr Tyr Gly Val Asp Ala Trp Gly Gln Gly Thr Ser Val Thr Val Ser
        115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Lys Val Glu Pro Lys Ser Cys Asp Lys Thr His Thr Cys Pro Pro
225                 230                 235                 240

Cys Pro Ala Pro Glu Ala Ala Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
    290                 295                 300

Glu Glu Gln Tyr Ala Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Ser Arg Cys
        355                 360                 365

Glu Leu Thr Lys Asn Gln Val Ser Leu Ser Cys Ala Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Val Ser Lys Leu Thr Val Asp Lys Ser Arg Trp Gln Gln Gly
            420                 425                 430

Asn Val Phe Ser Cys Ser Val Met His Glu Ala Leu His Asn His Tyr
        435                 440                 445

Thr Gln Lys Ser Leu Ser Leu Ser Pro Asp Tyr Lys Asp Asp Asp Asp
    450                 455                 460

Lys
465


<210> SEQ ID NO 31
<211> LENGTH: 465
<212> TYPE: PRT
<213> ORGANISM: Artificial sequence
<220> FEATURE:
<223> OTHER INFORMATION: An artificially synthesized peptide sequence
```

<400> SEQUENCE: 31

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Lys Ser Asn Asn Tyr Ala Thr Tyr Tyr Ala Glu
    50                  55                  60

Ser Val Lys Gly Arg Phe Thr Ile Ser Arg Asp Asp Ser Lys Ser Asn
65                  70                  75                  80

Ile Tyr Leu Gln Met Asn Ser Leu Lys Glu Glu Asp Thr Ala Val Tyr
                85                  90                  95

Tyr Cys Arg Tyr Val His Tyr Gly Ala Gly Cys Arg Gly Asp Cys Leu
            100                 105                 110

Tyr Tyr Gly Val Asp Ala Trp Gly Gln Gly Thr Ser Val Thr Val Ser
        115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Lys Val Glu Pro Lys Ser Cys Asp Lys Thr His Thr Cys Pro Pro
225                 230                 235                 240

Cys Pro Ala Pro Glu Ala Ala Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
    290                 295                 300

Glu Glu Gln Tyr Ala Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Ser Arg Cys
        355                 360                 365

Glu Leu Thr Lys Asn Gln Val Ser Leu Ser Cys Ala Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe

-continued 405 410 415

Phe Leu Val Ser Lys Leu Thr Val Asp Lys Ser Arg Trp Gln Gln Gly
420 425 430

Asn Val Phe Ser Cys Ser Val Met His Glu Ala Leu His Asn His Tyr
435 440 445

Thr Gln Lys Ser Leu Ser Leu Ser Pro Asp Tyr Lys Asp Asp Asp Asp
450 455 460

Lys
465

<210> SEQ ID NO 32
<211> LENGTH: 465
<212> TYPE: PRT
<213> ORGANISM: Artificial sequence
<220> FEATURE:
<223> OTHER INFORMATION: An artificially synthesized peptide sequence

<400> SEQUENCE: 32

Glu Val Gln Leu Val Glu Thr Gly Gly Ser Leu Val Gln Pro Gly Lys
1 5 10 15

Ser Leu Lys Leu Thr Cys Ala Thr Ser Gly Phe Thr Phe Ser Asn Ala
20 25 30

Trp Met His Trp Val Arg Gln Ser Pro Glu Lys Gln Leu Glu Trp Val
35 40 45

Ala Gln Ile Lys Ala Lys Ser Asn Asn Tyr Ala Thr Tyr Tyr Ala Glu
50 55 60

Ser Val Lys Gly Arg Phe Thr Ile Ser Arg Asp Asp Ser Lys Ser Asn
65 70 75 80

Ile Tyr Leu Gln Met Asn Ser Leu Lys Glu Glu Asp Thr Ala Val Tyr
85 90 95

Tyr Cys Arg Tyr Val His Tyr Gly Ala Tyr Gly Cys Arg Gly Asp Cys
100 105 110

Leu Tyr Gly Val Asp Ala Trp Gly Gln Gly Thr Ser Val Thr Val Ser
115 120 125

Ser Ala Ser Thr Lys Gly Pro Ser Val Phe Pro Leu Ala Pro Ser Ser
130 135 140

Lys Ser Thr Ser Gly Gly Thr Ala Ala Leu Gly Cys Leu Val Lys Asp
145 150 155 160

Tyr Phe Pro Glu Pro Val Thr Val Ser Trp Asn Ser Gly Ala Leu Thr
165 170 175

Ser Gly Val His Thr Phe Pro Ala Val Leu Gln Ser Ser Gly Leu Tyr
180 185 190

Ser Leu Ser Ser Val Val Thr Val Pro Ser Ser Ser Leu Gly Thr Gln
195 200 205

Thr Tyr Ile Cys Asn Val Asn His Lys Pro Ser Asn Thr Lys Val Asp
210 215 220

Lys Lys Val Glu Pro Lys Ser Cys Asp Lys Thr His Thr Cys Pro Pro
225 230 235 240

Cys Pro Ala Pro Glu Ala Ala Gly Gly Pro Ser Val Phe Leu Phe Pro
245 250 255

Pro Lys Pro Lys Asp Thr Leu Met Ile Ser Arg Thr Pro Glu Val Thr
260 265 270

Cys Val Val Val Asp Val Ser His Glu Asp Pro Glu Val Lys Phe Asn
275 280 285

Trp Tyr Val Asp Gly Val Glu Val His Asn Ala Lys Thr Lys Pro Arg

```
    290                 295                 300

Glu Glu Gln Tyr Ala Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Ser Arg Cys
        355                 360                 365

Glu Leu Thr Lys Asn Gln Val Ser Leu Ser Cys Ala Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Val Ser Lys Leu Thr Val Asp Lys Ser Arg Trp Gln Gln Gly
            420                 425                 430

Asn Val Phe Ser Cys Ser Val Met His Glu Ala Leu His Asn His Tyr
        435                 440                 445

Thr Gln Lys Ser Leu Ser Leu Ser Pro Asp Tyr Lys Asp Asp Asp Asp
    450                 455                 460

Lys
465


<210> SEQ ID NO 33
<211> LENGTH: 444
<212> TYPE: PRT
<213> ORGANISM: Artificial sequence
<220> FEATURE:
<223> OTHER INFORMATION: An artificially synthesized peptide sequence

<400> SEQUENCE: 33

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Lys Gln Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
```

-continued

```
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Tyr Gln Trp Gly Pro Met Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Asp Glu Glu Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ala Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Cys Thr Leu Pro Pro
            340                 345                 350

Ser Arg Asp Glu Leu Thr Lys Asn Gln Val Ser Leu Trp Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440


<210> SEQ ID NO 34
<211> LENGTH: 444
<212> TYPE: PRT
<213> ORGANISM: Artificial sequence
<220> FEATURE:
<223> OTHER INFORMATION: An artificially synthesized peptide sequence

<400> SEQUENCE: 34

Gln Asp Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile Gln Trp Val Arg Gln Ala Pro Gly Gln Gly Leu Glu Trp Met
        35                  40                  45

Gly Arg Ile Asp Pro Leu Arg Lys Gln Thr Lys Tyr Arg Glu Lys Phe
    50                  55                  60

Glu Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Ser Gly Arg Glu Phe Asp Tyr Trp Gly Gln Gly Thr Leu Val
```

-continued

```
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Glu Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Asp Ala Leu Pro Met Pro Ile Glu Glu Thr Ile Ser
                325                 330                 335

Lys Ala Lys Gly Gln Pro Arg Glu Pro Gln Val Tyr Thr Leu Pro Pro
            340                 345                 350

Ser Arg Cys Glu Leu Thr Lys Asn Gln Val Ser Leu Ser Cys Ala Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
        435                 440


<210> SEQ ID NO 35
<211> LENGTH: 213
<212> TYPE: PRT
<213> ORGANISM: Artificial sequence
<220> FEATURE:
<223> OTHER INFORMATION: An artificially synthesized peptide sequence

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile His Lys Tyr
```

```
            20                  25                  30

Ile Ala Trp Tyr Gln Gln Lys Pro Gly Gln Ala Pro Arg Leu Leu Ile
        35                  40                  45

Gln Tyr Thr Ser Thr Leu Gln Pro Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Leu Gln Tyr Glu Gln Leu Arg Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 36
<211> LENGTH: 22
<212> TYPE: PRT
<213> ORGANISM: Artificial sequence
<220> FEATURE:
<223> OTHER INFORMATION: An artificially synthesized peptide sequence

<400> SEQUENCE: 36

Arg Trp Gly Tyr His Leu Arg Asp Arg Lys Tyr Lys Gly Val Arg Ser
1               5                   10                  15

His Lys Gly Val Pro Arg
            20


<210> SEQ ID NO 37
<211> LENGTH: 480
<212> TYPE: PRT
<213> ORGANISM: Artificial sequence
<220> FEATURE:
<223> OTHER INFORMATION: An artificially synthesized peptide sequence

<400> SEQUENCE: 37

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Lys Arg Trp Gly Tyr His Leu Arg Asp Arg Lys
    50                  55                  60

Tyr Lys Gly Val Arg Ser His Lys Gly Val Pro Arg Ser Asn Asn Tyr
65                  70                  75                  80
```

-continued

```
Ala Thr Tyr Tyr Ala Glu Ser Val Lys Gly Arg Phe Thr Ile Ser Arg
                85                  90                  95

Asp Asp Ser Lys Ser Asn Ile Tyr Leu Gln Met Asn Ser Leu Lys Glu
            100                 105                 110

Glu Asp Thr Ala Val Tyr Tyr Cys Arg Tyr Val His Tyr Gly Ala Tyr
        115                 120                 125

Tyr Gly Val Asp Ala Trp Gly Gln Gly Thr Ser Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Pro Pro Cys
                245                 250                 255

Pro Ala Pro Glu Ala Ala Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Ala Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Cys Glu
    370                 375                 380

Leu Thr Lys Asn Gln Val Ser Leu Ser Cys Ala Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Val Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Asp Tyr Lys Asp Asp Asp Asp Lys
465                 470                 475                 480
```

<210> SEQ ID NO 38
<211> LENGTH: 482
<212> TYPE: PRT

```
<213> ORGANISM: Artificial sequence
<220> FEATURE:
<223> OTHER INFORMATION: An artificially synthesized peptide sequence

<400> SEQUENCE: 38

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Lys Cys Arg Trp Gly Tyr His Leu Arg Asp Arg
    50                  55                  60

Lys Tyr Lys Gly Val Arg Ser His Lys Gly Val Pro Arg Cys Ser Asn
65                  70                  75                  80

Asn Tyr Ala Thr Tyr Tyr Ala Glu Ser Val Lys Gly Arg Phe Thr Ile
                85                  90                  95

Ser Arg Asp Asp Ser Lys Ser Asn Ile Tyr Leu Gln Met Asn Ser Leu
            100                 105                 110

Lys Glu Glu Asp Thr Ala Val Tyr Tyr Cys Arg Tyr Val His Tyr Gly
        115                 120                 125

Ala Tyr Tyr Gly Val Asp Ala Trp Gly Gln Gly Thr Ser Val Thr Val
    130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
    210                 215                 220

Gln Thr Tyr Ile Cys Asn Val Asn His Lys Pro Ser Asn Thr Lys Val
225                 230                 235                 240

Asp Lys Lys Val Glu Pro Lys Ser Cys Asp Lys Thr His Thr Cys Pro
                245                 250                 255

Pro Cys Pro Ala Pro Glu Ala Ala Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Ala Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
    370                 375                 380

Cys Glu Leu Thr Lys Asn Gln Val Ser Leu Ser Cys Ala Val Lys Gly
```

385 390 395 400

Phe Tyr Pro Ser Asp Ile Ala Val Glu Trp Glu Ser Asn Gly Gln Pro
405 410 415

Glu Asn Asn Tyr Lys Thr Thr Pro Pro Val Leu Asp Ser Asp Gly Ser
420 425 430

Phe Phe Leu Val Ser Lys Leu Thr Val Asp Lys Ser Arg Trp Gln Gln
435 440 445

Gly Asn Val Phe Ser Cys Ser Val Met His Glu Ala Leu His Asn His
450 455 460

Tyr Thr Gln Lys Ser Leu Ser Leu Ser Pro Asp Tyr Lys Asp Asp Asp
465 470 475 480

Asp Lys

<210> SEQ ID NO 39
<211> LENGTH: 480
<212> TYPE: PRT
<213> ORGANISM: Artificial sequence
<220> FEATURE:
<223> OTHER INFORMATION: An artificially synthesized peptide sequence

<400> SEQUENCE: 39

Glu Val Gln Leu Val Glu Thr Gly Gly Ser Leu Val Gln Pro Gly Lys
1 5 10 15

Ser Leu Lys Leu Thr Cys Ala Thr Ser Gly Phe Thr Phe Ser Asn Ala
20 25 30

Trp Met His Trp Val Arg Gln Ser Pro Glu Lys Gln Leu Glu Trp Val
35 40 45

Ala Gln Ile Lys Ala Lys Ser Asn Asn Tyr Ala Thr Tyr Tyr Ala Glu
50 55 60

Ser Val Lys Gly Arg Phe Thr Ile Ser Arg Asp Arg Trp Gly Tyr His
65 70 75 80

Leu Arg Asp Arg Lys Tyr Lys Gly Val Arg Ser His Lys Gly Val Pro
85 90 95

Arg Asp Ser Lys Ser Asn Ile Tyr Leu Gln Met Asn Ser Leu Lys Glu
100 105 110

Glu Asp Thr Ala Val Tyr Tyr Cys Arg Tyr Val His Tyr Gly Ala Tyr
115 120 125

Tyr Gly Val Asp Ala Trp Gly Gln Gly Thr Ser Val Thr Val Ser Ser
130 135 140

Ala Ser Thr Lys Gly Pro Ser Val Phe Pro Leu Ala Pro Ser Ser Lys
145 150 155 160

Ser Thr Ser Gly Gly Thr Ala Ala Leu Gly Cys Leu Val Lys Asp Tyr
165 170 175

Phe Pro Glu Pro Val Thr Val Ser Trp Asn Ser Gly Ala Leu Thr Ser
180 185 190

Gly Val His Thr Phe Pro Ala Val Leu Gln Ser Ser Gly Leu Tyr Ser
195 200 205

Leu Ser Ser Val Val Thr Val Pro Ser Ser Ser Leu Gly Thr Gln Thr
210 215 220

Tyr Ile Cys Asn Val Asn His Lys Pro Ser Asn Thr Lys Val Asp Lys
225 230 235 240

Lys Val Glu Pro Lys Ser Cys Asp Lys Thr His Thr Cys Pro Pro Cys
245 250 255

Pro Ala Pro Glu Ala Ala Gly Gly Pro Ser Val Phe Leu Phe Pro Pro
260 265 270

Lys Pro Lys Asp Thr Leu Met Ile Ser Arg Thr Pro Glu Val Thr Cys
275 280 285

Val Val Val Asp Val Ser His Glu Asp Pro Glu Val Lys Phe Asn Trp
290 295 300

Tyr Val Asp Gly Val Glu Val His Asn Ala Lys Thr Lys Pro Arg Glu
305 310 315 320

Glu Gln Tyr Ala Ser Thr Tyr Arg Val Val Ser Val Leu Thr Val Leu
325 330 335

His Gln Asp Trp Leu Asn Gly Lys Glu Tyr Lys Cys Lys Val Ser Asn
340 345 350

Lys Ala Leu Pro Ala Pro Ile Glu Lys Thr Ile Ser Lys Ala Lys Gly
355 360 365

Gln Pro Arg Glu Pro Gln Val Tyr Thr Leu Pro Pro Ser Arg Cys Glu
370 375 380

Leu Thr Lys Asn Gln Val Ser Leu Ser Cys Ala Val Lys Gly Phe Tyr
385 390 395 400

Pro Ser Asp Ile Ala Val Glu Trp Glu Ser Asn Gly Gln Pro Glu Asn
405 410 415

Asn Tyr Lys Thr Thr Pro Pro Val Leu Asp Ser Asp Gly Ser Phe Phe
420 425 430

Leu Val Ser Lys Leu Thr Val Asp Lys Ser Arg Trp Gln Gln Gly Asn
435 440 445

Val Phe Ser Cys Ser Val Met His Glu Ala Leu His Asn His Tyr Thr
450 455 460

Gln Lys Ser Leu Ser Leu Ser Pro Asp Tyr Lys Asp Asp Asp Asp Lys
465 470 475 480

<210> SEQ ID NO 40
<211> LENGTH: 482
<212> TYPE: PRT
<213> ORGANISM: Artificial sequence
<220> FEATURE:
<223> OTHER INFORMATION: An artificially synthesized peptide sequence

<400> SEQUENCE: 40

Glu Val Gln Leu Val Glu Thr Gly Gly Ser Leu Val Gln Pro Gly Lys
1 5 10 15

Ser Leu Lys Leu Thr Cys Ala Thr Ser Gly Phe Thr Phe Ser Asn Ala
20 25 30

Trp Met His Trp Val Arg Gln Ser Pro Glu Lys Gln Leu Glu Trp Val
35 40 45

Ala Gln Ile Lys Ala Lys Ser Asn Asn Tyr Ala Thr Tyr Tyr Ala Glu
50 55 60

Ser Val Lys Gly Arg Phe Thr Ile Ser Arg Asp Cys Arg Trp Gly Tyr
65 70 75 80

His Leu Arg Asp Arg Lys Tyr Lys Gly Val Arg Ser His Lys Gly Val
85 90 95

Pro Arg Cys Asp Ser Lys Ser Asn Ile Tyr Leu Gln Met Asn Ser Leu
100 105 110

Lys Glu Glu Asp Thr Ala Val Tyr Tyr Cys Arg Tyr Val His Tyr Gly
115 120 125

Ala Tyr Tyr Gly Val Asp Ala Trp Gly Gln Gly Thr Ser Val Thr Val
130 135 140

Ser Ser Ala Ser Thr Lys Gly Pro Ser Val Phe Pro Leu Ala Pro Ser
145 150 155 160

Ser Lys Ser Thr Ser Gly Gly Thr Ala Ala Leu Gly Cys Leu Val Lys
165 170 175

Asp Tyr Phe Pro Glu Pro Val Thr Val Ser Trp Asn Ser Gly Ala Leu
180 185 190

Thr Ser Gly Val His Thr Phe Pro Ala Val Leu Gln Ser Ser Gly Leu
195 200 205

Tyr Ser Leu Ser Ser Val Val Thr Val Pro Ser Ser Ser Leu Gly Thr
210 215 220

Gln Thr Tyr Ile Cys Asn Val Asn His Lys Pro Ser Asn Thr Lys Val
225 230 235 240

Asp Lys Lys Val Glu Pro Lys Ser Cys Asp Lys Thr His Thr Cys Pro
245 250 255

Pro Cys Pro Ala Pro Glu Ala Ala Gly Gly Pro Ser Val Phe Leu Phe
260 265 270

Pro Pro Lys Pro Lys Asp Thr Leu Met Ile Ser Arg Thr Pro Glu Val
275 280 285

Thr Cys Val Val Val Asp Val Ser His Glu Asp Pro Glu Val Lys Phe
290 295 300

Asn Trp Tyr Val Asp Gly Val Glu Val His Asn Ala Lys Thr Lys Pro
305 310 315 320

Arg Glu Glu Gln Tyr Ala Ser Thr Tyr Arg Val Val Ser Val Leu Thr
325 330 335

Val Leu His Gln Asp Trp Leu Asn Gly Lys Glu Tyr Lys Cys Lys Val
340 345 350

Ser Asn Lys Ala Leu Pro Ala Pro Ile Glu Lys Thr Ile Ser Lys Ala
355 360 365

Lys Gly Gln Pro Arg Glu Pro Gln Val Tyr Thr Leu Pro Pro Ser Arg
370 375 380

Cys Glu Leu Thr Lys Asn Gln Val Ser Leu Ser Cys Ala Val Lys Gly
385 390 395 400

Phe Tyr Pro Ser Asp Ile Ala Val Glu Trp Glu Ser Asn Gly Gln Pro
405 410 415

Glu Asn Asn Tyr Lys Thr Thr Pro Pro Val Leu Asp Ser Asp Gly Ser
420 425 430

Phe Phe Leu Val Ser Lys Leu Thr Val Asp Lys Ser Arg Trp Gln Gln
435 440 445

Gly Asn Val Phe Ser Cys Ser Val Met His Glu Ala Leu His Asn His
450 455 460

Tyr Thr Gln Lys Ser Leu Ser Leu Ser Pro Asp Tyr Lys Asp Asp Asp
465 470 475 480

Asp Lys

<210> SEQ ID NO 41
<211> LENGTH: 477
<212> TYPE: PRT
<213> ORGANISM: Artificial sequence
<220> FEATURE:
<223> OTHER INFORMATION: An artificially synthesized peptide sequence

<400> SEQUENCE: 41

Glu Val Gln Leu Val Glu Thr Gly Gly Ser Leu Val Gln Pro Gly Lys
1 5 10 15

Ser Leu Lys Leu Thr Cys Ala Thr Ser Gly Phe Thr Phe Ser Asn Ala
20 25 30

-continued

```
Trp Met His Trp Val Arg Gln Ser Pro Glu Lys Gln Leu Glu Trp Val
        35                  40                  45

Ala Gln Ile Lys Ala Lys Ser Asn Asn Tyr Ala Thr Tyr Tyr Ala Glu
    50                  55                  60

Ser Val Lys Gly Arg Phe Thr Ile Ser Arg Asp Asp Ser Lys Ser Asn
65                  70                  75                  80

Ile Tyr Leu Gln Met Asn Ser Leu Lys Glu Glu Asp Thr Ala Val Tyr
                85                  90                  95

Tyr Cys Arg Tyr Val His Tyr Gly Ala Tyr Tyr Gly Val Asp Ala Trp
            100                 105                 110

Gly Gln Gly Thr Ser Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Glu Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Asp Ala Leu Pro Met Pro
                325                 330                 335

Ile Glu Glu Thr Ile Ser Lys Ala Lys Gly Gln Pro Arg Glu Pro Gln
            340                 345                 350

Val Tyr Thr Leu Pro Pro Ser Arg Cys Glu Leu Thr Lys Asn Gln Val
        355                 360                 365

Ser Leu Ser Cys Ala Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Val Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Gly Gly Gly Ser Arg Trp Gly Tyr His Leu Arg Asp Arg
```

```
    450                 455                 460

Lys Tyr Lys Gly Val Arg Ser His Lys Gly Val Pro Arg
465                 470                 475
```

<210> SEQ ID NO 42
<211> LENGTH: 479
<212> TYPE: PRT
<213> ORGANISM: Artificial sequence
<220> FEATURE:
<223> OTHER INFORMATION: An artificially synthesized peptide sequence

<400> SEQUENCE: 42

```
Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Lys Ser Asn Asn Tyr Ala Thr Tyr Tyr Ala Glu
    50                  55                  60

Ser Val Lys Gly Arg Phe Thr Ile Ser Arg Asp Asp Ser Lys Ser Asn
65                  70                  75                  80

Ile Tyr Leu Gln Met Asn Ser Leu Lys Glu Glu Asp Thr Ala Val Tyr
                85                  90                  95

Tyr Cys Arg Tyr Val His Tyr Gly Ala Tyr Tyr Gly Val Asp Ala Trp
            100                 105                 110

Gly Gln Gly Thr Ser Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Glu Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Asp Ala Leu Pro Met Pro
                325                 330                 335

Ile Glu Glu Thr Ile Ser Lys Ala Lys Gly Gln Pro Arg Glu Pro Gln
```

```
            340                 345                 350

Val Tyr Thr Leu Pro Pro Ser Arg Cys Glu Leu Thr Lys Asn Gln Val
        355                 360                 365

Ser Leu Ser Cys Ala Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Val Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Gly Gly Gly Ser Cys Arg Trp Gly Tyr His Leu Arg Asp
    450                 455                 460

Arg Lys Tyr Lys Gly Val Arg Ser His Lys Gly Val Pro Arg Cys
465                 470                 475


<210> SEQ ID NO 43
<211> LENGTH: 461
<212> TYPE: PRT
<213> ORGANISM: Artificial sequence
<220> FEATURE:
<223> OTHER INFORMATION: An artificially synthesized peptide sequence

<400> SEQUENCE: 43

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Lys Gly Gly Ser Ser Asn Asn Tyr Ala Thr Tyr
    50                  55                  60

Tyr Ala Glu Ser Val Lys Gly Arg Phe Thr Ile Ser Arg Asp Asp Ser
65                  70                  75                  80

Lys Ser Asn Ile Tyr Leu Gln Met Asn Ser Leu Lys Glu Glu Asp Thr
                85                  90                  95

Ala Val Tyr Tyr Cys Arg Tyr Val His Tyr Gly Ala Tyr Tyr Gly Val
            100                 105                 110

Asp Ala Trp Gly Gln Gly Thr Ser Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
```

225 230 235 240

Glu Ala Ala Gly Gly Pro Ser Val Phe Leu Phe Pro Pro Lys Pro Lys
245 250 255

Asp Thr Leu Met Ile Ser Arg Thr Pro Glu Val Thr Cys Val Val Val
260 265 270

Asp Val Ser His Glu Asp Pro Glu Val Lys Phe Asn Trp Tyr Val Asp
275 280 285

Gly Val Glu Val His Asn Ala Lys Thr Lys Pro Arg Glu Glu Gln Tyr
290 295 300

Ala Ser Thr Tyr Arg Val Val Ser Val Leu Thr Val Leu His Gln Asp
305 310 315 320

Trp Leu Asn Gly Lys Glu Tyr Lys Cys Lys Val Ser Asn Lys Ala Leu
325 330 335

Pro Ala Pro Ile Glu Lys Thr Ile Ser Lys Ala Lys Gly Gln Pro Arg
340 345 350

Glu Pro Gln Val Tyr Thr Leu Pro Pro Ser Arg Cys Glu Leu Thr Lys
355 360 365

Asn Gln Val Ser Leu Ser Cys Ala Val Lys Gly Phe Tyr Pro Ser Asp
370 375 380

Ile Ala Val Glu Trp Glu Ser Asn Gly Gln Pro Glu Asn Asn Tyr Lys
385 390 395 400

Thr Thr Pro Pro Val Leu Asp Ser Asp Gly Ser Phe Phe Leu Val Ser
405 410 415

Lys Leu Thr Val Asp Lys Ser Arg Trp Gln Gln Gly Asn Val Phe Ser
420 425 430

Cys Ser Val Met His Glu Ala Leu His Asn His Tyr Thr Gln Lys Ser
435 440 445

Leu Ser Leu Ser Pro Asp Tyr Lys Asp Asp Asp Asp Lys
450 455 460

<210> SEQ ID NO 44
<211> LENGTH: 464
<212> TYPE: PRT
<213> ORGANISM: Artificial sequence
<220> FEATURE:
<223> OTHER INFORMATION: An artificially synthesized peptide sequence

<400> SEQUENCE: 44

Glu Val Gln Leu Val Glu Thr Gly Gly Ser Leu Val Gln Pro Gly Lys
1 5 10 15

Ser Leu Lys Leu Thr Cys Ala Thr Ser Gly Phe Thr Phe Ser Asn Ala
20 25 30

Trp Met His Trp Val Arg Gln Ser Pro Glu Lys Gln Leu Glu Trp Val
35 40 45

Ala Gln Ile Lys Ala Lys Gly Gly Ser Gly Gly Ser Ser Asn Asn Tyr
50 55 60

Ala Thr Tyr Tyr Ala Glu Ser Val Lys Gly Arg Phe Thr Ile Ser Arg
65 70 75 80

Asp Asp Ser Lys Ser Asn Ile Tyr Leu Gln Met Asn Ser Leu Lys Glu
85 90 95

Glu Asp Thr Ala Val Tyr Tyr Cys Arg Tyr Val His Tyr Gly Ala Tyr
100 105 110

Tyr Gly Val Asp Ala Trp Gly Gln Gly Thr Ser Val Thr Val Ser Ser
115 120 125

Ala Ser Thr Lys Gly Pro Ser Val Phe Pro Leu Ala Pro Ser Ser Lys 130 135 140

Ser Thr Ser Gly Gly Thr Ala Ala Leu Gly Cys Leu Val Lys Asp Tyr
145 150 155 160

Phe Pro Glu Pro Val Thr Val Ser Trp Asn Ser Gly Ala Leu Thr Ser
165 170 175

Gly Val His Thr Phe Pro Ala Val Leu Gln Ser Ser Gly Leu Tyr Ser
180 185 190

Leu Ser Ser Val Val Thr Val Pro Ser Ser Ser Leu Gly Thr Gln Thr
195 200 205

Tyr Ile Cys Asn Val Asn His Lys Pro Ser Asn Thr Lys Val Asp Lys
210 215 220

Lys Val Glu Pro Lys Ser Cys Asp Lys Thr His Thr Cys Pro Pro Cys
225 230 235 240

Pro Ala Pro Glu Ala Ala Gly Gly Pro Ser Val Phe Leu Phe Pro Pro
245 250 255

Lys Pro Lys Asp Thr Leu Met Ile Ser Arg Thr Pro Glu Val Thr Cys
260 265 270

Val Val Val Asp Val Ser His Glu Asp Pro Glu Val Lys Phe Asn Trp
275 280 285

Tyr Val Asp Gly Val Glu Val His Asn Ala Lys Thr Lys Pro Arg Glu
290 295 300

Glu Gln Tyr Ala Ser Thr Tyr Arg Val Val Ser Val Leu Thr Val Leu
305 310 315 320

His Gln Asp Trp Leu Asn Gly Lys Glu Tyr Lys Cys Lys Val Ser Asn
325 330 335

Lys Ala Leu Pro Ala Pro Ile Glu Lys Thr Ile Ser Lys Ala Lys Gly
340 345 350

Gln Pro Arg Glu Pro Gln Val Tyr Thr Leu Pro Pro Ser Arg Cys Glu
355 360 365

Leu Thr Lys Asn Gln Val Ser Leu Ser Cys Ala Val Lys Gly Phe Tyr
370 375 380

Pro Ser Asp Ile Ala Val Glu Trp Glu Ser Asn Gly Gln Pro Glu Asn
385 390 395 400

Asn Tyr Lys Thr Thr Pro Pro Val Leu Asp Ser Asp Gly Ser Phe Phe
405 410 415

Leu Val Ser Lys Leu Thr Val Asp Lys Ser Arg Trp Gln Gln Gly Asn
420 425 430

Val Phe Ser Cys Ser Val Met His Glu Ala Leu His Asn His Tyr Thr
435 440 445

Gln Lys Ser Leu Ser Leu Ser Pro Asp Tyr Lys Asp Asp Asp Asp Lys
450 455 460

<210> SEQ ID NO 45
<211> LENGTH: 467
<212> TYPE: PRT
<213> ORGANISM: Artificial sequence
<220> FEATURE:
<223> OTHER INFORMATION: An artificially synthesized peptide sequence

<400> SEQUENCE: 45

Glu Val Gln Leu Val Glu Thr Gly Gly Ser Leu Val Gln Pro Gly Lys
1 5 10 15

Ser Leu Lys Leu Thr Cys Ala Thr Ser Gly Phe Thr Phe Ser Asn Ala
20 25 30

Trp Met His Trp Val Arg Gln Ser Pro Glu Lys Gln Leu Glu Trp Val

-continued

```
        35                  40                  45

Ala Gln Ile Lys Ala Lys Gly Gly Ser Gly Gly Ser Gly Gly Ser Ser
    50                  55                  60

Asn Asn Tyr Ala Thr Tyr Tyr Ala Glu Ser Val Lys Gly Arg Phe Thr
65                  70                  75                  80

Ile Ser Arg Asp Asp Ser Lys Ser Asn Ile Tyr Leu Gln Met Asn Ser
                85                  90                  95

Leu Lys Glu Glu Asp Thr Ala Val Tyr Tyr Cys Arg Tyr Val His Tyr
            100                 105                 110

Gly Ala Tyr Tyr Gly Val Asp Ala Trp Gly Gln Gly Thr Ser Val Thr
        115                 120                 125

Val Ser Ser Ala Ser Thr Lys Gly Pro Ser Val Phe Pro Leu Ala Pro
    130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
    210                 215                 220

Val Asp Lys Lys Val Glu Pro Lys Ser Cys Asp Lys Thr His Thr Cys
225                 230                 235                 240

Pro Pro Cys Pro Ala Pro Glu Ala Ala Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Ala Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Arg Cys Glu Leu Thr Lys Asn Gln Val Ser Leu Ser Cys Ala Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Val Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Asp Tyr Lys Asp Asp
    450                 455                 460
```

Asp Asp Lys
465

<210> SEQ ID NO 46
<211> LENGTH: 461
<212> TYPE: PRT
<213> ORGANISM: Artificial sequence
<220> FEATURE:
<223> OTHER INFORMATION: An artificially synthesized peptide sequence

<400> SEQUENCE: 46

Glu Val Gln Leu Val Glu Thr Gly Gly Ser Leu Val Gln Pro Gly Lys
1 5 10 15

Ser Leu Lys Leu Thr Cys Ala Thr Ser Gly Phe Thr Phe Ser Asn Ala
20 25 30

Trp Met His Trp Val Arg Gln Ser Pro Glu Lys Gln Leu Glu Trp Val
35 40 45

Ala Gln Ile Lys Ala Lys Ser Asn Asn Tyr Ala Thr Tyr Tyr Ala Glu
50 55 60

Ser Val Lys Gly Arg Phe Thr Ile Ser Arg Asp Gly Gly Ser Asp Ser
65 70 75 80

Lys Ser Asn Ile Tyr Leu Gln Met Asn Ser Leu Lys Glu Glu Asp Thr
85 90 95

Ala Val Tyr Tyr Cys Arg Tyr Val His Tyr Gly Ala Tyr Tyr Gly Val
100 105 110

Asp Ala Trp Gly Gln Gly Thr Ser Val Thr Val Ser Ser Ala Ser Thr
115 120 125

Lys Gly Pro Ser Val Phe Pro Leu Ala Pro Ser Ser Lys Ser Thr Ser
130 135 140

Gly Gly Thr Ala Ala Leu Gly Cys Leu Val Lys Asp Tyr Phe Pro Glu
145 150 155 160

Pro Val Thr Val Ser Trp Asn Ser Gly Ala Leu Thr Ser Gly Val His
165 170 175

Thr Phe Pro Ala Val Leu Gln Ser Ser Gly Leu Tyr Ser Leu Ser Ser
180 185 190

Val Val Thr Val Pro Ser Ser Ser Leu Gly Thr Gln Thr Tyr Ile Cys
195 200 205

Asn Val Asn His Lys Pro Ser Asn Thr Lys Val Asp Lys Lys Val Glu
210 215 220

Pro Lys Ser Cys Asp Lys Thr His Thr Cys Pro Pro Cys Pro Ala Pro
225 230 235 240

Glu Ala Ala Gly Gly Pro Ser Val Phe Leu Phe Pro Pro Lys Pro Lys
245 250 255

Asp Thr Leu Met Ile Ser Arg Thr Pro Glu Val Thr Cys Val Val Val
260 265 270

Asp Val Ser His Glu Asp Pro Glu Val Lys Phe Asn Trp Tyr Val Asp
275 280 285

Gly Val Glu Val His Asn Ala Lys Thr Lys Pro Arg Glu Glu Gln Tyr
290 295 300

Ala Ser Thr Tyr Arg Val Val Ser Val Leu Thr Val Leu His Gln Asp
305 310 315 320

Trp Leu Asn Gly Lys Glu Tyr Lys Cys Lys Val Ser Asn Lys Ala Leu
325 330 335

Pro Ala Pro Ile Glu Lys Thr Ile Ser Lys Ala Lys Gly Gln Pro Arg
340 345 350

```
Glu Pro Gln Val Tyr Thr Leu Pro Pro Ser Arg Cys Glu Leu Thr Lys
        355                 360                 365

Asn Gln Val Ser Leu Ser Cys Ala Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Val Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Asp Tyr Lys Asp Asp Asp Asp Lys
    450                 455                 460


<210> SEQ ID NO 47
<211> LENGTH: 464
<212> TYPE: PRT
<213> ORGANISM: Artificial sequence
<220> FEATURE:
<223> OTHER INFORMATION: An artificially synthesized peptide sequence

<400> SEQUENCE: 47

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Lys Ser Asn Asn Tyr Ala Thr Tyr Tyr Ala Glu
    50                  55                  60

Ser Val Lys Gly Arg Phe Thr Ile Ser Arg Asp Gly Gly Ser Gly Gly
65                  70                  75                  80

Ser Asp Ser Lys Ser Asn Ile Tyr Leu Gln Met Asn Ser Leu Lys Glu
                85                  90                  95

Glu Asp Thr Ala Val Tyr Tyr Cys Arg Tyr Val His Tyr Gly Ala Tyr
            100                 105                 110

Tyr Gly Val Asp Ala Trp Gly Gln Gly Thr Ser Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Ala Ala Gly Gly Pro Ser Val Phe Leu Phe Pro Pro
                245                 250                 255
```

```
Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Ala Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Cys Glu
        355                 360                 365

Leu Thr Lys Asn Gln Val Ser Leu Ser Cys Ala Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Val Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Asp Tyr Lys Asp Asp Asp Asp Lys
    450                 455                 460
```

<210> SEQ ID NO 48
<211> LENGTH: 467
<212> TYPE: PRT
<213> ORGANISM: Artificial sequence
<220> FEATURE:
<223> OTHER INFORMATION: An artificially synthesized peptide sequence

<400> SEQUENCE: 48

```
Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Lys Ser Asn Asn Tyr Ala Thr Tyr Tyr Ala Glu
    50                  55                  60

Ser Val Lys Gly Arg Phe Thr Ile Ser Arg Asp Gly Gly Ser Gly Gly
65                  70                  75                  80

Ser Gly Gly Ser Asp Ser Lys Ser Asn Ile Tyr Leu Gln Met Asn Ser
                85                  90                  95

Leu Lys Glu Glu Asp Thr Ala Val Tyr Tyr Cys Arg Tyr Val His Tyr
            100                 105                 110

Gly Ala Tyr Tyr Gly Val Asp Ala Trp Gly Gln Gly Thr Ser Val Thr
        115                 120                 125

Val Ser Ser Ala Ser Thr Lys Gly Pro Ser Val Phe Pro Leu Ala Pro
    130                 135                 140

Ser Ser Lys Ser Thr Ser Gly Gly Thr Ala Ala Leu Gly Cys Leu Val
145                 150                 155                 160
```

-continued

```
Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
    210                 215                 220

Val Asp Lys Lys Val Glu Pro Lys Ser Cys Asp Lys Thr His Thr Cys
225                 230                 235                 240

Pro Pro Cys Pro Ala Pro Glu Ala Ala Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Ala Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Arg Cys Glu Leu Thr Lys Asn Gln Val Ser Leu Ser Cys Ala Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Val Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Asp Tyr Lys Asp Asp
    450                 455                 460

Asp Asp Lys
465
```

<210> SEQ ID NO 49
<211> LENGTH: 461
<212> TYPE: PRT
<213> ORGANISM: Artificial sequence
<220> FEATURE:
<223> OTHER INFORMATION: An artificially synthesized peptide sequence

<400> SEQUENCE: 49

```
Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45
```

-continued

```
Ala Gln Ile Lys Ala Lys Ser Asn Asn Tyr Ala Thr Tyr Tyr Ala Glu
    50                  55                  60

Ser Val Lys Gly Arg Phe Thr Ile Ser Arg Asp Asp Ser Lys Ser Asn
65                  70                  75                  80

Ile Tyr Leu Gln Met Asn Ser Leu Lys Glu Glu Asp Thr Ala Val Tyr
                85                  90                  95

Tyr Cys Arg Tyr Val His Tyr Gly Ala Gly Gly Ser Tyr Tyr Gly Val
            100                 105                 110

Asp Ala Trp Gly Gln Gly Thr Ser Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Ala Ala Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Ala Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Cys Glu Leu Thr Lys
        355                 360                 365

Asn Gln Val Ser Leu Ser Cys Ala Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Val Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Asp Tyr Lys Asp Asp Asp Asp Lys
    450                 455                 460
```

<210> SEQ ID NO 50
<211> LENGTH: 464
<212> TYPE: PRT
<213> ORGANISM: Artificial sequence
<220> FEATURE:
<223> OTHER INFORMATION: An artificially synthesized peptide sequence

<400> SEQUENCE: 50

```
Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Lys Ser Asn Asn Tyr Ala Thr Tyr Tyr Ala Glu
    50                  55                  60

Ser Val Lys Gly Arg Phe Thr Ile Ser Arg Asp Asp Ser Lys Ser Asn
65                  70                  75                  80

Ile Tyr Leu Gln Met Asn Ser Leu Lys Glu Glu Asp Thr Ala Val Tyr
                85                  90                  95

Tyr Cys Arg Tyr Val His Tyr Gly Ala Gly Gly Ser Gly Gly Ser Tyr
            100                 105                 110

Tyr Gly Val Asp Ala Trp Gly Gln Gly Thr Ser Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Ala Ala Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Ala Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Cys Glu
        355                 360                 365
```

-continued

```
Leu Thr Lys Asn Gln Val Ser Leu Ser Cys Ala Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Val Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Asp Tyr Lys Asp Asp Asp Asp Lys
    450                 455                 460


<210> SEQ ID NO 51
<211> LENGTH: 467
<212> TYPE: PRT
<213> ORGANISM: Artificial sequence
<220> FEATURE:
<223> OTHER INFORMATION: An artificially synthesized peptide sequence

<400> SEQUENCE: 51

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Lys Ser Asn Asn Tyr Ala Thr Tyr Tyr Ala Glu
    50                  55                  60

Ser Val Lys Gly Arg Phe Thr Ile Ser Arg Asp Asp Ser Lys Ser Asn
65                  70                  75                  80

Ile Tyr Leu Gln Met Asn Ser Leu Lys Glu Glu Asp Thr Ala Val Tyr
                85                  90                  95

Tyr Cys Arg Tyr Val His Tyr Gly Ala Gly Gly Ser Gly Gly Ser Gly
            100                 105                 110

Gly Ser Tyr Tyr Gly Val Asp Ala Trp Gly Gln Gly Thr Ser Val Thr
        115                 120                 125

Val Ser Ser Ala Ser Thr Lys Gly Pro Ser Val Phe Pro Leu Ala Pro
    130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
    210                 215                 220

Val Asp Lys Lys Val Glu Pro Lys Ser Cys Asp Lys Thr His Thr Cys
225                 230                 235                 240

Pro Pro Cys Pro Ala Pro Glu Ala Ala Gly Gly Pro Ser Val Phe Leu
                245                 250                 255

Phe Pro Pro Lys Pro Lys Asp Thr Leu Met Ile Ser Arg Thr Pro Glu
            260                 265                 270
```

```
Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Ala Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Arg Cys Glu Leu Thr Lys Asn Gln Val Ser Leu Ser Cys Ala Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Val Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Asp Tyr Lys Asp Asp
    450                 455                 460

Asp Asp Lys
465


<210> SEQ ID NO 52
<211> LENGTH: 122
<212> TYPE: PRT
<213> ORGANISM: Artificial sequence
<220> FEATURE:
<223> OTHER INFORMATION: An artificially synthesized peptide sequence

<400> SEQUENCE: 52

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Ala Lys Ser Asn Asn Tyr Ala Thr Tyr Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Arg Tyr Val His Tyr Gly Ala Tyr Tyr Gly Val Asp Ala Trp
            100                 105                 110

Gly Gln Gly Thr Thr Val Thr Val Ser Ser
        115                 120


<210> SEQ ID NO 53
<211> LENGTH: 112
<212> TYPE: PRT
<213> ORGANISM: Artificial sequence
<220> FEATURE:
```

<223> OTHER INFORMATION: An artificially synthesized peptide sequence

<400> SEQUENCE: 53

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Val His Ser
20 25 30

Asn Arg Asn Thr Tyr Leu His Trp Tyr Gln Gln Lys Pro Gly Gln Ala
35 40 45

Pro Arg Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Gly Gln Gly
85 90 95

Thr Gln Val Pro Tyr Thr Phe Gly Gln Gly Thr Lys Leu Glu Ile Lys
100 105 110

<210> SEQ ID NO 54
<211> LENGTH: 336
<212> TYPE: PRT
<213> ORGANISM: Artificial sequence
<220> FEATURE:
<223> OTHER INFORMATION: An artificially synthesized peptide sequence

<400> SEQUENCE: 54

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Ala Ala Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Ala Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Cys Glu
225 230 235 240

```
Leu Thr Lys Asn Gln Val Ser Leu Ser Cys Ala Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Val Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Asp Tyr Lys Asp Asp Asp Asp Lys
                325                 330                 335


<210> SEQ ID NO 55
<211> LENGTH: 107
<212> TYPE: PRT
<213> ORGANISM: Homo sapiens

<400> SEQUENCE: 55

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 56
<211> LENGTH: 230
<212> TYPE: PRT
<213> ORGANISM: Artificial sequence
<220> FEATURE:
<223> OTHER INFORMATION: An artificially synthesized peptide sequence

<400> SEQUENCE: 56

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110
```

-continued

```
Leu Pro Ala Pro Ile Glu Lys Thr Ile Ser Lys Ala Lys Gly Gln Pro
        115                 120                 125

Arg Glu Pro Gln Val Cys Thr Leu Pro Pro Ser Arg Asp Glu Leu Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn Arg Tyr Thr Gln Lys
    210                 215                 220

Ser Leu Ser Leu Ser Pro
225                 230


<210> SEQ ID NO 57
<211> LENGTH: 449
<212> TYPE: PRT
<213> ORGANISM: Artificial sequence
<220> FEATURE:
<223> OTHER INFORMATION: An artificially synthesized peptide sequence

<400> SEQUENCE: 57

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240
```

```
Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 58
<211> LENGTH: 214
<212> TYPE: PRT
<213> ORGANISM: Artificial sequence
<220> FEATURE:
<223> OTHER INFORMATION: An artificially synthesized peptide sequence

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

```
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 59
<211> LENGTH: 458
<212> TYPE: PRT
<213> ORGANISM: Artificial sequence
<220> FEATURE:
<223> OTHER INFORMATION: An artificially synthesized peptide sequence

<400> SEQUENCE: 59

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Lys Ser Asn Asn Tyr Ala Thr Tyr Tyr Ala Glu
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Ala Ala Tyr Tyr Gly Val Asp Ala Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Ala Ser Thr
```

```
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Cys Glu Leu Thr Lys Asn Gln Val
        355                 360                 365

Ser Leu Ser Cys Ala Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Val Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Asp Tyr Lys Asp Asp Asp Asp Lys
    450                 455


<210> SEQ ID NO 60
<211> LENGTH: 15
<212> TYPE: PRT
<213> ORGANISM: Artificial sequence
<220> FEATURE:
<223> OTHER INFORMATION: An artificially synthesized peptide sequence

<400> SEQUENCE: 60

Gln Asp Gly Asn Glu Glu Met Gly Gly Ile Thr Gln Thr Pro Tyr
1               5                   10                  15


<210> SEQ ID NO 61
<211> LENGTH: 467
<212> TYPE: PRT
<213> ORGANISM: Artificial sequence
<220> FEATURE:
<223> OTHER INFORMATION: An artificially synthesized peptide sequence

<400> SEQUENCE: 61

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Ser Ala
            20                  25                  30

Trp Met His Trp Val Arg Gln Ala Pro Gly Lys Gly Leu Glu Trp Val
        35                  40                  45

Ala Gln Ile Lys Asp Lys Gly Asn Gly Tyr Asn Ala Tyr Tyr Ala Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Thr Thr Ser Tyr Phe Gly Leu Phe Gly
            100                 105                 110

Gly Gly Gly Gly Gly Val Asp Ala Trp Gly Gln Gly Thr Thr Val Thr
        115                 120                 125
```

```
Val Ser Ser Ala Ser Thr Lys Gly Pro Ser Val Phe Pro Leu Ala Pro
    130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
    210                 215                 220

Val Asp Lys Lys Val Glu Pro Lys Ser Cys Asp Lys Thr His Thr Cys
225                 230                 235                 240

Pro Pro Cys Pro Ala Pro Glu Ala Ala Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Ala Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Arg Cys Glu Leu Thr Lys Asn Gln Val Ser Leu Ser Cys Ala Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Val Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Asp Tyr Lys Asp Asp
    450                 455                 460

Asp Asp Lys
465


<210> SEQ ID NO 62
<211> LENGTH: 467
<212> TYPE: PRT
<213> ORGANISM: Artificial sequence
<220> FEATURE:
<223> OTHER INFORMATION: An artificially synthesized peptide sequence

<400> SEQUENCE: 62

Gln Val Gln Leu Val Glu Ser Gly Gly Gly Leu Val Gln Pro Gly Arg
1               5                   10                  15
```

-continued

```
Ser Leu Arg Leu Ser Cys Ala Ala Ser Gly Phe Thr Phe Ser Ser Ala
            20                  25                  30

Trp Met His Trp Val Arg Gln Ala Pro Gly Lys Gly Leu Glu Trp Val
        35                  40                  45

Ala Gln Ile Lys Asp Lys Gly Asn Gly Tyr Asn Ala Tyr Tyr Ala Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Thr Thr Ser Tyr Phe Gly Leu Phe Gly
            100                 105                 110

Gly Gly Gly Gly Gly Val Asp Ala Trp Gly Gln Gly Thr Thr Val Thr
        115                 120                 125

Val Ser Ser Ala Ser Thr Lys Gly Pro Ser Val Phe Pro Leu Ala Pro
    130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
    210                 215                 220

Val Asp Lys Lys Val Glu Pro Lys Ser Cys Asp Lys Thr His Thr Cys
225                 230                 235                 240

Pro Pro Cys Pro Ala Pro Glu Ala Ala Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Ala Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Arg Cys Glu Leu Thr Lys Asn Gln Val Ser Leu Ser Cys Ala Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Val Ser Lys Leu Thr Val Asp Lys Ser Arg Trp Gln
            420                 425                 430

Gln Gly Asn Val Phe Ser Cys Ser Val Met His Glu Ala Leu His Asn
```

```
        435                 440                 445

His Tyr Thr Gln Lys Ser Leu Ser Leu Ser Pro Asp Tyr Lys Asp Asp
    450                 455                 460

Asp Asp Lys
465


<210> SEQ ID NO 63
<211> LENGTH: 464
<212> TYPE: PRT
<213> ORGANISM: Artificial sequence
<220> FEATURE:
<223> OTHER INFORMATION: An artificially synthesized peptide sequence

<400> SEQUENCE: 63

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Lys Gly Gln Gln Tyr Ala Ala Tyr Tyr Ala Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Gln Thr Tyr Ser Asp Gly Ser Phe Tyr
            100                 105                 110

Phe Gly Val Asp Ala Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Ala Ala Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Ala Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
```

```
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Cys Glu
        355                 360                 365

Leu Thr Lys Asn Gln Val Ser Leu Ser Cys Ala Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Val Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Asp Tyr Lys Asp Asp Asp Asp Lys
    450                 455                 460


<210> SEQ ID NO 64
<211> LENGTH: 464
<212> TYPE: PRT
<213> ORGANISM: Artificial sequence
<220> FEATURE:
<223> OTHER INFORMATION: An artificially synthesized peptide sequence

<400> SEQUENCE: 64

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Arg Val Asn Gln Tyr Ala Asn Tyr Tyr Ala Glu
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Gly Leu Thr Gly Tyr Phe Ser Gly Gln
            100                 105                 110

Gly Gly Val Asp Ala Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
```

```
225                 230                 235                 240

Pro Ala Pro Glu Ala Ala Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Ala Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Cys Glu
        355                 360                 365

Leu Thr Lys Asn Gln Val Ser Leu Ser Cys Ala Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Val Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Asp Tyr Lys Asp Asp Asp Asp Lys
    450                 455                 460


<210> SEQ ID NO 65
<211> LENGTH: 464
<212> TYPE: PRT
<213> ORGANISM: Artificial sequence
<220> FEATURE:
<223> OTHER INFORMATION: An artificially synthesized peptide sequence

<400> SEQUENCE: 65

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Arg Val Asn Gln Tyr Ala Asn Tyr Tyr Ala Glu
    50                  55                  60

Ser Val Lys Gly Arg Leu Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Gly Leu Thr Gly Tyr Phe Ser Gly Gln
            100                 105                 110

Gly Gly Val Asp Ala Trp Gly Gln Gly Thr Thr Val Thr Val Ser Ser
        115                 120                 125

Ala Ser Thr Lys Gly Pro Ser Val Phe Pro Leu Ala Pro Ser Ser Lys
```

130 135 140

Ser Thr Ser Gly Gly Thr Ala Ala Leu Gly Cys Leu Val Lys Asp Tyr
145 150 155 160

Phe Pro Glu Pro Val Thr Val Ser Trp Asn Ser Gly Ala Leu Thr Ser
165 170 175

Gly Val His Thr Phe Pro Ala Val Leu Gln Ser Ser Gly Leu Tyr Ser
180 185 190

Leu Ser Ser Val Val Thr Val Pro Ser Ser Ser Leu Gly Thr Gln Thr
195 200 205

Tyr Ile Cys Asn Val Asn His Lys Pro Ser Asn Thr Lys Val Asp Lys
210 215 220

Lys Val Glu Pro Lys Ser Cys Asp Lys Thr His Thr Cys Pro Pro Cys
225 230 235 240

Pro Ala Pro Glu Ala Ala Gly Gly Pro Ser Val Phe Leu Phe Pro Pro
245 250 255

Lys Pro Lys Asp Thr Leu Met Ile Ser Arg Thr Pro Glu Val Thr Cys
260 265 270

Val Val Val Asp Val Ser His Glu Asp Pro Glu Val Lys Phe Asn Trp
275 280 285

Tyr Val Asp Gly Val Glu Val His Asn Ala Lys Thr Lys Pro Arg Glu
290 295 300

Glu Gln Tyr Ala Ser Thr Tyr Arg Val Val Ser Val Leu Thr Val Leu
305 310 315 320

His Gln Asp Trp Leu Asn Gly Lys Glu Tyr Lys Cys Lys Val Ser Asn
325 330 335

Lys Ala Leu Pro Ala Pro Ile Glu Lys Thr Ile Ser Lys Ala Lys Gly
340 345 350

Gln Pro Arg Glu Pro Gln Val Tyr Thr Leu Pro Pro Ser Arg Cys Glu
355 360 365

Leu Thr Lys Asn Gln Val Ser Leu Ser Cys Ala Val Lys Gly Phe Tyr
370 375 380

Pro Ser Asp Ile Ala Val Glu Trp Glu Ser Asn Gly Gln Pro Glu Asn
385 390 395 400

Asn Tyr Lys Thr Thr Pro Pro Val Leu Asp Ser Asp Gly Ser Phe Phe
405 410 415

Leu Val Ser Lys Leu Thr Val Asp Lys Ser Arg Trp Gln Gln Gly Asn
420 425 430

Val Phe Ser Cys Ser Val Met His Glu Ala Leu His Asn His Tyr Thr
435 440 445

Gln Lys Ser Leu Ser Leu Ser Pro Asp Tyr Lys Asp Asp Asp Asp Lys
450 455 460

<210> SEQ ID NO 66
<211> LENGTH: 464
<212> TYPE: PRT
<213> ORGANISM: Artificial sequence
<220> FEATURE:
<223> OTHER INFORMATION: An artificially synthesized peptide sequence

<400> SEQUENCE: 66

Gln Val Gln Leu Val Glu Ser Gly Gly Gly Leu Val Gln Pro Gly Arg
1 5 10 15

Ser Leu Arg Leu Ser Cys Ala Ala Ser Gly Phe Ala Phe Ser Asn Ala
20 25 30

Trp Met His Trp Val Arg Gln Ala Pro Gly Lys Gly Leu Glu Trp Val

-continued

```
        35                  40                  45

Ala Gln Ile Lys Asp Arg Val Asn Gln Tyr Ala Asn Tyr Tyr Ala Glu
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Gly Leu Thr Gly Tyr Phe Ser Gly Gln
            100                 105                 110

Gly Gly Val Asp Ala Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Ala Ala Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Ala Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Cys Glu
        355                 360                 365

Leu Thr Lys Asn Gln Val Ser Leu Ser Cys Ala Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Val Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Asp Tyr Lys Asp Asp Asp Asp Lys
    450                 455                 460
```

<210> SEQ ID NO 67
<211> LENGTH: 464
<212> TYPE: PRT
<213> ORGANISM: Artificial sequence
<220> FEATURE:
<223> OTHER INFORMATION: An artificially synthesized peptide sequence

<400> SEQUENCE: 67

Gln Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe Ser Asn Ala
20 25 30

Trp Met His Trp Val Arg Gln Ala Pro Gly Lys Gly Leu Glu Trp Val
35 40 45

Ala Gln Ile Lys Asp Arg Val Asn Gln Tyr Ala Asn Tyr Tyr Ala Glu
50 55 60

Cys Val Lys Gly Arg Phe Thr Ile Ser Arg Asp Asp Ser Lys Asn Ser
65 70 75 80

Ile Tyr Leu Gln Met Asn Ser Leu Lys Thr Glu Asp Thr Ala Val Tyr
85 90 95

Tyr Cys Arg Tyr Val His Tyr Gly Leu Thr Gly Tyr Phe Ser Gly Gln
100 105 110

Gly Gly Val Asp Ala Trp Gly Gln Gly Thr Thr Val Thr Val Ser Ser
115 120 125

Ala Ser Thr Lys Gly Pro Ser Val Phe Pro Leu Ala Pro Ser Ser Lys
130 135 140

Ser Thr Ser Gly Gly Thr Ala Ala Leu Gly Cys Leu Val Lys Asp Tyr
145 150 155 160

Phe Pro Glu Pro Val Thr Val Ser Trp Asn Ser Gly Ala Leu Thr Ser
165 170 175

Gly Val His Thr Phe Pro Ala Val Leu Gln Ser Ser Gly Leu Tyr Ser
180 185 190

Leu Ser Ser Val Val Thr Val Pro Ser Ser Ser Leu Gly Thr Gln Thr
195 200 205

Tyr Ile Cys Asn Val Asn His Lys Pro Ser Asn Thr Lys Val Asp Lys
210 215 220

Lys Val Glu Pro Lys Ser Cys Asp Lys Thr His Thr Cys Pro Pro Cys
225 230 235 240

Pro Ala Pro Glu Ala Ala Gly Gly Pro Ser Val Phe Leu Phe Pro Pro
245 250 255

Lys Pro Lys Asp Thr Leu Met Ile Ser Arg Thr Pro Glu Val Thr Cys
260 265 270

Val Val Val Asp Val Ser His Glu Asp Pro Glu Val Lys Phe Asn Trp
275 280 285

Tyr Val Asp Gly Val Glu Val His Asn Ala Lys Thr Lys Pro Arg Glu
290 295 300

Glu Gln Tyr Ala Ser Thr Tyr Arg Val Val Ser Val Leu Thr Val Leu
305 310 315 320

His Gln Asp Trp Leu Asn Gly Lys Glu Tyr Lys Cys Lys Val Ser Asn
325 330 335

Lys Ala Leu Pro Ala Pro Ile Glu Lys Thr Ile Ser Lys Ala Lys Gly
340 345 350

Gln Pro Arg Glu Pro Gln Val Tyr Thr Leu Pro Pro Ser Arg Cys Glu
355 360 365

```
Leu Thr Lys Asn Gln Val Ser Leu Ser Cys Ala Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Val Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Asp Tyr Lys Asp Asp Asp Asp Lys
    450                 455                 460


<210> SEQ ID NO 68
<211> LENGTH: 464
<212> TYPE: PRT
<213> ORGANISM: Artificial sequence
<220> FEATURE:
<223> OTHER INFORMATION: An artificially synthesized peptide sequence

<400> SEQUENCE: 68

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Ser Ala
            20                  25                  30

Trp Met His Trp Val Arg Gln Ala Pro Gly Lys Gly Leu Glu Trp Val
        35                  40                  45

Ala Gln Ile Lys Asp Lys Gln Asn Gln Tyr Asn Ala Tyr Tyr Ala Glu
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Ala Thr Ser Asp Gly Phe Leu Pro Tyr
            100                 105                 110

Phe Gly Val Asp Ala Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Ala Ala Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270
```

```
Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Ala Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Cys Glu
        355                 360                 365

Leu Thr Lys Asn Gln Val Ser Leu Ser Cys Ala Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Val Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Asp Tyr Lys Asp Asp Asp Asp Lys
    450                 455                 460


<210> SEQ ID NO 69
<211> LENGTH: 464
<212> TYPE: PRT
<213> ORGANISM: Artificial sequence
<220> FEATURE:
<223> OTHER INFORMATION: An artificially synthesized peptide sequence

<400> SEQUENCE: 69

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Arg Ala Ser Gly Tyr Asn Asn Tyr Tyr Ala Glu
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Ala Gln Ser Val Ser Ala Phe Phe Gln
            100                 105                 110

Tyr Gly Val Asp Ala Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175
```

```
Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Ala Ala Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Ala Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Cys Glu
        355                 360                 365

Leu Thr Lys Asn Gln Val Ser Leu Ser Cys Ala Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Val Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Asp Tyr Lys Asp Asp Asp Asp Lys
    450                 455                 460
```

<210> SEQ ID NO 70
<211> LENGTH: 464
<212> TYPE: PRT
<213> ORGANISM: Artificial sequence
<220> FEATURE:
<223> OTHER INFORMATION: An artificially synthesized peptide sequence

<400> SEQUENCE: 70

```
Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Lys Gln Ser Gln Tyr Ala Asn Tyr Tyr Ala Pro
    50                  55                  60

Ser Val Lys Gly Arg Phe Thr Ile Ser Arg Asp Asp Ser Lys Asn Ser
65                  70                  75                  80
```

-continued

```
Ile Tyr Leu Gln Met Asn Ser Leu Lys Thr Glu Asp Thr Ala Val Tyr
                85                  90                  95

Tyr Cys Arg Tyr Val His Tyr Gln Ser Thr Ser Tyr Ser Phe Tyr Gln
            100                 105                 110

Gly Gly Val Asp Ala Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Ala Ala Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Ala Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Cys Glu
        355                 360                 365

Leu Thr Lys Asn Gln Val Ser Leu Ser Cys Ala Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Val Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Asp Tyr Lys Asp Asp Asp Asp Lys
    450                 455                 460
```

<210> SEQ ID NO 71
<211> LENGTH: 464
<212> TYPE: PRT
<213> ORGANISM: Artificial sequence
<220> FEATURE:

-continued

<223> OTHER INFORMATION: An artificially synthesized peptide sequence

<400> SEQUENCE: 71

```
Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Lys Gln Ser Gln Tyr Ala Asn Tyr Tyr Ala Pro
    50                  55                  60

Ser Val Lys Gly Arg Phe Thr Ile Ser Arg Asp Asp Ser Lys Ser Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Gln Ser Thr Ser Tyr Ser Phe Tyr Gln
            100                 105                 110

Gly Gly Val Asp Ala Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Ala Ala Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Ala Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Cys Glu
        355                 360                 365

Leu Thr Lys Asn Gln Val Ser Leu Ser Cys Ala Val Lys Gly Phe Tyr
    370                 375                 380

Pro Ser Asp Ile Ala Val Glu Trp Glu Ser Asn Gly Gln Pro Glu Asn
385                 390                 395                 400
```

```
Asn Tyr Lys Thr Thr Pro Pro Val Leu Asp Ser Asp Gly Ser Phe Phe
                405                 410                 415

Leu Val Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Asp Tyr Lys Asp Asp Asp Asp Lys
    450                 455                 460


<210> SEQ ID NO 72
<211> LENGTH: 464
<212> TYPE: PRT
<213> ORGANISM: Artificial sequence
<220> FEATURE:
<223> OTHER INFORMATION: An artificially synthesized peptide sequence

<400> SEQUENCE: 72

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Arg Gly Asn Asn Tyr Ala Ala Tyr Tyr Ala Glu
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Gly Ser Tyr Phe Phe Ala Ser Phe Tyr
            100                 105                 110

Phe Gly Val Asp Ile Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Ala Ala Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300
```

-continued

```
Glu Gln Tyr Ala Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Cys Glu
        355                 360                 365

Leu Thr Lys Asn Gln Val Ser Leu Ser Cys Ala Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Val Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Asp Tyr Lys Asp Asp Asp Asp Lys
    450                 455                 460


<210> SEQ ID NO 73
<211> LENGTH: 464
<212> TYPE: PRT
<213> ORGANISM: Artificial sequence
<220> FEATURE:
<223> OTHER INFORMATION: An artificially synthesized peptide sequence

<400> SEQUENCE: 73

Gln Val Gln Leu Val Glu Ser Gly Gly Gly Leu Val Gln Pro Gly His
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Arg Gly Asn Asn Tyr Ala Ala Tyr Tyr Ala Glu
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Gly Ser Tyr Phe Phe Ala Ser Phe Tyr
            100                 105                 110

Phe Gly Val Asp Ile Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205
```

-continued

```
Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Ala Ala Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Ala Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Cys Glu
        355                 360                 365

Leu Thr Lys Asn Gln Val Ser Leu Ser Cys Ala Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Val Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Asp Tyr Lys Asp Asp Asp Asp Lys
    450                 455                 460
```

<210> SEQ ID NO 74
<211> LENGTH: 464
<212> TYPE: PRT
<213> ORGANISM: Artificial sequence
<220> FEATURE:
<223> OTHER INFORMATION: An artificially synthesized peptide sequence

<400> SEQUENCE: 74

```
Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Arg Gly Asn Asn Tyr Asn Thr Tyr Tyr Ala Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Gly Ser Tyr Phe Phe Ser Gly Ser Ser
            100                 105                 110
```

-continued

```
Phe Gly Val Asp Ile Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Ala Ala Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Ala Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Cys Glu
        355                 360                 365

Leu Thr Lys Asn Gln Val Ser Leu Ser Cys Ala Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Val Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Asp Tyr Lys Asp Asp Asp Asp Lys
    450                 455                 460
```

<210> SEQ ID NO 75
<211> LENGTH: 464
<212> TYPE: PRT
<213> ORGANISM: Artificial sequence
<220> FEATURE:
<223> OTHER INFORMATION: An artificially synthesized peptide sequence

<400> SEQUENCE: 75

```
Gln Val Gln Leu Val Glu Ser Gly Gly Gly Leu Val Gln Pro Gly Arg
1               5                   10                  15
```

-continued

```
Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Arg Gly Asn Asn Tyr Asn Thr Tyr Tyr Ala Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Ala His Tyr Gly Ser Tyr Phe Phe Ser Gly Ser Ser
            100                 105                 110

Phe Gly Val Asp Ile Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Ala Ala Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Ala Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Cys Glu
        355                 360                 365

Leu Thr Lys Asn Gln Val Ser Leu Ser Cys Ala Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Val Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
```

```
        435                 440                 445

Gln Lys Ser Leu Ser Leu Ser Pro Asp Tyr Lys Asp Asp Asp Asp Lys
    450                 455                 460


<210> SEQ ID NO 76
<211> LENGTH: 464
<212> TYPE: PRT
<213> ORGANISM: Artificial sequence
<220> FEATURE:
<223> OTHER INFORMATION: An artificially synthesized peptide sequence

<400> SEQUENCE: 76

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Lys Gly Asn Gln Tyr Ala Thr Tyr Tyr Ala Glu
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Gly Thr Tyr Phe Phe Ala Leu Pro Ala
            100                 105                 110

Phe Gly Val Asp Ile Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Ala Ala Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Ala Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
```

```
            340                 345                 350

Gln Pro Arg Glu Pro Gln Val Tyr Thr Leu Pro Pro Ser Arg Cys Glu
        355                 360                 365

Leu Thr Lys Asn Gln Val Ser Leu Ser Cys Ala Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Val Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Asp Tyr Lys Asp Asp Asp Asp Lys
    450                 455                 460


<210> SEQ ID NO 77
<211> LENGTH: 464
<212> TYPE: PRT
<213> ORGANISM: Artificial sequence
<220> FEATURE:
<223> OTHER INFORMATION: An artificially synthesized peptide sequence

<400> SEQUENCE: 77

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Lys Gly Asn Gln Tyr Ala Thr Tyr Tyr Ala Glu
    50                  55                  60

Ser Val Lys Gly Arg Tyr Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Gly Thr Tyr Phe Phe Ala Leu Pro Ala
            100                 105                 110

Phe Gly Val Asp Ile Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Ala Ala Gly Gly Pro Ser Val Phe Leu Phe Pro Pro
```

```
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Ala Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Cys Glu
        355                 360                 365

Leu Thr Lys Asn Gln Val Ser Leu Ser Cys Ala Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Val Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Asp Tyr Lys Asp Asp Asp Asp Lys
    450                 455                 460


<210> SEQ ID NO 78
<211> LENGTH: 464
<212> TYPE: PRT
<213> ORGANISM: Artificial sequence
<220> FEATURE:
<223> OTHER INFORMATION: An artificially synthesized peptide sequence

<400> SEQUENCE: 78

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Arg Gly Asn Asn Tyr Ala Ala Tyr Tyr Ala Glu
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Gly Ser Tyr Phe Phe Ala Ser Phe Tyr
            100                 105                 110

Phe Gly Val Asp Ile Trp Gly Gln Gly Thr Ala Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
```

-continued 145 150 155 160

Phe Pro Glu Pro Val Thr Val Ser Trp Asn Ser Gly Ala Leu Thr Ser
165 170 175

Gly Val His Thr Phe Pro Ala Val Leu Gln Ser Ser Gly Leu Tyr Ser
180 185 190

Leu Ser Ser Val Val Thr Val Pro Ser Ser Ser Leu Gly Thr Gln Thr
195 200 205

Tyr Ile Cys Asn Val Asn His Lys Pro Ser Asn Thr Lys Val Asp Lys
210 215 220

Lys Val Glu Pro Lys Ser Cys Asp Lys Thr His Thr Cys Pro Pro Cys
225 230 235 240

Pro Ala Pro Glu Ala Ala Gly Gly Pro Ser Val Phe Leu Phe Pro Pro
245 250 255

Lys Pro Lys Asp Thr Leu Met Ile Ser Arg Thr Pro Glu Val Thr Cys
260 265 270

Val Val Val Asp Val Ser His Glu Asp Pro Glu Val Lys Phe Asn Trp
275 280 285

Tyr Val Asp Gly Val Glu Val His Asn Ala Lys Thr Lys Pro Arg Glu
290 295 300

Glu Gln Tyr Ala Ser Thr Tyr Arg Val Val Ser Val Leu Thr Val Leu
305 310 315 320

His Gln Asp Trp Leu Asn Gly Lys Glu Tyr Lys Cys Lys Val Ser Asn
325 330 335

Lys Ala Leu Pro Ala Pro Ile Glu Lys Thr Ile Ser Lys Ala Lys Gly
340 345 350

Gln Pro Arg Glu Pro Gln Val Tyr Thr Leu Pro Pro Ser Arg Cys Glu
355 360 365

Leu Thr Lys Asn Gln Val Ser Leu Ser Cys Ala Val Lys Gly Phe Tyr
370 375 380

Pro Ser Asp Ile Ala Val Glu Trp Glu Ser Asn Gly Gln Pro Glu Asn
385 390 395 400

Asn Tyr Lys Thr Thr Pro Pro Val Leu Asp Ser Asp Gly Ser Phe Phe
405 410 415

Leu Val Ser Lys Leu Thr Val Asp Lys Ser Arg Trp Gln Gln Gly Asn
420 425 430

Val Phe Ser Cys Ser Val Met His Glu Ala Leu His Asn His Tyr Thr
435 440 445

Gln Lys Ser Leu Ser Leu Ser Pro Asp Tyr Lys Asp Asp Asp Asp Lys
450 455 460

<210> SEQ ID NO 79
<211> LENGTH: 15
<212> TYPE: PRT
<213> ORGANISM: Artificial sequence
<220> FEATURE:
<223> OTHER INFORMATION: An artificially synthesized peptide sequence

<400> SEQUENCE: 79

Gly Leu Asn Asp Ile Phe Glu Ala Gln Lys Ile Glu Trp His Glu
1 5 10 15

<210> SEQ ID NO 80
<211> LENGTH: 233
<212> TYPE: PRT
<213> ORGANISM: Artificial sequence
<220> FEATURE:
<223> OTHER INFORMATION: An artificially synthesized peptide sequence

<400> SEQUENCE: 80

Cys His Pro Arg Leu Ser Leu His Arg Pro Ala Leu Glu Asp Leu Leu
1 5 10 15

Leu Gly Ser Glu Ala Asn Leu Thr Cys Thr Leu Thr Gly Leu Arg Asp
20 25 30

Ala Ser Gly Val Thr Phe Thr Trp Thr Pro Ser Ser Gly Lys Ser Ala
35 40 45

Val Gln Gly Pro Pro Glu Arg Asp Leu Cys Gly Cys Tyr Ser Val Ser
50 55 60

Ser Val Leu Pro Gly Cys Ala Glu Pro Trp Asn His Gly Lys Thr Phe
65 70 75 80

Thr Cys Thr Ala Ala Tyr Pro Glu Ser Lys Thr Pro Leu Thr Ala Thr
85 90 95

Leu Ser Lys Ser Gly Asn Thr Phe Arg Pro Glu Val His Leu Leu Pro
100 105 110

Pro Pro Ser Glu Glu Leu Ala Leu Asn Glu Leu Val Thr Leu Thr Cys
115 120 125

Leu Ala Arg Gly Phe Ser Pro Lys Asp Val Leu Val Arg Trp Leu Gln
130 135 140

Gly Ser Gln Glu Leu Pro Arg Glu Lys Tyr Leu Thr Trp Ala Ser Arg
145 150 155 160

Gln Glu Pro Ser Gln Gly Thr Thr Thr Phe Ala Val Thr Ser Ile Leu
165 170 175

Arg Val Ala Ala Glu Asp Trp Lys Lys Gly Asp Thr Phe Ser Cys Met
180 185 190

Val Gly His Glu Ala Leu Pro Leu Ala Phe Thr Gln Lys Thr Ile Asp
195 200 205

Arg Leu Ala Gly Lys Gly Gly Gly Gly Ser Gly Leu Asn Asp Ile Phe
210 215 220

Glu Ala Gln Lys Ile Glu Trp His Glu
225 230

<210> SEQ ID NO 81
<211> LENGTH: 641
<212> TYPE: PRT
<213> ORGANISM: Human herpesvirus 4

<400> SEQUENCE: 81

Met Ser Asp Glu Gly Pro Gly Thr Gly Pro Gly Asn Gly Leu Gly Glu
1 5 10 15

Lys Gly Asp Thr Ser Gly Pro Glu Gly Ser Gly Gly Ser Gly Pro Gln
20 25 30

Arg Arg Gly Gly Asp Asn His Gly Arg Gly Arg Gly Arg Gly Arg Gly
35 40 45

Arg Gly Gly Gly Arg Pro Gly Ala Pro Gly Gly Ser Gly Ser Gly Pro
50 55 60

Arg His Arg Asp Gly Val Arg Arg Pro Gln Lys Arg Pro Ser Cys Ile
65 70 75 80

Gly Cys Lys Gly Thr His Gly Gly Thr Gly Ala Gly Ala Gly Ala Gly
85 90 95

Gly Ala Gly Ala Gly Gly Ala Gly Ala Gly Gly Gly Ala Gly Ala Gly
100 105 110

Gly Gly Ala Gly Gly Ala Gly Gly Ala Gly Gly Ala Gly Ala Gly Gly
115 120 125

-continued

```
Gly Ala Gly Ala Gly Gly Gly Ala Gly Gly Ala Gly Gly Ala Gly Ala
    130                 135                 140

Gly Gly Gly Ala Gly Ala Gly Gly Gly Ala Gly Gly Ala Gly Ala Gly
145                 150                 155                 160

Gly Gly Ala Gly Gly Ala Gly Gly Ala Gly Ala Gly Gly Gly Ala Gly
                165                 170                 175

Ala Gly Gly Gly Ala Gly Gly Ala Gly Ala Gly Gly Gly Ala Gly Gly
            180                 185                 190

Ala Gly Gly Ala Gly Ala Gly Gly Gly Ala Gly Ala Gly Gly Ala Gly
        195                 200                 205

Gly Ala Gly Gly Ala Gly Ala Gly Gly Ala Gly Ala Gly Gly Gly Ala
    210                 215                 220

Gly Gly Ala Gly Gly Ala Gly Ala Gly Gly Ala Gly Ala Gly Gly Ala
225                 230                 235                 240

Gly Ala Gly Gly Ala Gly Ala Gly Gly Ala Gly Gly Ala Gly Ala Gly
                245                 250                 255

Gly Ala Gly Gly Ala Gly Ala Gly Gly Ala Gly Gly Ala Gly Ala Gly
            260                 265                 270

Gly Gly Ala Gly Gly Ala Gly Ala Gly Gly Gly Ala Gly Gly Ala Gly
        275                 280                 285

Ala Gly Gly Ala Gly Gly Ala Gly Ala Gly Gly Ala Gly Gly Ala Gly
    290                 295                 300

Ala Gly Gly Ala Gly Gly Ala Gly Ala Gly Gly Gly Ala Gly Ala Gly
305                 310                 315                 320

Gly Ala Gly Ala Gly Gly Gly Gly Arg Gly Arg Gly Gly Ser Gly Gly
                325                 330                 335

Arg Gly Arg Gly Gly Ser Gly Gly Arg Gly Arg Gly Gly Ser Gly Gly
            340                 345                 350

Arg Arg Gly Arg Gly Arg Glu Arg Ala Arg Gly Gly Ser Arg Glu Arg
        355                 360                 365

Ala Arg Gly Arg Gly Arg Gly Arg Gly Glu Lys Arg Pro Arg Ser Pro
    370                 375                 380

Ser Ser Gln Ser Ser Ser Ser Gly Ser Pro Pro Arg Arg Pro Pro Pro
385                 390                 395                 400

Gly Arg Arg Pro Phe Phe His Pro Val Gly Glu Ala Asp Tyr Phe Glu
                405                 410                 415

Tyr His Gln Glu Gly Gly Pro Asp Gly Glu Pro Asp Val Pro Pro Gly
            420                 425                 430

Ala Ile Glu Gln Gly Pro Ala Asp Asp Pro Gly Glu Gly Pro Ser Thr
        435                 440                 445

Gly Pro Arg Gly Gln Gly Asp Gly Gly Arg Arg Lys Lys Gly Gly Trp
    450                 455                 460

Phe Gly Lys His Arg Gly Gln Gly Gly Ser Asn Pro Lys Phe Glu Asn
465                 470                 475                 480

Ile Ala Glu Gly Leu Arg Ala Leu Leu Ala Arg Ser His Val Glu Arg
                485                 490                 495

Thr Thr Asp Glu Gly Thr Trp Val Ala Gly Val Phe Val Tyr Gly Gly
            500                 505                 510

Ser Lys Thr Ser Leu Tyr Asn Leu Arg Arg Gly Thr Ala Leu Ala Ile
        515                 520                 525

Pro Gln Cys Arg Leu Thr Pro Leu Ser Arg Leu Pro Phe Gly Met Ala
    530                 535                 540
```

-continued

```
Pro Gly Pro Gly Pro Gln Pro Gly Pro Leu Arg Glu Ser Ile Val Cys
545                 550                 555                 560

Tyr Phe Met Val Phe Leu Gln Thr His Ile Phe Ala Glu Val Leu Lys
                565                 570                 575

Asp Ala Ile Lys Asp Leu Val Met Thr Lys Pro Ala Pro Thr Cys Asn
            580                 585                 590

Ile Arg Val Thr Val Cys Ser Phe Asp Asp Gly Val Asp Leu Pro Pro
        595                 600                 605

Trp Phe Pro Pro Met Val Glu Gly Ala Ala Ala Glu Gly Asp Asp Gly
    610                 615                 620

Asp Asp Gly Asp Glu Gly Gly Asp Gly Asp Glu Gly Glu Glu Gly Gln
625                 630                 635                 640

Glu


<210> SEQ ID NO 82
<211> LENGTH: 321
<212> TYPE: PRT
<213> ORGANISM: Escherichia coli

<400> SEQUENCE: 82

Met Lys Asp Asn Thr Val Pro Leu Lys Leu Ile Ala Leu Leu Ala Asn
1               5                   10                  15

Gly Glu Phe His Ser Gly Glu Gln Leu Gly Glu Thr Leu Gly Met Ser
            20                  25                  30

Arg Ala Ala Ile Asn Lys His Ile Gln Thr Leu Arg Asp Trp Gly Val
        35                  40                  45

Asp Val Phe Thr Val Pro Gly Lys Gly Tyr Ser Leu Pro Glu Pro Ile
    50                  55                  60

Gln Leu Leu Asn Ala Lys Gln Ile Leu Gly Gln Leu Asp Gly Gly Ser
65                  70                  75                  80

Val Ala Val Leu Pro Val Ile Asp Ser Thr Asn Gln Tyr Leu Leu Asp
                85                  90                  95

Arg Ile Gly Glu Leu Lys Ser Gly Asp Ala Cys Ile Ala Glu Tyr Gln
            100                 105                 110

Gln Ala Gly Arg Gly Arg Arg Gly Arg Lys Trp Phe Ser Pro Phe Gly
        115                 120                 125

Ala Asn Leu Tyr Leu Ser Met Phe Trp Arg Leu Glu Gln Gly Pro Ala
    130                 135                 140

Ala Ala Ile Gly Leu Ser Leu Val Ile Gly Ile Val Met Ala Glu Val
145                 150                 155                 160

Leu Arg Lys Leu Gly Ala Asp Lys Val Arg Val Lys Trp Pro Asn Asp
                165                 170                 175

Leu Tyr Leu Gln Asp Arg Lys Leu Ala Gly Ile Leu Val Glu Leu Thr
            180                 185                 190

Gly Lys Thr Gly Asp Ala Ala Gln Ile Val Ile Gly Ala Gly Ile Asn
        195                 200                 205

Met Ala Met Arg Arg Val Glu Glu Ser Val Val Asn Gln Gly Trp Ile
    210                 215                 220

Thr Leu Gln Glu Ala Gly Ile Asn Leu Asp Arg Asn Thr Leu Ala Ala
225                 230                 235                 240

Met Leu Ile Arg Glu Leu Arg Ala Ala Leu Glu Leu Phe Glu Gln Glu
                245                 250                 255

Gly Leu Ala Pro Tyr Leu Ser Arg Trp Glu Lys Leu Asp Asn Phe Ile
            260                 265                 270
```

```
Asn Arg Pro Val Lys Leu Ile Ile Gly Asp Lys Glu Ile Phe Gly Ile
        275                 280                 285

Ser Arg Gly Ile Asp Lys Gln Gly Ala Leu Leu Leu Glu Gln Asp Gly
    290                 295                 300

Ile Ile Lys Pro Trp Met Gly Gly Glu Ile Ser Leu Arg Ser Ala Glu
305                 310                 315                 320

Lys


<210> SEQ ID NO 83
<211> LENGTH: 549
<212> TYPE: DNA
<213> ORGANISM: Homo sapiens

<400> SEQUENCE: 83

atggaacagg ggaagggcct ggctgtcctc atcctggcta tcattcttct tcaaggtact      60

ttggcccagt caatcaaagg aaaccacttg gttaaggtgt atgactatca agaagatggt     120

tcggtacttc tgacttgtga tgcagaagcc aaaaatatca catggtttaa agatgggaag     180

atgatcggct tcctaactga agataaaaaa aaatggaatc tgggaagtaa tgccaaggac     240

cctcgaggga tgtatcagtg taaaggatca cagaacaagt caaaaccact ccaagtgtat     300

tacagaatgt gtcagaactg cattgaacta aatgcagcca ccatatctgg ctttctcttt     360

gctgaaatcg tcagcatttt cgtccttgct gttggggtct acttcattgc tggacaggat     420

ggagttcgcc agtcgagagc ttcagacaag cagactctgt tgcccaatga ccagctctac     480

cagcccctca aggatcgaga agatgaccag tacagccacc ttcaaggaaa ccagttgagg     540

aggaattga                                                              549


<210> SEQ ID NO 84
<211> LENGTH: 182
<212> TYPE: PRT
<213> ORGANISM: Homo sapiens

<400> SEQUENCE: 84

Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
            20                  25                  30

Val Tyr Asp Tyr Gln Glu Asp Gly Ser Val Leu Leu Thr Cys Asp Ala
        35                  40                  45

Glu Ala Lys Asn Ile Thr Trp Phe Lys Asp Gly Lys Met Ile Gly Phe
    50                  55                  60

Leu Thr Glu Asp Lys Lys Lys Trp Asn Leu Gly Ser Asn Ala Lys Asp
65                  70                  75                  80

Pro Arg Gly Met Tyr Gln Cys Lys Gly Ser Gln Asn Lys Ser Lys Pro
                85                  90                  95

Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
        115                 120                 125

Leu Ala Val Gly Val Tyr Phe Ile Ala Gly Gln Asp Gly Val Arg Gln
    130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Asp Gln Tyr Ser His Leu Gln Gly
                165                 170                 175
```

```
Asn Gln Leu Arg Arg Asn
            180


<210> SEQ ID NO 85
<211> LENGTH: 516
<212> TYPE: DNA
<213> ORGANISM: Homo sapiens

<400> SEQUENCE: 85

atggaacata gcacgtttct ctctggcctg gtactggcta cccttctctc gcaagtgagc      60

cccttcaaga tacctataga ggaacttgag gacagagtgt ttgtgaattg caataccagc     120

atcacatggg tagagggaac ggtgggaaca ctgctctcag acattacaag actggacctg     180

ggaaaacgca tcctggaccc acgaggaata tataggtgta atgggacaga tatatacaag     240

gacaaagaat ctaccgtgca agttcattat cgaatgtgcc agagctgtgt ggagctggat     300

ccagccaccg tggctggcat cattgtcact gatgtcattg ccactctgct ccttgctttg     360

ggagtcttct gctttgctgg acatgagact ggaaggctgt ctggggctgc cgacacacaa     420

gctctgttga ggaatgacca ggtctatcag cccctccgag atcgagatga tgctcagtac     480

agccaccttg gaggaaactg ggctcggaac aagtga                                516


<210> SEQ ID NO 86
<211> LENGTH: 171
<212> TYPE: PRT
<213> ORGANISM: Homo sapiens

<400> SEQUENCE: 86

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170


<210> SEQ ID NO 87
<211> LENGTH: 624
<212> TYPE: DNA
<213> ORGANISM: Homo sapiens

<400> SEQUENCE: 87
```

-continued

```
atgcagtcgg gcactcactg gagagttctg ggcctctgcc tcttatcagt tggcgtttgg     60

gggcaagatg gtaatgaaga aatgggtggt attacacaga caccatataa agtctccatc    120

tctggaacca cagtaatatt gacatgccct cagtatcctg gatctgaaat actatggcaa    180

cacaatgata aaaacatagg cggtgatgag gatgataaaa acataggcag tgatgaggat    240

cacctgtcac tgaaggaatt ttcagaattg gagcaaagtg gttattatgt ctgctacccc    300

agaggaagca aaccagaaga tgcgaacttt tatctctacc tgagggcaag agtgtgtgag    360

aactgcatgg agatggatgt gatgtcggtg gccacaattg tcatagtgga catctgcatc    420

actgggggct tgctgctgct ggtttactac tggagcaaga atagaaaggc caaggccaag    480

cctgtgacac gaggagcggg tgctggcggc aggcaaaggg gacaaaacaa ggagaggcca    540

ccacctgttc ccaacccaga ctatgagccc atccggaaag gccagcggga cctgtattct    600

ggcctgaatc agagacgcat ctga                                           624
```

<210> SEQ ID NO 88
<211> LENGTH: 207
<212> TYPE: PRT
<213> ORGANISM: Homo sapiens

<400> SEQUENCE: 88

```
Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205
```

<210> SEQ ID NO 89
<211> LENGTH: 8
<212> TYPE: PRT
<213> ORGANISM: Artificial Sequence
<220> FEATURE:
<223> OTHER INFORMATION: An artificially synthesized peptide sequence

<400> SEQUENCE: 89

-continued

Asp Tyr Lys Asp Asp Asp Asp Lys
1 5

<210> SEQ ID NO 90
<211> LENGTH: 6
<212> TYPE: PRT
<213> ORGANISM: Artificial sequence
<220> FEATURE:
<223> OTHER INFORMATION: An artificially synthesized peptide sequence

<400> SEQUENCE: 90

Gly Gly Ser Gly Gly Ser
1 5

<210> SEQ ID NO 91
<211> LENGTH: 9
<212> TYPE: PRT
<213> ORGANISM: Artificial sequence
<220> FEATURE:
<223> OTHER INFORMATION: An artificially synthesized peptide sequence

<400> SEQUENCE: 91

Gly Gly Ser Gly Gly Ser Gly Gly Ser
1 5

<210> SEQ ID NO 92
<211> LENGTH: 7
<212> TYPE: PRT
<213> ORGANISM: Artificial sequence
<220> FEATURE:
<223> OTHER INFORMATION: An artificially synthesized peptide sequence

<400> SEQUENCE: 92

Gly Gly Ser Gly Gly Gly Ser
1 5

<210> SEQ ID NO 93
<211> LENGTH: 8
<212> TYPE: PRT
<213> ORGANISM: Artificial sequence
<220> FEATURE:
<223> OTHER INFORMATION: An artificially synthesized peptide sequence

<400> SEQUENCE: 93

Gly Gly Gly Ser Gly Gly Gly Ser
1 5

<210> SEQ ID NO 94
<211> LENGTH: 122
<212> TYPE: PRT
<213> ORGANISM: Artificial sequence
<220> FEATURE:
<223> OTHER INFORMATION: An artificially synthesized peptide sequence

<400> SEQUENCE: 94

Gln Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe Ser Asn Ala
20 25 30

Trp Met His Trp Val Arg Gln Ala Pro Gly Lys Gly Leu Glu Trp Val
35 40 45

Ala Gln Ile Lys Ala Lys Ser Asn Asn Tyr Ala Thr Tyr Tyr Ala Glu
50 55 60

Ser Val Lys Gly Arg Phe Thr Ile Ser Arg Asp Asp Ser Lys Asn Ser
65 70 75 80

```
Ile Tyr Leu Gln Met Asn Ser Leu Lys Thr Glu Asp Thr Ala Val Tyr
                85                  90                  95

Tyr Cys Arg Tyr Val His Tyr Gly Ala Tyr Tyr Gly Val Asp Ala Trp
            100                 105                 110

Gly Gln Gly Thr Thr Val Thr Val Ser Ser
        115                 120


<210> SEQ ID NO 95
<211> LENGTH: 122
<212> TYPE: PRT
<213> ORGANISM: Artificial sequence
<220> FEATURE:
<223> OTHER INFORMATION: An artificially synthesized peptide sequence

<400> SEQUENCE: 95

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Lys Ser Asn Asn Tyr Ala Thr Tyr Tyr Ala Glu
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Gly Ala Tyr Tyr Gly Val Asp Ala Trp
            100                 105                 110

Gly Gln Gly Thr Thr Val Thr Val Ser Ser
        115                 120


<210> SEQ ID NO 96
<211> LENGTH: 128
<212> TYPE: PRT
<213> ORGANISM: Artificial sequence
<220> FEATURE:
<223> OTHER INFORMATION: An artificially synthesized peptide sequence

<400> SEQUENCE: 96

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Lys Ser Asn Asn Tyr Ala Thr Tyr Tyr Ala Glu
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Gly Ala Gly Gly Ser Gly Gly Ser Tyr
            100                 105                 110

Tyr Gly Val Asp Ala Trp Gly Gln Gly Thr Thr Val Thr Val Ser Ser
        115                 120                 125
```

```
<210> SEQ ID NO 97
<211> LENGTH: 122
<212> TYPE: PRT
<213> ORGANISM: Artificial sequence
<220> FEATURE:
<223> OTHER INFORMATION: An artificially synthesized peptide sequence

<400> SEQUENCE: 97

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Lys Ser Asn Asn Tyr Ala Thr Tyr Tyr Ala Glu
    50                  55                  60

Ser Val Lys Gly Arg Phe Thr Ile Ser Arg Asp Asp Ser Lys Ser Asn
65                  70                  75                  80

Ile Tyr Leu Gln Met Asn Ser Leu Lys Glu Glu Asp Thr Ala Val Tyr
                85                  90                  95

Tyr Cys Arg Tyr Val His Tyr Gly Ala Tyr Tyr Gly Val Asp Ala Trp
            100                 105                 110

Gly Gln Gly Thr Ser Val Thr Val Ser Ser
        115                 120


<210> SEQ ID NO 98
<211> LENGTH: 112
<212> TYPE: PRT
<213> ORGANISM: Artificial sequence
<220> FEATURE:
<223> OTHER INFORMATION: An artificially synthesized peptide sequence

<400> SEQUENCE: 98

Asp Val Val Met Thr Gln Thr Pro Val Ser Met Ser Val Ser Leu Gly
1               5                   10                  15

Gly Gln Val Ser Ile Ser Cys Arg Ser Ser Gln Ser Leu Val His Asn
            20                  25                  30

Asn Gly Asn Thr Tyr Val Ser Trp Tyr Ile Gln Lys Pro Ser Gln Ser
        35                  40                  45

Pro Gln Leu Leu Ile Tyr Lys Val Ser Asn Arg Phe Ser Gly Ile Ser
    50                  55                  60

Asp Arg Phe Ser Gly Ser Gly Ser Gly Thr Asp Phe Thr Leu Lys Ile
65                  70                  75                  80

Ser Arg Val Glu Pro Asp Asp Leu Gly Val Tyr Tyr Cys Gly Gln Gly
                85                  90                  95

Thr Gln Asp Pro Tyr Thr Phe Gly Ala Gly Thr Lys Leu Glu Leu Lys
            100                 105                 110


<210> SEQ ID NO 99
<211> LENGTH: 5
<212> TYPE: PRT
<213> ORGANISM: Artificial sequence
<220> FEATURE:
<223> OTHER INFORMATION: An artificially synthesized peptide sequence

<400> SEQUENCE: 99

Asn Ala Trp Met His
1               5


<210> SEQ ID NO 100
```

<211> LENGTH: 19
<212> TYPE: PRT
<213> ORGANISM: Artificial sequence
<220> FEATURE:
<223> OTHER INFORMATION: An artificially synthesized peptide sequence

<400> SEQUENCE: 100

Gln Ile Lys Asp Lys Ser Asn Asn Tyr Ala Thr Tyr Tyr Ala Glu Ser
1 5 10 15

Val Lys Gly

<210> SEQ ID NO 101
<211> LENGTH: 11
<212> TYPE: PRT
<213> ORGANISM: Artificial sequence
<220> FEATURE:
<223> OTHER INFORMATION: An artificially synthesized peptide sequence

<400> SEQUENCE: 101

Val His Tyr Gly Ala Tyr Tyr Gly Val Asp Ala
1 5 10

<210> SEQ ID NO 102
<211> LENGTH: 17
<212> TYPE: PRT
<213> ORGANISM: Artificial sequence
<220> FEATURE:
<223> OTHER INFORMATION: An artificially synthesized peptide sequence

<400> SEQUENCE: 102

Val His Tyr Gly Ala Gly Gly Ser Gly Gly Ser Tyr Tyr Gly Val Asp
1 5 10 15

Ala

<210> SEQ ID NO 103
<211> LENGTH: 16
<212> TYPE: PRT
<213> ORGANISM: Artificial sequence
<220> FEATURE:
<223> OTHER INFORMATION: An artificially synthesized peptide sequence

<400> SEQUENCE: 103

Arg Ser Ser Gln Ser Leu Val His Ser Asn Arg Asn Thr Tyr Leu His
1 5 10 15

<210> SEQ ID NO 104
<211> LENGTH: 7
<212> TYPE: PRT
<213> ORGANISM: Artificial sequence
<220> FEATURE:
<223> OTHER INFORMATION: An artificially synthesized peptide sequence

<400> SEQUENCE: 104

Lys Val Ser Asn Arg Phe Ser
1 5

<210> SEQ ID NO 105
<211> LENGTH: 9
<212> TYPE: PRT
<213> ORGANISM: Artificial sequence
<220> FEATURE:
<223> OTHER INFORMATION: An artificially synthesized peptide sequence

<400> SEQUENCE: 105

Gly Gln Gly Thr Gln Val Pro Tyr Thr
1 5

<210> SEQ ID NO 106
<211> LENGTH: 128
<212> TYPE: PRT
<213> ORGANISM: Artificial sequence
<220> FEATURE:
<223> OTHER INFORMATION: An artificially synthesized peptide sequence

<400> SEQUENCE: 106

```
Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Lys Ala Asn Gly Tyr Asn Thr Tyr Tyr Ala Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Thr Thr Tyr Tyr Tyr Ala Ser Gly Ser
            100                 105                 110

Tyr Gly Val Asp Ala Trp Gly Gln Gly Thr Thr Val Thr Val Ser Ser
        115                 120                 125
```

<210> SEQ ID NO 107
<211> LENGTH: 128
<212> TYPE: PRT
<213> ORGANISM: Artificial sequence
<220> FEATURE:
<223> OTHER INFORMATION: An artificially synthesized peptide sequence

<400> SEQUENCE: 107

```
Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Arg Ser Asn Gly Tyr Ala Thr Tyr Tyr Ala Glu
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Thr Thr Phe Thr Gly Val Ser Phe Gln
            100                 105                 110

Tyr Gly Val Asp Ala Trp Gly Gln Gly Thr Thr Val Thr Val Ser Ser
        115                 120                 125
```

<210> SEQ ID NO 108
<211> LENGTH: 128
<212> TYPE: PRT
<213> ORGANISM: Artificial sequence
<220> FEATURE:
<223> OTHER INFORMATION: An artificially synthesized peptide sequence

<400> SEQUENCE: 108

Gln Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe Ser Asn Ala
20 25 30

Trp Met His Trp Val Arg Gln Ala Pro Gly Lys Gly Leu Glu Trp Val
35 40 45

Ala Gln Ile Lys Asp Arg Ala Ser Gly Tyr Ala Thr Tyr Tyr Ala Pro
50 55 60

Ser Val Lys Gly Arg Phe Thr Ile Ser Arg Asp Asp Ser Lys Asn Ser
65 70 75 80

Ile Tyr Leu Gln Met Asn Ser Leu Lys Thr Glu Asp Thr Ala Val Tyr
85 90 95

Tyr Cys Arg Tyr Val His Tyr Thr Thr Tyr Val Asp Gly Leu Tyr Ser
100 105 110

Phe Gly Val Asp Ala Trp Gly Gln Gly Thr Thr Val Thr Val Ser Ser
115 120 125

<210> SEQ ID NO 109
<211> LENGTH: 128
<212> TYPE: PRT
<213> ORGANISM: Artificial sequence
<220> FEATURE:
<223> OTHER INFORMATION: An artificially synthesized peptide sequence

<400> SEQUENCE: 109

Gln Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe Ser Asn Ala
20 25 30

Trp Met His Trp Val Arg Gln Ala Pro Gly Lys Gly Leu Glu Trp Val
35 40 45

Ala Gln Ile Lys Asp Lys Ala Asn Gly Tyr Asn Thr Tyr Tyr Ala Pro
50 55 60

Ser Val Lys Gly Arg Phe Thr Ile Ser Arg Asp Asp Ser Lys Asn Ser
65 70 75 80

Ile Tyr Leu Gln Met Asn Ser Leu Lys Thr Glu Asp Thr Ala Val Tyr
85 90 95

Tyr Cys Arg Tyr Val His Tyr Thr Leu Tyr Phe Gly Gly Tyr Tyr Gln
100 105 110

Tyr Gly Val Asp Ala Trp Gly Gln Gly Thr Thr Val Thr Val Ser Ser
115 120 125

<210> SEQ ID NO 110
<211> LENGTH: 128
<212> TYPE: PRT
<213> ORGANISM: Artificial sequence
<220> FEATURE:
<223> OTHER INFORMATION: An artificially synthesized peptide sequence

<400> SEQUENCE: 110

Gln Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe Ser Asn Ala
20 25 30

Trp Met His Trp Val Arg Gln Ala Pro Gly Lys Gly Leu Glu Trp Val
35 40 45

Ala Gln Ile Lys Asp Lys Ala Asn Gly Tyr Asn Thr Tyr Tyr Ala Glu
50 55 60

```
Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Thr Thr Phe Gly Gly Phe Gly Phe Ser
            100                 105                 110

Tyr Gly Val Asp Ala Trp Gly Gln Gly Thr Thr Val Thr Val Ser Ser
        115                 120                 125


<210> SEQ ID NO 111
<211> LENGTH: 128
<212> TYPE: PRT
<213> ORGANISM: Artificial sequence
<220> FEATURE:
<223> OTHER INFORMATION: An artificially synthesized peptide sequence

<400> SEQUENCE: 111

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Arg Gln Asn Gly Tyr Asn Thr Tyr Tyr Ala Glu
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Thr Thr Thr Tyr Gly Ser Tyr Tyr Gln
            100                 105                 110

Phe Gly Val Asp Ala Trp Gly Gln Gly Thr Thr Val Thr Val Ser Ser
        115                 120                 125


<210> SEQ ID NO 112
<211> LENGTH: 128
<212> TYPE: PRT
<213> ORGANISM: Artificial sequence
<220> FEATURE:
<223> OTHER INFORMATION: An artificially synthesized peptide sequence

<400> SEQUENCE: 112

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Arg Gln Asn Gly Tyr Ala Ala Tyr Tyr Ala Glu
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Arg Thr Phe Thr Gly Leu Ser Pro Lys
            100                 105                 110

Phe Gly Val Asp Ala Trp Gly Gln Gly Thr Pro Val Thr Val Ser Ser
```

```
        115                 120                 125


<210> SEQ ID NO 113
<211> LENGTH: 128
<212> TYPE: PRT
<213> ORGANISM: Artificial sequence
<220> FEATURE:
<223> OTHER INFORMATION: An artificially synthesized peptide sequence

<400> SEQUENCE: 113

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Lys Gln Asn Ser Tyr Ala Ala Tyr Tyr Ala Glu
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Thr Thr Tyr Ser Gly Gly Phe Phe Ser
            100                 105                 110

Tyr Gly Val Asp Ala Trp Gly Gln Gly Thr Thr Val Thr Val Ser Ser
        115                 120                 125


<210> SEQ ID NO 114
<211> LENGTH: 128
<212> TYPE: PRT
<213> ORGANISM: Artificial sequence
<220> FEATURE:
<223> OTHER INFORMATION: An artificially synthesized peptide sequence

<400> SEQUENCE: 114

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Arg Ala Asn Ser Tyr Asn Thr Tyr Tyr Ala Glu
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Thr Thr Tyr Ala Gly Ser Ser Phe Ser
            100                 105                 110

Tyr Gly Val Asp Ala Trp Gly Gln Gly Thr Thr Val Thr Val Ser Ser
        115                 120                 125


<210> SEQ ID NO 115
<211> LENGTH: 128
<212> TYPE: PRT
<213> ORGANISM: Artificial sequence
<220> FEATURE:
<223> OTHER INFORMATION: An artificially synthesized peptide sequence

<400> SEQUENCE: 115
```

-continued

```
Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Lys Ala Asn Gly Tyr Asn Ala Tyr Tyr Ala Glu
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Thr Thr Tyr Ala Gly Phe Ser Tyr Lys
            100                 105                 110

Phe Gly Val Asp Ala Trp Gly Gln Gly Thr Thr Val Thr Val Ser Ser
        115                 120                 125


<210> SEQ ID NO 116
<211> LENGTH: 128
<212> TYPE: PRT
<213> ORGANISM: Artificial sequence
<220> FEATURE:
<223> OTHER INFORMATION: An artificially synthesized peptide sequence

<400> SEQUENCE: 116

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Arg Gly Asn Gly Tyr Asn Thr Tyr Tyr Ala Glu
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Thr Thr Phe Gly Asp Gly Phe Tyr Lys
            100                 105                 110

Phe Gly Val Asp Ala Trp Gly Gln Gly Thr Thr Val Thr Val Ser Ser
        115                 120                 125


<210> SEQ ID NO 117
<211> LENGTH: 126
<212> TYPE: PRT
<213> ORGANISM: Artificial sequence
<220> FEATURE:
<223> OTHER INFORMATION: An artificially synthesized peptide sequence

<400> SEQUENCE: 117

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Arg Ser Asn Gly Tyr Ala Ala Tyr Tyr Ala Pro
```

```
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Thr Thr Phe Leu Ser Phe Ala Tyr Gly
            100                 105                 110

Val Asp Ala Trp Gly Gln Gly Thr Thr Val Thr Val Ser Ser
        115                 120                 125


<210> SEQ ID NO 118
<211> LENGTH: 128
<212> TYPE: PRT
<213> ORGANISM: Artificial sequence
<220> FEATURE:
<223> OTHER INFORMATION: An artificially synthesized peptide sequence

<400> SEQUENCE: 118

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Arg Gly Asn Gly Tyr Asn Thr Tyr Tyr Ala Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Arg Thr Ser Ser Tyr Gly Gly Phe Lys
            100                 105                 110

Phe Gly Val Asp Ala Trp Gly Gln Gly Thr Thr Val Thr Val Ser Ser
        115                 120                 125


<210> SEQ ID NO 119
<211> LENGTH: 128
<212> TYPE: PRT
<213> ORGANISM: Artificial sequence
<220> FEATURE:
<223> OTHER INFORMATION: An artificially synthesized peptide sequence

<400> SEQUENCE: 119

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Arg Ser Asn Gly Tyr Ala Thr Tyr Tyr Ala Glu
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Thr Ser Phe Ala Phe Phe Phe Gly Gln
            100                 105                 110
```

-continued

```
Phe Gly Val Asp Ala Trp Gly Gln Gly Thr Thr Val Thr Val Ser Ser
        115                 120                 125


<210> SEQ ID NO 120
<211> LENGTH: 126
<212> TYPE: PRT
<213> ORGANISM: Artificial sequence
<220> FEATURE:
<223> OTHER INFORMATION: An artificially synthesized peptide sequence

<400> SEQUENCE: 120

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Lys Gly Asn Gln Tyr Asn Thr Tyr Tyr Ala Glu
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Thr Gln Tyr Ser Phe Gly Gln Tyr Gly
            100                 105                 110

Val Asp Ala Trp Gly Gln Gly Thr Thr Val Thr Val Ser Ser
        115                 120                 125


<210> SEQ ID NO 121
<211> LENGTH: 128
<212> TYPE: PRT
<213> ORGANISM: Artificial sequence
<220> FEATURE:
<223> OTHER INFORMATION: An artificially synthesized peptide sequence

<400> SEQUENCE: 121

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Lys Gly Asn Gln Tyr Asn Ala Tyr Tyr Ala Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Val Ser Ser Ser Ser Gly Ser Tyr Gln
            100                 105                 110

Phe Gly Val Asp Ala Trp Gly Gln Gly Thr Thr Val Thr Val Ser Ser
        115                 120                 125


<210> SEQ ID NO 122
<211> LENGTH: 128
<212> TYPE: PRT
<213> ORGANISM: Artificial sequence
<220> FEATURE:
<223> OTHER INFORMATION: An artificially synthesized peptide sequence
```

-continued

<400> SEQUENCE: 122

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Arg Gly Ser Ala Tyr Ala Ala Tyr Tyr Ala Glu
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Thr Ser Gly Tyr Phe Gly Tyr Phe Gln
            100                 105                 110

Tyr Gly Val Asp Ala Trp Gly Gln Gly Thr Thr Val Thr Val Ser Ser
        115                 120                 125

<210> SEQ ID NO 123
<211> LENGTH: 128
<212> TYPE: PRT
<213> ORGANISM: Artificial sequence
<220> FEATURE:
<223> OTHER INFORMATION: An artificially synthesized peptide sequence

<400> SEQUENCE: 123

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Arg Gly Asn Asn Tyr Leu Thr Tyr Tyr Ala Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Thr Thr Tyr Tyr Gly Gly Phe Tyr Ser
            100                 105                 110

Phe Gly Val Asp Ala Trp Gly Gln Gly Thr Thr Val Thr Val Ser Ser
        115                 120                 125

<210> SEQ ID NO 124
<211> LENGTH: 127
<212> TYPE: PRT
<213> ORGANISM: Artificial sequence
<220> FEATURE:
<223> OTHER INFORMATION: An artificially synthesized peptide sequence

<400> SEQUENCE: 124

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

```
Ala Gln Ile Lys Asp Arg Ser Ser Gly Tyr Ala Ala Tyr Tyr Ala Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Ser Arg Pro Phe Phe Gly Gly Lys Tyr
            100                 105                 110

Gly Val Asp Ala Trp Gly Gln Gly Thr Thr Val Thr Val Ser Ser
        115                 120                 125


<210> SEQ ID NO 125
<211> LENGTH: 128
<212> TYPE: PRT
<213> ORGANISM: Artificial sequence
<220> FEATURE:
<223> OTHER INFORMATION: An artificially synthesized peptide sequence

<400> SEQUENCE: 125

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Lys Ala Asn Gln Tyr Asn Thr Tyr Tyr Ala Glu
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Thr Thr Ser Phe Gly Phe Phe Tyr Ser
            100                 105                 110

Phe Gly Val Asp Ala Trp Gly Gln Gly Thr Thr Val Thr Val Ser Ser
        115                 120                 125


<210> SEQ ID NO 126
<211> LENGTH: 128
<212> TYPE: PRT
<213> ORGANISM: Artificial sequence
<220> FEATURE:
<223> OTHER INFORMATION: An artificially synthesized peptide sequence

<400> SEQUENCE: 126

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Lys Ser Ser Gly Tyr Ala Thr Tyr Tyr Ala Glu
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Thr Thr Phe Val Gly Gly Tyr Pro Ser
            100                 105                 110
```

```
Tyr Gly Val Asp Ala Trp Gly Gln Gly Thr Thr Val Thr Val Ser Ser
        115                 120                 125


<210> SEQ ID NO 127
<211> LENGTH: 127
<212> TYPE: PRT
<213> ORGANISM: Artificial sequence
<220> FEATURE:
<223> OTHER INFORMATION: An artificially synthesized peptide sequence

<400> SEQUENCE: 127

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Arg Gly Asn Ser Tyr Asn Ala Tyr Tyr Ala Glu
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Thr Thr Thr Tyr Ser Gly Tyr Gln Tyr
            100                 105                 110

Gly Val Asp Ala Trp Gly Gln Gly Thr Thr Val Thr Val Ser Ser
        115                 120                 125


<210> SEQ ID NO 128
<211> LENGTH: 127
<212> TYPE: PRT
<213> ORGANISM: Artificial sequence
<220> FEATURE:
<223> OTHER INFORMATION: An artificially synthesized peptide sequence

<400> SEQUENCE: 128

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Arg Gln Asn Asn Tyr Ala Thr Tyr Tyr Ala Glu
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Thr Thr Tyr Phe Gly Gly Ser Tyr Gly
            100                 105                 110

Gly Val Asp Ala Trp Gly Gln Gly Thr Thr Val Thr Val Ser Ser
        115                 120                 125


<210> SEQ ID NO 129
<211> LENGTH: 128
<212> TYPE: PRT
<213> ORGANISM: Artificial sequence
<220> FEATURE:
<223> OTHER INFORMATION: An artificially synthesized peptide sequence
```

<400> SEQUENCE: 129

```
Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Arg Gln Asn Gln Tyr Ala Thr Tyr Tyr Ala Glu
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Thr Ser Phe Ala Gly Ser Gly Ser Ser
            100                 105                 110

Phe Gly Val Asp Ala Trp Gly Gln Gly Thr Thr Val Thr Val Ser Ser
        115                 120                 125
```

<210> SEQ ID NO 130
<211> LENGTH: 128
<212> TYPE: PRT
<213> ORGANISM: Artificial sequence
<220> FEATURE:
<223> OTHER INFORMATION: An artificially synthesized peptide sequence

<400> SEQUENCE: 130

```
Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Arg Gln Gln Gly Tyr Ala Asn Tyr Tyr Ala Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Thr Thr Ser Phe Asp Gly Ser Tyr Gln
            100                 105                 110

Tyr Gly Val Asp Val Trp Gly Gln Gly Thr Thr Val Thr Val Ser Ser
        115                 120                 125
```

<210> SEQ ID NO 131
<211> LENGTH: 128
<212> TYPE: PRT
<213> ORGANISM: Artificial sequence
<220> FEATURE:
<223> OTHER INFORMATION: An artificially synthesized peptide sequence

<400> SEQUENCE: 131

```
Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45
```

```
Ala Gln Ile Lys Asp Lys Ala Asn Gly Tyr Asn Ala Tyr Tyr Ala Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Thr Thr Phe Gly Phe Gly Leu Ser Tyr
            100                 105                 110

Gly Gly Val Asp Ala Trp Gly Gln Gly Thr Thr Val Thr Val Ser Ser
        115                 120                 125


<210> SEQ ID NO 132
<211> LENGTH: 128
<212> TYPE: PRT
<213> ORGANISM: Artificial sequence
<220> FEATURE:
<223> OTHER INFORMATION: An artificially synthesized peptide sequence

<400> SEQUENCE: 132

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Arg Gln Asn Asn Tyr Ala Thr Tyr Tyr Ala Glu
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Ala Thr Tyr Phe Ser Gly Leu Tyr Lys
            100                 105                 110

Phe Gly Val Asp Ala Trp Gly Gln Gly Thr Thr Val Thr Val Ser Ser
        115                 120                 125


<210> SEQ ID NO 133
<211> LENGTH: 128
<212> TYPE: PRT
<213> ORGANISM: Artificial sequence
<220> FEATURE:
<223> OTHER INFORMATION: An artificially synthesized peptide sequence

<400> SEQUENCE: 133

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Arg Gln Asn Gly Tyr Ala Thr Tyr Tyr Ala Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Thr Thr Tyr Tyr Gly Gly Tyr Phe Gln
```

```
            100                 105                 110

Phe Gly Val Asp Ala Trp Gly Gln Gly Thr Thr Val Thr Val Ser Ser
        115                 120                 125


<210> SEQ ID NO 134
<211> LENGTH: 128
<212> TYPE: PRT
<213> ORGANISM: Artificial sequence
<220> FEATURE:
<223> OTHER INFORMATION: An artificially synthesized peptide sequence

<400> SEQUENCE: 134

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Lys Gly Asn Ser Tyr Ala Thr Tyr Tyr Ala Pro
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Thr Thr Val Ser Phe Leu Gly Phe Lys
            100                 105                 110

Tyr Gly Val Asp Ala Trp Gly Gln Gly Thr Thr Val Thr Val Ser Ser
        115                 120                 125


<210> SEQ ID NO 135
<211> LENGTH: 128
<212> TYPE: PRT
<213> ORGANISM: Artificial Sequence
<220> FEATURE:
<223> OTHER INFORMATION: An artificially synthesized peptide sequence

<400> SEQUENCE: 135

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Arg Gly Asn Ala Tyr Asn Ala Tyr Tyr Ala Glu
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Ala Ser Tyr Ala Phe Gly Phe Phe Ser
            100                 105                 110

Tyr Gly Val Asp Ala Trp Gly Gln Gly Thr Thr Val Thr Val Ser Ser
        115                 120                 125


<210> SEQ ID NO 136
<211> LENGTH: 471
<212> TYPE: PRT
<213> ORGANISM: Artificial Sequence
<220> FEATURE:
```

<223> OTHER INFORMATION: An artificially synthesized peptide sequence

<400> SEQUENCE: 136

Gln Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe Ser Asn Ala
20 25 30

Trp Met His Trp Val Arg Gln Ala Pro Gly Lys Gly Leu Glu Trp Val
35 40 45

Ala Gln Ile Lys Asp Lys Gly Gln Gln Tyr Ala Ala Tyr Tyr Ala Pro
50 55 60

Ser Val Lys Gly Arg Phe Thr Ile Ser Arg Asp Gly Cys Arg Gly Asp
65 70 75 80

Cys Leu Asp Ser Lys Asn Ser Ile Tyr Leu Gln Met Asn Ser Leu Lys
85 90 95

Thr Glu Asp Thr Ala Val Tyr Tyr Cys Arg Tyr Val His Tyr Gln Thr
100 105 110

Tyr Ser Asp Gly Ser Phe Tyr Phe Gly Val Asp Ala Trp Gly Gln Gly
115 120 125

Thr Thr Val Thr Val Ser Ser Ala Ser Thr Lys Gly Pro Ser Val Phe
130 135 140

Pro Leu Ala Pro Ser Ser Lys Ser Thr Ser Gly Gly Thr Ala Ala Leu
145 150 155 160

Gly Cys Leu Val Lys Asp Tyr Phe Pro Glu Pro Val Thr Val Ser Trp
165 170 175

Asn Ser Gly Ala Leu Thr Ser Gly Val His Thr Phe Pro Ala Val Leu
180 185 190

Gln Ser Ser Gly Leu Tyr Ser Leu Ser Ser Val Val Thr Val Pro Ser
195 200 205

Ser Ser Leu Gly Thr Gln Thr Tyr Ile Cys Asn Val Asn His Lys Pro
210 215 220

Ser Asn Thr Lys Val Asp Lys Lys Val Glu Pro Lys Ser Cys Asp Lys
225 230 235 240

Thr His Thr Cys Pro Pro Cys Pro Ala Pro Glu Ala Ala Gly Gly Pro
245 250 255

Ser Val Phe Leu Phe Pro Pro Lys Pro Lys Asp Thr Leu Met Ile Ser
260 265 270

Arg Thr Pro Glu Val Thr Cys Val Val Val Asp Val Ser His Glu Asp
275 280 285

Pro Glu Val Lys Phe Asn Trp Tyr Val Asp Gly Val Glu Val His Asn
290 295 300

Ala Lys Thr Lys Pro Arg Glu Glu Gln Tyr Ala Ser Thr Tyr Arg Val
305 310 315 320

Val Ser Val Leu Thr Val Leu His Gln Asp Trp Leu Asn Gly Lys Glu
325 330 335

Tyr Lys Cys Lys Val Ser Asn Lys Ala Leu Pro Ala Pro Ile Glu Lys
340 345 350

Thr Ile Ser Lys Ala Lys Gly Gln Pro Arg Glu Pro Gln Val Tyr Thr
355 360 365

Leu Pro Pro Ser Arg Cys Glu Leu Thr Lys Asn Gln Val Ser Leu Ser
370 375 380

Cys Ala Val Lys Gly Phe Tyr Pro Ser Asp Ile Ala Val Glu Trp Glu
385 390 395 400

-continued

```
Ser Asn Gly Gln Pro Glu Asn Asn Tyr Lys Thr Thr Pro Pro Val Leu
            405                 410                 415

Asp Ser Asp Gly Ser Phe Phe Leu Val Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Asp
    450                 455                 460

Tyr Lys Asp Asp Asp Asp Lys
465                 470


<210> SEQ ID NO 137
<211> LENGTH: 22
<212> TYPE: PRT
<213> ORGANISM: Artificial Sequence
<220> FEATURE:
<223> OTHER INFORMATION: An artificially synthesized peptide sequence

<400> SEQUENCE: 137

Arg Trp Gly Tyr His Leu Arg Asp Arg Lys Tyr Lys Gly Val Arg Ser
1               5                   10                  15

His Lys Gly Val Pro Arg
            20


<210> SEQ ID NO 138
<211> LENGTH: 122
<212> TYPE: PRT
<213> ORGANISM: Artificial Sequence
<220> FEATURE:
<223> OTHER INFORMATION: An artificially synthesized peptide sequence
<220> FEATURE:
<221> NAME/KEY: MISC_FEATURE
<222> LOCATION: (11)..(11)
<223> OTHER INFORMATION: Xaa can be Alanine, Aspartic Acid, Glutamic
      Acid, Phenylalanine, Glycine, Histidine, Isoleucine, Lysine,
      Leucine, Methionine, Asparagine, Proline, Glutamine, Arginine,
      Serine, Threonine, Valine, Tryptophan, or Tyrosine
<220> FEATURE:
<221> NAME/KEY: MISC_FEATURE
<222> LOCATION: (16)..(16)
<223> OTHER INFORMATION: Xaa can be Alanine, Aspartic Acid, Glutamic
      Acid, Phenylalanine, Glycine, Histidine, Isoleucine, Lysine,
      Leucine, Methionine, Asparagine, Proline, Glutamine, Arginine,
      Serine, Threonine, Valine, Tryptophan, or Tyrosine
<220> FEATURE:
<221> NAME/KEY: MISC_FEATURE
<222> LOCATION: (19)..(19)
<223> OTHER INFORMATION: Xaa can be Alanine, Aspartic Acid, Glutamic
      Acid, Phenylalanine, Glycine, Histidine, Isoleucine, Lysine,
      Leucine, Methionine, Asparagine, Proline, Glutamine, Arginine,
      Serine, Threonine, Valine, Tryptophan, or Tyrosine
<220> FEATURE:
<221> NAME/KEY: MISC_FEATURE
<222> LOCATION: (28)..(28)
<223> OTHER INFORMATION: Xaa can be Alanine, Aspartic Acid, Glutamic
      Acid, Phenylalanine, Glycine, Histidine, Isoleucine, Lysine,
      Leucine, Methionine, Asparagine, Proline, Glutamine, Arginine,
      Serine, Threonine, Valine, Tryptophan, or Tyrosine
<220> FEATURE:
<221> NAME/KEY: MISC_FEATURE
<222> LOCATION: (29)..(29)
<223> OTHER INFORMATION: Xaa can be Alanine, Aspartic Acid, Glutamic
      Acid, Phenylalanine, Glycine, Histidine, Isoleucine, Lysine,
      Leucine, Methionine, Asparagine, Proline, Glutamine, Arginine,
      Serine, Threonine, Valine, Tryptophan, or Tyrosine
<220> FEATURE:
<221> NAME/KEY: MISC_FEATURE
<222> LOCATION: (30)..(30)
<223> OTHER INFORMATION: Xaa can be Alanine, Aspartic Acid, Glutamic
      Acid, Phenylalanine, Glycine, Histidine, Isoleucine, Lysine,
      Leucine, Methionine, Asparagine, Proline, Glutamine, Arginine,
```

```
      Serine, Threonine, Valine, Tryptophan, or Tyrosine
<220> FEATURE:
<221> NAME/KEY: MISC_FEATURE
<222> LOCATION: (31)..(31)
<223> OTHER INFORMATION: Xaa can be Alanine, Aspartic Acid, Glutamic
      Acid, Phenylalanine, Glycine, Histidine, Isoleucine, Lysine,
      Leucine, Methionine, Asparagine, Proline, Glutamine, Arginine,
      Serine, Threonine, Valine, Tryptophan, or Tyrosine
<220> FEATURE:
<221> NAME/KEY: MISC_FEATURE
<222> LOCATION: (32)..(32)
<223> OTHER INFORMATION: Xaa can be Alanine, Aspartic Acid, Glutamic
      Acid, Phenylalanine, Glycine, Histidine, Isoleucine, Lysine,
      Leucine, Methionine, Asparagine, Proline, Glutamine, Arginine,
      Serine, Threonine, Valine, Tryptophan, or Tyrosine
<220> FEATURE:
<221> NAME/KEY: MISC_FEATURE
<222> LOCATION: (33)..(33)
<223> OTHER INFORMATION: Xaa can be Alanine, Aspartic Acid, Glutamic
      Acid, Phenylalanine, Glycine, Histidine, Isoleucine, Lysine,
      Leucine, Methionine, Asparagine, Proline, Glutamine, Arginine,
      Serine, Threonine, Valine, Tryptophan, or Tyrosine
<220> FEATURE:
<221> NAME/KEY: MISC_FEATURE
<222> LOCATION: (35)..(35)
<223> OTHER INFORMATION: Xaa can be Alanine, Aspartic Acid, Glutamic
      Acid, Phenylalanine, Glycine, Histidine, Isoleucine, Lysine,
      Leucine, Methionine, Asparagine, Proline, Glutamine, Arginine,
      Serine, Threonine, Valine, Tryptophan, or Tyrosine
<220> FEATURE:
<221> NAME/KEY: MISC_FEATURE
<222> LOCATION: (43)..(43)
<223> OTHER INFORMATION: Xaa can be Alanine, Aspartic Acid, Glutamic
      Acid, Phenylalanine, Glycine, Histidine, Isoleucine, Lysine,
      Leucine, Methionine, Asparagine, Proline, Glutamine, Arginine,
      Serine, Threonine, Valine, Tryptophan, or Tyrosine
<220> FEATURE:
<221> NAME/KEY: MISC_FEATURE
<222> LOCATION: (50)..(50)
<223> OTHER INFORMATION: Xaa can be Alanine, Aspartic Acid, Glutamic
      Acid, Phenylalanine, Glycine, Histidine, Isoleucine, Lysine,
      Leucine, Methionine, Asparagine, Proline, Glutamine, Arginine,
      Serine, Threonine, Valine, Tryptophan, or Tyrosine
<220> FEATURE:
<221> NAME/KEY: MISC_FEATURE
<222> LOCATION: (51)..(51)
<223> OTHER INFORMATION: Xaa can be Alanine, Aspartic Acid, Glutamic
      Acid, Phenylalanine, Glycine, Histidine, Isoleucine, Lysine,
      Leucine, Methionine, Asparagine, Proline, Glutamine, Arginine,
      Serine, Threonine, Valine, Tryptophan, or Tyrosine
<220> FEATURE:
<221> NAME/KEY: MISC_FEATURE
<222> LOCATION: (52)..(52)
<223> OTHER INFORMATION: Xaa can be Alanine, Aspartic Acid, Glutamic
      Acid, Phenylalanine, Glycine, Histidine, Isoleucine, Lysine,
      Leucine, Methionine, Asparagine, Proline, Glutamine, Arginine,
      Serine, Threonine, Valine, Tryptophan, or Tyrosine
<220> FEATURE:
<221> NAME/KEY: MISC_FEATURE
<222> LOCATION: (53)..(53)
<223> OTHER INFORMATION: Xaa can be Alanine, Aspartic Acid, Glutamic
      Acid, Phenylalanine, Glycine, Histidine, Isoleucine, Lysine,
      Leucine, Methionine, Asparagine, Proline, Glutamine, Arginine,
      Serine, Threonine, Valine, Tryptophan, or Tyrosine
<220> FEATURE:
<221> NAME/KEY: MISC_FEATURE
<222> LOCATION: (54)..(54)
<223> OTHER INFORMATION: Xaa can be Alanine, Aspartic Acid, Glutamic
      Acid, Phenylalanine, Glycine, Histidine, Isoleucine, Lysine,
      Leucine, Methionine, Asparagine, Proline, Glutamine, Arginine,
      Serine, Threonine, Valine, Tryptophan, or Tyrosine
<220> FEATURE:
<221> NAME/KEY: MISC_FEATURE
<222> LOCATION: (55)..(55)
<223> OTHER INFORMATION: Xaa can be Alanine, Aspartic Acid, Glutamic
      Acid, Phenylalanine, Glycine, Histidine, Isoleucine, Lysine,
      Leucine, Methionine, Asparagine, Proline, Glutamine, Arginine,
      Serine, Threonine, Valine, Tryptophan, or Tyrosine
<220> FEATURE:
```

<221> NAME/KEY: MISC_FEATURE
<222> LOCATION: (56)..(56)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (57)..(57)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (58)..(58)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (59)..(59)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (60)..(60)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (61)..(61)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (62)..(62)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (63)..(63)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (64)..(64)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (65)..(65)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (67)..(67)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (68)..(68)

<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (72)..(72)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (73)..(73)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (74)..(74)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (75)..(75)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (76)..(76)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (77)..(77)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (78)..(78)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (81)..(81)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (86)..(86)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (101)..(101)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (102)..(102)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (103)..(103)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (104)..(104)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (105)..(105)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (106)..(106)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (107)..(107)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (108)..(108)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (109)..(109)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (110)..(110)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (111)..(111)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (114)..(114)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine

<400> SEQUENCE: 138

```
Gln Val Gln Leu Val Glu Ser Gly Gly Gly Xaa Val Gln Pro Gly Xaa
1               5                   10                  15

Ser Leu Xaa Leu Ser Cys Ala Ala Ser Gly Phe Xaa Xaa Xaa Xaa Xaa
```

```
            20                  25                  30

Xaa Met Xaa Trp Val Arg Gln Ala Pro Gly Xaa Gly Leu Glu Trp Val
        35                  40                  45

Ala Xaa Xaa Xaa Xaa Xaa Xaa Xaa Xaa Xaa Xaa Xaa Xaa Xaa Xaa Xaa
    50                  55                  60

Xaa Val Xaa Xaa Arg Phe Thr Xaa Xaa Xaa Xaa Xaa Xaa Xaa Asn Ser
65                  70                  75                  80

Xaa Tyr Leu Gln Met Xaa Ser Leu Lys Thr Glu Asp Thr Ala Val Tyr
                85                  90                  95

Tyr Cys Arg Tyr Xaa Xaa Xaa Xaa Xaa Xaa Xaa Xaa Xaa Xaa Xaa Trp
            100                 105                 110

Gly Xaa Gly Thr Thr Val Thr Val Ser Ser
        115                 120
```

<210> SEQ ID NO 139
<211> LENGTH: 112
<212> TYPE: PRT
<213> ORGANISM: Artificial Sequence
<220> FEATURE:
<223> OTHER INFORMATION: An artificially synthesized peptide sequence
<220> FEATURE:
<221> NAME/KEY: MISC_FEATURE
<222> LOCATION: (24)..(24)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (25)..(25)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (26)..(26)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (27)..(27)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (28)..(28)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (29)..(29)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (30)..(30)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (31)..(31)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (32)..(32)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (33)..(33)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (34)..(34)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (35)..(35)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (36)..(36)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (37)..(37)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (38)..(38)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (39)..(39)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (50)..(50)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (55)..(55)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (56)..(56)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (57)..(57)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (58)..(58)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (59)..(59)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (60)..(60)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (61)..(61)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (79)..(79)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (82)..(82)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (94)..(94)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (95)..(95)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (96)..(96)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (97)..(97)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (98)..(98)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (99)..(99)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (100)..(100)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (101)..(101)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (102)..(102)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine
<220> FEATURE:
<221> NAME/KEY: MISC_FEATURE
<222> LOCATION: (112)..(112)
<223> OTHER INFORMATION: Xaa can be Alanine, Aspartic Acid, Glutamic Acid, Phenylalanine, Glycine, Histidine, Isoleucine, Lysine, Leucine, Methionine, Asparagine, Proline, Glutamine, Arginine, Serine, Threonine, Valine, Tryptophan, or Tyrosine

<400> SEQUENCE: 139

```
Asp Ile Val Met Thr Gln Ser Pro Leu Ser Leu Pro Val Thr Pro Gly
1               5                   10                  15

Glu Pro Ala Ser Ile Ser Cys Xaa Xaa Xaa Xaa Xaa Xaa Xaa Xaa Xaa
            20                  25                  30

Xaa Xaa Xaa Xaa Xaa Xaa Xaa Trp Tyr Gln Gln Lys Pro Gly Gln Ala
        35                  40                  45

Pro Xaa Leu Leu Ile Tyr Xaa Xaa Xaa Xaa Xaa Xaa Xaa Gly Val Pro
    50                  55                  60

Asp Arg Phe Ser Gly Ser Gly Ser Gly Thr Asp Phe Thr Leu Xaa Ile
65                  70                  75                  80

Ser Xaa Val Glu Ala Glu Asp Val Gly Val Tyr Tyr Cys Xaa Xaa Xaa
                85                  90                  95

Xaa Xaa Xaa Xaa Xaa Xaa Phe Gly Gln Gly Thr Lys Leu Glu Ile Xaa
            100                 105                 110
```

<210> SEQ ID NO 140
<211> LENGTH: 464
<212> TYPE: PRT
<213> ORGANISM: Artificial sequence

```
<220> FEATURE:
<223> OTHER INFORMATION: An artificially synthesized peptide sequence
<220> FEATURE:
<221> NAME/KEY: MISC_FEATURE
<222> LOCATION: (106)..(106)
<223> OTHER INFORMATION: Xaa can be Alanine, Glutamic Acid,
      Phenylalanine, Glycine, Histidine, Isoleucine, Leucine,
      Asparagine, Arginine, Serine, Valine, Tryptophan, Or Tyrosine
<220> FEATURE:
<221> NAME/KEY: MISC_FEATURE
<222> LOCATION: (107)..(107)
<223> OTHER INFORMATION: Xaa can be Glutamic Acid, Phenylalanine,
      Glycine, Leucine, Methionine, Threonine, Valine, Tryptophan, or
      Tyrosine
<220> FEATURE:
<221> NAME/KEY: MISC_FEATURE
<222> LOCATION: (108)..(108)
<223> OTHER INFORMATION: Xaa can be Alanine, Glutamic Acid, Glycine,
      Isoleucine, Leucine, Methionine, Glutamine, Arginine, Serine,
      Valine, Tryptophan, or Tyrosine
<220> FEATURE:
<221> NAME/KEY: MISC_FEATURE
<222> LOCATION: (109)..(109)
<223> OTHER INFORMATION: Xaa can be Glycine, Leucine, Proline,
      Glutamine, Arginine, Serine, Threonine, Valine, or Tryptophan
<220> FEATURE:
<221> NAME/KEY: MISC_FEATURE
<222> LOCATION: (110)..(110)
<223> OTHER INFORMATION: Xaa can be Alanine, Glutamic Acid, Glycine,
      Leucine, Arginine, Serine, Threonine, Valine, or Tryptophan
<220> FEATURE:
<221> NAME/KEY: MISC_FEATURE
<222> LOCATION: (111)..(111)
<223> OTHER INFORMATION: Xaa can be Alanine, Glycine, Histidine,
      Asparagine, Arginine, Serine, Valine, or Tryptophan

<400> SEQUENCE: 140

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Lys Ser Asn Asn Tyr Ala Thr Tyr Tyr Ala Glu
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Ala Ala Xaa Xaa Xaa Xaa Xaa Xaa Tyr
            100                 105                 110

Tyr Gly Val Asp Ala Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220
```

```
Lys Val Glu Pro Lys Ser Cys Asp Lys Thr His Thr Cys Pro Pro Cys
225                 230                 235                 240

Pro Ala Pro Glu Ala Ala Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Ala Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Cys Glu
        355                 360                 365

Leu Thr Lys Asn Gln Val Ser Leu Ser Cys Ala Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Val Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Asp Tyr Lys Asp Asp Asp Asp Lys
    450                 455                 460
```

<210> SEQ ID NO 141
<211> LENGTH: 128
<212> TYPE: PRT
<213> ORGANISM: Artificial Sequence
<220> FEATURE:
<223> OTHER INFORMATION: An artificially synthesized peptide sequence
<220> FEATURE:
<221> NAME/KEY: MISC_FEATURE
<222> LOCATION: (31)..(31)
<223> OTHER INFORMATION: Xaa can be Isoleucine, Asparagine, or Serine
<220> FEATURE:
<221> NAME/KEY: MISC_FEATURE
<222> LOCATION: (54)..(54)
<223> OTHER INFORMATION: Xaa can be Lysine or Arginine
<220> FEATURE:
<221> NAME/KEY: MISC_FEATURE
<222> LOCATION: (55)..(55)
<223> OTHER INFORMATION: Xaa can be Alanine, Glycine, Leucine, Glutamine, Serine, or Valine
<220> FEATURE:
<221> NAME/KEY: MISC_FEATURE
<222> LOCATION: (56)..(56)
<223> OTHER INFORMATION: Xaa can be Asparagine, Glutamine, or Serine
<220> FEATURE:
<221> NAME/KEY: MISC_FEATURE
<222> LOCATION: (57)..(57)
<223> OTHER INFORMATION: Xaa can be Alanine, Glycine, Leucine, Glutamine, Serine, or Asparagine
<220> FEATURE:
<221> NAME/KEY: MISC_FEATURE
<222> LOCATION: (59)..(59)
<223> OTHER INFORMATION: Xaa can be Alanine, Leucine, or Asparagine
<220> FEATURE:
<221> NAME/KEY: MISC_FEATURE
<222> LOCATION: (60)..(60)
<223> OTHER INFORMATION: Xaa can be Alanine, Asparagine, or Threonine
<220> FEATURE:
<221> NAME/KEY: MISC_FEATURE
<222> LOCATION: (64)..(64)
<223> OTHER INFORMATION: Xaa can be Glutamic Acid or Proline
<220> FEATURE:
<221> NAME/KEY: MISC_FEATURE
<222> LOCATION: (104)..(104)
<223> OTHER INFORMATION: Xaa can be Alanine, Glycine, Histidine, Proline, Glutamine, Serine, or Threonine
<220> FEATURE:
<221> NAME/KEY: MISC_FEATURE
<222> LOCATION: (105)..(105)
<223> OTHER INFORMATION: Xaa can be Alanine, Leucine, Glutamine, Serine, or Threonine
<220> FEATURE:
<221> NAME/KEY: MISC_FEATURE
<222> LOCATION: (106)..(106)
<223> OTHER INFORMATION: Xaa can be Alanine, Phenylalanine, Glycine, Serine, Threonine, Valine, or Tyrosine
<220> FEATURE:
<221> NAME/KEY: MISC_FEATURE
<222> LOCATION: (107)..(107)
<223> OTHER INFORMATION: Xaa can be Alanine, Aspartic Acid, Phenylalanine, Glycine, Serine, Threonine, Valine, or Tyrosine
<220> FEATURE:
<221> NAME/KEY: MISC_FEATURE
<222> LOCATION: (108)..(108)
<223> OTHER INFORMATION: Xaa can be Aspartic Acid, Phenylalanine, Glycine, Serine, Threonine, or Tyrosine
<220> FEATURE:
<221> NAME/KEY: MISC_FEATURE
<222> LOCATION: (109)..(109)
<223> OTHER INFORMATION: Xaa can be Alanine, Phenylalanine, Glycine, Leucine, Serine, Valine, or Tyrosine
<220> FEATURE:
<221> NAME/KEY: MISC_FEATURE
<222> LOCATION: (110)..(110)
<223> OTHER INFORMATION: Xaa can be Phenylalanine, Glycine, Leucine, Serine, or Tyrosine
<220> FEATURE:
<221> NAME/KEY: MISC_FEATURE
<222> LOCATION: (111)..(111)
<223> OTHER INFORMATION: Xaa can be Phenylalanine, Glycine, Proline, Serine, or Tyrosine
<220> FEATURE:
<221> NAME/KEY: MISC_FEATURE
<222> LOCATION: (112)..(112)
<223> OTHER INFORMATION: Xaa can be Alanine, Glycine, Lysine, Glutamine, Serine, or Tyrosine
<220> FEATURE:
<221> NAME/KEY: MISC_FEATURE
<222> LOCATION: (113)..(113)
<223> OTHER INFORMATION: Xaa can be Phenylalanine, Glycine, or Tyrosine

<400> SEQUENCE: 141

```
Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Xaa Ala
            20                  25                  30

Trp Met His Trp Val Arg Gln Ala Pro Gly Lys Gly Leu Glu Trp Val
        35                  40                  45

Ala Gln Ile Lys Asp Xaa Xaa Xaa Xaa Tyr Xaa Xaa Tyr Tyr Ala Xaa
    50                  55                  60

Ser Val Lys Gly Arg Phe Thr Ile Ser Arg Asp Asp Ser Lys Asn Ser
65                  70                  75                  80

Ile Tyr Leu Gln Met Asn Ser Leu Lys Thr Glu Asp Thr Ala Val Tyr
                85                  90                  95
```

-continued

```
Tyr Cys Arg Tyr Val His Tyr Xaa Xaa Xaa Xaa Xaa Xaa Xaa Xaa Xaa
            100                 105                 110

Xaa Gly Val Asp Ala Trp Gly Gln Gly Thr Thr Val Thr Val Ser Ser
        115                 120                 125
```

LIBRARY OF ANTIGEN-BINDING MOLECULES INCLUDING MODIFIED ANTIBODY VARIABLE REGION

CROSS-REFERENCE TO RELATED APPLICATIONS

This application is the National Stage of International Application Serial No. PCT/JP2015/081693, filed on Nov. 11, 2015, which claims the benefit of PCT/JP2014/079785, filed on Nov. 11, 2014, and Japanese Application Serial No. 2015-097884, filed on May 13, 2015.

REFERENCE TO SEQUENCE LISTING SUBMITTED ELECTRONICALLY

The content of the electronically submitted sequence listing, file name: 38856-0258US1_Replacement_SL_ST25.txt; size: 348.353 bytes; and date of creation: Jan. 28, 2020, is incorporated herein by reference in its entirety.

TECHNICAL FIELD

The present invention provides a population (library) of antigen-binding molecules each comprising an antibody variable region that is capable of binding to two different antigens (first antigen and second antigen), but does not bind to these antigens at the same time, a method for producing the library, a method for producing a bispecific antibody comprising common L chain variable domains using the library, and a method for selecting an antigen-binding molecule comprising a variable region having enhanced binding to the first antigen. The present invention also relates to an antigen-binding molecule comprising an antibody variable region that is capable of binding to three different antigens (first antigen, second antigen, and fourth antigen), but does not bind to the three antigens at the same time, a pharmaceutical composition comprising the antigen-binding molecule, and a method for producing the same.

BACKGROUND ART

Antibodies have received attention as drugs because of having high stability in plasma and producing few adverse reactions (Nat. Biotechnol. (2005) 23, 1073-1078 (Non Patent Literature 1) and Eur J Pharm Biopharm. (2005) 59 (3), 389-396 (Non Patent Literature 2)). The antibodies not only have an antigen-binding effect and an agonist or antagonist effect, but induce cytotoxic activity mediated by effector cells (also referred to as effector functions), such as ADCC (antibody dependent cytotoxicity), ADCP (antibody dependent cell phagocytosis), or CDC (complement dependent cytotoxicity). Particularly, antibodies of IgG1 subclass exhibit the effector functions for cancer cells. Therefore, a large number of antibody drugs have been developed in the field of oncology.

For exerting the ADCC, ADCP, or CDC of the antibodies, their Fc regions must bind to antibody receptors (FcγR) present on effector cells (such as NK cells or macrophages) and various complement components. In humans, FcγRIa, FcγRIIa, FcγRIIb, FcγRIIIa, and FcγRIIIb isoforms have been reported as the protein family of FcγR, and their respective allotypes have also been reported (Immunol. Lett. (2002) 82, 57-65 (Non Patent Literature 3)). Of these isoforms, FcγRIa, FcγRIIa, and FcγRIIIa have, in their intracellular domains, a domain called ITAM (immunoreceptor tyrosine-based activation motif), which transduces activation signals. By contrast, only FcγRIIb has, in its intracellular domain, a domain called ITIM (immunoreceptor tyrosine-based inhibitory motif), which transduces inhibition signals. These isoforms of FcγR are all known to transduce signals through cross-linking by immune complexes or the like (Nat. Rev. Immunol. (2008) 8, 34-47 (Non Patent Literature 4)). In fact, when the antibodies exert effector functions against cancer cells, FcγR molecules on effector cell membranes are clustered by the Fc regions of a plurality of antibodies bound onto cancer cell membranes and thereby transduce activation signals through the effector cells. As a result, a cell-killing effect is exerted. In this respect, the cross-linking of FcγR is restricted to effector cells located near the cancer cells, showing that the activation of immunity is localized to the cancer cells (Ann. Rev. Immunol. (1988). 6. 251-81 (Non Patent Literature 5)).

Naturally occurring immunoglobulins bind to antigens through their variable regions and bind to receptors such as FcγR, FcRn, FcαR, and FcεR or complements through their constant regions. Each molecule of FcRn (binding molecule that interacts with an IgG Fc region) binds to each heavy chain of an antibody in a one-to-one connection. Hence, two molecules of FcRn reportedly bind to one IgG-type antibody molecule. Unlike FcRn, etc., FcγR interacts with an antibody hinge region and CH2 domains, and only one molecule of FcγR binds to one IgG-type antibody molecule (J. Bio. Chem., (20001) 276, 16469-16477). For the binding between FcγR and the Fc region of an antibody, some amino acid residues in the hinge region and the CH2 domains of the antibody and sugar chains added to Asn 297 (EU numbering) of the CH2 domains have been found to be important (Chem. Immunol. (1997), 65, 88-110 (Non Patent Literature 6), Eur. J. Immunol. (1993) 23, 1098-1104 (Non Patent Literature 7), and Immunol. (1995) 86, 319-324 (Non Patent Literature 8)). Fc region variants having various FcγR-binding properties have previously been studied by focusing on this binding site, to yield Fc region variants having higher binding activity against activating FcγR (WO2000/042072 (Patent Literature 1) and WO2006/019447 (Patent Literature 2)). For example, Lazar et al. have successfully increased the binding activity of human IgG1 against human FcγRIIIa (V158) to approximately 370 times by substituting Ser 239, Ala 330, and Ile 332 (EU numbering) of the human IgG1 by Asn, Leu, and Glu, respectively (Proc. Natl. Acad. Sci. U.S.A. (2006) 103, 4005-4010 (Non Patent Literature 9) and WO2006/019447 (Patent Literature 2)). This altered form has approximately 9 times the binding activity of a wild type in terms of the ratio of FcγRIIIa to FcγIIb (A/I ratio). Alternatively, Shinkawa et al. have successfully increased binding activity against FcγRIIIa to approximately 100 times by deleting fucose of the sugar chains added to Asn 297 (EU numbering) (J. Biol. Chem. (2003) 278, 3466-3473 (Non Patent Literature 10)). These methods can drastically improve the ADCC activity of human IgG1 compared with naturally occurring human IgG1.

A naturally occurring IgG-type antibody typically recognizes and binds to one epitope through its variable region (Fab) and can therefore bind to only one antigen. Meanwhile, many types of proteins are known to participate in cancer or inflammation, and these proteins may crosstalk with each other. For example, some inflammatory cytokines (TNF, ILL and IL6) are known to participate in immunological disease (Nat. Biotech., (2011) 28, 502-10 (Non Patent Literature 11)). Also, the activation of other receptors is known as one mechanism underlying the acquisition of drug resistance by cancer (Endocr Relat Cancer (2006) 13, 45-51 (Non Patent Literature 12)). In such a case, the usual antibody, which recognizes one epitope, cannot inhibit a plurality of proteins.

Antibodies that bind to two or more types of antigens by one molecule (these antibodies are referred to as bispecific antibodies) have been studied as molecules inhibiting a plurality of targets. Binding activity against two different antigens (first antigen and second antigen) can be conferred by the modification of naturally occurring IgG-type antibodies (mAbs. (2012) Mar. 1, 4 (2)). Therefore, such an antibody has not only the effect of neutralizing these two or more types of antigens by one molecule but the effect of enhancing antitumor activity through the cross-linking of cells having cytotoxic activity to cancer cells. A molecule with an antigen-binding site added to the N or C terminus of an antibody (DVD-Ig and scFv-IgG), a molecule having different sequences of two Fab regions of an antibody (common L-chain bispecific antibody and hybrid hybridoma), a molecule in which one Fab region recognizes two antigens (two-in-one IgG), and a molecule having a CH3 domain loop as another antigen-binding site (Fcab) have previously been reported as molecular forms of the bispecific antibody (Nat. Rev. (2010), 10, 301-316 (Non Patent Literature 13) and Peds (2010), 23 (4), 289-297 (Non Patent Literature 14)). Since any of these bispecific antibodies interact at their Fc regions with FcγR, antibody effector functions are preserved therein. Thus, the bispecific antibody binds to any antigen recognized thereby at the same time with binding to FcγR and exhibits ADCC activity against cells expressing the antigen.

Provided that all the antigens recognized by the bispecific antibody are antigens specifically expressed in cancer, the bispecific antibody binding to any of the antigens exhibits cytotoxic activity against cancer cells and can therefore be expected to have a more efficient anticancer effect than that of the conventional antibody drug that recognizes one antigen. However, in the case where any one of the antigens recognized by the bispecific antibody is expressed in a normal tissue or is a cell expressed on immunocytes, damage on the normal tissue or release of cytokines occurs due to cross-linking with FcγR (J. Immunol. (1999) Aug. 1, 163 (3), 1246-52 (Non Patent Literature 15)). As a result, strong adverse reactions are induced.

For example, catumaxomab is known as a bispecific antibody that recognizes a protein expressed on T cells and a protein expressed on cancer cells (cancer antigen). Catumaxomab binds, at two Fabs, the cancer antigen (EpCAM) and a CD3ε chain expressed on T cells, respectively. Catumaxomab induces T cell-mediated cytotoxic activity through binding to the cancer antigen and the CD3ε at the same time and induces NK cell- or antigen-presenting cell (e.g., macrophage)-mediated cytotoxic activity through binding to the cancer antigen and FcγR at the same time. By use of these two cytotoxic activities, catumaxomab exhibits a high therapeutic effect on malignant ascites by intraperitoneal administration and has thus been approved in Europe (Cancer Treat Rev. (2010) October 36 (6), 458-67 (Non Patent Literature 16)). In addition, the administration of catumaxomab reportedly yields cancer cell-reactive antibodies in some cases, demonstrating that acquired immunity is induced (Future Oncol. (2012) Jan. 8 (1), 73-85 (Non Patent Literature 17)). From this result, such antibodies having both of T cell-mediated cytotoxic activity and the effect brought about by cells such as NK cells or macrophages via FcγR (these antibodies are particularly referred to as trifunctional antibodies) have received attention because a strong antitumor effect and induction of acquired immunity can be expected.

The trifunctional antibodies, however, bind to CD3ε and FcγR at the same time even in the absence of a cancer antigen and therefore cross-link CD3ε-expressing T cells to FcγR-expressing cells even in a cancer cell-free environment to produce various cytokines in large amounts. Such cancer antigen-independent induction of production of various cytokines restricts the current administration of the trifunctional antibodies to an intraperitoneal route (Cancer Treat Rev. 2010 October 36 (6), 458-67 (Non Patent Literature 16)). The trifunctional antibodies are very difficult to administer systemically due to serious cytokine storm-like adverse reactions (Cancer Immunol Immunother. 2007 September; 56 (9): 1397-406 (Non Patent Literature 18)).

The bispecific antibody of the conventional technique is capable of binding to both antigens, i.e., a first antigen cancer antigen (EpCAM) and a second antigen CD3c, at the same time with binding to FcγR, and therefore, cannot circumvent, in view of its molecular structure, such adverse reactions caused by the binding to FcγR and the second antigen CD3ε at the same time.

In recent years, a modified antibody that causes cytotoxic activity mediated by T cells while circumventing adverse reactions has been provided by use of an Fc region having reduced binding activity against FcγR (WO2012/073985).

Even such an antibody, however, fails to act on two immunoreceptors, i.e., CD3ε and FcγR, while binding to the cancer antigen, in view of its molecular structure.

An antibody that exerts both of cytotoxic activity mediated by T cells and cytotoxic activity mediated by cells other than the T cells in a cancer antigen-specific manner while circumventing adverse reactions has not yet been known.

CITATION LIST

Patent Literature

Patent Literature 1: WO2000/042072
Patent Literature 2: WO2006/019447

Non Patent Literature

Non Patent Literature 1: Nat. Biotechnol. (2005) 23, 1073-1078
Non Patent Literature 2: Eur J Pharm Biopharm. (2005) 59 (3), 389-396
Non Patent Literature 3: Immunol. Lett. (2002) 82, 57-65
Non Patent Literature 4: Nat. Rev. Immunol. (2008) 8, 34-47
Non Patent Literature 5: Ann. Rev. Immunol. (1988). 6. 251-81
Non Patent Literature 6: Chem. Immunol. (1997), 65, 88-110
Non Patent Literature 7: Eur. J. Immunol. (1993) 23, 1098-1104
Non Patent Literature 8: Immunol. (1995) 86, 319-324
Non Patent Literature 9: Proc. Natl. Acad. Sci. U.S.A. (2006) 103, 4005-4010
Non Patent Literature 10: J. Biol. Chem. (2003) 278, 3466-3473
Non Patent Literature 11: Nat. Biotech., (2011) 28, 502-10
Non Patent Literature 12: Endocr Relat Cancer (2006) 13, 45-51
Non Patent Literature 13: Nat. Rev. (2010), 10, 301-316
Non Patent Literature 14: Peds (2010), 23 (4), 289-297

Non Patent Literature 15: J. Immunol. (1999) Aug. 1, 163 (3), 1246-52
Non Patent Literature 16: Cancer Treat Rev. (2010) October 36 (6), 458-67
Non Patent Literature 17: Future Oncol. (2012) Jan. 8 (1), 73-85
Non Patent Literature 18: Cancer Immunol Immunother. 2007 September; 56 (9): 1397-406

SUMMARY OF INVENTION

Technical Problem

The present invention has been made in light of these circumstances. An object of the present invention is to provide a population (library) of antigen-binding molecules each comprising an antibody variable region that has binding activity against two different antigens (first antigen and second antigen), but does not bind to these antigens at the same time, a method for producing the library, a method for selecting or producing a desired antigen-binding molecule using the library, and a method for selecting an antigen-binding molecule comprising a variable region having enhanced binding to the first antigen. Another object of the present invention is to provide an antigen-binding molecule comprising an antibody variable region that is capable of binding to three different antigens (first antigen, second antigen, and fourth antigen), but does not bind to the three antigens at the same time, a pharmaceutical composition comprising the antigen-binding molecule, and a method for producing the same.

Solution to Problem

The present inventors have conducted diligent studies to attain the object. As a result, the present inventors have successfully prepared an antigen-binding molecule comprising: an antibody variable region that has binding activity against two different antigens (first antigen and second antigen), but does not bind to these antigens at the same time; and a variable region binding to an antigen (third antigen) different from these antigens, and enhanced activity brought about by this antigen-binding molecule through the use of the binding activity of the antigen-binding molecule against the three different antigens. In addition, the present inventors have successfully prepared an antigen-binding molecule capable of circumventing the cross-linking between different cells resulting from the binding of a conventional multispecific antigen-binding molecule to antigens expressed on the different cells, which is considered to be responsible for adverse reactions when the multispecific antigen-binding molecule is used as a drug. Moreover, the present inventors have successfully prepared a library of antigen-binding molecules each comprising an antibody variable region that is capable of binding to two different antigens (first antigen and second antigen), but does not bind to these antigens at the same time. In addition, by use of the library, the present inventors have successfully obtained (selected) an antigen-binding molecule having binding activity against desired two antigens, and obtained (selected) a variable region having enhanced binding to a desired antigen. Furthermore, the present inventors have successfully prepared an antigen-binding molecule comprising an antibody variable region that is capable of binding to three different antigens (first antigen, second antigen, and fourth antigen), but does not bind to the three antigens at the same time.

More specifically, the present invention relates to the following:

[1] A library consisting essentially of a plurality of antigen-binding molecules differing in sequence from each other, wherein an antigen-binding region in each of the antigen-binding molecules is an antibody variable region that is capable of binding to a first antigen and a second antigen different from the first antigen, but does not bind to the first antigen and the second antigen at the same time, any one of the first antigen and the second antigen is CD3, and the other antigen is a molecule expressed on the surface of a T cell or any other immunocyte.

[2] The library according to [1], wherein the variable region that does not bind to the first antigen and the second antigen at the same time is a variable region that does not bind to the first antigen and the second antigen each expressed on a different cell, at the same time.

[3] The library according to [1] or [2], wherein the variable region is a variable region having alteration of at least one amino acid, and the altered amino acid is an amino acid in the CDR1, CDR2, CDR3, or FR3 region of the antibody variable region.

[4] The library according to [3], wherein the altered amino acid is an amino acid at at least one position selected from Kabat numbering positions 31 to 35, 50 to 65, 71 to 74, and 95 to 102 in an antibody H chain variable domain, and Kabat numbering positions 24 to 34, 50 to 56, and 89 to 97 in an L chain variable domain.

[5] The library according to any one of [1] to [4], wherein the other antigen is FcγR, TLR, lectin, IgA, an immune checkpoint molecule, a TNF superfamily molecule, a TNFR superfamily molecule, or an NK receptor molecule.

[6] The library according to any one of [1] to [5], wherein the antigen-binding molecules are fusion polypeptides each comprising the antibody variable region and at least a portion of a viral coat protein.

[7] The library according to any one of [3] to [6], wherein the alteration of at least one amino acid is introduced into a template sequence consisting of a heavy chain variable domain sequence described in SEQ ID NO: 96 and/or a light chain variable domain sequence described in SEQ ID NO: 53, and the altered amino acid is an amino acid at any one or more positions selected from the following:

H chain: 31, 52b, 52c, 53, 54, 56, 57, 61, 98, 99, 100, 100a, 100b, 100c, 100d, 100e, 100f, and 100g (Kabat numbering); and L chain: 24, 25, 26, 27, 27a, 27b, 27c, 27e, 30, 31, 33, 34, 51, 52, 53, 54, 55, 56, 74, 77, 89, 90, 92, 93, 94, and 96 (Kabat numbering).

[8] A method for producing a library according to any one of [1] to [7], the method comprising the following steps (a) and (b):

(a) using an antibody variable region sequence binding to the first antigen as a library template sequence to identify amino acid alteration that satisfies any one or more of the following conditions (i) to (iii):

(i) the alteration does not substantially change the ability to bind to the first antigen;

(ii) the alteration does not substantially change the ability to bind to ECM; and (iii) the alteration is insertion of a peptide consisting of 1 to 25 amino acid residues to the CDR1, CDR2, CDR3, or FR3 domain of a heavy chain variable domain; and (b) designing a library comprising a nucleic acid encoding the template sequence, and nucleic acids encoding variable regions differing in sequence from each other and each having at least one amino acid alteration identified in the step (a) in the template sequence.

[9] The method for producing a library according to [8], wherein the library is produced using a heavy chain variable domain sequence described in SEQ ID NO: 96 and/or a light chain variable domain sequence described in SEQ ID NO: 53 as the library template sequence.

[10] A method for producing an antigen-binding molecule comprising a variable region that is capable of binding to a first antigen which is CD3 and a second antigen different from the first antigen, but does not bind to the first antigen and the second antigen at the same time, the method comprising the following steps (a) to (c):

(a) contacting a library according to any one of [1] to [7] with the second antigen;

(b) recovering antigen-binding molecules bound with the second antigen in the step (a); and (c) selecting an antigen-binding molecule comprising a variable region that does not bind to the first antigen and the second antigen at the same time from a population of the antigen-binding molecules recovered in the step (b).

[11] The method for producing an antigen-binding molecule according to [10], wherein the second antigen is FcγR, TLR, lectin, IgA, an immune checkpoint molecule, a TNF superfamily molecule, a TNFR superfamily molecule, or an NK receptor molecule.

[12] A method for producing a bispecific antibody using a library consisting essentially of a plurality of antigen-binding molecules differing in sequence from each other, wherein an antigen-binding region in each of the antigen-binding molecules is an antibody variable region consisting of a template sequence, or an antibody variable region that has alteration of at least one amino acid in the template sequence and is capable of binding to a first antigen and a second antigen different from the first antigen, but does not bind to the first antigen and the second antigen at the same time, the method comprising the following steps (a) to (c):

(a) selecting the library template sequence as a variable region binding to the first antigen;

(b) selecting a variable region that binds to the second antigen, but does not bind to the first antigen, as a variable region binding to the second antigen, the step (b) comprising the following steps (i) to (iv):

(i) contacting the library with the second antigen;

(ii) recovering antigen-binding molecules bound with the second antigen in the step (i);

(iii) contacting a population of the antigen-binding molecules recovered in the step (ii) with the first antigen; and (iv) selecting an antigen-binding molecule that does not bind to the first antigen in the step (iii); and (c) producing a bispecific antibody comprising the variable region binding to the first antigen selected in the step (a), and the variable region binding to the second antigen selected in the step (b).

[13] The method for producing a bispecific antibody according to [12], wherein the first antigen is CD3, and the second antigen is a molecule specifically expressed in a cancer tissue.

[14] A method for selecting a variable region having enhanced binding to a first antigen, the method comprising the following steps (a) to (c):

(a) contacting a library according to any one of [1] to [7] with the first antigen;

(b) recovering antigen-binding molecules bound with the first antigen in the step (a); and (c) selecting an antigen-binding molecule comprising the variable region having enhanced binding to the first antigen from a population of the antigen-binding molecules bound with the first antigen in the step (b).

[15] An antigen-binding molecule comprising an antibody variable region that is capable of binding to three different antigens (a first antigen, a second antigen different from the first antigen, and a fourth antigen different from the first antigen and the second antigen), but does not bind to the three antigens at the same time.

[16] The antigen-binding molecule according to [15], further comprising a variable region binding to a third antigen different from the three antigens.

[17] The antigen-binding molecule according to [15] or [16], wherein the variable region that does not bind to the three antigens at the same time is a variable region that does not bind to the first antigen, the second antigen, and the fourth antigen each expressed on a different cell, at the same time.

[18] The antigen-binding molecule according to any of [15] to [17], further comprising an antibody Fc region.

[19] The antigen-binding molecule according to [18], wherein the Fc region has lower binding activity against FcγR than that of the Fc region of a naturally occurring human IgG1 antibody against FcγR.

[20] The antigen-binding molecule according to any of [15] to [19], wherein the antibody variable region capable of binding to the three antigens is a variable region having alteration of at least one amino acid, and the altered amino acid is an amino acid in the CDR1, CDR2, CDR3, or FR3 region of the antibody variable region.

[21] The antigen-binding molecule according to [20], wherein the altered amino acid is an amino acid at at least one position selected from Kabat numbering positions 31 to 35, 50 to 65, 71 to 74, and 95 to 102 in an antibody H chain variable domain, and Kabat numbering positions 24 to 34, 50 to 56, and 89 to 97 in an L chain variable domain.

[22] The antigen-binding molecule according to any of [15] to [21], wherein any one of the first antigen, the second antigen, and the fourth antigen is a molecule specifically expressed on the surface of a T cell, and each of the remaining two antigens is a molecule expressed on the surface of a T cell or any other immunocyte.

[23] The antigen-binding molecule according to [22], wherein each of the remaining two antigens is FcγR, TLR, lectin, IgA, an immune checkpoint molecule, a TNF superfamily molecule, a TNFR superfamily molecule, or an NK receptor molecule.

[24] The antigen-binding molecule according to any one of [16] to [23], wherein the third antigen is a molecule specifically expressed in a cancer tissue.

[25] A pharmaceutical composition comprising an antigen-binding molecule according to any of [15] to [24] and a pharmaceutically acceptable carrier.

[26] A method for producing an antigen-binding molecule according to any of [15] to [24], the method comprising the following steps (i) to (iv):

(i) preparing a library of antigen-binding molecules with at least one amino acid altered in their antibody variable regions each binding to three different antigens (a first antigen, a second antigen different from the first antigen, and a fourth antigen different from the first antigen and the second antigen), wherein the altered variable regions differ in at least one amino acid from each other;

(ii) selecting, from the prepared library, an antigen-binding molecule comprising a variable region that has binding activity against the three antigens, but does not bind to the three antigens at the same time;

(iii) culturing a host cell comprising a nucleic acid encoding the variable region of the antigen-binding molecule selected in the step (ii) to express an antigen-binding molecule comprising the antibody variable region that is capable of binding to the three antigens, but does not bind to the three antigens at the same time; and (iv) recovering the antigen-binding molecule from the host cell cultures.

[27] The method according to [26], wherein the variable region that does not bind to the three antigens at the same time, contained in the antigen-binding molecule selected in the step (ii) is a variable region that does not bind to the three antigens each expressed on a different cell, at the same time.

[28] The method according to [26] or [27], wherein the host cell cultured in the step (iii) further comprises a nucleic acid encoding an antibody Fc region.

[29] The method according to [28], wherein the Fc region has lower binding activity against FcγR than that of the Fc region of a naturally occurring human IgG1 antibody against FcγR.

[30] The method according to any of [26] to [29], wherein the antigen-binding molecule to be produced is a multispecific antibody.

[31] The method according to any of [26] to [30], wherein the at least one amino acid altered in the variable regions in the step (i) is a substituted or inserted amino acid.

[32] The method according to [31], wherein the number of inserted amino acids is 1 to 25.

[33] The method according to any of [26] to [32], wherein the alteration is alteration of an amino acid in a CDR1, CDR2, CDR3, or FR3 region of the antibody variable region.

[34] The method according to any of [26] to [33], wherein the alteration is alteration of an amino acid in a loop.

[35] The method according to any of [26] to [33], wherein the alteration is alteration of at least one amino acid selected from Kabat numbering positions 31 to 35, 50 to 65, 71 to 74, and 95 to 102 in an antibody H chain variable domain, and Kabat numbering positions 24 to 34, 50 to 56, and 89 to 97 in an L chain variable domain.

[36] The method according to any of [26] to [35], wherein any one of the first antigen, the second antigen, and the fourth antigen is a molecule specifically expressed on the surface of a T cell, and each of the remaining two antigens is a molecule expressed on the surface of a T cell or any other immunocyte.

[37] The method according to [36], wherein any one of the first antigen, the second antigen, and the fourth antigen is CD3, and each of the remaining two antigens is FcγR, TLR, IgA, lectin, an immune checkpoint molecule, a TNF superfamily molecule, a TNFR superfamily molecule, or an NK receptor molecule.

[38] The method according to any of [26] to [37], wherein the antigen-binding molecule further comprises a variable region binding to a third antigen different from the three antigens.

[39] The method according to [38], wherein the third antigen is a molecule specifically expressed in a cancer tissue.

[40] A method for treating cancer, comprising the step of administering an antigen-binding molecule according to any of [15] to [24].

[41] The antigen-binding molecule according to any of [15] to [24] for use in the treatment of cancer.

[42] Use of an antigen-binding molecule according to any of [15] to [24] in the production of a therapeutic agent for cancer.

[43] A process for producing a therapeutic agent for cancer, comprising the step of using an antigen-binding molecule according to any of [15] to [24].

Those skilled in the art should understand that one of or any combination of two or more of the aspects described above is also included in the present invention unless a technical contradiction arises on the basis of the technical common sense of those skilled in the art.

BRIEF DESCRIPTION OF DRAWINGS

FIG. 20 is a diagram showing the binding of a Fab domain displayed by a phage to CD3ε and human IgA (hIgA). NC denotes its binding to an antigen-unimmobilized plate.

FIG. 23 is a diagram showing the binding of a Fab domain displayed by a phage to CD3ε and human CD154. NC denotes its binding to an antigen-unimmobilized plate.

DESCRIPTION OF EMBODIMENTS

Figure 1:
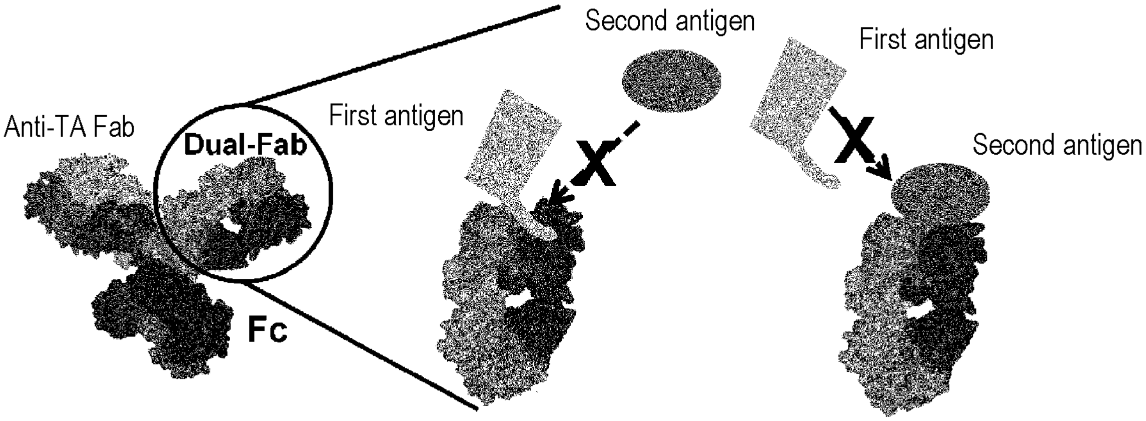
FIG. 1 is a conceptual diagram of an antibody that binds to a first antigen and a second antigen, but does not bind to these antigens at the same time.

According to one aspect, the present invention relates to a library consisting essentially of a plurality of antigen-binding molecules differing in sequence from each other, wherein an antigen-binding region in each of the antigen-binding molecules is an antibody variable region that is capable of binding to a first antigen and a second antigen different from the first antigen, but does not bind to the first antigen and the second antigen at the same time (hereinafter, also referred to as the antibody variable region of the present invention). For the antigen-binding region contained in the library of the present invention, preferably, any one of the first antigen and the second antigen is CD3, and the other antigen is a molecule expressed on the surface of a T cell or any other immunocyte.

According to another aspect, the present invention relates to an antigen-binding molecule comprising an antibody variable region that is capable of binding to three different antigens (first antigen, second antigen, and fourth antigen), but does not bind to the three antigens at the same time. In this context, the "three different antigens" according to the present invention refer to a first antigen, a second antigen different from the first antigen, and a fourth antigen different from the first antigen and the second antigen.

In the present specification, the respective antigens included in the term "two different antigens" are indicated by the terms "first antigen" and "second antigen", and the respective antigens included in the term "three different antigens" are indicated by the terms "first antigen", "second antigen", and "fourth antigen".

The present invention further relates to the antigen-binding molecule further comprising a variable region binding to a "third antigen" which is an antigen different from the "three different antigens".

In the present invention, the "antibody variable region" usually means a region comprising a domain constituted by four framework regions (FRs) and three complementarity-determining regions (CDRs) flanked thereby, and also includes a partial sequence thereof as long as the partial sequence has the activity of binding to a portion or the whole of an antigen. Particularly, a region comprising an antibody light chain variable domain (VL) and an antibody heavy chain variable domain (VH) is preferred. The antibody variable region of the present invention may have an arbitrary sequence and may be a variable region derived from any antibody such as a mouse antibody, a rat antibody, a rabbit antibody, a goat antibody, a camel antibody, and a humanized antibody obtained by the humanization of any of these nonhuman antibodies, and a human antibody. The "humanized antibody", also called reshaped human antibody, is obtained by grafting complementarity determining regions (CDRs) of a non-human mammal-derived antibody, for example, a mouse antibody to human antibody CDRs. Methods for identifying CDRs are known in the art (Kabat et al., Sequence of Proteins of Immunological Interest (1987), National Institute of Health, Bethesda, Md.; and Chothia et al., Nature (1989) 342: 877). General gene recombination approaches therefor are also known in the art (see European Patent Application Publication No. EP 125023 and WO 96/02576).

The "antibody variable region" of the present invention that does "not bind to the first antigen and the second antigen at the same time" means that the antibody variable region of the present invention cannot bind to the second antigen in a state bound with the first antigen whereas the variable region cannot bind to the first antigen in a state bound with the second antigen. Specifically, the "antibody variable region" of the present invention that "is capable of binding to the first antigen and the second antigen, but does not bind to the first antigen and the second antigen at the same time" or that "binds to the first antigen and the second antigen, but does not bind to the first antigen and the second antigen at the same time" means that the antibody variable region of the present invention cannot bind to the second antigen in a state bound with the first antigen and can bind to the second antigen in a state unbound with the first antigen whereas the variable region cannot bind to the first antigen in a state bound with the second antigen and can bind to the first antigen in a state unbound with the second antigen. In this context, the phrase "not bind to the first antigen and the second antigen at the same time" also includes not cross-linking a cell expressing the first antigen to a cell expressing the second antigen, or not binding to the first antigen and the second antigen each expressed on a different cell, at the same time. This phrase further includes the case where the variable region is capable of binding to both the first antigen and the second antigen at the same time when the first antigen and the second antigen are not expressed on cell membranes, as with soluble proteins, or both reside on the same cell, but cannot bind to the first antigen and the second antigen each expressed on a different cell, at the same time. Such an antibody variable region is not particularly limited as long as the antibody variable region has these functions. Examples thereof can include variable regions derived from an IgG-type antibody variable region by the alteration of a portion of its amino acids so as to bind to the desired antigen. The amino acid to be altered is selected from, for example, amino acids whose alteration does not cancel the binding to the antigen, in an antibody variable region binding to the first antigen or the second antigen.

In this context, the phrase "expressed on different cells" merely means that the antigens are expressed on separate cells. The combination of such cells may be, for example, the same types of cells such as a T cell and another T cell, or may be different types of cells such as a T cell and an NK cell.

The "antibody variable region" of the present invention that does "not bind to three different antigens (first antigen, second antigen, and fourth antigen) at the same time" means that the antigens to which the antibody variable region of the present invention can bind at the same time are (A) any one type of antigen or (B) a combination of any two types of antigens among the three different antigens (i.e., three types of antigens).

In other words, the antibody variable region of the present invention that does "not bind to three different antigens (first antigen, second antigen, and fourth antigen) at the same time" means that the antibody variable region (A) cannot bind to remaining two types of antigens in a state bound with any one type of antigen among the three different antigens (three types of antigens) or (B) cannot bind to remaining one type of antigen in a state bound with any two types of antigens among the three different antigens (three types of antigens). The case (A) specifically means that (i) the antibody variable region of the present invention can bind to neither the second antigen nor the fourth antigen in a state bound with the first antigen, (ii) the variable region can bind to neither the first antigen nor the fourth antigen in a state bound with the second antigen, and (iii) the variable region can bind to neither the first antigen nor the second antigen in a state bound with the fourth antigen. The case (B) specifically means that (i) the antibody variable region of the present invention cannot bind to the fourth antigen in a state bound with the first antigen and the second antigen, (ii) the antibody variable region of the present invention cannot bind to the second antigen in a state bound with the first antigen and the fourth antigen, and (iii) the antibody variable region of the present invention cannot bind to the first antigen in a state bound with the second antigen and the fourth antigen.

Preferably, the antibody variable region of the present invention does not bind to the three different antigens at the same time, i.e., does not bind to the first antigen, the second antigen, and the fourth antigen at the same time, and additionally, does not bind to the first antigen and the second antigen at the same time, does not bind to the first antigen and the fourth antigen at the same time, and/or does not bind to the second antigen and the fourth antigen at the same time.

Most preferably, the antibody variable region of the present invention does not bind to at least two or more antigens selected from the group consisting of the first antigen, the second antigen, and the fourth antigen, at the same time (i.e., does not bind to the combination of the first antigen and the second antigen, the combination of the first antigen and the fourth antigen, the combination of the second antigen and the fourth antigen, or the combination of the first antigen, the second antigen, and the fourth antigen, at the same time).

In this context, the phrase "not bind to the three different antigens (first antigen, second antigen, and fourth antigen) at the same time" also includes not cross-linking two or more cells selected from the group consisting of a cell expressing the first antigen, a cell expressing the second antigen, and a cell expressing the fourth antigen, or not binding to two or more antigens selected from the first antigen, the second antigen, and the fourth antigen each expressed on a different cell, at the same time. This phrase further includes the case where the variable region is capable of binding to the three different antigens (first antigen, second antigen and fourth antigen) at the same time when any one or more of the three different antigens are not expressed on cell membranes, as with soluble proteins, or any two or more of the three different antigens reside on the same cell, but cannot bind to the three different antigens each expressed on a different cell, at the same time. Such an antibody variable region is not particularly limited as long as the antibody variable region has these functions. Examples thereof can include variable regions derived from an IgG-type antibody variable region by the alteration of a portion of its amino acids so as to bind to the desired antigen.

In the present invention, one amino acid alteration may be used alone, or a plurality of amino acid alterations may be used in combination.

In the case of using a plurality of amino acid alterations in combination, the number of the alterations to be combined is not particularly limited and can be appropriately set within a range that can attain the object of the invention. The number of the alterations to be combined is, for example, 2 or more and 30 or less, preferably 2 or more and 25 or less, 2 or more and 22 or less, 2 or more and 20 or less, 2 or more and 15 or less, 2 or more and 10 or less, 2 or more and 5 or less, or 2 or more and 3 or less.

The plurality of amino acid alterations to be combined may be added to only the antibody heavy chain variable domain or light chain variable domain or may be appropriately distributed to both of the heavy chain variable domain and the light chain variable domain.

One or more amino acid residues in the variable region are acceptable as the amino acid residue to be altered (the altered amino acid) as long as the antigen-binding activity is maintained. In the case of altering an amino acid in the variable region, the resulting variable region preferably maintains the binding activity of the corresponding unaltered antibody and preferably has, for example, 50% or higher, more preferably 80% or higher, further preferably 100% or higher, of the binding activity before the alteration, though the variable region according to the present invention is not limited thereto. The binding activity may be increased by the amino acid alteration and may be, for example, 2 times, 5 times, or 10 times the binding activity before the alteration.

Examples of the region preferred for the amino acid alteration include solvent-exposed regions and loops in the variable region. Among others, CDR1, CDR2, CDR3, FR3, and loops are preferred. Specifically, Kabat numbering positions 31 to 35, 50 to 65, 71 to 74, and 95 to 102 in the H chain variable domain and Kabat numbering positions 24 to 34, 50 to 56, and 89 to 97 in the L chain variable domain are preferred. Kabat numbering positions 31, 52a to 61, 71 to 74, and 97 to 101 in the H chain variable domain and Kabat numbering positions 24 to 34, 51 to 56, and 89 to 96 in the L chain variable domain are more preferred. Also, an amino acid that increases antigen-binding activity may be further introduced at the time of the amino acid alteration.

In the present invention, the "loop" means a region containing residues that are not involved in the maintenance of an immunoglobulin β barrel structure.

In the present invention, the amino acid alteration means substitution, deletion, addition, insertion, or modification, or a combination thereof. In the present invention, the amino acid alteration can be used interchangeably with amino acid mutation and used in the same sense therewith.

The substitution of an amino acid residue is carried out by replacement with another amino acid residue for the purpose of altering, for example, any of the following (a) to (c): (a) the polypeptide backbone structure of a region having a sheet structure or helix structure; (b) the electric charge or hydrophobicity of a target site; and (c) the size of a side chain.

Amino acid residues are classified into the following groups on the basis of general side chain properties: (1) hydrophobic residues: norleucine, Met, Ala, Val, Leu, and Ile; (2) neutral hydrophilic residues: Cys, Ser, Thr, Asn, and Gln; (3) acidic residues: Asp and Glu; (4) basic residues: His, Lys, and Arg; (5) residues that influence chain orientation: Gly and Pro; and (6) aromatic residues: Trp, Tyr, and Phe.

The substitution of amino acid residues within each of these groups is called conservative substitution, while the substitution of an amino acid residue in one of these groups by an amino acid residue in another group is called non-conservative substitution.

The substitution according to the present invention may be the conservative substitution or may be the non-conservative substitution. Alternatively, the conservative substitution and the non-conservative substitution may be combined.

The alteration of an amino acid residue also includes: the selection of a variable region that is capable of binding to the first antigen and the second antigen, but cannot bind to these antigens at the same time, from those obtained by the random alteration of amino acids whose alteration does not cancel the binding to the antigen, in the antibody variable region binding to the first antigen or the second antigen; and alteration to insert a peptide previously known to have binding activity against the desired antigen, to the region mentioned above. This alteration also includes: the selection of a variable region that is capable of binding to the first antigen, the second antigen, and the fourth antigen, but cannot bind to these antigens at the same time, from those obtained by the random alteration of amino acids whose alteration does not cancel the binding to the antigen, in the antibody variable region binding to the first antigen, the second antigen, or the fourth antigen; and alteration to insert a peptide previously known to have binding activity against the desired antigen, to the region mentioned above. Examples of the peptide previously known to have binding activity against the desired antigen include peptides shown in Table 1.

TABLE 1

| Binding partner/ protein of interest | References |
|---|---|
| VEGFR | J Biol Chem. 2002 Nov 8; 277(45): 43137-42. Epub 2002 Aug 14., EMBO J. 2000 Apr 3; 19(7): 1525-33., J Med Chem. 2010 Jun 10; 53(11): 4428-40. |
| TNFR | Mol Immunol. 2004 Jul; 41(8): 741-9., Eur J Pharmacol. 2011 Apr 10; 656(1-3): 119-24. |
| TLR5 | J Immunol 2010; 185; 1744-1754 |
| TLR4 | PLoS ONE, February 2012\|Volume 7\|Issue 2\|e30839 |
| TLR2 | WO2006/083706A2, |
| T cell VLA receptor | Int Immunopharmacol. 2003 Mar; 3(3): 435-43. |
| PDGFR | Biochemical Pharmacology(2003), 66(7), 1307-1317, FEBS Lett. 1997 Dec 15; 419(2-3): 166-70. |
| Naip5(NLR) | NATURE IMMUNOLOGY VOLUME 9 NUMBER 10 OCTOBER 2008 1171- |
| Integrin | WO 95/14714, WO 97/08203, WO 98/10795, WO 99/24462, J. Biol. Chem. 274: 1979-1985 |
| FcgRIIa | J Biol Chem. 2009 Jan 9; 284(2): 1126-35 |
| EGFR | Journal of Biotechnology(2005), 116(3) 211-219 |
| DR5 agonist | Journal of Biotechnology(2006), 361(3) 522-536 |
| CXCR4 | Science 330, 1066 (2010); Vol. 330 no. 6007 pp. 1066-1071 |
| CD40 | Eur J Biochem. 2003 May; 270(10): 2287-94. |
| CD154 | J Mol Med (Berl). 2009 Feb; 87(2): 181-97. |

According to one aspect, the present invention provides an antigen-binding molecule comprising an antibody variable region with an amino acid altered in a heavy chain variable domain such that the variable region is capable of binding to a first antigen and a second antigen different from the first antigen, but does not bind to the first antigen and the second antigen at the same time. According to another aspect, the present invention provides an antigen-binding molecule comprising an antibody variable region with an amino acid altered in a heavy chain variable domain such that the variable region is capable of binding to three different antigens (first antigen, second antigen, and fourth antigen), but does not bind to the three antigens at the same time. The antibody variable region that is capable of binding to a first antigen and a second antigen different from the first antigen, but does not bind to the first antigen and the second antigen at the same time, or the antibody variable region that is capable of binding to three different antigens (first antigen, second antigen, and fourth antigen), but does not bind to the three antigens at the same time can be prepared, for example, by introducing the amino acid alteration (substitution, deletion, addition, insertion, or modification, or a combination thereof) mentioned above to a heavy chain variable domain. The position to which the amino acid alteration is introduced is preferably a heavy chain variable domain. Examples of a more preferred region include solvent-exposed regions and loops in the variable domain. Among others, CDR1, CDR2, CDR3, FR3, and loops are preferred. Specifically, Kabat numbering positions 31 to 35, 50 to 65, 71 to 74, and 95 to 102 in the H chain variable domain are preferred. Kabat numbering positions 31, 52a to 61, 71 to 74, and 97 to 101 in the H chain variable domain are more preferred. Also, an amino acid that increases antigen-binding activity may be further introduced at the time of the amino acid alteration.

In the antibody variable region of the present invention, the alteration mentioned above may be combined with alteration known in the art. For example, the modification of N-terminal glutamine of the variable region to pyroglutamic acid by pyroglutamylation is a modification well known to those skilled in the art. Thus, the antibody of the present invention having glutamine at the N terminus of its heavy chain may contain a variable region with this N-terminal glutamine modified to pyroglutamic acid.

Such an antibody variable region may further have amino acid alteration to improve, for example, antigen binding, pharmacokinetics, stability, or antigenicity. The antibody variable region of the present invention may be altered so as to have pH dependent binding activity against an antigen and be thereby capable of repetitively binding to the antigen (WO2009/125825).

Also, amino acid alteration to change antigen-binding activity according to the concentration of a target tissue-specific compound may be added to, for example, such an antibody variable region binding to a third antigen (WO2013/180200).

The variable region may be further altered for the purpose of, for example, enhancing binding activity, improving specificity, reducing pI, conferring pH-dependent antigen-binding properties, improving the thermal stability of binding, improving solubility, improving stability against chemical modification, improving heterogeneity derived from a sugar chain, avoiding a T cell epitope identified by use of in silico prediction or in vitro T cell-based assay for reduction in immunogenicity, or introducing a T cell epitope for activating regulatory T cells (mAbs 3: 243-247, 2011).

Whether the antibody variable region of the present invention is "capable of binding to the first antigen and the second antigen" can be determined by a method known in the art.

This can be determined by, for example, an electrochemiluminescence method (ECL method) (BMC Research Notes 2011, 4: 281).

Specifically, for example, a low-molecular antibody composed of a region capable of binding to the first antigen and the second antigen, for example, a Fab region, of a biotin-labeled antigen-binding molecule to be tested, or a monovalent antibody (antibody lacking one of the two Fab regions carried by a usual antibody) thereof is mixed with the first antigen or the second antigen labeled with sulfo-tag (Ru complex), and the mixture is added onto a streptavidin-immobilized plate. In this operation, the biotin-labeled antigen-binding molecule to be tested binds to streptavidin on the plate. Light is developed from the sulfo-tag, and the luminescence signal can be detected using Sector Imager 600 or 2400 (MSD K.K.) or the like to thereby confirm the binding of the aforementioned region of the antigen-binding molecule to be tested to the first antigen or the second antigen.

Alternatively, this assay may be conducted by ELISA, FACS (fluorescence activated cell sorting), ALPHAScreen (amplified luminescent proximity homogeneous assay screen), the BIACORE method based on a surface plasmon resonance (SPR) phenomenon, etc. (Proc. Natl. Acad. Sci. USA (2006) 103 (11), 4005-4010).

Specifically, the assay can be conducted using, for example, an interaction analyzer Biacore (GE Healthcare Japan Corp.) based on a surface plasmon resonance (SPR) phenomenon. The Biacore analyzer includes any model such as Biacore T100, T200, X100, A100, 4000, 3000, 2000, 1000, or C. Any sensor chip for Biacore, such as a CM7, CM5, CM4, CM3, C1, SA, NTA, L1, HPA, or Au chip, can be used as a sensor chip. Proteins for capturing the antigen-binding molecule of the present invention, such as protein A, protein G, protein L, anti-human IgG antibodies, anti-human IgG-Fab, anti-human L chain antibodies, anti-human Fc antibodies, antigenic proteins, or antigenic peptides, are immobilized onto the sensor chip by a coupling method such as amine coupling, disulfide coupling, or aldehyde coupling. The first antigen or the second antigen is injected thereon as an analyte, and the interaction is measured to obtain a sensorgram. In this operation, the concentration of the first antigen or the second antigen can be selected within the range of a few μM to a few pM according to the interaction strength (e.g., KD) of the assay sample.

Alternatively, the first antigen or the second antigen may be immobilized instead of the antigen-binding molecule onto the sensor chip, with which the antibody sample to be evaluated is in turn allowed to interact. Whether the antibody variable region of the antigen-binding molecule of the present invention has binding activity against the first antigen or the second antigen can be confirmed on the basis of a dissociation constant (KD) value calculated from the sensorgram of the interaction or on the basis of the degree of increase in the sensorgram after the action of the antigen-binding molecule sample over the level before the action.

The ALPHAScreen is carried out by the ALPHA technology using two types of beads (donor and acceptor) on the basis of the following principle: luminescence signals are detected only when these two beads are located in proximity through the biological interaction between a molecule bound with the donor bead and a molecule bound with the acceptor bead. A laser-excited photosensitizer in the donor bead converts ambient oxygen to singlet oxygen having an excited state. The singlet oxygen diffuses around the donor bead and reaches the acceptor bead located in proximity thereto to thereby cause chemiluminescent reaction in the bead, which finally emits light. In the absence of the interaction between the molecule bound with the donor bead and the molecule bound with the acceptor bead, singlet oxygen produced by the donor bead does not reach the acceptor bead. Thus, no chemiluminescent reaction occurs.

One (ligand) of the substances between which the interaction is to be observed is immobilized onto a thin gold film of a sensor chip. The sensor chip is irradiated with light from the back such that total reflection occurs at the interface between the thin gold film and glass. As a result, a site having a drop in reflection intensity (SPR signal) is formed in a portion of reflected light. The other (analyte) of the substances between which the interaction is to be observed is injected on the surface of the sensor chip. Upon binding of the analyte to the ligand, the mass of the immobilized ligand molecule is increased to change the refractive index of the solvent on the sensor chip surface. This change in the refractive index shifts the position of the SPR signal (on the contrary, the dissociation of the bound molecules gets the signal back to the original position). The Biacore system plots on the ordinate the amount of the shift, i.e., change in mass on the sensor chip surface, and displays time-dependent change in mass as assay data (sensorgram). The amount of the analyte bound to the ligand captured on the sensor chip surface (amount of change in response on the sensorgram between before and after the interaction of the analyte) can be determined from the sensorgram. However, since the amount bound also depends on the amount of the ligand, the comparison must be performed under conditions where substantially the same amounts of the ligand are used. Kinetics, i.e., an association rate constant (ka) and a dissociation rate constant (kd), can be determined from the curve of the sensorgram, while affinity (KD) can be determined from the ratio between these constants. Inhibition assay is also preferably used in the BIACORE method. Examples of the inhibition assay are described in Proc. Natl. Acad. Sci. USA (2006) 103 (11), 4005-4010.

Whether the antibody variable region of the present invention is "capable of binding to the three different antigens (first antigen, second antigen, and fourth antigen)" can be appropriately determined by those skilled in the art using, for example, the electrochemiluminescence (ECL) method according to the aforementioned method known in the art.

Whether the antigen-binding molecule of the present invention does "not bind to the first antigen and the second antigen at the same time" can be confirmed by: confirming the antigen-binding molecule to have binding activity against the first antigen and the second antigen; then allowing either of the first antigen or the second antigen to bind in advance to the antigen-binding molecule comprising the variable region having this binding activity; and then determining the presence or absence of its binding activity against the other antigen by the method mentioned above.

Alternatively, this can also be confirmed by determining whether the binding of the antigen-binding molecule to either of the first antigen or the second antigen immobilized on an ELISA plate or a sensor chip is inhibited by the addition of the other antigen into the solution.

Specifically, in the case of using, for example, the ECL method, a biotin-labeled antigen-binding molecule to be tested, the first antigen labeled with sulfo-tag (Ru complex), and an unlabeled second antigen are prepared. When the antigen-binding molecule to be tested is capable of binding to the first antigen and the second antigen, but does not bind to the first antigen and the second antigen at the same time, the luminescence signal of the sulfo-tag is detected in the absence of the unlabeled second antigen by adding the mixture of the antigen-binding molecule to be tested and the first antigen onto a streptavidin-immobilized plate, followed by light development. By contrast, the luminescence signal is decreased in the presence of the second antigen. This decrease in luminescence signal can be quantified to determine relative binding activity.

In the case of the ALPHAScreen, the antigen-binding molecule to be tested interacts with the first antigen in the absence of the competing second antigen to generate signals of 520 to 620 nm. The untagged second antigen competes with the first antigen for the interaction with the antigen-binding molecule to be tested. Decrease in fluorescence caused as a result of the competition can be quantified to thereby determine relative binding activity. The polypeptide biotinylation using sulfo-NHS-biotin or the like is known in the art. The first antigen can be tagged with GST by an appropriately adopted method which involves, for example: fusing a polynucleotide encoding the first antigen in flame with a polynucleotide encoding GST; and allowing the resulting fusion gene to be expressed by cells or the like harboring vectors capable of expression thereof, followed by purification using a glutathione column. The obtained signals are preferably analyzed using, for example, software GRAPHPAD PRISM (GraphPad Software, Inc., San Diego) adapted to a one-site competition model based on nonlinear regression analysis. This analysis may be similarly conducted using the tagged second antigen and the untagged first antigen.

Alternatively, a method using fluorescence resonance energy transfer (FRET) may be used. FRET is a phenomenon in which excitation energy is transferred directly between two fluorescent molecules located in proximity to each other by electron resonance. When FRET occurs, the excitation energy of a donor (fluorescent molecule having an excited state) is transferred to an acceptor (another fluorescent molecule located near the donor) so that the fluorescence emitted from the donor disappears (to be precise, the lifetime of the fluorescence is shortened) and instead, the fluorescence is emitted from the acceptor. By use of this phenomenon, whether or not to be dual-Fab can be analyzed. For example, when the first antigen carrying a fluorescence donor and the second antigen carrying a fluorescence acceptor bind to the antigen-binding molecule to be tested at the same time, the fluorescence of the donor disappears while the fluorescence is emitted from the acceptor. Therefore, change in fluorescence wavelength is observed. Such an antibody is confirmed not to be dual-Fab. On the other hand, if the mixing of the first antigen, the second antigen, and the antigen-binding molecule to be tested does not change the fluorescence wavelength of the fluorescence donor bound with the first antigen, this antigen-binding molecule to be tested can be regarded as dual-Fab.

For example, a biotin-labeled antigen-binding molecule to be tested is allowed to bind to streptavidin on the donor bead, while the first antigen tagged with glutathione S transferase (GST) is allowed to bind to the acceptor bead. The antigen-binding molecule to be tested interacts with the first antigen in the absence of the competing second antigen to generate signals of 520 to 620 nm. The untagged second antigen competes with the first antigen for the interaction with the antigen-binding molecule to be tested. Decrease in fluorescence caused as a result of the competition can be quantified to thereby determine relative binding activity. The polypeptide biotinylation using sulfo-NHS-biotin or the like is known in the art. The first antigen can be tagged with GST by an appropriately adopted method which involves, for example: fusing a polynucleotide encoding the first antigen in flame with a polynucleotide encoding GST; and allowing the resulting fusion gene to be expressed by cells or the like harboring vectors capable of expression thereof, followed by purification using a glutathione column. The obtained signals are preferably analyzed using, for example, software GRAPHPAD PRISM (GraphPad Software, Inc., San Diego) adapted to a one-site competition model based on nonlinear regression analysis.

The tagging is not limited to the GST tagging and may be carried out with any tag such as, but not limited to, a histidine tag, MBP, CBP, a Flag tag, an HA tag, a V5 tag, or a c-myc tag. The binding of the antigen-binding molecule to be tested to the donor bead is not limited to the binding using biotin-streptavidin reaction. Particularly, when the antigen-binding molecule to be tested comprises Fc, a possible method involves allowing the antigen-binding molecule to be tested to bind via an Fc-recognizing protein such as protein A or protein G on the donor bead.

Also, the case where the variable region is capable of binding to the first antigen and the second antigen at the same time when the first antigen and the second antigen are not expressed on cell membranes, as with soluble proteins, or both reside on the same cell, but cannot bind to the first antigen and the second antigen each expressed on a different cell, at the same time can also be assayed by a method known in the art.

Specifically, the antigen-binding molecule to be tested has been confirmed to be positive in ECL-ELISA for detecting binding to the first antigen and the second antigen at the same time is also mixed with a cell expressing the first antigen and a cell expressing the second antigen. The antigen-binding molecule to be tested can be shown to be incapable of binding to the first antigen and the second antigen expressed on different cells, at the same time unless the antigen-binding molecule and these cells bind to each other at the same time. This assay can be conducted by, for example, cell-based ECL-ELISA. The cell expressing the first antigen is immobilized onto a plate in advance. After binding of the antigen-binding molecule to be tested thereto, the cell expressing the second antigen is added to the plate. A different antigen expressed only on the cell expressing the second antigen is detected using a sulfo-tag-labeled antibody against this antigen. A signal is observed when the antigen-binding molecule binds to the two antigens respectively expressed on the two cells, at the same time. No signal is observed when the antigen-binding molecule does not bind to these antigens at the same time.

Alternatively, this assay may be conducted by the ALPHAScreen method. The antigen-binding molecule to be tested is mixed with a cell expressing the first antigen bound with the donor bead and a cell expressing the second antigen bound with the acceptor bead. A signal is observed when the antigen-binding molecule binds to the two antigens expressed on the two cells respectively, at the same time. No signal is observed when the antigen-binding molecule does not bind to these antigens at the same time.

Alternatively, this assay may also be conducted by an Octet interaction analysis method. First, a cell expressing the first antigen tagged with a peptide tag is allowed to bind to a biosensor that recognizes the peptide tag. A cell expressing the second antigen and the antigen-binding molecule to be tested are placed in wells and analyzed for interaction. A large wavelength shift caused by the binding of the antigen-binding molecule to be tested and the cell expressing the second antigen to the biosensor is observed when the antigen-binding molecule binds to the two antigens expressed on the two cells respectively, at the same time. A small wavelength shift caused by the binding of only the antigen-binding molecule to be tested to the biosensor is observed when the antigen-binding molecule does not bind to these antigens at the same time.

Instead of these methods based on the binding activity, assay based on biological activity may be conducted. For example, a cell expressing the first antigen and a cell expressing the second antigen are mixed with the antigen-binding molecule to be tested, and cultured. The two antigens expressed on the two cells respectively are mutually activated via the antigen-binding molecule to be tested when the antigen-binding molecule binds to these two antigens at the same time. Therefore, change in activation signal, such as increase in the respective downstream phosphorylation levels of the antigens, can be detected. Alternatively, cytokine production is induced as a result of the activation. Therefore, the amount of cytokines produced can be measured to thereby confirm whether or not to bind to the two cells at the same time.

Whether the antigen-binding molecule of the present invention does "not bind to the three different antigens at the same time" can be appropriately determined by those skilled in the art using, for example, the electrochemiluminescence (ECL) method according to the aforementioned method known in the art, for example, after confirmation of the antigen-binding molecule to have binding activity against the three different antigens (first antigen, second antigen, and fourth antigen).

In the present invention, the "Fc region" refers to a region comprising a fragment consisting of a hinge or a portion thereof and CH2 and CH3 domains in an antibody molecule. The Fc region of IgG class means, but is not limited to, a region from, for example, cysteine 226 (EU numbering (also referred to as EU index herein)) to the C terminus or proline 230 (EU numbering) to the C terminus. The Fc region can be preferably obtained by the partial digestion of, for example, an IgG1, IgG2, IgG3, or IgG4 monoclonal antibody with a proteolytic enzyme such as pepsin followed by the re-elution of a fraction adsorbed on a protein A column or a protein G column. Such a proteolytic enzyme is not particularly limited as long as the enzyme is capable of digesting a whole antibody to restrictively form Fab or $F(ab')_2$ under appropriately set reaction conditions (e.g., pH) of the enzyme. Examples thereof can include pepsin and papain.

In the present invention, the "antigen-binding molecule" is not particularly limited as long as the molecule comprises the "antibody variable region" of the present invention. The antigen-binding molecule may further comprise a peptide or a protein having a length of approximately 5 or more amino acids. The peptide or the protein is not limited to a peptide or a protein derived from an organism, and may be, for example, a polypeptide consisting of an artificially designed sequence. Also, a natural polypeptide, a synthetic polypeptide, a recombinant polypeptide, or the like may be used.

Preferred examples of the antigen-binding molecule of the present invention can include an antigen-binding molecule comprising an antibody Fc region.

An Fc region derived from, for example, naturally occurring IgG can be used as the "Fc region" of the present invention. In this context, the naturally occurring IgG means a polypeptide that contains an amino acid sequence identical to that of IgG found in nature and belongs to a class of an antibody substantially encoded by an immunoglobulin gamma gene. The naturally occurring human IgG means, for example, naturally occurring human IgG1, naturally occurring human IgG2, naturally occurring human IgG3, or naturally occurring human IgG4. The naturally occurring IgG also includes variants or the like spontaneously derived therefrom. A plurality of allotype sequences based on gene polymorphism are described as the constant regions of human IgG1, human IgG2, human IgG3, and human IgG4 antibodies in Sequences of proteins of immunological interest, NIH Publication No. 91-3242, any of which can be used in the present invention. Particularly, the sequence of human IgG1 may have DEL or EEM as an amino acid sequence of EU numbering positions 356 to 358.

The antibody Fc region is found as, for example, an Fc region of IgA1, IgA2, IgD, IgE, IgG1, IgG2, IgG3, IgG4, or IgM type. For example, an Fc region derived from a naturally occurring human IgG antibody can be used as the antibody Fc region of the present invention. For example, an Fc region derived from a constant region of naturally occurring IgG, specifically, a constant region (SEQ ID NO: 1) originated from naturally occurring human IgG1, a constant region (SEQ ID NO: 2) originated from naturally occurring human IgG2, a constant region (SEQ ID NO: 3) originated from naturally occurring human IgG3, or a constant region (SEQ ID NO: 4) originated from naturally occurring human IgG4 can be used as the Fc region of the present invention. The constant region of naturally occurring IgG also includes variants or the like spontaneously derived therefrom.

The Fc region of the present invention is particularly preferably an Fc region having reduced binding activity against an Fcγ receptor. In this context, the Fcγ receptor (also referred to as FcγR herein) refers to a receptor capable of binding to the Fc region of IgG1, IgG2, IgG3, or IgG4 and means any member of the protein family substantially encoded by Fcγ receptor genes. In humans, this family includes, but is not limited to: FcγRI (CD64) including isoforms FcγRIa, FcγRIb, and FcγRIc; FcγRII (CD32) including isoforms FcγRIIa (including allotypes H131 (H type) and R131 (R type)), FcγRIIb (including FcγRIIb-1 and FcγRIIb-2), and FcγRIIc; and FcγRIII (CD16) including isoforms FcγRIIIa (including allotypes V158 and F158) and FcγRIIIb (including allotypes FcγRIIIb-NA1 and FcγRIIIb-NA2); and any yet-to-be-discovered human FcγR or FcγR isoform or allotype. The FcγR includes those derived from humans, mice, rats, rabbits, and monkeys. The FcγR is not limited to these molecules and may be derived from any organism. The mouse FcγRs include, but are not limited to, FcγRI (CD64), FcγRII (CD32), FcγRIII (CD16), and FcγRIII-2 (CD16-2), and any yet-to-be-discovered mouse FcγR or FcγR isoform or allotype. Preferred examples of such Fcγ receptors include human FcγRI (CD64), FcγRIIa (CD32), FcγRIIb (CD32), FcγRIIIa (CD16), and/or FcγRIIIb (CD16).

The FcγR is found in the forms of an activating receptor having ITAM (immunoreceptor tyrosine-based activation motif) and an inhibitory receptor having ITIM (immunoreceptor tyrosine-based inhibitory motif). The FcγR is classified into activating FcγR (FcγRI, FcγRIIa R, FcγRIIa H, FcγRIIIa, and FcγRIIIb) and inhibitory FcγR (FcγRIIb).

The polynucleotide sequence and the amino acid sequence of FcγRI are described in NM_000566.3 and NP_000557.1, respectively; the polynucleotide sequence and the amino acid sequence of FcγRIIa are described in BC020823.1 and AAH20823.1, respectively; the polynucleotide sequence and the amino acid sequence of FcγRIIb are described in BC146678.1 and AAI46679.1, respectively; the polynucleotide sequence and the amino acid sequence of FcγRIIIa are described in BC033678.1 and AAH33678.1, respectively; and the polynucleotide sequence and the amino acid sequence of FcγRIIIb are described in BC128562.1 and AAI28563.1, respectively (RefSeq registration numbers). FcγRIIa has two types of gene polymorphisms that substitute the 131st amino acid of FcγRIIa by histidine (H type) or arginine (R type) (J. Exp. Med, 172, 19-25, 1990). FcγRIIb has two types of gene polymorphisms that substitute the 232nd amino acid of FcγRIIb by isoleucine (I type) or threonine (T type) (Arthritis. Rheum. 46: 1242-1254

(2002)). FcγRIIIa has two types of gene polymorphisms that substitute the 158th amino acid of FcγRIIIa by valine (V type) or phenylalanine (F type) (J. Clin. Invest. 100 (5): 1059-1070 (1997)). FcγRIIIb has two types of gene polymorphisms (NA1 type and NA2 type) (J. Clin. Invest. 85: 1287-1295 (1990)).

The reduced binding activity against an Fcγ receptor can be confirmed by a well-known method such as FACS, ELISA format, ALPHAScreen (amplified luminescent proximity homogeneous assay screen), or the BIACORE method based on a surface plasmon resonance (SPR) phenomenon (Proc. Natl. Acad. Sci. USA (2006) 103 (11), 4005-4010).

The ALPHAScreen method is carried out by the ALPHA technology using two types of beads (donor and acceptor) on the basis of the following principle: luminescence signals are detected only when these two beads are located in proximity through the biological interaction between a molecule bound with the donor bead and a molecule bound with the acceptor bead. A laser-excited photosensitizer in the donor bead converts ambient oxygen to singlet oxygen having an excited state. The singlet oxygen diffuses around the donor bead and reaches the acceptor bead located in proximity thereto to thereby cause chemiluminescent reaction in the bead, which finally emits light. In the absence of the interaction between the molecule bound with the donor bead and the molecule bound with the acceptor bead, singlet oxygen produced by the donor bead does not reach the acceptor bead. Thus, no chemiluminescent reaction occurs.

For example, a biotin-labeled antigen-binding molecule is allowed to bind to the donor bead, while a glutathione S transferase (GST)-tagged Fcγ receptor is allowed to bind to the acceptor bead. In the absence of a competing antigen-binding molecule having a mutated Fc region, an antigen-binding molecule having a wild-type Fc region interacts with the Fcγ receptor to generate signals of 520 to 620 nm. The untagged antigen-binding molecule having a mutated Fc region competes with the antigen-binding molecule having a wild-type Fc region for the interaction with the Fcγ receptor. Decrease in fluorescence caused as a result of the competition can be quantified to thereby determine relative binding affinity. The antigen-binding molecule (e.g., antibody) biotinylation using sulfo-NHS-biotin or the like is known in the art. The Fcγ receptor can be tagged with GST by an appropriately adopted method which involves, for example: fusing a polynucleotide encoding the Fcγ receptor in flame with a polynucleotide encoding GST; and allowing the resulting fusion gene to be expressed by cells or the like harboring vectors capable of expression thereof, followed by purification using a glutathione column. The obtained signals are preferably analyzed using, for example, software GRAPHPAD PRISM (GraphPad Software, Inc., San Diego) adapted to a one-site competition model based on nonlinear regression analysis.

One (ligand) of the substances between which the interaction is to be observed is immobilized onto a thin gold film of a sensor chip. The sensor chip is irradiated with light from the back such that total reflection occurs at the interface between the thin gold film and glass. As a result, a site having a drop in reflection intensity (SPR signal) is formed in a portion of reflected light. The other (analyte) of the substances between which the interaction is to be observed is injected on the surface of the sensor chip. Upon binding of the analyte to the ligand, the mass of the immobilized ligand molecule is increased to change the refractive index of the solvent on the sensor chip surface. This change in the refractive index shifts the position of the SPR signal (on the contrary, the dissociation of the bound molecules gets the signal back to the original position). The Biacore system plots on the ordinate the amount of the shift, i.e., change in mass on the sensor chip surface, and displays time-dependent change in mass as assay data (sensorgram). Kinetics, i.e., an association rate constant (ka) and a dissociation rate constant (kd), can be determined from the curve of the sensorgram, while affinity (KD) can be determined from the ratio between these constants. Inhibition assay is also preferably used in the BIACORE method. Examples of the inhibition assay are described in Proc. Natl. Acad. Sci. USA (2006) 103 (11), 4005-4010.

In the present specification, the reduced binding activity against an Fcγ receptor means that the antigen-binding molecule to be tested exhibits binding activity of, for example, 50% or lower, preferably 45% or lower, 40% or lower, 35% or lower, 30% or lower, 20% or lower, or 15% or lower, particularly preferably 10% or lower, 9% or lower, 8% or lower, 7% or lower, 6% or lower, 5% or lower, 4% or lower, 3% or lower, 2% or lower, or 1% or lower, compared with the binding activity of a control antigen-binding molecule comprising an Fc region on the basis of the analysis method described above.

An antigen-binding molecule having an IgG1, IgG2, IgG3, or IgG4 monoclonal antibody Fc region can be appropriately used as the control antigen-binding molecule. The structure of the Fc region is described in SEQ ID NO: 1 (RefSeq registration No. AAC82527.1 with A added to the N terminus), SEQ ID NO: 2 (RefSeq registration No. AAB59393.1 with A added to the N terminus), SEQ ID NO: 3 (RefSeq registration No. CAA27268.1 with A added to the N terminus), or SEQ ID NO: 4 (RefSeq registration No. AAB59394.1 with A added to the N terminus). In the case of using an antigen-binding molecule having a variant of the Fc region of an antibody of a certain isotype as a test substance, an antigen-binding molecule having the Fc region of the antibody of this certain isotype is used as a control to test the effect of the mutation in the variant on the binding activity against an Fcγ receptor. The antigen-binding molecule having the Fc region variant thus confirmed to have reduced binding activity against an Fcγ receptor is appropriately prepared.

For example, a 231A-238S deletion (WO 2009/011941), C226S, C229S, P238S, (C220S) (J. Rheumatol (2007) 34, 11), C226S, C229S (Hum. Antibod. Hybridomas (1990) 1 (1), 47-54), C226S, C229S, E233P, L234V, or L235A (Blood (2007) 109, 1185-1192) (these amino acids are defined according to the EU numbering) variant is known in the art as such a variant.

Preferred examples thereof include antigen-binding molecules having an Fc region derived from the Fc region of an antibody of a certain isotype by the substitution of any of the following constituent amino acids: amino acids at positions 220, 226, 229, 231, 232, 233, 234, 235, 236, 237, 238, 239, 240, 264, 265, 266, 267, 269, 270, 295, 296, 297, 298, 299, 300, 325, 327, 328, 329, 330, 331, and 332 defined according to the EU numbering. The isotype of the antibody from which the Fc region is originated is not particularly limited, and an Fc region originated from an IgG1, IgG2, IgG3, or IgG4 monoclonal antibody can be appropriately used. An Fc region originated from a naturally occurring human IgG1 antibody is preferably used.

For example, an antigen-binding molecule having an Fc region derived from an IgG1 antibody Fc region by any of the following substitution groups of the constituent amino acids (the number represents the position of an amino acid residue defined according to the EU numbering; the one-letter amino acid code positioned before the number represents an amino acid residue before the substitution; and the one-letter amino acid code positioned after the number represents an amino acid residue before the substitution):

(a) L234F, L235E, and P331S,
(b) C226S, C229S, and P238S,
(c) C226S and C229S, and
(d) C226S, C229S, E233P, L234V, and L235A or by the deletion of an amino acid sequence from positions 231 to 238 defined according to the EU numbering can also be appropriately used.

An antigen-binding molecule having an Fc region derived from an IgG2 antibody Fc region by any of the following substitution groups of the constituent amino acids (the number represents the position of an amino acid residue defined according to the EU numbering; the one-letter amino acid code positioned before the number represents an amino acid residue before the substitution; and the one-letter amino acid code positioned after the number represents an amino acid residue before the substitution):

(e) H268Q, V309L, A330S, and P331S,
(f) V234A,
(g) G237A,
(h) V234A and G237A,
(i) A235E and G237A, and
(j) V234A, A235E, and G237A defined according to the EU numbering can also be appropriately used.

An antigen-binding molecule having an Fc region derived from an IgG3 antibody Fc region by any of the following substitution groups of the constituent amino acids (the number represents the position of an amino acid residue defined according to the EU numbering; the one-letter amino acid code positioned before the number represents an amino acid residue before the substitution; and the one-letter amino acid code positioned after the number represents an amino acid residue before the substitution):

(k) F241A,
(l) D265A, and
(m) V264A defined according to the EU numbering can also be appropriately used.

An antigen-binding molecule having an Fc region derived from an IgG4 antibody Fc region by any of the following substitution groups of the constituent amino acids (the number represents the position of an amino acid residue defined according to the EU numbering; the one-letter amino acid code positioned before the number represents an amino acid residue before the substitution; and the one-letter amino acid code positioned after the number represents an amino acid residue before the substitution):

(n) L235A, G237A, and E318A,
(o) L235E, and
(p) F234A and L235A defined according to the EU numbering can also be appropriately used.

Other preferred examples thereof include antigen-binding molecules having an Fc region derived from the Fc region of a naturally occurring human IgG1 antibody by the substitution of any of the following constituent amino acids: amino acids at positions 233, 234, 235, 236, 237, 327, 330, and 331 defined according to the EU numbering, by an amino acid at the corresponding EU numbering position in the Fc region of the counterpart IgG2 or IgG4.

Other preferred examples thereof include antigen-binding molecules having an Fc region derived from the Fc region of a naturally occurring human IgG1 antibody by the substitution of any one or more of the following constituent amino acids: amino acids at positions 234, 235, and 297 defined according to the EU numbering, by a different amino acid. The type of the amino acid present after the substitution is not particularly limited. An antigen-binding molecule having an Fc region with any one or more of amino acids at positions 234, 235, and 297 substituted by alanine is particularly preferred.

Other preferred examples thereof include antigen-binding molecules having an Fc region derived from an IgG1 antibody Fc region by the substitution of the constituent amino acid at position 265 defined according to the EU numbering, by a different amino acid. The type of the amino acid present after the substitution is not particularly limited. An antigen-binding molecule having an Fc region with an amino acid at position 265 substituted by alanine is particularly preferred.

One preferred form of the “antigen-binding molecule” of the present invention can be, for example, a multispecific antibody comprising the antibody variable region of the present invention.

A technique of suppressing the unintended association between H chains by introducing electric charge repulsion to the interface between the second constant domains (CH2) or the third constant domains (CH3) of the antibody H chains (WO2006/106905) can be applied to association for the multispecific antibody.

In the technique of suppressing the unintended association between H chains by introducing electric charge repulsion to the CH2 or CH3 interface, examples of amino acid residues contacting with each other at the interface between the H chain constant domains can include a residue at EU numbering position 356, a residue at EU numbering position 439, a residue at EU numbering position 357, a residue at EU numbering position 370, a residue at EU numbering position 399, and a residue at EU numbering position 409 in one CH3 domain, and their partner residues in another CH3 domain.

More specifically, for example, an antibody comprising two H chain CH3 domains can be prepared as an antibody in which one to three pairs of amino acid residues selected from the following amino acid residue pairs (1) to (3) in the first H chain CH3 domain carry the same electric charge: (1) amino acid residues at EU numbering positions 356 and 439 contained in the H chain CH3 domain; (2) amino acid residues at EU numbering positions 357 and 370 contained in the H chain CH3 domain; and (3) amino acid residues at EU numbering positions 399 and 409 contained in the H chain CH3 domain.

The antibody can be further prepared as an antibody in which one to three pairs of amino acid residues are selected from the amino acid residue pairs (1) to (3) in the second H chain CH3 domain different from the first H chain CH3 domain so as to correspond to the amino acid residue pairs (1) to (3) carrying the same electric charge in the first H chain CH3 domain and to carry opposite electric charge from their corresponding amino acid residues in the first H chain CH3 domain.

Each amino acid residue described in the pairs (1) to (3) is located close to its partner in the associated H chains. Those skilled in the art can find positions corresponding to the amino acid residues described in each of the pairs (1) to (3) as to the desired H chain CH3 domains or H chain constant domains by homology modeling or the like using commercially available software and can appropriately alter amino acid residues at the positions.

In the antibody described above, each of the “amino acid residues carrying electric charge” is preferably selected from, for example, amino acid residues included in any of the following groups (a) and (b):

(a) glutamic acid (E) and aspartic acid (D); and (b) lysine (K), arginine (R), and histidine (H).

In the antibody described above, the phrase "carrying the same electric charge" means that, for example, all of two or more amino acid residues are amino acid residues included in any one of the groups (a) and (b). The phrase "carrying opposite electric charge" means that, for example, at least one amino acid residue among two or more amino acid residues may be an amino acid residue included in any one of the groups (a) and (b), while the remaining amino acid residue(s) is amino acid residue(s) included in the other group.

In a preferred embodiment, the antibody may have the first H chain CH3 domain and the second H chain CH3 domain cross-linked through a disulfide bond.

The amino acid residue to be altered according to the present invention is not limited to the amino acid residues in the antibody variable region or the antibody constant region mentioned above. Those skilled in the art can find amino acid residues constituting the interface as to a polypeptide variant or a heteromultimer by homology modeling or the like using commercially available software and can alter amino acid residues at the positions so as to regulate the association.

The association for the multispecific antibody of the present invention can also be carried out by an alternative technique known in the art. An amino acid side chain present in the variable domain of one antibody H chain is substituted by a larger side chain (knob), and its partner amino acid side chain present in the variable domain of the other H chain is substituted by a smaller side chain (hole). The knob can be placed into the hole to efficiently associate the polypeptides of the Fc domains differing in amino acid sequence (WO1996/027011; Ridgway J B et al., Protein Engineering (1996) 9, 617-621; and Merchant A M et al. Nature Biotechnology (1998) 16, 677-681).

In addition to this technique, a further alternative technique known in the art may be used for forming the multispecific antibody of the present invention. A portion of CH3 of one antibody H chain is converted to its counterpart IgA-derived sequence, and its complementary portion in CH3 of the other H chain is converted to its counterpart IgA-derived sequence. Use of the resulting strand-exchange engineered domain CH3 can cause efficient association between the polypeptides differing in sequence through complementary CH3 association (Protein Engineering Design & Selection, 23; 195-202, 2010). By use of this technique known in the art, the multispecific antibody of interest can also be efficiently formed.

Alternatively, the multispecific antibody may be formed by, for example, an antibody preparation technique using antibody CH1-CL association and VH-VL association as described in WO2011/028952, a technique of preparing a bispecific antibody using separately prepared monoclonal antibodies (Fab arm exchange) as described in WO2008/119353 and WO2011/131746, a technique of controlling the association between antibody heavy chain CH3 domains as described in WO2012/058768 and WO2013/063702, a technique of preparing a bispecific antibody constituted by two types of light chains and one type of heavy chain as described in WO2012/023053, or a technique of preparing a bispecific antibody using two bacterial cell lines each expressing an antibody half-molecule consisting of one H chain and one L chain as described in Christoph et al. (Nature Biotechnology Vol. 31, p. 753-758 (2013)). In addition to these association techniques, CrossMab technology, a known hetero light chain association technique of associating a light chain forming a variable region binding to a first epitope and a light chain forming a variable region binding to a second epitope to a heavy chain forming the variable region binding to the first epitope and a heavy chain forming the variable region binding to the second epitope, respectively (Scaefer et al., Proc. Natl. Acad. Sci. U.S.A. (2011) 108, 11187-11192), can also be used for preparing a multispecific or multiparatopic antigen-binding molecule provided by the present invention. Examples of the technique of preparing a bispecific antibody using separately prepared monoclonal antibodies can include a method which involves promoting antibody heterodimerization by placing monoclonal antibodies with a particular amino acid substituted in a heavy chain CH3 domain under reductive conditions to obtain the desired bispecific antibody. Examples of the amino acid substitution site preferred for this method can include a residue at EU numbering position 392 and a residue at EU numbering position 397 in the CH3 domain. Furthermore, the bispecific antibody can also be prepared by use of an antibody in which one to three pairs of amino acid residues selected from the following amino acid residue pairs (1) to (3) in the first H chain CH3 domain carry the same electric charge: (1) amino acid residues at EU numbering positions 356 and 439 contained in the H chain CH3 domain; (2) amino acid residues at EU numbering positions 357 and 370 contained in the H chain CH3 domain; and (3) amino acid residues at EU numbering positions 399 and 409 contained in the H chain CH3 domain. The bispecific antibody can also be prepared by use of the antibody in which one to three pairs of amino acid residues are selected from the amino acid residue pairs (1) to (3) in the second H chain CH3 domain different from the first H chain CH3 domain so as to correspond to the amino acid residue pairs (1) to (3) carrying the same electric charge in the first H chain CH3 domain and to carry opposite electric charge from their corresponding amino acid residues in the first H chain CH3 domain (WO2015/046467).

Even if the multispecific antibody of interest cannot be formed efficiently, the multispecific antibody of the present invention may be obtained by the separation and purification of the multispecific antibody of interest from among produced antibodies. For example, the previously reported method involves introducing amino acid substitution to the variable domains of two types of H chains to impart thereto difference in isoelectric point so that two types of homodimers and the heterodimerized antibody of interest can be separately purified by ion-exchanged chromatography (WO2007114325). A method using protein A to purify a heterodimerized antibody consisting of a mouse IgG2a H chain capable of binding to protein A and a rat IgG2b H chain incapable of binding to protein A has previously been reported as a method for purifying the heterodimer (WO98050431 and WO95033844). Alternatively, amino acid residues at EU numbering positions 435 and 436 that constitute the protein A-binding site of IgG may be substituted by amino acids, such as Tyr and His, which offer the different strength of protein A binding, and the resulting H chain is used to change the interaction of each H chain with protein A. As a result, only the heterodimerized antibody can be efficiently purified by use of a protein A column.

A plurality of, for example, two or more of these techniques may be used in combination. Also, these techniques can be appropriately applied separately to the two H chains to be associated. On the basis of, but separately from the form thus altered, the antigen-binding molecule of the present invention may be prepared as an antigen-binding molecule having an amino acid sequence identical thereto.

The alteration of an amino acid sequence can be performed by various methods known in the art. Examples of these methods that may be performed can include, but are not limited to, methods such as site-directed mutagenesis (Hashimoto-Gotoh, T, Mizuno, T, Ogasahara, Y, and Nakagawa, M. (1995) An oligodeoxyribonucleotide-directed dual amber method for site-directed mutagenesis. Gene 152, 271-275; Zoller, M J, and Smith, M. (1983) Oligonucleotide-directed mutagenesis of DNA fragments cloned into M13 vectors. Methods Enzymol. 100, 468-500; Kramer, W, Drutsa, V, Jansen, H W, Kramer, B, Pflugfelder, M, and Fritz, H J (1984) The gapped duplex DNA approach to oligonucleotide-directed mutation construction. Nucleic Acids Res. 12, 9441-9456; Kramer W, and Fritz H J (1987) Oligonucleotide-directed construction of mutations via gapped duplex DNA Methods. Enzymol. 154, 350-367; and Kunkel, T A (1985) Rapid and efficient site-specific mutagenesis without phenotypic selection. Proc Natl Acad Sci USA. 82, 488-492), PCR mutagenesis, and cassette mutagenesis.

The "antigen-binding molecule" of the present invention may be an antibody fragment that comprises both of a heavy chain and a light chain constituting the "antibody variable region" of the present invention in a single polypeptide chain, but lacks a constant region. Such an antibody fragment may be, for example, diabody (Db), a single-chain antibody, or sc(Fab')2.

Db is a dimer constituted by two polypeptide chains (e.g., Holliger P et al., Proc. Natl. Acad. Sci. USA 90: 6444-6448 (1993); EP404,097; and WO93/11161). These polypeptide chains are linked through a linker as short as, for example, approximately 5 residues, such that an L chain variable domain (VL) and an H chain variable domain (VH) on the same polypeptide chain cannot be paired with each other.

Because of this short linker, VL and VH encoded on the same polypeptide chain cannot form single-chain Fv and instead, are dimerized with VH and VL, respectively, on another polypeptide chain, to form two antigen-binding sites.

Examples of the single-chain antibody include sc(Fv)2. The sc(Fv)2 is a single-chain antibody having one chain constituted by four variable domains, i.e., two VLs and two VHs, linked via linkers such as peptide linkers (J Immunol. Methods (1999) 231 (1-2), 177-189). These two VHs and VLs may be derived from different monoclonal antibodies. Preferred examples thereof include bispecific sc(Fv)2, which recognizes two types of epitopes present in the same antigen, as disclosed in Journal of Immunology (1994) 152 (11), 5368-5374. The sc(Fv)2 can be prepared by a method generally known to those skilled in the art. For example, the sc(Fv)2 can be prepared by connecting two scFvs via a linker such as a peptide linker.

Examples of the configuration of the antigen-binding domains constituting the sc(Fv)2 described herein include an antibody in which two VHs and two VLs are aligned as VH, VL, VH, and VL (i.e., [VH]-linker-[VL]-linker-[VH]-linker-[VL]) in this order starting at the N-terminus of the single-chain polypeptide. The order of two VHs and two VLs is not particularly limited to the configuration described above and may be any order of arrangement. Examples thereof can also include the following arrangements:

[VL]-linker-[VH]-linker-[VH]-linker-[VL],
[VH]-linker-[VL]-linker-[VL]-linker-[VH],
[VH]-linker-[VH]-linker-[VL]-linker-[VL],
[VL]-linker-[VL]-linker-[VH]-linker-[VH], and
[VL]-linker-[VH]-linker-[VL]-linker-[VH].

The molecular form of the sc(Fv)2 is also described in detail in WO2006/132352. On the basis of the description therein, those skilled in the art can appropriately prepare the desired sc(Fv)2 in order to prepare the antigen-binding molecule disclosed in the present specification.

The antigen-binding molecule of the present invention may be conjugated with a carrier polymer such as PEG or an organic compound such as an anticancer agent. Also, a sugar chain can be preferably added to the antigen-binding molecule of the present invention by the insertion of a glycosylation sequence for the purpose of producing the desired effects.

For example, an arbitrary peptide linker that can be introduced by genetic engineering, or a synthetic compound linker (e.g., a linker disclosed in Protein Engineering, 9 (3), 299-305, 1996) can be used as the linker to link the antibody variable domains. In the present invention, a peptide linker is preferred. The length of the peptide linker is not particularly limited and can be appropriately selected by those skilled in the art according to the purpose. The length is preferably 5 or more amino acids (the upper limit is not particularly limited and is usually 30 or less amino acids, preferably 20 or less amino acids), particularly preferably 15 amino acids. When the sc(Fv)2 contains three peptide linkers, all of these peptide linkers used may have the same lengths or may have different lengths.

Examples of the peptide linker can include

```
Ser,

Gly-Ser,

Gly-Gly-Ser,

Ser-Gly-Gly,

                                        (SEQ ID NO: 5)
Gly-Gly-Gly-Ser,

                                        (SEQ ID NO: 6)
Ser-Gly-Gly-Gly,

                                        (SEQ ID NO: 7)
Gly-Gly-Gly-Gly-Ser,

                                        (SEQ ID NO: 8)
Ser-Gly-Gly-Gly-Gly,

                                        (SEQ ID NO: 9)
Gly-Gly-Gly-Gly-Gly-Ser,

                                       (SEQ ID NO: 10)
Ser-Gly-Gly-Gly-Gly-Gly,

                                       (SEQ ID NO: 11)
Gly-Gly-Gly-Gly-Gly-Gly-Ser,

                                       (SEQ ID NO: 12)
Ser-Gly-Gly-Gly-Gly-Gly-Gly,

(Gly-Gly-Gly-Gly-Ser (SEQ ID NO: 7))n,
and

(Ser-Gly-Gly-Gly-Gly (SEQ ID NO: 8))n,
```

wherein n is an integer of 1 or larger.

However, the length or sequence of the peptide linker can be appropriately selected by those skilled in the art according to the purpose.

The synthetic compound linker (chemical cross-linking agent) is a cross-linking agent usually used in the cross-linking of peptides, for example, N-hydroxysuccinimide (NHS), disuccinimidyl suberate (DSS), bis(sulfosuccinimidyl) suberate (BS3), dithiobis(succinimidyl propionate) (DSP), dithiobis(sulfosuccinimidyl propionate) (DTSSP), ethylene glycol bis(succinimidyl succinate) (EGS), ethylene glycol bis(sulfosuccinimidyl succinate) (sulfo-EGS), disuccinimidyl tartrate (DST), disulfosuccinimidyl tartrate (sulfo-DST), bis[2-(succinimidoxycarbonyloxy)ethyl]sulfone (BSOCOES), or bis[2-(sulfosuccinimidoxycarbonyloxy) ethyl]sulfone (sulfo-BSOCOES).

These cross-linking agents are commercially available.

Three linkers are usually necessary for linking four antibody variable domains. All of these linkers used may be the same linkers or may be different linkers.

The F(ab')2 comprises two light chains and two heavy chains containing a constant region (CH1 domains and a portion of CH2 domains) so as to form the interchain disulfide bond between these two heavy chains. The F(ab')2 constituting a polypeptide associate disclosed in the present specification can be preferably obtained by the partial digestion of, for example, a whole monoclonal antibody having the desired antigen-binding domains with a proteolytic enzyme such as pepsin followed by the removal of an Fc fragment adsorbed on a protein A column. Such a proteolytic enzyme is not particularly limited as long as the enzyme is capable of digesting a whole antibody to restrictively form $F(ab')_2$ under appropriately set reaction conditions (e.g., pH) of the enzyme. Examples thereof can include pepsin and ficin.

The antigen-binding molecule of the present invention can further contain additional alteration in addition to the amino acid alteration mentioned above. The additional alteration can be selected from, for example, amino acid substitution, deletion, and modification, and a combination thereof.

For example, the antigen-binding molecule of the present invention can be further altered arbitrarily, substantially without changing the intended functions of the molecule. Such a mutation can be performed, for example, by the conservative substitution of amino acid residues. Alternatively, even alteration to change the intended functions of the antigen-binding molecule of the present invention may be carried out as long as the functions changed by such alteration fall within the object of the present invention.

The alteration of an amino acid sequence according to the present invention also includes posttranslational modification. Specifically, the posttranslational modification can refer to the addition or deletion of a sugar chain. The antigen-binding molecule of the present invention, for example, having an IgG1-type constant region, can have a sugar chain-modified amino acid residue at EU numbering position 297. The sugar chain structure for use in the modification is not limited. In general, antibodies expressed by eukaryotic cells involve sugar chain modification in their constant regions. Thus, antibodies expressed by the following cells are usually modified with some sugar chain:

mammalian antibody-producing cells; and eukaryotic cells transformed with expression vectors comprising antibody-encoding DNAs.

In this context, the eukaryotic cells include yeast and animal cells. For example, CHO cells or HEK293H cells are typical animal cells for transformation with expression vectors comprising antibody-encoding DNAs. On the other hand, the antibody of the present invention also includes antibodies lacking sugar chain modification at the position. The antibodies having sugar chain-unmodified constant regions can be obtained by the expression of genes encoding these antibodies in prokaryotic cells such as *E. coli.*

The additional alteration according to the present invention may be more specifically, for example, the addition of sialic acid to a sugar chain in an Fc region (mAbs. 2010 September-October; 2 (5): 519-27).

When the antigen-binding molecule of the present invention has an Fc region, for example, amino acid substitution to improve binding activity against FcRn (J Immunol. 2006 Jan. 1; 176 (1): 346-56; J Biol Chem. 2006 Aug. 18; 281 (33): 23514-24; Int Immunol. 2006 December; 18 (12): 1759-69; Nat Biotechnol. 2010 February; 28 (2): 157-9; WO2006/019447; WO2006/053301; and WO2009/086320) or amino acid substitution to improve antibody heterogeneity or stability ((WO2009/041613)) may be added thereto.

In the present invention, the term “antibody” is used in the broadest sense and also includes any antibody such as monoclonal antibodies (including whole monoclonal antibodies), polyclonal antibodies, antibody variants, antibody fragments, multispecific antibodies (e.g., bispecific antibodies), chimeric antibodies, and humanized antibodies as long as the antibody exhibits the desired biological activity.

The antibody of the present invention is not limited by the type of its antigen, its origin, etc., and may be any antibody. Examples of the origin of the antibody can include, but are not particularly limited to, human antibodies, mouse antibodies, rat antibodies, and rabbit antibodies.

The antibody can be prepared by a method well known to those skilled in the art. For example, the monoclonal antibodies may be produced by a hybridoma method (Kohler and Milstein, Nature 256: 495 (1975)) or a recombination method (U.S. Pat. No. 4,816,567). Alternatively, the monoclonal antibodies may be isolated from phage-displayed antibody libraries (Clackson et al., Nature 352: 624-628 (1991); and Marks et al., J. Mol. Biol. 222: 581-597 (1991)). Also, the monoclonal antibodies may be isolated from single B cell clones (N. Biotechnol. 28 (5): 253-457 (2011)).

The humanized antibodies are also called reshaped human antibodies. Specifically, for example, a humanized antibody consisting of a non-human animal (e.g., mouse) antibody CDR-grafted human antibody is known in the art. General gene recombination approaches are also known for obtaining the humanized antibodies. Specifically, for example, overlap extension PCR is known in the art as a method for grafting mouse antibody CDRs to human FRs.

DNAs encoding antibody variable domains each comprising three CDRs and four FRs linked and DNAs encoding human antibody constant domains can be inserted into expression vectors such that the variable domain DNAs are fused in frame with the constant domain DNAs to prepare vectors for humanized antibody expression. These vectors having the inserts are transferred to hosts to establish recombinant cells. Then, the recombinant cells are cultured for the expression of the DNAs encoding the humanized antibodies to produce the humanized antibodies into the cultures of the cultured cells (see European Patent Publication No. EP 239400 and International Publication No. WO1996/002576).

If necessary, FR amino acid residue(s) may be substituted such that the CDRs of the reshaped human antibody form an appropriate antigen-binding site. For example, the amino acid sequence of FR can be mutated by the application of the PCR method used in the mouse CDR grafting to the human FRs.

The desired human antibody can be obtained by DNA immunization using transgenic animals having all repertoires of human antibody genes (see International Publication Nos. WO1993/012227, WO1992/003918, WO1994/

002602, WO1994/025585, WO1996/034096, and WO1996/033735) as immunized animals.

In addition, a technique of obtaining human antibodies by panning using human antibody libraries is also known. For example, a human antibody V region is expressed as a single-chain antibody (scFv) on the surface of phages by a phage display method. A phage expressing antigen-binding scFv can be selected. The gene of the selected phage can be analyzed to determine a DNA sequence encoding the V region of the antigen-binding human antibody. After the determination of the DNA sequence of the antigen-binding scFv, the V region sequence can be fused in frame with the sequence of the desired human antibody C region and then inserted to appropriate expression vectors to prepare expression vectors. The expression vectors are transferred to the preferred expression cells listed above for the expression of the genes encoding the human antibodies to obtain the human antibodies. These methods are already known in the art (see International Publication Nos. WO1992/001047, WO1992/020791, WO1993/006213, WO1993/011236, WO1993/019172, WO1995/001438, and WO1995/015388).

In addition to the phage display technique, for example, a technique using a cell-free translation system, a technique of displaying an antigen-binding molecule on the surface of a cell or a virus, and a technique using an emulsion are known as techniques for obtaining a human antibody by panning using a human antibody library. For example, a ribosome display method which involves forming a complex of mRNA and a translated protein via a ribosome by the removal of a stop codon, etc., a cDNA or mRNA display method which involves covalently binding a translated protein to a gene sequence using a compound such as puromycin, or a CIS display method which involves forming a complex of a gene and a translated protein using a nucleic acid-binding protein can be used as the technique using a cell-free translation system. The phage display method as well as an *E. coli* display method, a gram-positive bacterium display method, a yeast display method, a mammalian cell display method, a virus display method, or the like can be used as the technique of displaying an antigen-binding molecule on the surface of a cell or a virus. For example, an in vitro virus display method using a gene and a translation-related molecule enclosed in an emulsion can be used as the technique using an emulsion. These methods have already been known in the art (Nat Biotechnol. 2000 December; 18 (12): 1287-92; Nucleic Acids Res. 2006; 34 (19): e127; Proc Natl Acad Sci USA. 2004 Mar. 2; 101 (9): 2806-10; Proc Natl Acad Sci USA. 2004 Jun. 22; 101 (25): 9193-8; Protein Eng Des Sel. 2008 April; 21 (4): 247-55; Proc Natl Acad Sci USA. 2000 Sep. 26; 97 (20): 10701-5; MAbs. 2010 September-October; 2 (5): 508-18; and Methods Mol Biol. 2012; 911: 183-98).

The variable regions constituting the antibody of the present invention can be variable regions that recognize an arbitrary antigen.

In the present specification, the "antigen" is not particularly limited and may be any antigen. Examples of the antigen include 17-IA, 4-1 BB, 4Dc, 6-keto-PGF1a, 8-iso-PGF2a, 8-oxo-dG, A1 Adenosine Receptor, A33, ACE, ACE-2, Activin, Activin A, Activin AB, Activin B, Activin C, Activin RIA, Activin RIA ALK-2, Activin RIB ALK-4, Activin RITA, Activin RIIB, ADAM, ADAM10, ADAM12, ADAM15, ADAM17/TACE, ADAMS, ADAMS, ADAMTS, ADAMTS4, ADAMTS5, Addressins, adiponectin, ADP ribosyl cyclase-1, aFGF, AGE, ALCAM, ALK, ALK-1, ALK-7, allergen, alpha1-antichemotrypsin, alpha1-antitrypsin, alpha-synuclein, alpha-V/beta-1 antagonist, aminin, amylin, amyloid beta, amyloid immunoglobulin heavy chain variable region. amyloid immunoglobulin light chain variable region, Androgen, ANG, angiotensinogen, Angiopoietin ligand-2, anti-Id, antithrombinIII, Anthrax, APAF-1, APE, APJ, apo A1, apo serum amyloid A, Apo-SAA, APP, APRIL, AR, ARC, ART, Artemin, ASPARTIC, Atrial natriuretic factor, Atrial natriuretic peptide, atrial natriuretic peptides A, atrial natriuretic peptides B, atrial natriuretic peptides C, av/b3 integrin, Axl, B7-1, B7-2, B7-H, BACE, BACE-1, *Bacillus anthracia* protective antigen, Bad, BAFF, BAFF-R, Bag-1, BAK, Bax, BCA-1, BCAM, BcI, BCMA, BDNF, b-ECGF, beta-2-microglobulin, betalactamase, bFGF, BID, Bik, BIM, BLC, BL-CAM, BLK, B-lymphocyte Stimulator (BIyS), BMP, BMP-2 (BMP-2a), BMP-3 (Osteogenin), BMP-4 (BMP-2b), BMP-5, BMP-6 (Vgr-1), BMP-7 (OP-1), BMP-8 (BMP-8a), BMPR, BMPR-IA (ALK-3), BMPR-IB (ALK-6), BMPR-II (BRK-3), BMPs, BOK, Bombesin, Bone-derived neurotrophic factor, bovine growth hormone, BPDE, BPDE-DNA, BRK-2, BTC, B-lymphocyte cell adhesion molecule, C10, C1-inhibitor, C1q, C3, C3a, C4, C5, C5a (complement 5a), CA125, CAD-8, Cadherin-3, Calcitonin, cAMP, Carbonic anhydrase-IX, carcinoembryonic antigen (CEA), carcinoma-associated antigen, Cardiotrophin-1, Cathepsin A, Cathepsin B, Cathepsin C/DPPI, Cathepsin D, Cathepsin E, Cathepsin H, Cathepsin L, Cathepsin O, Cathepsin S, Cathepsin V, Cathepsin X/Z/P, CBL, CCI, CCK2, CCL, CCL1/I-309, CCL11/Eotaxin, CCL12/MCP-5, CCL13/MCP-4, CCL14/HCC-1, CCL15/HCC-2, CCL16/HCC-4, CCL17/TARC, CCL18/PARC, CCL19/ELC, CCL2/MCP-1, CCL20/MIP-3-alpha, CCL21/SLC, CCL22/MDC, CCL23/MPIF-1, CCL24/Eotaxin-2, CCL25/TECK, CCL26/Eotaxin-3, CCL27/CTACK, CCL28/MEC, CCL3/M1P-1-alpha, CCL3L1/LD-78-beta, CCL4/MIP-1-beta, CCL5/RANTES, CCL6/C10, CCL7/MCP-3, CCL8/MCP-2, CCL9/10/MTP-1-gamma, CCR, CCR1, CCR10, CCR2, CCR3, CCR4, CCR5, CCR6, CCR7, CCR8, CCR9, CD1, CD10, CD105, CD11a, CD11b, CD11c, CD123, CD13, CD137, CD138, CD14, CD140a, CD146, CD147, CD148, CD15, CD152, CD16, CD164, CD18, CD19, CD2, CD20, CD21, CD22, CD23, CD25, CD26, CD27L, CD28, CD29, CD3, CD30, CD30L, CD32, CD33 (p67 proteins), CD34, CD37, CD38, CD3E, CD4, CD40, CD40L, CD44, CD45, CD46, CD49a, CD49b, CD5, CD51, CD52, CD54, CD55, CD56, CD6, CD61, CD64, CD66e, CD7, CD70, CD74, CD8, CD80 (B7-1), CD89, CD95, CD105, CD158a, CEA, CEACAM5, CFTR, cGMP, CGRP receptor, CINC, CKb8-1, Claudin18, CLC, *Clostridium botulinum* toxin, *Clostridium difficile* toxin, *Clostridium perfringens* toxin, c-Met, CMV, CMV UL, CNTF, CNTN-1, complement factor 3 (C3), complement factor D, corticosteroid-binding globulin, Colony stimulating factor-1 receptor, COX, C-Ret, CRG-2, CRTH2, CT-1, CTACK, CTGF, CTLA-4, CX3CL1/Fractalkine, CX3CR1, CXCL, CXCL1/Gro-alpha, CXCL10, CXCL11/I-TAC, CXCL12/SDF-1-alpha/beta, CXCL13/BCA-1, CXCL14/BRAK, CXCL15/Lungkine. CXCL16, CXCL16, CXCL2/Gro-beta CXCL3/Gro-gamma, CXCL3, CXCL4/PF4, CXCL5/ENA-78, CXCL6/GCP-2, CXCL7/NAP-2, CXCL8/IL-8, CXCL9/Mig, CXCL10/IP-10, CXCR, CXCR1, CXCR2, CXCR3, CXCR4, CXCR5, CXCR6, cystatin C, cytokeratin tumor-associated antigen, DAN, DCC, DcR3, DC-SIGN, Decay accelerating factor, Delta-like protein ligand 4, des(1-3)-IGF-1 (brain IGF-1), Dhh, DHICA oxidase, Dickkopf-1, digoxin, Dipeptidyl peptidase IV, DK1, DNAM-1, Dnase, Dpp, DPPIV/CD26, Dtk, ECAD, EDA, EDA-A1, EDA-A2, EDAR, EGF, EGFR (ErbB-1), EGF like domain containing protein 7, Elastase, elastin, EMA, EMMPRIN, ENA, ENA-78, Endosialin, endothelin receptor, endotoxin, Enkephalinase, eNOS, Eot, Eotaxin, Eotaxin-2, eotaxini, EpCAM, Ephrin B2/EphB4, Epha2 tyrosine kinase receptor, epidermal growth factor receptor (EGFR), ErbB2 receptor, ErbB3 tyrosine kinase receptor, ERCC, EREG, erythropoietin (EPO), Erythropoietin receptor, E-selectin, ET-1, Exodus-2, F protein of RSV, F10, F11, F12, F13, F5, F9, Factor Ia, Factor IX, Factor Xa, Factor VII, factor VIII, Factor VIIIc, Fas, FcalphaR, FcepsilonRI, FcgammaIIb, FcgammaRI, FcgammaRIIa, FcgammaRIIIa, FcgammaRIIIb, FcRn, FEN-1, Ferritin, FGF, FGF-19, FGF-2, FGF-2 receptor, FGF-3, FGF-8, FGF-acidic, FGF-basic, FGFR, FGFR-3, Fibrin, fibroblast activation protein (FAP), fibroblast growth factor, fibroblast growth factor-10, fibronectin, FL, FLIP, Flt-3, FLT3 ligand, Folate receptor, follicle stimulating hormone (FSH), Fractalkine (CX3C), free heavy chain, free light chain, FZD1, FZD10, FZD2, FZD3, FZD4, FZD5, FZD6, FZD7, FZD8, FZD9, G250, Gas 6, GCP-2, GCSF, G-CSF, G-CSF receptor, GD2, GD3, GDF, GDF-1, GDF-15 (MIC-1), GDF-3 (Vgr-2), GDF-5 (BMP-14/CDMP-1), GDF-6 (BMP-13/CDMP-2), GDF-7 (BMP-12/CDMP-3), GDF-8 (Myostatin), GDF-9, GDNF, Gelsolin, GFAP, GF-CSF, GFR-alpha1, GFR-alpha2, GFR-alpha3, GF-β1, gH envelope glycoprotein, GITR, Glucagon, Glucagon receptor, Glucagon-like peptide 1 receptor, Glut 4, Glutamate carboxypeptidase II, glycoprotein hormone receptors, glycoprotein IIb/IIIa (GP IIb/IIIa), Glypican-3, GM-CSF, GM-CSF receptor, gp130, gp140, gp72, granulocyte-CSF (G-CSF), GRO/MGSA, Growth hormone releasing factor, GRO-β, GRO-γ, *H. pylori*, Hapten (NP-cap or NIP-cap), HB-EGF, HCC, HCC 1, HCMV gB envelope glycoprotein, HCMV UL, Hemopoietic growth factor (HGF), Hep B gp120, heparanase, heparin cofactor II, hepatic growth factor, *Bacillus anthracis* protective antigen, Hepatitis C virus E2 glycoprotein, Hepatitis E, Hepcidin, Her1, Her2/neu (ErbB-2), Her3 (ErbB-3), Her4 (ErbB-4), herpes simplex virus (HSV) gB glycoprotein, HGF, HGFA, High molecular weight melanoma-associated antigen (HMW-MAA), HIV envelope proteins such as GP120, HIV MIB gp 120 V3 loop, HLA, HLA-DR, HM1.24, HMFG PEM, HMGB-1, HRG, Hrk, HSP47, Hsp90, HSV gD glycoprotein, human cardiac myosin, human cytomegalovirus (HCMV), human growth hormone (hGH), human serum albumin, human tissue-type plasminogen activator (t-PA), Huntingtin, HVEM, IAP, ICAM, ICAM-1, ICAM-3, ICE, ICOS, IFN-alpha, IFN-beta, IFN-gamma, IgA, IgA receptor, IgE, IGF, IGF binding proteins, IGF-1, IGF-1 R, IGF-2, IGFBP, IGFR, IL, IL-1, IL-10, IL-10 receptors, IL-11, IL-11 receptors, IL-12, IL-12 receptors, IL-13, IL-13 receptors, IL-15, IL-15 receptors, IL-16, IL-16 receptors, IL-17, IL-17 receptors, IL-18 (IGIF), IL-18 receptors, IL-1alpha, IL-1beta, IL-1 receptors, IL-2, IL-2 receptors, IL-20, IL-20 receptors, IL-21, IL-21 receptors, IL-23, IL-23 receptors, IL-2 receptors, IL-3, IL-3 receptors, IL-31, IL-31 receptors, IL-3 receptors, IL-4, IL-4 receptors IL-5, IL-5 receptors, IL-6, IL-6 receptors, IL-7, IL-7 receptors, IL-8, IL-8 receptors, IL-9, IL-9 receptors, immunoglobulin immune complex, immunoglobulins, INF-alpha, INF-alpha receptors, INF-beta, INF-beta receptors, INF-gamma, INF-gamma receptors, IFN type-I, IFN type-I receptor, influenza, inhibin, Inhibin α, Inhibin β, iNOS, insulin, Insulin A-chain, Insulin B-chain, Insulin-like growth factor 1, insulin-like growth factor 2, insulin-like growth factor binding proteins, integrin, integrin alpha2, integrin alpha3, integrin alpha4, integrin alpha4/beta1, integrin alpha-V/beta-3, integrin alpha-V/beta-6, integrin alpha4/beta7, integrin alpha5/beta1, integrin alpha5/beta3, integrin alpha5/beta6, integrin alpha σ (alphaV), integrin alpha θ, integrin beta1, integrin beta2, integrin beta3(GPIIb-IIIa), IP-10, I-TAC, JE, kalliklein, Kallikrein 11, Kallikrein 12, Kallikrein 14, Kallikrein 15, Kallikrein 2, Kallikrein 5, Kallikrein 6, Kallikrein L1, Kallikrein L2, Kallikrein L3, Kallikrein L4, kallistatin, KC, KDR, Keratinocyte Growth Factor (KGF), Keratinocyte Growth Factor-2 (KGF-2), KGF, killer immunoglobulin-like receptor, kit ligand (KL), Kit tyrosine kinase, laminin 5, LAMP, LAPP (Amylin, islet-amyloid polypeptide), LAP (TGF-1), latency associated peptide, Latent TGF-1, Latent TGF-1 bp1, LBP, LDGF, LDL, LDL receptor, LECT2, Lefty, Leptin, leutinizing hormone (LH), Lewis-Y antigen, Lewis-Y related antigen, LFA-1, LFA-3, LFA-3 receptors, Lfo, LIF, LIGHT, lipoproteins, LIX, LKN, Lptn, L-Selectin, LT-a, LT-b, LTB4, LTBP-1, Lung surfactant, Luteinizing hormone, Lymphotactin, Lymphotoxin Beta Receptor, Lysosphingolipid receptor, Mac-1, macrophage-CSF (M-CSF), MAdCAM, MAG, MAP2, MARC, maspin, MCAM, MCK-2, MCP, MCP-1, MCP-2, MCP-3, MCP-4, MCP-I (MCAF), M-CSF, MDC, MDC (67 a.a.), MDC (69 a.a.), megsin, Mer, MET tyrosine kinase receptor family, METALLOPROTEASES, Membrane glycoprotein OX2, Mesothelin, MGDF receptor, MGMT, MHC (HLA-DR), microbial protein, MIF, MIG, MIP, MIP-1α, MIP-1β, MIP-3α, MIP-4, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, monocyte attractant protein, monocyte colony inhibitory factor, mouse gonadotropin-associated peptide, MPIF, Mpo, MSK, MSP, MUC-16, MUC18, mucin (Mud), Muellerian-inhibiting substance, Mug, MuSK, Myelin associated glycoprotein, myeloid progenitor inhibitor factor-1 (MPIF-I), NAIP, Nanobody, NAP, NAP-2, NCA 90, NCAD, N-Cadherin, NCAM, Neprilysin, Neural cell adhesion molecule, neroserpin, Neuronal growth factor (NGF), Neurotrophin-3, Neurotrophin-4, Neurotrophin-6, Neuropilin 1, Neurturin, NGF-beta, NGFR, NKG20, N-methionyl human growth hormone, nNOS, NO, Nogo-A, Nogo receptor, non-structural protein type 3 (NS3) from the hepatitis C virus, NOS, Npn, NRG-3, NT, NT-3, NT-4, NTN, OB, OGG1, Oncostatin M, OP-2, OPG, OPN, OSM, OSM receptors, osteoinductive factors, osteopontin, OX40L, OX40R, oxidized LDL, p150, p95, PADPr, parathyroid hormone, PARC, PARP, PBR, PBSF, PCAD, P-Cadherin, PCNA, PCSK9, PDGF, PDGF receptor, PDGF-AA, PDGF-AB, PDGF-BB, PDGF-D, PDK-1, PECAM, PEDF, PEM, PF-4, PGE, PGF, PGI2, PGJ2, PIGF, PIN, PLA2, Placenta growth factor, placental alkaline phosphatase (PLAP), placental lactogen, plasminogen activator inhibitor-1, platelet-growth factor, plgR, PLP, poly glycol chains of different size (e.g. PEG-20, PEG-30, PEG40), PP14, prekallikrein, prion protein, procalcitonin, Programmed cell death protein 1, proinsulin, prolactin, Proprotein convertase PC9, prorelaxin, prostate specific membrane antigen (PSMA), Protein A, Protein C, Protein D, Protein S, Protein Z, PS, PSA, PSCA, PsmAr, PTEN, PTHrp, Ptk, PTN, P-selectin glycoprotein ligand-1, R51, RAGE, RANK, RANKL, RANTES, relaxin, Relaxin A-chain, Relaxin B-chain, renin, respiratory syncytial virus (RSV) F, Ret, reticulon 4, Rheumatoid factors, RLI P76, RPA2, RPK-1, RSK, RSV Fgp, S100, RON-8, SCF/KL, SCGF, Sclerostin, SDF-1, SDF1α, SDF1β, SERINE, Serum Amyloid P, Serum albumin, sFRP-3, Shh, Shiga like toxin II, SIGIRR, SK-1, SLAM, SLPI, SMAC, SMDF, SMOH, SOD, SPARC, sphingosine 1-phosphate receptor 1, Staphylococcal lipoteichoic acid, Stat, STEAP, STEAP-II, stem cell factor (SCF), streptokinase, superoxide dismutase, syndecan-1, TACE, TACI, TAG-72 (tumor-associated glycoprotein-72), TARC, TB, TCA-3, T-cell receptor alpha/beta, TdT, TECK, TEM1, TEM5, TEM7, TEM8, Tenascin, TERT, testicular PLAP-like alkaline phosphatase, TfR, TGF, TGF-alpha, TGF-beta, TGF-beta Pan Specific, TGF-beta RII, TGF-beta RIIb, TGF-beta RIII, TGF-beta R1 (ALK-5), TGF-beta1, TGF-beta2, TGF-beta3, TGF-beta4, TGF-beta5, TGF-I, Thrombin, thrombopoietin (TPO), Thymic stromal lymphoprotein receptor, Thymus Ck-1, thyroid stimulating hormone (TSH), thyroxine, thyroxine-binding globulin, Tie, TIMP, TIQ, Tissue Factor, tissue factor protease inhibitor, tissue factor protein, TMEFF2, Tmpo, TMPRSS2, TNF receptor I, TNF receptor II, TNF-alpha, TNF-beta, TNF-beta2, TNFc, TNF-RI, TNF-RII, TNFRSF10A (TRAIL R1 Apo-2/DR4), TNFRSF10B (TRAIL R2 DR5/KILLER/TRICK-2A/TRICK-B), TNFRSF10C (TRAIL R3 DcR1/LIT/TRID), TNFRSF10D (TRAIL R4 DcR2/TRUNDD), TNFRSF11A (RANK ODF R/TRANCE R), TNFRSF11B (OPG OCIF/TR1), TNFRSF12 (TWEAK R FN14), TNFRSF12A, TNFRSF13B (TACI), TNFRSF13C (BAFF R), TNFRSF14 (HVEM ATAR/HveA/LIGHT R/TR2), TNFRSF16 (NGFR p75NTR), TNFRSF17 (BCMA), TNFRSF18 (GITR AITR), TNFRSF19 (TROY TAJ/TRADE), TNFRSF19L (RELT), TNFRSF1A (TNF R1 CD120a/p55-60), TNFRSF1B (TNF RII CD120b/p75-80), TNFRSF21 (DR6), TNFRSF22 (DcTRAIL R2 TNFRH2), TNFRSF25 (DR3 Apo-3/LARD/TR-3/TRAMP/WSL-1), TNFRSF26 (TNFRH3), TNFRSF3 (LTbR TNF RIII/TNFC R), TNFRSF4 (OX40 ACT35/TXGP1 R), TNFRSF5 (CD40 p50), TNFRSF6 (Fas Apo-1/APT1/CD95), TNFRSF6B (DcR3 M68/TR6), TNFRSF7 (CD27), TNFRSF8 (CD30), TNFRSF9 (4-1 BB CD137/ILA), TNFRST23 (DcTRAIL R1 TNFRH1), TNFSF10 (TRAIL Apo-2 Ligand/TL2), TNFSF11 (TRANCE/RANK Ligand ODF/OPG Ligand), TNFSF12 (TWEAK Apo-3 Ligand/DR3 Ligand), TNFSF13 (APRIL TALL2), TNFSF13B (BAFF BLYS/TALL1/THANK/TNFSF20), TNFSF14 (LIGHT HVEM Ligand/LTg), TNFSF15 (TL1A/VEGI), TNFSF18 (GITR Ligand AITR Ligand/TL6), TNFSF1A (TNF-a Conectin/DIF/TNFSF2), TNFSF1B (TNF-b LTa/TNFSF1), TNFSF3 (LTb TNFC/p33), TNFSF4 (OX40 Ligand gp34/TXGP1), TNFSF5 (CD40 Ligand CD154/gp39/HIGM1/IMD3/TRAP), TNFSF6 (Fas Ligand Apo-1 Ligand/APT1 Ligand), TNFSF7 (CD27 Ligand CD70), TNFSF8 (CD30 Ligand CD153), TNFSF9 (4-1 BB Ligand CD137 Ligand), TNF-α, TNF-β, TNIL-I, toxic metabolite, TP-1, t-PA, Tpo, TRAIL, TRAIL R, TRAIL-R1, TRAIL-R2, TRANCE, transferrin receptor, transforming growth factors (TGF) such as TGF-alpha and TGF-beta, Transmembrane glycoprotein NMB, Transthyretin, TRF, Trk, TROP-2, Trophoblast glycoprotein, TSG, TSLP, Tumor Necrosis Factor (TNF), tumor-associated antigen CA 125, tumor-associated antigen expressing Lewis Y related carbohydrate, TWEAK, TXB2, Ung, uPAR, uPAR-1, Urokinase, VAP-1, vascular endothelial growth factor (VEGF), vaspin, VCAM, VCAM-1, VECAD, VE-Cadherin, VE-Cadherin-2, VEFGR-1 (flt-1), VEFGR-2, VEGF receptor (VEGFR), VEGFR-3 (flt-4), VEGI, VIM, Viral antigens, VitB12 receptor, Vitronectin receptor, VLA, VLA-1, VLA-4, VNR integrin, von Willebrand Factor (vWF), WIF-1, WNT1, WNT10A, WNT10B, WNT11, WNT16, WNT2, WNT2B/13, WNT3, WNT3A, WNT4, WNT5A, WNT5B, WNT6, WNT7A, WNT7B, WNT8A, WNT8B, WNT9A, WNT9B, XCL1, XCL2/SCM-1-beta, XCL1/Lymphotactin, XCR1, XEDAR, XIAP, and XPD.

One of the variable regions of the antibody included in the antigen-binding molecule of the present invention is capable of binding to "two different antigens", but cannot bind to these antigens at the same time, or is capable of binding to "three different antigens", but cannot bind to these antigens at the same time. The "first antigen" or the "second antigen" to which the variable region binds, or the "first antigen", the "second antigen", or the "fourth antigen" to which the variable region binds is preferably, for example, an immunocyte surface molecule (e.g., a T cell surface molecule, an NK cell surface molecule, a dendritic cell surface molecule, a B cell surface molecule, an NKT cell surface molecule, an MDSC cell surface molecule, and a macrophage surface molecule), or an antigen expressed not only on tumor cells, tumor vessels, stromal cells, and the like but on normal tissues (integrin, tissue factor, VEGFR, PDGFR, EGFR, IGFR, MET chemokine receptor, heparan sulfate proteoglycan, CD44, fibronectin, DR5, TNFRSF, etc.). As for the combination of the "first antigen" and the "second antigen" to which the variable region that is capable of binding to "two different antigens", but cannot bind to these antigens at the same time, binds, preferably, any one of the first antigen and the second antigen is, for example, a molecule specifically expressed on a T cell, and the other antigen is a molecule expressed on the surface of a T cell or any other immunocyte. In another embodiment of the combination of the "first antigen" and the "second antigen", preferably, any one of the first antigen and the second antigen is, for example, a molecule specifically expressed on a T cell, and the other antigen is a molecule that is expressed on an immunocyte and is different from the preliminarily selected antigen. Specific examples of the molecule specifically expressed on a T cell include CD3 and T cell receptors. Particularly, CD3 is preferred. In the case of, for example, human CD3, a site in the CD3 to which the antigen-binding molecule of the present invention binds may be any epitope present in a γ chain, δchain, or ε chain sequence constituting the human CD3. Particularly, an epitope present in the extracellular region of an ε chain in a human CD3 complex is preferred. The polynucleotide sequences of the γ chain, δ chain, and ε chain structures constituting CD3 are shown in SEQ ID NOs: 83 (NM_000073.2), 85 (NM_000732.4), and 87 (NM_000733.3), and the polypeptide sequences thereof are shown in SEQ ID NOs: 84 (NP_000064.1), 86 (NP_000723.1), and 88 (NP_000724.1) (RefSeq registration numbers are shown within the parentheses). Examples of the other antigen include Fcγ receptors, TLR, lectin, IgA, immune checkpoint molecules, TNF superfamily molecules, TNFR superfamily molecules, and NK receptor molecules.

As for the combination of the "first antigen", the "second antigen", and the "fourth antigen" to which the variable region that is capable of binding to "three different antigens", but cannot bind to these antigens at the same time, binds, preferably, any one of the first antigen, the second antigen, and the fourth antigen is, for example, a molecule specifically expressed on a T cell, and each of the remaining two antigens is a molecule expressed on the surface of a T cell or any other immunocyte. In another embodiment of the combination of the "first antigen", the "second antigen", and the "fourth antigen", preferably, any one of the first antigen, the second antigen, and the fourth antigen is, for example, a molecule specifically expressed on a T cell, and each of the remaining two antigens is a molecule that is expressed on an immunocyte and is different from the preliminarily selected antigen. Specific examples of the molecule specifically expressed on a T cell include CD3 and T cell receptors. Particularly, CD3 is preferred. In the case of, for example, human CD3, a site in the CD3 to which the antigen-binding molecule of the present invention binds may be any epitope present in a γ chain, δ chain, or c chain sequence constituting the human CD3. Particularly, an epitope present in the extracellular region of an ε chain in a human CD3 complex is preferred. The polynucleotide sequences of the γ chain, δ chain, and ε chain structures constituting CD3 are shown in SEQ ID NOs: 83 (NM_000073.2), 85 (NM_000732.4), and 87 (NM_000733.3), and the polypeptide sequences thereof are shown in SEQ ID NOs: 84 (NP_000064.1), 86 (NP_000723.1), and 88 (NP_000724.1) (RefSeq registration numbers are shown within the parentheses). Examples of the other antigen include Fcγ receptors, TLR, lectin, IgA, immune checkpoint molecules, TNF superfamily molecules, TNFR superfamily molecules, and NK receptor molecules.

Of the variable regions of the antibody included in the antigen-binding molecule of the present invention, the other variable region binds to a “third antigen” that is different from the “first antigen”, the “second antigen” and the “fourth antigen” mentioned above. The third antigen is preferably, for example, a tumor cell-specific antigen and also includes an antigen expressed in association with the malignant alteration of cells as well as an abnormal sugar chain that appears on cell surface or a protein molecule during the malignant transformation of cells. Specific examples thereof include ALK receptor (pleiotrophin receptor), pleiotrophin, KS 1/4 pancreatic cancer antigen, ovary cancer antigen (CA125), prostatic acid phosphate, prostate-specific antigen (PSA), melanoma-associated antigen p97, melanoma antigen gp75, high-molecular-weight melanoma antigen (HMW-MAA), prostate-specific membrane antigen, carcinoembryonic antigen (CEA), polymorphic epithelial mucin antigen, human milk fat globule antigen, colorectal tumor-associated antigen (e.g., CEA, TAG-72, CO17-1A, GICA 19-9, CTA-1, and LEA), Burkitt's lymphoma antigen 38.13, CD19, human B lymphoma antigen CD20, CD33, melanoma-specific antigen (e.g., ganglioside GD2, ganglioside GD3, ganglioside GM2, and ganglioside GM3), tumor-specific transplantation antigen (TSTA), T antigen, virus-induced tumor antigen (e.g., envelope antigens of DNA tumor virus and RNA tumor virus), colon CEA, oncofetal antigen α-fetoprotein (e.g., oncofetal trophoblastic glycoprotein 5T4 and oncofetal bladder tumor antigen), differentiation antigen (e.g., human lung cancer antigens L6 and L20), fibrosarcoma antigen, human T cell leukemia-associated antigen Gp37, newborn glycoprotein, sphingolipid, breast cancer antigen (e.g., EGFR (epithelial growth factor receptor)), NY-BR-16, NY-BR-16 and HER2 antigen (p185HER2), polymorphic epithelial mucin (PEM), malignant human lymphocyte antigen APO-1, differentiation antigen such as I antigen found in fetal erythrocytes, primary endoderm I antigen found in adult erythrocytes, I (Ma) found in embryos before transplantation or gastric cancer, M18 found in mammary gland epithelium, M39, SSEA-1 found in bone marrow cells, VEP8, VEP9, Myl, VIM-D5, D156-22 found in colorectal cancer, TRA-1-85 (blood group H), SCP-1 found in testis and ovary cancers, C14 found in colon cancer, F3 found in lung cancer, AH6 found in gastric cancer, Y hapten, Ley found in embryonic cancer cells, TL5 (blood group A), EGF receptor found in A431 cells, E1 series (blood group B) found in pancreatic cancer, FC10.2 found in embryonic cancer cells, gastric cancer antigen, CO-514 (blood group Lea) found in adenocarcinoma, NS-10 found in adenocarcinoma, CO-43 (blood group Leb), G49 found in A431 cell EGF receptor, MH2 (blood group ALeb/Ley) found in colon cancer, 19.9 found in colon cancer, gastric cancer mucin, T5A7 found in bone marrow cells, R24 found in melanoma, 4.2, GD3, D1.1, OFA-1, GM2, OFA-2, GD2, and M1:22:25:8 found in embryonic cancer cells, SSEA-3 and SSEA-4 found in 4-cell to 8-cell embryos, cutaneous T cell lymphoma-associated antigen, MART-1 antigen, sialyl Tn (STn) antigen, colon cancer antigen NY-CO-45, lung cancer antigen NY-LU-12 variant A, adenocarcinoma antigen ART1, paraneoplastic associated brain-testis-cancer antigen (onconeuronal antigen MA2 and paraneoplastic neuronal antigen), neuro-oncological ventral antigen 2 (NOVA2), blood cell cancer antigen gene 520, tumor-associated antigen CO-029, tumor-associated antigen MAGE-C1 (cancer/testis antigen CT7), MAGE-B1 (MAGE-XP antigen), MAGE-B2 (DAM6), MAGE-2, MAGE-4a, MAGE-4b MAGE-X2, cancer-testis antigen (NY-EOS-1), YKL-40, and any fragment of these polypeptides, and modified structures thereof (aforementioned modified phosphate groups, sugar chains, etc.), EpCAM, EREG, CA19-9, CA15-3, sialyl SSEA-1 (SLX), HER2, PSMA, CEA, and CLEC12A.

The antigen-binding molecule of the present invention can be produced by a method generally known to those skilled in the art. For example, the antibody can be prepared by a method given below, though the method for preparing the antibody of the present invention is not limited thereto. Many combinations of host cells and expression vectors are known in the art for antibody preparation by the transfer of isolated genes encoding polypeptides into appropriate hosts. All of these expression systems can be applied to the isolation of the antigen-binding molecule of the present invention. In the case of using eukaryotic cells as the host cells, animal cells, plant cells, or fungus cells can be appropriately used. Specifically, examples of the animal cells can include the following cells:

(1) mammalian cells such as CHO (Chinese hamster ovary cell line), COS (monkey kidney cell line), myeloma cells (Sp2/O, NS0, etc.), BHK (baby hamster kidney cell line), HEK293 (human embryonic kidney cell line with sheared adenovirus (Ad)5 DNA), PER. C6 cell (human embryonic retinal cell line transformed with the adenovirus type 5 (Ad5) E1A and E1B genes), Hela, and Vero (Current Protocols in Protein Science (May, 2001, Unit 5.9, Table 5.9.1));
(2) amphibian cells such as *Xenopus oocytes*; and
(3) insect cells such as sf9, sf21, and Tn5.

The antibody can also be prepared using *E. coli* (mAbs 2012 March-April; 4 (2): 217-225) or yeast (WO2000023579). The antibody prepared using *E. coli* is not glycosylated. On the other hand, the antibody prepared using yeast is glycosylated.

An antibody heavy chain-encoding DNA that encodes a heavy chain with one or more amino acid residues in a variable domain substituted by different amino acids of interest, and a DNA encoding a light chain of the antibody are expressed. The DNA that encodes a heavy chain or a light chain with one or more amino acid residues in a variable domain substituted by different amino acids of interest can be obtained, for example, by obtaining a DNA encoding an antibody variable domain prepared by a method known in the art against a certain antigen, and appropriately introducing substitution such that codons encoding the particular amino acids in the domain encode the different amino acids of interest.

Alternatively, a DNA encoding a protein in which one or more amino acid residues in an antibody variable domain prepared by a method known in the art against a certain antigen are substituted by different amino acids of interest may be designed in advance and chemically synthesized to obtain the DNA that encodes a heavy chain with one or more amino acid residues in a variable domain substituted by different amino acids of interest. The amino acid substitution site and the type of the substitution are not particularly limited. Examples of the region preferred for the amino acid alteration include solvent-exposed regions and loops in the variable region. Among others, CDR1, CDR2, CDR3, FR3, and loops are preferred. Specifically, Kabat numbering positions 31 to 35, 50 to 65, 71 to 74, and 95 to 102 in the H chain variable domain and Kabat numbering positions 24 to 34, 50 to 56, and 89 to 97 in the L chain variable domain are preferred. Kabat numbering positions 31, 52a to 61, 71 to 74, and 97 to 101 in the H chain variable domain and Kabat numbering positions 24 to 34, 51 to 56, and 89 to 96 in the L chain variable domain are more preferred.

The amino acid alteration is not limited to the substitution and may be deletion, addition, insertion, or modification, or a combination thereof.

The DNA that encodes a heavy chain with one or more amino acid residues in a variable domain substituted by different amino acids of interest can also be produced as separate partial DNAs. Examples of the combination of the partial DNAs include, but are not limited to: a DNA encoding a variable domain and a DNA encoding a constant domain; and a DNA encoding a Fab domain and a DNA encoding an Fc domain. Likewise, the light chain-encoding DNA can also be produced as separate partial DNAs.

These DNAs can be expressed by the following method: for example, a DNA encoding a heavy chain variable domain, together with a DNA encoding a heavy chain constant domain, is integrated to an expression vector to construct a heavy chain expression vector. Likewise, a DNA encoding a light chain variable domain, together with a DNA encoding a light chain constant domain, is integrated to an expression vector to construct a light chain expression vector. These heavy chain and light chain genes may be integrated to a single vector.

The DNA encoding the antibody of interest is integrated to expression vectors so as to be expressed under the control of expression control regions, for example, an enhancer and a promoter. Next, host cells are transformed with the resulting expression vectors and allowed to express antibodies. In this case, appropriate hosts and expression vectors can be used in combination.

Examples of the vectors include M13 series vectors, pUC series vectors, pBR322, pBluescript, and pCR-Script. In addition to these vectors, for example, pGEM-T, pDIRECT, or pT7 can also be used for the purpose of cDNA subcloning and excision.

Particularly, expression vectors are useful for using the vectors for the purpose of producing the antibody of the present invention. For example, when the host is *E. coli* such as JM109, DH5α, HB101, or XL1-Blue, the expression vectors indispensably have a promoter that permits efficient expression in *E. coli*, for example, lacZ promoter (Ward et al., Nature (1989) 341, 544-546; and FASEB J. (1992) 6, 2422-2427, which are incorporated herein by reference in their entirety), araB promoter (Better et al., Science (1988) 240, 1041-1043, which is incorporated herein by reference in its entirety), or T7 promoter. Examples of such vectors include the vectors mentioned above as well as pGEX-5X-1 (manufactured by Pharmacia), "QIAexpress system" (manufactured by Qiagen N. V.), pEGFP, and pET (in this case, the host is preferably BL21 expressing T7 RNA polymerase).

The vectors may contain a signal sequence for polypeptide secretion. In the case of production in the periplasm of *E. coli*, pelB signal sequence (Lei, S. P. et al., J. Bacteriol. (1987) 169, 4397, which is incorporated herein by reference in its entirety) can be used as the signal sequence for polypeptide secretion. The vectors can be transferred to the host cells by use of, for example, a Lipofectin method, a calcium phosphate method, or a DEAE-dextran method.

In addition to the expression vectors for *E. coli*, examples of the vectors for producing the polypeptide of the present invention include mammal-derived expression vectors (e.g., pcDNA3 (manufactured by Invitrogen Corp.), pEGF-BOS (Nucleic Acids. Res. 1990, 18 (17), p. 5322, which is incorporated herein by reference in its entirety), pEF, and pCDM8), insect cell-derived expression vectors (e.g., "Bac-to-BAC baculovirus expression system" (manufactured by GIBCO BRL), and pBacPAK8), plant-derived expression vectors (e.g., pMH1 and pMH2), animal virus-derived expression vectors (e.g., pHSV, pMV, and pAdexLcw), retrovirus-derived expression vectors (e.g., pZIPneo), yeast-derived expression vectors (e.g., "*Pichia* Expression Kit" (manufactured by Invitrogen Corp.), pNV11, and SP-Q01), and *Bacillus subtilis*-derived expression vectors (e.g., pPL608 and pKTH50).

For the purpose of expression in animal cells such as CHO cells, COS cells, NIH3T3 cells, or HEK293 cells, the vectors indispensably have a promoter necessary for intracellular expression, for example, SV40 promoter (Mulligan et al., Nature (1979) 277, 108, which is incorporated herein by reference in its entirety), MMTV-LTR promoter, EF1α promoter (Mizushima et al., Nucleic Acids Res. (1990) 18, 5322, which is incorporated herein by reference in its entirety), CAG promoter (Gene. (1991) 108, 193, which is incorporated herein by reference in its entirety), or CMV promoter and, more preferably, have a gene for screening for transformed cells (e.g., a drug resistance gene that can work as a marker by a drug (neomycin, G418, etc.)). Examples of the vectors having such properties include pMAM, pDR2, pBK-RSV, pBK-CMV, pOPRSV, and pOP13. In addition, EBNA1 protein may be coexpressed therewith for the purpose of increasing the number of gene copies. In this case, vectors having a replication origin OriP are used (Biotechnol Bioeng. 2001 Oct. 20; 75 (2): 197-203; and Biotechnol Bioeng. 2005 Sep. 20; 91 (6): 670-7).

An exemplary method intended to stably express the gene and increase the number of intracellular gene copies involves transforming CHO cells deficient in nucleic acid synthesis pathway with vectors having a DHFR gene serving as a complement thereto (e.g., pCHOI) and using methotrexate (MTX) in the gene amplification. An exemplary method intended to transiently express the gene involves using COS cells having an SV40 T antigen gene on their chromosomes to transform the cells with vectors having a replication origin of SV40 (pcD, etc.). A replication origin derived from polyomavirus, adenovirus, bovine papillomavirus (BPV), or the like can also be used. In order to increase the number of gene copies in the host cell system, the expression vectors can contain a selective marker such as an aminoglycoside phosphotransferase (APH) gene, a thymidine kinase (TK) gene, an *E. coli* xanthine guanine phosphoribosyltransferase (Ecogpt) gene, or a dihydrofolate reductase (dhfr) gene.

The antibody can be recovered, for example, by culturing the transformed cells and then separating the antibody from within the molecule-transformed cells or from the culture solution thereof. The antibody can be separated and purified by appropriately using in combination methods such as centrifugation, ammonium sulfate fractionation, salting out, ultrafiltration, C1q, FcRn, protein A and protein G columns, affinity chromatography, ion-exchanged chromatography, and gel filtration chromatography.

The technique mentioned above, such as the knobs-into-holes technology (WO1996/027011; Ridgway J B et al., Protein Engineering (1996) 9, 617-621; and Merchant A M et al., Nature Biotechnology (1998) 16, 677-681) or the technique of suppressing the unintended association between H chains by the introduction of electric charge repulsion (WO2006/106905), can be applied to a method for efficiently preparing the multispecific antibody.

The present invention further provides a method for producing the antigen-binding molecule of the present invention and specifically provides a method for producing an antigen-binding molecule comprising: an antibody variable region that is capable of binding to two different antigens (first antigen and second antigen), but does not bind to the first antigen and the second antigen at the same time (this variable region is referred to as a first variable region); and a variable region binding to a third antigen different from the first antigen and the second antigen (this variable region is referred to as a second variable region), the method comprising the step of preparing an antigen-binding molecule library containing diverse amino acid sequences of the first variable region.

Examples thereof can include a production method comprising the following steps:

(i) preparing a library of antigen-binding molecules with at least one amino acid altered in their antibody variable regions each binding to the first antigen or the second antigen, wherein the altered variable regions differ in at least one amino acid from each other;

(ii) selecting, from the prepared library, an antigen-binding molecule comprising a variable region that has binding activity against the first antigen and the second antigen, but does not bind to the first antigen and the second antigen at the same time;

(iii) culturing a host cell comprising a nucleic acid encoding the variable region of the antigen-binding molecule selected in the step (ii), and a nucleic acid encoding a variable region of an antigen-binding molecule binding to the third antigen, to express an antigen-binding molecule comprising the antibody variable region that is capable of binding to the first antigen and the second antigen, but does not bind to the first antigen and the second antigen at the same time, and the variable region binding to the third antigen; and (iv) recovering the antigen-binding molecule from the host cell cultures.

In this production method, the step (ii) may be the following selection step:

(v) selecting, from the prepared library, an antigen-binding molecule comprising a variable region that has binding activity against the first antigen and the second antigen, but does not bind to the first antigen and the second antigen each expressed on a different cell, at the same time.

The antigen-binding molecules used in the step (i) are not particularly limited as long as these molecules each comprise an antibody variable region. The antigen-binding molecules may be antibody fragments such as Fv, Fab, or Fab' or may be Fc region-containing antibodies.

The amino acid to be altered is selected from, for example, amino acids whose alteration does not cancel the binding to the antigen, in the antibody variable region binding to the first antigen or the second antigen.

In the present invention, one amino acid alteration may be used alone, or a plurality of amino acid alterations may be used in combination.

In the case of using a plurality of amino acid alterations in combination, the number of the alterations to be combined is not particularly limited and is, for example, 2 or more and 30 or less, preferably 2 or more and 25 or less, 2 or more and 22 or less, 2 or more and 20 or less, 2 or more and 15 or less, 2 or more and 10 or less, 2 or more and 5 or less, or 2 or more and 3 or less.

The plurality of amino acid alterations to be combined may be added to only the antibody heavy chain variable domain or light chain variable domain or may be appropriately distributed to both of the heavy chain variable domain and the light chain variable domain.

Examples of the region preferred for the amino acid alteration include solvent-exposed regions and loops in the variable region. Among others, CDR1, CDR2, CDR3, FR3, and loops are preferred. Specifically, Kabat numbering positions 31 to 35, 50 to 65, 71 to 74, and 95 to 102 in the H chain variable domain and Kabat numbering positions 24 to 34, 50 to 56, and 89 to 97 in the L chain variable domain are preferred. Kabat numbering positions 31, 52a to 61, 71 to 74, and 97 to 101 in the H chain variable domain and Kabat numbering positions 24 to 34, 51 to 56, and 89 to 96 in the L chain variable domain are more preferred.

The alteration of an amino acid residue also include: the random alteration of amino acids in the region mentioned above in the antibody variable region binding to the first antigen or the second antigen; and the insertion of a peptide previously known to have binding activity against the desired antigen, to the region mentioned above. The antigen-binding molecule of the present invention can be obtained by selecting a variable region that is capable of binding to the first antigen and the second antigen, but cannot bind to these antigens at the same time, from among the antigen-binding molecules thus altered. Examples of the peptide previously known to have binding activity against the desired antigen include peptides shown in Table 1 above.

Whether the variable region is capable of binding to the first antigen and the second antigen, but cannot bind to these antigens at the same time, and further, whether the variable region is capable of binding to both the first antigen and the second antigen at the same time when any one of the first antigen and the second antigen resides on a cell and the other antigen exists alone, both of the antigens each exist alone, or both of the antigens reside on the same cell, but cannot bind to these antigens each expressed on a different cell, at the same time, can also be confirmed according to the method mentioned above.

The present invention further provides a method for producing the antigen-binding molecule of the present invention and specifically provides a method for producing an antigen-binding molecule comprising an antibody variable region that is capable of binding to two different antigens (first antigen and second antigen), but does not bind to the first antigen and the second antigen at the same time (this variable region is referred to as a first variable region), the method comprising the step of preparing an antigen-binding molecule library containing diverse amino acid sequences of the first variable region.

Examples of the method for producing such an antigen-binding molecule can include a production method comprising the following steps:

(i) preparing a library of antigen-binding molecules with at least one amino acid altered in their antibody variable regions each binding to the first antigen or the second antigen, wherein the altered variable regions differ in at least one amino acid from each other;

(ii) selecting, from the prepared library, an antigen-binding molecule comprising a variable region that has binding activity against the first antigen and the second antigen, but does not bind to the first antigen and the second antigen at the same time;

(iii) culturing a host cell comprising a nucleic acid encoding the variable region of the antigen-binding molecule selected in the step (ii), to express an antigen-binding molecule comprising the antibody variable region that is capable of binding to the first antigen and the second antigen, but does not bind to the first antigen and the second antigen at the same time; and (iv) recovering the antigen-binding molecule from the host cell cultures.

Examples of the region preferred for the amino acid alteration include a heavy chain variable domain. More preferred examples thereof include solvent-exposed regions and loops in the variable domain. Among others, CDR1, CDR2, CDR3, FR3, and loops are preferred. Specifically, Kabat numbering positions 31 to 35, 50 to 65, 71 to 74, and 95 to 102 in the H chain variable domain and Kabat numbering positions 24 to 34, 50 to 56, and 89 to 97 in the L chain variable domain are preferred. Kabat numbering positions 31, 52a to 61, 71 to 74, and 97 to 101 in the H chain variable domain and Kabat numbering positions 24 to 34, 51 to 56, and 89 to 96 in the L chain variable domain are more preferred.

In this production method, the step (ii) may be the following selection step:

(v) selecting, from the prepared library, an antigen-binding molecule comprising a variable region that has binding activity against the first antigen and the second antigen, but does not bind to the first antigen and the second antigen each expressed on a different cell, at the same time.

The antigen-binding molecules used in the step (i) are not particularly limited as long as these molecules each comprise an antibody variable region. The antigen-binding molecules may be antibody fragments such as Fv, Fab, or Fab' or may be Fc region-containing antibodies.

The amino acid to be altered is selected from, for example, amino acids whose alteration does not cancel the binding to the antigen, in the antibody variable region binding to the first antigen or the second antigen.

In the present invention, one amino acid alteration may be used alone, or a plurality of amino acid alterations may be used in combination.

In the case of using a plurality of amino acid alterations in combination, the number of the alterations to be combined is not particularly limited and is, for example, 2 or more and 30 or less, preferably 2 or more and 25 or less, 2 or more and 22 or less, 2 or more and 20 or less, 2 or more and 15 or less, 2 or more and 10 or less, 2 or more and 5 or less, or 2 or more and 3 or less.

The plurality of amino acid alterations to be combined may be added only to either the antibody heavy chain variable domain or light chain variable domain or may be appropriately distributed to both of the heavy chain variable domain and the light chain variable domain.

The alteration of an amino acid residue also include: the random alteration of amino acids in the region mentioned above in the antibody variable region binding to the first antigen or the second antigen; and the insertion of a peptide previously known to have binding activity against the desired antigen, to the region mentioned above. The antigen-binding molecule of the present invention can be obtained by selecting a variable region that is capable of binding to the first antigen and the second antigen, but cannot bind to these antigens at the same time, from among the antigen-binding molecules thus altered. Examples of the peptide previously known to have binding activity against the desired antigen include peptides shown in Table 1 above.

Whether the variable region is capable of binding to the first antigen and the second antigen, but cannot bind to these antigens at the same time, and further, whether the variable region is capable of binding to both the first antigen and the second antigen at the same time when any one of the first antigen and the second antigen resides on a cell and the other antigen exists alone, both of the antigens each exist alone, or both of the antigens reside on the same cell, but cannot bind to these antigens each expressed on a different cell, at the same time, can also be confirmed according to the method mentioned above.

The antigen-binding molecule produced by any of these production methods is also included in the present invention.

The type or range of the amino acid alteration introduced by the method of the present invention is not particularly limited.

In a non-limiting embodiment, examples of the library of the present invention include a library consisting of antigen-binding molecules binding to CD3 (in the case of human CD3, γ chain, δ chain, or ε chain constituting the human CD3) selected as the first antigen, and an arbitrary second antigen.

In a preferred embodiment, examples of the library of the present invention include a library consisting essentially of a plurality of antigen-binding molecules differing in sequence from each other, wherein an antigen-binding region in each of the antigen-binding molecules is an antibody variable region that is capable of binding to a first antigen and a second antigen different from the first antigen, but does not bind to the first antigen and the second antigen at the same time, any one of the first antigen and the second antigen is CD3, and the other antigen is a molecule expressed on the surface of a T cell or any other immunocyte.

When any one of the first antigen and the second antigen is human CD3, each of the antigen-binding molecules preferably binds to a γ chain, δ chain, or ε chain sequence constituting the human CD3. The variable region is preferably a variable region that does not bind to the first antigen and the second antigen each expressed on a different cell, at the same time. In this context, the phrase "expressed on different cells" merely means that the antigens are expressed on separate cells. The combination of such cells may be, for example, the same types of cells such as a T cell and another T cell, or may be different types of cells such as a T cell and an NK cell.

The present invention further provides a method for producing the antigen-binding molecule of the present invention and specifically provides a method for producing an antigen-binding molecule comprising: an antibody variable region that is capable of binding to three different antigens (a first antigen, a second antigen different from the first antigen, and a fourth antigen different from the first antigen and the second antigen), but does not bind to the three antigens at the same time (this variable region is referred to as a first variable region); and a variable region binding to a third antigen different from the three antigens (this variable region is referred to as a second variable region), the method comprising the step of preparing an antigen-binding molecule library containing diverse amino acid sequences of the first variable region.

Examples thereof can include a production method comprising the following steps:

(i) preparing a library of antigen-binding molecules with at least one amino acid altered in their antibody variable regions each binding to the three different antigens (a first antigen, a second antigen different from the first antigen, and a fourth antigen different from the first antigen and the second antigen), wherein the altered variable regions differ in at least one amino acid from each other;

(ii) selecting, from the prepared library, an antigen-binding molecule comprising a variable region that has binding activity against the three antigens, but does not bind to the three antigens at the same time;

(iii) culturing a host cell comprising a nucleic acid encoding the variable region of the antigen-binding molecule selected in the step (ii), and a nucleic acid encoding a variable region of an antigen-binding molecule binding to the third antigen, to express an antigen-binding molecule comprising the antibody variable region that is capable of binding to the three antigens, but does not bind to the three antigens at the same time, and the variable region binding to the third antigen; and (iv) recovering the antigen-binding molecule from the host cell cultures.

In this production method, the step (ii) may be the following selection step:

(v) selecting, from the prepared library, an antigen-binding molecule comprising a variable region that has binding activity against the three antigens, but does not bind to the three antigens each expressed on a different cell, at the same time.

The antigen-binding molecules used in the step (i) are not particularly limited as long as these molecules each comprise an antibody variable region. The antigen-binding molecules may be antibody fragments such as Fv, Fab, or Fab' or may be Fc region-containing antibodies.

The amino acid to be altered is selected from, for example, amino acids whose alteration does not cancel the binding to the antigen, in the antibody variable region binding to the three antigens.

In the present invention, one amino acid alteration may be used alone, or a plurality of amino acid alterations may be used in combination.

In the case of using a plurality of amino acid alterations in combination, the number of the alterations to be combined is not particularly limited and is, for example, 2 or more and 30 or less, preferably 2 or more and 25 or less, 2 or more and 22 or less, 2 or more and 20 or less, 2 or more and 15 or less, 2 or more and 10 or less, 2 or more and 5 or less, or 2 or more and 3 or less.

The plurality of amino acid alterations to be combined may be added to only the antibody heavy chain variable domain or light chain variable domain or may be appropriately distributed to both of the heavy chain variable domain and the light chain variable domain.

Examples of the region preferred for the amino acid alteration include solvent-exposed regions and loops in the variable region. Among others, CDR1, CDR2, CDR3, FR3, and loops are preferred. Specifically, Kabat numbering positions 31 to 35, 50 to 65, 71 to 74, and 95 to 102 in the H chain variable domain and Kabat numbering positions 24 to 34, 50 to 56, and 89 to 97 in the L chain variable domain are preferred. Kabat numbering positions 31, 52a to 61, 71 to 74, and 97 to 101 in the H chain variable domain and Kabat numbering positions 24 to 34, 51 to 56, and 89 to 96 in the L chain variable domain are more preferred.

The alteration of an amino acid residue also includes: the random alteration of amino acids in the region mentioned above in the antibody variable region binding to the three antigens; and the insertion of a peptide previously known to have binding activity against the desired antigen, to the region mentioned above. The antigen-binding molecule of the present invention can be obtained by selecting a variable region that is capable of binding to three different antigens (a first antigen, a second antigen different from the first antigen, and a fourth antigen different from the first antigen and the second antigen), but cannot bind to these antigens at the same time, from among the antigen-binding molecules thus altered. Examples of the peptide previously known to have binding activity against the desired antigen include peptides shown in Table 1 above.

Whether the variable region is capable of binding to the three antigens, but cannot bind to these antigens at the same time, and further, whether the variable region is capable of binding to the three different antigens (first antigen, second antigen, and fourth antigen) at the same time when any one or more of the three different antigens exist alone without residing on a cell, or any two or more of the three different antigens reside on the same cell, but cannot bind to these antigens each expressed on a different cell, at the same time, can also be confirmed according to the method mentioned above.

The present invention further provides a method for producing the antigen-binding molecule of the present invention and specifically provides a method for producing an antigen-binding molecule comprising an antibody variable region that is capable of binding to three different antigens (a first antigen, a second antigen different from the first antigen, and a fourth antigen different from the first antigen and the second antigen), but does not bind to the three antigens at the same time (this variable region is referred to as a first variable region), the method comprising the step of preparing an antigen-binding molecule library containing diverse amino acid sequences of the first variable region.

Examples of the method for producing such an antigen-binding molecule can include a production method comprising the following steps:

(i) preparing a library of antigen-binding molecules with at least one amino acid altered in their antibody variable regions each binding to the three different antigens (a first antigen, a second antigen different from the first antigen, and a fourth antigen different from the first antigen and the second antigen), wherein the altered variable regions differ in at least one amino acid from each other;

(ii) selecting, from the prepared library, an antigen-binding molecule comprising a variable region that has binding activity against the three antigens, but does not bind to the three antigens at the same time;

(iii) culturing a host cell comprising a nucleic acid encoding the variable region of the antigen-binding molecule selected in the step (ii), to express an antigen-binding molecule comprising the antibody variable region that is capable of binding to the three antigens, but does not bind to the three antigens at the same time; and (iv) recovering the antigen-binding molecule from the host cell cultures.

Examples of the region preferred for the amino acid alteration include a heavy chain variable domain. More preferred examples thereof include solvent-exposed regions and loops in the variable domain. Among others, CDR1, CDR2, CDR3, FR3, and loops are preferred. Specifically, Kabat numbering positions 31 to 35, 50 to 65, 71 to 74, and 95 to 102 in the H chain variable domain and Kabat numbering positions 24 to 34, 50 to 56, and 89 to 97 in the L chain variable domain are preferred. Kabat numbering positions 31, 52a to 61, 71 to 74, and 97 to 101 in the H chain variable domain and Kabat numbering positions 24 to 34, 51 to 56, and 89 to 96 in the L chain variable domain are more preferred.

In this production method, the step (ii) may be the following selection step:
(v) selecting, from the prepared library, an antigen-binding molecule comprising a variable region that has binding activity against the three antigens, but does not bind to the three antigens each expressed on a different cell, at the same time.

The antigen-binding molecules used in the step (i) are not particularly limited as long as these molecules each comprise an antibody variable region. The antigen-binding molecules may be antibody fragments such as Fv, Fab, or Fab' or may be Fc region-containing antibodies.

The amino acid to be altered is selected from, for example, amino acids whose alteration does not cancel the binding to the antigen, in the antibody variable region binding to the three antigens.

In the present invention, one amino acid alteration may be used alone, or a plurality of amino acid alterations may be used in combination.

In the case of using a plurality of amino acid alterations in combination, the number of the alterations to be combined is not particularly limited and is, for example, 2 or more and 30 or less, preferably 2 or more and 25 or less, 2 or more and 22 or less, 2 or more and 20 or less, 2 or more and 15 or less, 2 or more and 10 or less, 2 or more and 5 or less, or 2 or more and 3 or less.

The plurality of amino acid alterations to be combined may be added only to either the antibody heavy chain variable domain or light chain variable domain or may be appropriately distributed to both of the heavy chain variable domain and the light chain variable domain.

The alteration of an amino acid residue also includes: the random alteration of amino acids in the region mentioned above in the antibody variable region binding to the three antigens; and the insertion of a peptide previously known to have binding activity against the desired antigen, to the region mentioned above. The antigen-binding molecule of the present invention can be obtained by selecting a variable region that is capable of binding to the three antigens, but cannot bind to these antigens at the same time, from among the antigen-binding molecules thus altered. Examples of the peptide previously known to have binding activity against the desired antigen include peptides shown in Table 1 above.

Whether the variable region is capable of binding to the three antigens, but cannot bind to these antigens at the same time, and further, whether the variable region is capable of binding to the three different antigens (first antigen, second antigen, and fourth antigen) at the same time when any one or more of the three different antigens exist alone without residing on a cell, or any two or more of the three different antigens reside on the same cell, but cannot bind to these antigens each expressed on a different cell, at the same time, can also be confirmed according to the method mentioned above.

The antigen-binding molecule produced by any of these production methods is also included in the present invention.

The type or range of the amino acid alteration introduced by the method of the present invention is not particularly limited.

In a non-limiting embodiment, examples of the library of the present invention include a library consisting of antigen-binding molecules binding to CD3 (in the case of human CD3, γ chain, δ chain, or ε chain constituting the human CD3) selected as the first antigen, and an arbitrary second antigen and fourth antigen.

In a preferred embodiment, examples of the library of the present invention include a library consisting essentially of a plurality of antigen-binding molecules differing in sequence from each other, wherein an antigen-binding region in each of the antigen-binding molecules is an antibody variable region that is capable of binding to three different antigens (a first antigen, a second antigen different from the first antigen, and a fourth antigen different from the first antigen and the second antigen), but does not bind to the three antigens at the same time, any one of the three antigens is CD3, and each of the remaining two antigens is a molecule expressed on the surface of a T cell or any other immunocyte.

When any one of the three antigens is human CD3, each of the antigen-binding molecules preferably binds to a γ chain, δ chain, or ε chain sequence constituting the human CD3. The variable region is preferably a variable region that does not bind to the three antigens each expressed on a different cell, at the same time. In this context, the phrase “expressed on different cells” merely means that the antigens are expressed on separate cells. The combination of such cells may be, for example, the same types of cells such as a T cell and another T cell, or may be different types of cells such as a T cell and an NK cell.

In the present specification, the “library” refers to a plurality of antigen-binding molecules or a plurality of fusion polypeptides comprising the antigen-binding molecules, or nucleic acids or polynucleotides encoding these sequences. The plurality of antigen-binding molecules or the plurality of fusion polypeptides comprising the antigen-binding molecules, included in the library are antigen-binding molecules differing in sequence from each other, not having single sequences, or fusion polypeptides comprising the antigen-binding molecules.

In one embodiment of the present invention, a fusion polypeptide of the antigen-binding molecule of the present invention and a heterologous polypeptide can be prepared. In one embodiment, the fusion polypeptide can comprise the antigen-binding molecule of the present invention fused with at least a portion of a viral coat protein selected from the group consisting of, for example, viral coat proteins pIII, pVIII, pVII, pIX, Soc, Hoc, gpD, and pVI, and variants thereof.

In one embodiment, the antigen-binding molecule of the present invention can be ScFv, a Fab fragment, $F(ab)_2$, or $F(ab')_2$. In another embodiment, the present invention provides a library consisting essentially of a plurality of fusion polypeptides differing in sequence from each other, the fusion polypeptides each comprising any of these antigen-binding molecules and a heterologous polypeptide. Specifically, the present invention provides a library consisting essentially of a plurality of fusion polypeptides differing in sequence from each other, the fusion polypeptides each comprising any of these antigen-binding molecules fused with at least a portion of a viral coat protein selected from the group consisting of, for example, viral coat proteins pIII, pVIII, pVII, pIX, Soc, Hoc, gpD, and pVI, and variants thereof. The antigen-binding molecule of the present invention may further comprise a dimerization domain. In one embodiment, the dimerization domain can be located between the antibody heavy chain or light chain variable domain and at least a portion of the viral coat protein. This dimerization domain may comprise at least one dimerization sequence and/or a sequence comprising one or more cysteine residues. This dimerization domain can be preferably linked to the C terminus of the heavy chain variable domain or constant domain. The dimerization domain can assume various structures, depending on whether the antibody variable domain is prepared as a fusion polypeptide component with the viral coat protein component (an amber stop codon following the dimerization domain is absent) or depending on whether the antibody variable domain is prepared predominantly without comprising the viral coat protein component (e.g., an amber stop codon following the dimerization domain is present). When the antibody variable domain is prepared predominantly as a fusion polypeptide with the viral coat protein component, bivalent display is brought about by one or more disulfide bonds and/or a single dimerization sequence.

The term “differing in sequence from each other” in a plurality of antigen-binding molecules differing in sequence from each other as described herein means that the individual antigen-binding molecules in the library have distinct sequences. Specifically, the number of the distinct sequences in the library reflects the number of independent clones differing in sequences in the library and may also be referred to as a “library size”. The library size of a usual phage display library is $10^6$ to $10^{12}$ and can be expanded to 10' by the application of a technique known in the art such as a ribosome display method. The actual number of phage particles for use in panning selection for the phage library, however, is usually 10 to 10,000 times larger than the library size. This excessive multiple, also called the “number of equivalents of the library”, represents that 10 to 10,000 individual clones may have the same amino acid sequence. Accordingly, the term “differing in sequence from each other” described in the present invention means that the individual antigen-binding molecules in the library excluding the number of equivalents of the library have distinct sequences and more specifically means that the library has $10^6$ to $10^{14}$, preferably $10^7$ to $10^{12}$, more preferably $10^8$ to $10^{11}$, particularly preferably $10^8$ to $10^{10}$ antigen-binding molecules differing in sequence from each other.

The term “consisting essentially of” in the library consisting essentially of a plurality of antigen-binding molecules as described in the present invention reflects the number of antigen-binding molecules differing in binding activity against the first and/or second antigen (or antigen-binding molecules differing in binding activity against the first, second, and/or fourth antigen), among the independent clones differing in sequence in the library. Specifically, the library preferably has at least $10^4$ antigen-binding molecules that exhibit such binding activity. More preferably, the present invention provides the library having at least $10^5$ antigen-binding molecules that exhibit such binding activity. Further preferably, the present invention provides the library having at least $10^6$ antigen-binding molecules that exhibit such binding activity. Particularly preferably, the present invention provides the library having at least $10^7$ antigen-binding molecules that exhibit such binding activity. Also preferably, the present invention provides the library having at least $10^8$ antigen-binding molecules that exhibit such binding activity. In other words, the term may be preferably indicated by the ratio of the number of the antigen-binding molecules differing in binding activity against the first and/or second antigen (or antigen-binding molecules differing in binding activity against the first, second, and/or fourth antigen) to the number of the independent clones differing in sequence in the library. Specifically, the present invention provides the library comprising antigen-binding molecules that exhibit such binding activity at a ratio of 0.1% to 80%, preferably 0.5% to 60%, more preferably 1% to 40%, further preferably 2% to 20%, particularly preferably 4% to 10% to the number of the independent clones differing in sequence in the library. Fusion polypeptides, polynucleotide molecules, or vectors can also be indicated by the number of molecules or the ratio to all molecules, as in the above case. Likewise, viruses can also be indicated by the number of virus individuals or the ratio to all individuals, as in the above case.

The library of the present invention preferably has at least 1 molecule, 10 molecules, 100 molecules, 1000 molecules, $10^4$ molecules, $10^5$ molecules, $10^6$ molecules, $10^7$ molecules, or $10^8$ molecules as a plurality of antigen-binding molecules each comprising an antibody variable region that is capable of binding to a first antigen and a second antigen different from the first antigen, but does not bind to the first antigen and the second antigen at the same time (or a plurality of antigen-binding molecules each comprising an antibody variable region that is capable of binding to three different antigens, but does not bind to the three antigens at the same time). The present invention provides the library comprising a plurality of antigen-binding molecules each comprising an antibody variable region that is capable of binding to a first antigen and a second antigen different from the first antigen, but does not bind to the first antigen and the second antigen at the same time (or a plurality of antigen-binding molecules each comprising an antibody variable region that is capable of binding to three different antigens, but does not bind to the three antigens at the same time), at a ratio of $10^{-7}$% to 80%, preferably $10^{-6}$% to 60%, more preferably $10^{-5}$% to 40%, $10^{-4}$% to 30%, $10^{-3}$% to 20%, $10^{-2}$% to 10%, or $10^{-1}$% to 1% to the number of the independent clones differing in sequence in the library.

In one embodiment, the “library consisting essentially of a plurality of antigen-binding molecules differing in sequence from each other” according to the present invention is a library consisting essentially of (i) a plurality of antibody variable regions differing in sequence from each other, or antigen-binding molecules comprising the variable regions, or (ii) nucleic acids encoding the plurality of antibody variable regions differing in sequence from each other, or antigen-binding molecules comprising the variable regions.

In this context, the plurality of antigen-binding molecules differing in sequence from each other are antigen-binding molecules each comprising a variable region having alteration of at least one amino acid in a library template sequence (e.g., an antibody variable region). Examples of the region preferred for the amino acid alteration include a heavy chain variable domain and/or a light chain variable domain. More preferred examples thereof include solvent-exposed regions and loops in the variable region. Among others, CDR1, CDR2, CDR3, FR3, and loops are preferred. Specifically, Kabat numbering positions 31 to 35, 50 to 65, 71 to 74, and 95 to 102 in the H chain variable domain and Kabat numbering positions 24 to 34, 50 to 56, and 89 to 97 in the L chain variable domain are preferred. Kabat numbering positions 31, 52a to 61, 71 to 74, and 97 to 101 in the H chain variable domain and Kabat numbering positions 24 to 34, 51 to 56, and 89 to 96 in the L chain variable domain are more preferred.

The antigen-binding molecules are not particularly limited as long as these molecules each comprise an antibody variable region. The antigen-binding molecules may be antibody fragments such as Fv, Fab, or Fab' or may be Fc region-containing antibodies.

The amino acid to be altered is selected from, for example, amino acids whose alteration does not cancel the binding to the antigen, in the antibody variable region binding to the first antigen or the second antigen. Alternatively, the amino acid to be altered is selected from, for example, amino acids whose alteration does not cancel the binding to the three antigens, in the antibody variable region binding to the three different antigens.

In the present invention, one amino acid alteration may be used alone, or a plurality of amino acid alterations may be used in combination.

In the case of using a plurality of amino acid alterations in combination, the number of the alterations to be combined is not particularly limited and is, for example, 2 or more and 30 or less, preferably 2 or more and 25 or less, 2 or more and 22 or less, 2 or more and 20 or less, 2 or more and 15 or less, 2 or more and 10 or less, 2 or more and 5 or less, or 2 or more and 3 or less.

The plurality of amino acid alterations to be combined may be added to only the antibody heavy chain variable domain or light chain variable domain or may be appropriately distributed to both of the heavy chain variable domain and the light chain variable domain.

The alteration of an amino acid residue also includes: the random alteration of amino acids in the region mentioned above in the antibody variable region binding to the first antigen or the second antigen (or the antibody variable region binding to the first, second, or fourth antigen); and the insertion of a peptide previously known to have binding activity against the desired antigen, to the region mentioned above. The antigen-binding molecule of the present invention can be obtained by selecting a variable region that is capable of binding to the first antigen and the second antigen, but cannot bind to these antigens at the same time (or a variable region that is capable of binding to the three different antigens, but cannot bind to the three antigens at the same time), from among the antigen-binding molecules thus altered. Examples of the peptide previously known to have binding activity against the desired antigen include peptides shown in Table 1 above.

Whether the variable region is capable of binding to the first antigen and the second antigen, but cannot bind to these antigens at the same time (or whether the variable region is capable of binding to the three different antigens, but cannot bind to the three antigens at the same time), and further, whether the variable region is capable of binding to both the first antigen and the second antigen at the same time when any one of the first antigen and the second antigen resides on a cell and the other antigen exists alone, both of the antigens each exist alone, or both of the antigens reside on the same cell, but cannot bind to these antigens each expressed on a different cell, at the same time (or whether the variable region is capable of binding to the three different antigens at the same time when any one or more of the three different antigens exist alone without residing on a cell, or any two or more of the three different antigens reside on the same cell, but cannot bind to these antigens each expressed on a different cell, at the same time), can also be confirmed according to the method mentioned above.

The "phage display" as described herein refers to an approach by which variant polypeptides are displayed as fusion proteins with at least a portion of coat proteins on the particle surface of phages, for example, filamentous phages. The phage display is useful because a large library of randomized protein variants can be rapidly and efficiently screened for a sequence binding to a target antigen with high affinity. The display of peptide and protein libraries on the phages has been used for screening millions of polypeptides for ones with specific binding properties. A polyvalent phage display method has been used for displaying small random peptides and small proteins through fusion with filamentous phage gene III or gene VIII (Wells and Lowman, Curr. Opin. Struct. Biol. (1992) 3, 355-362; and references cited therein). Monovalent phage display involves fusing a protein or peptide library to gene III or a portion thereof, and expressing fusion proteins at low levels in the presence of wild-type gene III protein so that each phage particle displays one copy or none of the fusion proteins. The monovalent phages have a lower avidity effect than that of the polyvalent phages and are therefore screened on the basis of endogenous ligand affinity using phagemid vectors, which simplify DNA manipulation (Lowman and Wells, Methods: A Companion to Methods in Enzymology (1991) 3, 205-216).

The "phagemid" refers to a plasmid vector having a bacterial replication origin, for example, ColE1, and a copy of an intergenic region of a bacteriophage. A phagemid derived from any bacteriophage known in the art, for example, a filamentous bacteriophage or a lambdoid bacteriophage, can be appropriately used. Usually, the plasmid also contains a selective marker for antibiotic resistance. DNA fragments cloned into these vectors can grow as plasmids. When cells harboring these vectors possess all genes necessary for the production of phage particles, the replication pattern of plasmids is shifted to rolling circle replication to form copies of one plasmid DNA strand and package phage particles. The phagemid can form infectious or non-infectious phage particles. This term includes a phagemid comprising a phage coat protein gene or a fragment thereof bound with a heterologous polypeptide gene by gene fusion such that the heterologous polypeptide is displayed on the surface of the phage particle.

The term "phage vector" means a double-stranded replicative bacteriophage that comprises a heterologous gene and is capable of replicating. The phage vector has a phage replication origin that permits phage replication and phage particle formation. The phage is preferably a filamentous bacteriophage, for example, an M13, fl, fd, or Pf3 phage or a derivative thereof, or a lambdoid phage, for example, lambda, 21, phi80, phi81, 82, 424, 434, or any other phage or a derivative thereof.

The term "oligonucleotide" refers to a short single- or double-stranded polydeoxynucleotide that is chemically synthesized by a method known in the art (e.g., phosphotriester, phosphite, or phosphoramidite chemistry using a solid-phase approach such as an approach described in EP266032; or a method via deoxynucleotide H-phosphonate intermediates described in Froeshler et al., Nucl. Acids. Res. (1986) 14, 5399-5407). Other methods for oligonucleotide synthesis include the polymerase chain reaction described below and other autoprimer methods and oligonucleotide syntheses on solid supports. All of these methods are described in Engels et al., Agnew. Chem. Int. Ed. Engl. (1989) 28, 716-734. These methods are used if the whole nucleic acid sequence of the gene is known or if a nucleic acid sequence complementary to the coding strand is available. Alternatively, a possible nucleic acid sequence may be appropriately predicted using known and preferred residues encoding each amino acid residue, if the target amino acid sequence is known. The oligonucleotide can be purified using polyacrylamide gels or molecular sizing columns or by precipitation.

The terms "fusion protein" and "fusion polypeptide" refer to a polypeptide having two segments covalently linked to each other. These segments in the polypeptide differ in character. This character may be, for example, a biological property such as in vitro or in vivo activity. Alternatively, this character may be a single chemical or physical property, for example, binding to a target antigen or catalysis of reaction. These two segments may be linked either directly through a single peptide bond or via a peptide linker containing one or more amino acid residues. Usually, these two segments and the linker are located in the same reading frame. Preferably, the two segments of the polypeptide are obtained from heterologous or different polypeptides.

The term "coat protein" refers to a protein, at least a portion of which is present on the surface of a viral particle. From a functional standpoint, the coat protein is an arbitrary protein that binds to viral particles in the course of construction of viruses in host cells and remains bound therewith until viral infection of other host cells. The coat protein may be a major coat protein or may be a minor coat protein. The minor coat protein is usually a coat protein present in viral capsid at preferably at least approximately 5, more preferably at least approximately 7, further preferably at least approximately 10 or more protein copies per virion. The major coat protein can be present at tens, hundreds, or thousands of copies per virion. Examples of the major coat protein include filamentous phage p8 protein.

In a non-limiting embodiment of the present invention, examples of a method for preparing the library include the following 6 methods:

1. a method which involves inserting a peptide (this term is used to include a polypeptide and a protein) binding to the second antigen (or a peptide binding to the second antigen and a peptide binding to the fourth antigen) to antigen-binding molecules each binding to the first antigen;

2. a method which involves preparing a library such that various amino acids appear positions that permit alteration to a larger length (extension) of loops in antigen-binding molecules, and obtaining an antigen-binding molecule having binding activity against an arbitrary second antigen (or an arbitrary second antigen and an arbitrary fourth antigen) from the library by using the binding activity against the antigen as an index;

3. a method which involves identifying amino acids that maintain binding activity against the first antigen by use of an antibody prepared by site-directed mutagenesis from an antigen-binding molecule previously known to bind to the first antigen, and obtaining an antigen-binding molecule having binding activity against an arbitrary second antigen (or an arbitrary second antigen and an arbitrary fourth antigen) from a library in which the identified amino acids appear by using the binding activity against the antigen as an index;

4. the method 3 which further involves preparing an antibody library such that various amino acids appear positions that permit alteration to a larger length (extension) of loops in antigen-binding molecules, and obtaining an antigen-binding molecule having binding activity against an arbitrary second antigen (or an arbitrary second antigen and an arbitrary fourth antigen) from the library by using the binding activity against the antigen as an index;

5. the method 1, 2, 3, or 4 which further involves altering the antigen-binding molecules such that glycosylation sequences (e.g., NxS and NxT wherein x is an amino acid other than P) appear to add thereto sugar chains that are recognized by sugar chain receptors (e.g., high-mannose-type sugar chains are added thereto and thereby recognized by high-mannose receptors; it is known that the high-mannose-type sugar chains are obtained by the addition of kifunensine at the time of antibody expression (mAbs. 2012 July-August; 4 (4): 475-87)); and 6. the method 1, 2, 3, or 4 which further involves adding thereto domains each binding to the second antigen (or domains each binding to the second antigen and domains each binding to the fourth antigen) through a covalent bond by inserting Cys, Lys, or a non-natural amino acid to loops or sites found to be alterable to various amino acids or substituting these sites with Cys, Lys, or a non-natural amino acid (this method is typified by antibody drug conjugates and is a method for conjugation to Cys, Lys, or a non-natural amino acid through a covalent bond (mAbs 6: 1, 34-45; January/February 2014; WO2009/134891 A2; and Bioconjug Chem. 2014 Feb. 19; 25 (2): 351-61)).

In these 6 library preparation methods listed above, the amino acid substitution site in each antigen-binding molecule or the peptide insertion site in the antigen-binding molecule is preferably a site in a Fab or variable region in the antigen-binding molecule. Examples of the preferred region include solvent-exposed regions and loops in the variable region. Among others, CDR1, CDR2, CDR3, FR3, and loops are preferred. Specifically, Kabat numbering positions 31 to 35, 50 to 65, 71 to 74, and 95 to 102 in the H chain variable domain and Kabat numbering positions 24 to 34, 50 to 56, and 89 to 97 in the L chain variable domain are preferred. Kabat numbering positions 31, 52a to 61, 71 to 74, and 97 to 101 in the H chain variable domain and Kabat numbering positions 24 to 34, 51 to 56, and 89 to 96 in the L chain variable domain are more preferred.

In one embodiment, examples of the method 1 which involves inserting a peptide binding to the second antigen (or a peptide binding to the second antigen and a peptide binding to the fourth antigen) to antigen-binding molecules each binding to the first antigen can also include a method of inserting G-CSF as exemplified in Angew Chem Int Ed Engl. 2013 Aug. 5; 52 (32): 8295-8. In another embodiment, the peptide to be inserted can be obtained from a peptide-displaying library. Alternatively, the whole or a portion of a naturally occurring protein may be used.

According to one aspect, the present invention provides a method for producing the library, the method comprising the following steps (a) and (b):

(a) using an antibody variable region sequence binding to the first antigen as a library template sequence to identify amino acid alteration that satisfies any one or more of the following conditions (i) to (iii):

(i) the alteration does not substantially change the ability to bind to the first antigen;

(ii) the alteration does not substantially change the ability to bind to ECM; and (iii) the alteration is insertion of a peptide consisting of 1 to 25 amino acid residues to the CDR1, CDR2, CDR3, or FR3 domain of a heavy chain variable domain or a light chain variable domain; and (b) designing a library comprising a nucleic acid encoding the template sequence, and nucleic acids encoding variable regions differing in sequence from each other and each having at least one amino acid alteration identified in the step (a) in the template sequence.

The production method can produce a library consisting essentially of a plurality of antigen-binding molecules differing in sequence from each other, wherein an antigen-binding region in each of the antigen-binding molecules is an antibody variable region that is capable of binding to a first antigen and a second antigen different from the first antigen, but does not bind to the first antigen and the second antigen at the same time, and any one of the first antigen and the second antigen is CD3, and the other antigen is a molecule expressed on the surface of a T cell or any other immunocyte. Also, the production method can produce a library consisting essentially of a plurality of antigen-binding molecules differing in sequence from each other, wherein an antigen-binding region in each of the antigen-binding molecules is an antibody variable region that is capable of binding to three different antigens (first antigen, a second antigen different from the first antigen, and a fourth antigen different from the first antigen and the second antigen), but does not bind to the three antigens at the same time, any one of the three antigens is CD3, and each of the remaining two antigens is a molecule expressed on the surface of a T cell or any other immunocyte.

The "(library) template sequence" according to the present invention refers to an antibody amino acid sequence (e.g., an antibody variable region sequence or a CDR sequence) that is templated for preparing the library. The library of antigen-binding molecules can be prepared by identifying an altered amino acid that allows the formation of a library (e.g., which can be identified on the basis of the condition (i), (ii), and/or (iii) of the step (a)), using the sequence. When the first antigen is, for example, CD3, an antibody variable region sequence binding to the CD3 antigen can be appropriately selected as the library template sequence by those skilled in the art.

In order to identify an altered amino acid that does not substantially change the ability to bind to CD3 in the step (a)(i) (to identify amino acids that maintain binding activity against a first antigen CD3 (in the case of human CD3, γ chain, δ chain, or ε chain constituting the human CD3)), for example, one-amino acid alteration antibodies are prepared by amino acid alteration at sites presumed to participate in antigen binding, and these antibodies can be examined. The CD3 binding of the one-amino acid alteration antibodies can be evaluated by an appropriately selected method generally known to those skilled in the art and can be determined by, for example, ELISA, FACS (fluorescence activated cell sorting), ALPHAScreen (amplified luminescent proximity homogeneous assay screen), or the BIACORE method based on a surface plasmon resonance (SPR) phenomenon.

In order to identify an altered amino acid that does not substantially change the ability to bind to CD3 in the step (a)(i) (to identify the amino acids that maintain binding activity against CD3), results about the ratios of the amounts of, for example, various altered forms, bound to the amount of the corresponding unaltered antibody bound can be used. Specifically, when the amount of the corresponding unaltered antibody bound is defined as X and the amount of the one-amino acid altered form bound is defined as Y, a value of Z (ratio of amounts bound)=Y/X can be used. The altered form can be considered to maintain the binding relative to the corresponding unaltered antibody when Z (ratio of amount bound) is 0.5 or more, 0.6 or more, 0.7 or more, 0.8 or more, or 0.9 or more, preferably 0.8 or more. The antibody library can be prepared such that such amino acids that maintain binding appear.

ECM (extracellular matrix) is an extracellular constituent and resides at various sites in vivo. Therefore, an antibody strongly binding to ECM is known to have poorer kinetics in blood (shorter half-life) (WO2012093704 A1). Thus, amino acids that do not enhance ECM binding are preferably selected (an altered amino acid that does not substantially change the ability to bind to ECM is preferably identified) as the amino acids that appear in the antibody library.

In order to identify an altered amino acid that does not substantially change the ability to bind to ECM in the step (a)(ii) (to select the amino acids that do not enhance ECM binding), the ECM binding is evaluated, for example, according to a method of Reference Example 2. The ECM binding value (ECL reaction) of each altered form is divided by the ECM binding value of an antibody MRA (H chain: SEQ ID NO: 57, L chain: SEQ ID NO: 58), and the resulting value can be used. An effective value up to 5 times, 6 times, 7 times, 8 times, 9 times, 10 times, 15 times, 20 times, or 30 times can be adopted as this value in consideration of the effect of enhancing ECM binding by a plurality of alterations. Preferably, an effective value up to 10 times can be adopted to the library. The antibody library can be prepared such that the amino acids thus selected appear.

In the case of inserting, but not limited to, a peptide of 6 amino acids to CDR3, the binding to ECM is enhanced if the extended loop of CDR3 is rich in amino acids having a positively charged side chain. Therefore, it is preferred that three or more amino acids having a positively charged side chain should not appear in the loop.

In the library of the present invention, an altered amino acid to be inserted to each variable region can be identified in the step (a)(iii) (a peptide can be inserted to each variable region) in order to enhance the diversity of the library. Examples of the region preferred for the peptide insertion include solvent-exposed regions and loops in the variable region. Among others, CDR1, CDR2, CDR3, FR3, and loops are preferred. Specifically, Kabat numbering positions 31 to 35, 50 to 65, 71 to 74, and 95 to 102 in the H chain variable domain and Kabat numbering positions 24 to 34, 50 to 56, and 89 to 97 in the L chain variable domain are preferred. Kabat numbering positions 31, 52a to 61, 71 to 74, and 97 to 101 in the H chain variable domain and Kabat numbering positions 24 to 34, 51 to 56, and 89 to 96 in the L chain variable domain are more preferred. A region of Kabat numbering positions 99 and 100 in the H chain variable domain is further preferred. Also, an amino acid that increases antigen-binding activity may be further introduced at the time of the amino acid alteration.

In a non-limiting embodiment of the present invention, examples of the length of the peptide to be inserted include 1 to 3 amino acids, 4 to 6 amino acids, 7 to 9 amino acids, 10 to 12 amino acids, 13 to 15 amino acids, 15 to 20 amino acids, and 21 to 25 amino acids. The length of the peptide to be inserted is preferably 1 to 3 amino acids, 4 to 6 amino acids, or 7 to 9 amino acids.

The insertion site and the length of the peptide for enhancing the diversity of the library can be studied by preparing peptide-inserted molecules and evaluating the CD3 binding of the molecules. The CD3 binding can be evaluated by an appropriately selected method generally known to those skilled in the art and can be determined by, for example, ELISA, FACS (fluorescence activated cell sorting), ALPHAScreen (amplified luminescent proximity homogeneous assay screen), or the BIACORE method based on a surface plasmon resonance (SPR) phenomenon.

In a non-limiting embodiment of the present invention, an antibody library for obtaining an antibody binding to CD3 and the second antigen (or CD3 and the second antigen and the fourth antigen) can be designed as follows:

step 1: selecting amino acids that maintain the ability to bind to CD3 (to secure 80% or more of the amount of the unaltered antibody bound to CD3).

The library for obtaining an antibody binding to CD3 and the second antigen (or CD3 and the second antigen and the fourth antigen) can be prepared, for example, such that the amino acids selected in the step 1 appear.

In a non-limiting embodiment of the present invention, the antibody library for obtaining an antibody binding to CD3 and the second antigen (or CD3 and the second antigen and the fourth antigen) can be designed as follows:

step 1: selecting amino acids that maintain the ability to bind to CD3 (to secure 80% or more of the amount of the unaltered antibody bound to CD3); and step 2: inserting an amino acid to between positions 99 and 100 (Kabat numbering) in H chain CDR3.

The library for obtaining an antibody binding to CD3 and the second antigen (or CD3 and the second antigen and the fourth antigen) can be prepared with the library diversity enhanced, for example, by the step 1 as well as amino acid insertion to the CDR3 domain in the step 2.

In a non-limiting embodiment of the present invention, the antibody library for obtaining an antibody binding to CD3 and the second antigen (or CD3 and the second antigen and the fourth antigen) can be designed as follows:

step 1: selecting amino acids that maintain the ability to bind to CD3 (to secure 80% or more of the amount of the unaltered antibody bound to CD3);

step 2: selecting amino acids that keep ECM binding within 10 times that of MRA compared with before alteration; and step 3: inserting an amino acid to between positions 99 and 100 (Kabat numbering) in H chain CDR3.

The amino acids that do not enhance ECM binding can also be selected as the amino acids appearing in the library, for example, by the steps 1 and 3 as well as the step 2, though the present invention is not limited by this approach. Even library design without the step 2 allows an antigen-binding molecule obtained from the library to be assayed and evaluated for ECM binding.

In a non-limiting embodiment of the present invention, a VH domain CE115HA000 (SEQ ID NO: 52) may be used as a template sequence for CD3 (CD3ε)-binding antibody. In such a case, examples of altered amino acids for use in library design can include any one or more of amino acids at Kabat numbering positions 11, 31, 52a, 52b, 52c, 53, 54, 56, 57, 61, 72, 78, 98, 99, 100, 100a, 100b, 100c, 100d, 100e, 100f, 100g, and 101 contained in the heavy chain variable domain.

For the library, it is preferred to use a template sequence (SEQ ID NO: 94) derived from the VH domain CE115HA000 (SEQ ID NO: 52) by the introduction of amino acid alteration V11L/L78I, though the library according to the present invention is not limited thereto. For the library, it is further preferred to use a template sequence (SEQ ID NO: 95) derived from the VH domain CE115HA000 (SEQ ID NO: 52) by the introduction of amino acid alteration V11L/A52aD/L78I, or to use a template sequence (SEQ ID NO: 96) derived therefrom by the extension of the sequence of CDR3, though the library according to the present invention is not limited thereto. For example, a heavy chain variable domain sequence described in SEQ ID NO: 96 may be used as a template sequence. In such a case, examples of altered amino acids for use in library design can include any one or more of amino acids at Kabat numbering positions 31, 52b, 52c, 53, 54, 56, 57, 61, 98, 99, 100, 100a, 100b, 100c, 100d, 100e, 100f, and 100g contained in the heavy chain variable domain. In another embodiment, a rCE115H chain (SEQ ID NO: 97) can also be used as a template sequence for CD3-binding antibody.

In a non-limiting embodiment of the present invention, a VL domain GLS3000 (SEQ ID NO: 53) may be used as a template sequence for CD3 (CD3ε)-binding antibody. In such a case, examples of altered amino acids for use in library design can include any one or more of amino acids at Kabat numbering positions 24, 25, 26, 27, 27a, 27b, 27c, 27e, 30, 31, 33, 34, 51, 52, 53, 54, 55, 56, 74, 77, 89, 90, 92, 93, 94, and 96 contained in the light chain variable domain.

In another embodiment, a rCE115L chain (SEQ ID NO: 98) can also be used as a template sequence for CD3-binding antibody.

In a non-limiting embodiment of the present invention, a heavy chain variable domain sequence comprising heavy chain CDR1 (SEQ ID NO: 99), heavy chain CDR2 (SEQ ID NO: 100), and heavy chain CDR3 (SEQ ID NO: 101) may be used as a template sequence for CD3-binding antibody. In another embodiment, heavy chain CDR3 (SEQ ID NO: 102) having inserted 6 amino acid residues can also be used.

In a further alternative embodiment, a light chain variable domain sequence comprising light chain CDR1 (SEQ ID NO: 103), light chain CDR2 (SEQ ID NO: 104), and light chain CDR3 (SEQ ID NO: 105) may be used as a template sequence for CD3-binding antibody.

As for the amino acid sequences of framework regions contained in each variable region, for example, the sequences of currently known completely human framework regions included in a website such as IMGT (www.imgt.org/textes/IMGTrepertoire/) can be appropriately used as germline sequences contained in the antigen-binding molecule of the present invention, though the sequences are not limited thereto.

The library design according to the present invention includes, but is not particularly limited to, the design of a library comprising a plurality of altered forms of antigen-binding molecules comprising variable regions with an amino acid at a particular site altered to the desired amino acid by use of a library technique known in the art, for example, NNK or TRIM Library (Gonzalez-Munoz A et al., mAbs 2012; Lee C V et al., J Mol Biol. 2004; Knappik A. et al., J Mol Biol. 2000; and Tiller T et al., mAbs 2013).

In the present invention, the term "one or more amino acids" is not limited to a particular number of amino acids and may be 2 or more types of amino acids, 5 or more types of amino acids, 10 or more types of amino acids, 15 or more types of amino acids, or 20 types of amino acids.

According to one aspect, the present invention provides a method for selecting a variable region having enhanced binding to a first antigen, comprising the steps given below.

The method for selecting a variable region having enhanced binding to a first antigen comprises the following steps (a) to (c):

(a) contacting the library of the present invention with the first antigen;

(b) recovering antigen-binding molecules bound with the first antigen in the step (a); and (c) selecting an antigen-binding molecule comprising the variable region having enhanced binding to the first antigen from a population of the antigen-binding molecules bound with the first antigen in the step (b).

In this aspect, the first antigen is preferably CD3, though the first antigen is not particularly limited thereto.

The antigen-binding molecules used in the selection method are not particularly limited as long as these molecules each comprise an antibody variable region. The antigen-binding molecules may be antibody fragments such as Fv, Fab, or Fab' or may be Fc region-containing antibodies.

In the step (c), the antigen-binding molecule comprising the variable region having enhanced binding to the first antigen can be selected by measuring binding to the first antigen by a method generally known to those skilled in the art, for example, ELISA, FACS (fluorescence activated cell sorting), ALPHAScreen (amplified luminescent proximity homogeneous assay screen), or the BIACORE method based on a surface plasmon resonance (SPR) phenomenon. Specifically, when an antigen-binding molecule having higher binding activity than that of an antigen-binding molecule comprising a template variable region sequence is found by comparing the binding activity of the antigen-binding molecule comprising a variable region sequence selected as the library template sequence with the binding activity of the antigen-binding molecules bound with the first antigen recovered in the step (b), this antigen-binding molecule can be confirmed to be the antigen-binding molecule comprising the variable region having enhanced binding to the first antigen.

The library used in the step (a) is preferably a library produced by identifying amino acids that maintain 80% or more of the ability to bind to CD3, though the library is not limited thereto.

According to one aspect, the present invention provides a method for producing an antigen-binding molecule, comprising the steps given below.

The method for producing an antigen-binding molecule is a method for producing an antigen-binding molecule comprising a variable region that is capable of binding to a first antigen which is CD3 and a second antigen different from the first antigen, but does not bind to the first antigen and the second antigen at the same time, the method comprising the following steps (a) to (c):

(a) contacting the library of the present invention with the second antigen;

(b) recovering antigen-binding molecules bound with the second antigen in the step (a); and (c) selecting an antigen-binding molecule comprising a variable region that does not bind to the first antigen and the second antigen at the same time from a population of the antigen-binding molecules recovered in the step (b).

According to another aspect, the present invention provides a method for producing an antigen-binding molecule, comprising the steps given below.

The method for producing an antigen-binding molecule is a method for producing an antigen-binding molecule comprising a variable region that is capable of binding to a first antigen which is CD3, a second antigen different from the first antigen, and a fourth antigen different from the first antigen and the second antigen, but does not bind to the three antigens at the same time, the method comprising the following steps (a) to (f):

(a) contacting the library of the present invention with the second antigen;

(b) recovering antigen-binding molecules bound with the second antigen in the step (a);

(c) selecting antigen-binding molecules each comprising a variable region that does not bind to the first antigen and the second antigen at the same time from a population of the antigen-binding molecules recovered in the step (b);

(d) contacting a population of the antigen-binding molecules recovered in the step (c) with the fourth antigen;

(e) recovering antigen-binding molecules bound with the fourth antigen in the step (d); and (f) selecting an antigen-binding molecule comprising a variable region that does not bind to the first antigen, the second antigen, and the fourth antigen at the same time from a population of the antigen-binding molecules recovered in the step (e).

In these aspects, preferably, the first antigen is CD3, and the second antigen or the fourth antigen is a molecule expressed on the surface of a T cell or any other immunocyte. More preferably, the second antigen is FcγR, TLR, lectin, IgA, an immune checkpoint molecule, a TNF superfamily molecule, a TNFR superfamily molecule, or an NK receptor molecule.

The antigen-binding molecules are not particularly limited as long as these molecules each comprise an antibody variable region. The antigen-binding molecules may be antibody fragments such as Fv, Fab, or Fab' or may be Fc region-containing antibodies.

In the production method of the present invention, the step (c) may be the following selection step:

(d) selecting an antigen-binding molecule comprising a variable region that has binding activity against the first antigen and the second antigen, but does not bind to the first antigen and the second antigen each expressed on a different cell, at the same time, from the population of the antigen-binding molecules recovered in the step (b).

In the production method of the present invention, the step (f) may be the following selection step:

(g) selecting an antigen-binding molecule comprising a variable region that has binding activity against the first antigen, the second antigen, and the fourth antigen, but does not bind to the first antigen, the second antigen, and the fourth antigen each expressed on a different cell, at the same time, from the population of the antigen-binding molecules recovered in the step (c).

In one aspect, the present invention provides a method for producing a bispecific antibody comprising common L chain variable domains, comprising the steps given below.

The method for producing a bispecific antibody is a method for producing a bispecific antibody using a library consisting essentially of a plurality of antigen-binding molecules differing in sequence from each other, wherein an antigen-binding region in each of the antigen-binding molecules is a variable region consisting of a template sequence, or an antibody variable region that has alteration of at least one amino acid in the template sequence and is capable of binding to a first antigen and a second antigen different from the first antigen, but does not bind to the first antigen and the second antigen at the same time, the method comprising the following steps (a) to (c):

(a) selecting the library template sequence of the present invention as a variable region binding to the first antigen;

(b) selecting a variable region that binds to the second antigen, but does not bind to the first antigen, as a variable region binding to the second antigen, the step (b) comprising the following steps (i) to (iv):

(i) contacting the library of the present invention with the desired second antigen;

(ii) recovering antigen-binding molecules bound with the second antigen in the step (i);

(iii) contacting a population of the antigen-binding molecules recovered in the step (ii) with the first antigen; and (iv) selecting an antigen-binding molecule that does not bind to the first antigen in the step (iii); and (c) producing a bispecific antibody comprising the variable region binding to the first antigen selected in the step (a), and the variable region binding to the second antigen selected in the step (b).

In this aspect, preferably, the first antigen is CD3, and the second antigen is a molecule specifically expressed in a cancer tissue.

The production of a bispecific antibody by the method according to this aspect also allows the efficient obtainment of common L chain variable domains of a bispecific antibody comprising a variable region binding to a first antigen CD3, and a variable region binding to a second antigen molecule specifically expressed in a cancer tissue.

The antigen-binding molecules used in the step (b) are not particularly limited as long as these molecules each comprise an antibody variable region. The antigen-binding molecules may be antibody fragments such as Fv, Fab, or Fab' or may be Fc region-containing antibodies.

As for fusion polypeptide display, the fusion polypeptide of the variable region of the antigen-binding molecule can be displayed in various forms on the surface of cells, viruses, or phagemid particles. These forms include single-chain Fv fragments (scFvs), F(ab) fragments, and multivalent forms of these fragments. The multivalent forms are preferably ScFv, Fab, and F(ab') dimers, which are referred to as (ScFv)2, F(ab)2, and F(ab')2, respectively, herein. The display of the multivalent forms is preferred, probably in part because the displayed multivalent forms usually permit identification of low-affinity clones and/or have a plurality of antigen-binding sites that permit more efficient selection of rare clones in the course of selection.

Methods for displaying fusion polypeptides comprising antibody fragments on the surface of bacteriophages are known in the art and described in, for example, WO1992001047 and the present specification. Other related methods are described in WO1992020791, WO1993006213, WO1993011236, and 1993019172. Those skilled in the art can appropriately use these methods. Other public literatures (H. R. Hoogenboom & G. Winter (1992) J. Mol. Biol. 227, 381-388, WO1993006213, and WO1993011236) disclose the identification of antibodies using artificially rearranged variable region gene repertoires against various antigens displayed on the surface of phages.

In the case of constructing a vector for display in the form of scFv, this vector comprises nucleic acid sequences encoding the light chain variable domain and the heavy chain variable domain of the antigen-binding molecule. In general, the nucleic acid sequence encoding the heavy chain variable domain of the antigen-binding molecule is fused with a nucleic acid sequence encoding a viral coat protein constituent. The nucleic acid sequence encoding the light chain variable domain of the antigen-binding molecule is linked to the heavy chain variable domain nucleic acid of the antigen-binding molecule through a nucleic acid sequence encoding a peptide linker. The peptide linker generally contains approximately 5 to 15 amino acids. Optionally, an additional sequence encoding, for example, a tag useful in purification or detection, may be fused with the 3' end of the nucleic acid sequence encoding the light chain variable domain of the antigen-binding molecule or the nucleic acid sequence encoding the heavy chain variable domain of the antigen-binding molecule, or both.

In the case of constructing a vector for display in the form of F(ab), this vector comprises nucleic acid sequences encoding the variable domains of the antigen-binding molecule and the constant domains of the antigen-binding molecule. The nucleic acid sequence encoding the light chain variable domain is fused with the nucleic acid sequence encoding the light chain constant domain. The nucleic acid sequence encoding the heavy chain variable domain of the antigen-binding molecule is fused with the nucleic acid sequence encoding the heavy chain constant CH1 domain. In general, the nucleic acid sequence encoding the heavy chain variable domain and constant domain is fused with a nucleic acid sequence encoding the whole or a portion of a viral coat protein. The heavy chain variable domain and constant domain are preferably expressed as a fusion product with at least a portion of the viral coat protein, while the light chain variable domain and constant domain are expressed separately from the heavy chain-viral coat fusion protein. The heavy chain and the light chain may be associated with each other through a covalent bond or a non-covalent bond. Optionally, an additional sequence encoding, for example, a polypeptide tag useful in purification or detection, may be fused with the 3' end of the nucleic acid sequence encoding the light chain constant domain of the antigen-binding molecule or the nucleic acid sequence encoding the heavy chain constant domain of the antigen-binding molecule, or both.

As for vector transfer to host cells, the vectors constructed as described above are transferred to host cells for amplification and/or expression. The vectors can be transferred to host cells by a transformation method known in the art, including electroporation, calcium phosphate precipitation, and the like. When the vectors are infectious particles such as viruses, the vectors themselves invade the host cells. Fusion proteins are displayed on the surface of phage particles by the transfection of host cells with replicable expression vectors having inserts of polynucleotides encoding the fusion proteins and the production of the phage particles by an approach known in the art.

The replicable expression vectors can be transferred to host cells by use of various methods. In a non-limiting embodiment, the vectors can be transferred to the cells by electroporation as described in WO2000106717. The cells are cultured at 37° C., optionally for approximately 6 to 48 hours (or until OD at 600 nm reaches 0.6 to 0.8) in a standard culture medium. Next, the culture medium is centrifuged, and the culture supernatant is removed (e.g., by decantation). At the initial stage of purification, the cell pellet is preferably resuspended in a buffer solution (e.g., 1.0 mM HEPES (pH 7.4)). Next, the suspension is centrifuged again to remove the supernatant. The obtained cell pellet is resuspended in glycerin diluted to, for example, 5 to 20% V/V. The suspension is centrifuged again for the removal of the supernatant to obtain cell pellet. The cell pellet is resuspended in water or diluted glycerin. On the basis of the measured cell density of the resulting suspension, the final cell density is adjusted to a desired density using water or diluted glycerin.

Examples of preferred recipient cells include an *E. coli* strain SS320 capable of responding to electroporation (Sidhu et al., Methods Enzymol. (2000) 328, 333-363). The *E. coli* strain SS320 has been prepared by the coupling of MC1061 cells with XL1-BLUE cells under conditions sufficient for transferring fertility episome (F' plasmid) or XL1-BLUE into the MC1061 cells. The *E. coli* strain SS320 has been deposited with ATCC (10801 University Boulevard, Manassas, Va.) under deposition No. 98795. Any F' episome that permits phage replication in this strain can be used in the present invention. Appropriate episome may be obtained from strains deposited with ATCC or may be obtained as a commercially available product (TG1, CJ236, CSH18, DHF', ER2738, JM101, JM103, JM105, JM107, JM109, JM110, KS1000, XL1-BLUE, 71-18, etc.).

Use of higher DNA concentrations (approximately 10 times) in electroporation improves transformation frequency and increases the amount of DNAs transforming the host cells. Use of high cell densities also improves the efficiency (approximately 10 times). The increased amount of transferred DNAs can yield a library having greater diversity and a larger number of independent clones differing in sequence. The transformed cells are usually selected on the basis of the presence or absence of growth on a medium containing an antibiotic.

The present invention further provides a nucleic acid encoding the antigen-binding molecule of the present invention. The nucleic acid of the present invention may be in any form such as DNA or RNA.

The present invention further provides a vector comprising the nucleic acid of the present invention. The type of the vector can be appropriately selected by those skilled in the art according to host cells that receive the vector. For example, any of the vectors mentioned above can be used.

The present invention further relates to a host cell transformed with the vector of the present invention. The host cell can be appropriately selected by those skilled in the art. For example, any of the host cells mentioned above can be used.

The present invention also provides a pharmaceutical composition comprising the antigen-binding molecule of the present invention and a pharmaceutically acceptable carrier. The pharmaceutical composition of the present invention can be formulated according to a method known in the art by supplementing the antigen-binding molecule of the present invention with the pharmaceutically acceptable carrier. For example, the pharmaceutical composition can be used in the form of a parenteral injection of an aseptic solution or suspension with water or any other pharmaceutically acceptable solution. For example, the pharmaceutical composition may be formulated with the antigen-binding molecule mixed in a unit dosage form required for generally accepted pharmaceutical practice, in appropriate combination with pharmacologically acceptable carriers or media, specifically, sterilized water, physiological saline, plant oil, an emulsifier, a suspending agent, a surfactant, a stabilizer, a flavoring agent, an excipient, a vehicle, a preservative, a binder, etc. Specific examples of the carrier can include light anhydrous silicic acid, lactose, crystalline cellulose, mannitol, starch, carmellose calcium, carmellose sodium, hydroxypropylcellulose, hydroxypropylmethylcellulose, polyvinyl acetal diethylaminoacetate, polyvinylpyrrolidone, gelatin, medium-chain fatty acid triglyceride, polyoxyethylene hydrogenated castor oil 60, saccharide, carboxymethylcellulose, cornstarch, and inorganic salts. The amount of the active ingredient in such a preparation is determined such that an appropriate dose within the prescribed range can be achieved.

An aseptic composition for injection can be formulated according to conventional pharmaceutical practice using a vehicle such as injectable distilled water. Examples of aqueous solutions for injection include physiological saline, isotonic solutions containing glucose and other adjuvants, for example, D-sorbitol, D-mannose, D-mannitol, and sodium chloride. These solutions may be used in combination with an appropriate solubilizer, for example, an alcohol (specifically, ethanol) or a polyalcohol (e.g., propylene glycol and polyethylene glycol), or a nonionic surfactant, for example, polysorbate 80™ or HCO-50.

Examples of oily solutions include sesame oil and soybean oil. These solutions may be used in combination with benzyl benzoate or benzyl alcohol as a solubilizer. The solutions may be further mixed with a buffer (e.g., a phosphate buffer solution and a sodium acetate buffer solution), a soothing agent (e.g., procaine hydrochloride), a stabilizer (e.g., benzyl alcohol and phenol), and an antioxidant. The injection solutions thus prepared are usually charged into appropriate ampules. The pharmaceutical composition of the present invention is preferably administered parenterally. Specific examples of its dosage forms include injections, intranasal administration agents, transpulmonary administration agents, and percutaneous administration agents. Examples of the injections include intravenous injection, intramuscular injection, intraperitoneal injection, and subcutaneous injection, through which the pharmaceutical composition can be administered systemically or locally.

The administration method can be appropriately selected depending on the age and symptoms of a patient. The dose of a pharmaceutical composition containing a polypeptide or a polynucleotide encoding the polypeptide can be selected within a range of, for example, 0.0001 to 1000 mg/kg of body weight per dose. Alternatively, the dose can be selected within a range of, for example, 0.001 to 100000 mg/body of a patient, though the dose is not necessarily limited to these numeric values. Although the dose and the administration method vary depending on the weight, age, symptoms, etc. of a patient, those skilled in the art can appropriately select the dose and the method.

The present invention also provides a method for treating cancer, comprising the step of administering the antigen-binding molecule of the present invention, the antigen-binding molecule of the present invention for use in the treatment of cancer, use of the antigen-binding molecule of the present invention in the production of a therapeutic agent for cancer, and a process for producing a therapeutic agent for cancer, comprising the step of using the antigen-binding molecule of the present invention.

The three-letter codes and corresponding one-letter codes of amino acids used herein are defined as follows: alanine: Ala and A, arginine: Arg and R, asparagine: Asn and N, aspartic acid: Asp and D, cysteine: Cys and C, glutamine: Gln and Q, glutamic acid: Glu and E, glycine: Gly and G, histidine: His and H, isoleucine: Ile and I, leucine: Leu and L, lysine: Lys and K, methionine: Met and M, phenylalanine: Phe and F, proline: Pro and P, serine: Ser and S, threonine: Thr and T, tryptophan: Trp and W, tyrosine: Tyr and Y, and valine: Val and V.

Those skilled in the art should understand that one of or any combination of two or more of the aspects described herein is also included in the present invention unless a technical contradiction arises on the basis of the technical common sense of those skilled in the art.

All references cited herein are incorporated herein by reference in their entirety.

The present invention will be further illustrated with reference to Examples below. However, the present invention is not intended to be limited by Examples below.

EXAMPLES

[Example 1] Concept of Altered Immunoglobulin Variable (Fab) Region that Binds CD3 (First Antigen) and Another Antigen (Second Antigen), but does not Bind to CD3 (First Antigen) and Another Antigen (Second Antigen) on Different Cells at Same Time The binding of an immunoglobulin to two or more molecules of activating FcγR at the same time or to activating FcγR and another antigen at the same time causes the cross-linking reaction of the activating FcγR, which may in turn transduces FcγR ITAM signals, resulting in the possible activation of immunocytes. One molecule of an IgG-type antibody is capable of binding to only one FcγR molecule, as described above. Therefore, two or more molecules of activating FcγR are cross-linked only in the presence of an antigen to activate immunocytes.

When an IgG-type antibody binds to an antigen through its variable region (Fab), this antibody is also capable of binding to one molecule of FcγR through its Fc region at the same time therewith. This causes the cross-linking between a cell expressing the antigen and a cell expressing FcγR. Depending on the cell expressing the antigen, such cross-linking between the antigen and FcγR may not be favorable. Specifically, when the antigen is, for example, CD3, a T cell cross-linked with an FcγR-expressing cell may cause immune activation such as cytokine release (J. Immunol. (1999) Aug. 1, 163 (3), 1246-52). In such a case, the Fc region can lose its binding activity against FcγR by the introduction of alteration to prevent the cross-linking reaction between the antigen and FcγR (Advanced Drug Delivery Reviews (2006) 58, 640-656). Likewise, when antigens for IgG-type antibodies are, for example, TNFR superfamily molecules (e.g., CD40, OX40, and CD27) or CD3 and TLR (e.g., TLR2, TLR4, TLR8, and TLR9), the FcγR-mediated cross-linking causes systemic immune activation. Thus, the binding at the same time to these molecules expressed on separate cells is not favorable.

Meanwhile, a conventional multispecific antibody binds to a plurality of antigens at the same time. Depending on the combination of the antigens, the binding to a plurality of antigens at the same time may not be favorable. For example, integrin αvβ3, known as an adhesion molecule, is expressed in many cancer cells and peritumoral blood vessels and as such, is useful as a target molecule in tumor targeting (R. Haubner, PLoS Med., 2, e70 (2005)), whereas this molecule is also known to be expressed in various normal cells (Thromb Haemost. 1998 November; 80 (5): 726-34). Thus, the binding of the multispecific antibody to both CD3 and integrin αvβ3 at the same time might damage normal cells due to potent cytotoxic activity mediated by T cells.

Figure 2:
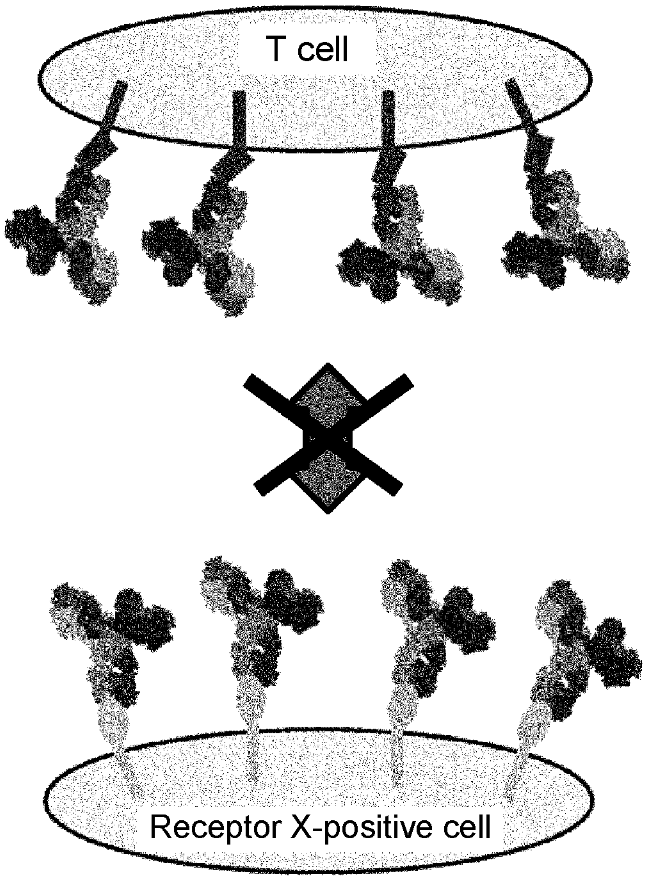
FIG. 2 is a conceptual diagram of an antibody that does not cause cross-linking because the antibody does not bind to two antigens at the same time.
Figure 3:
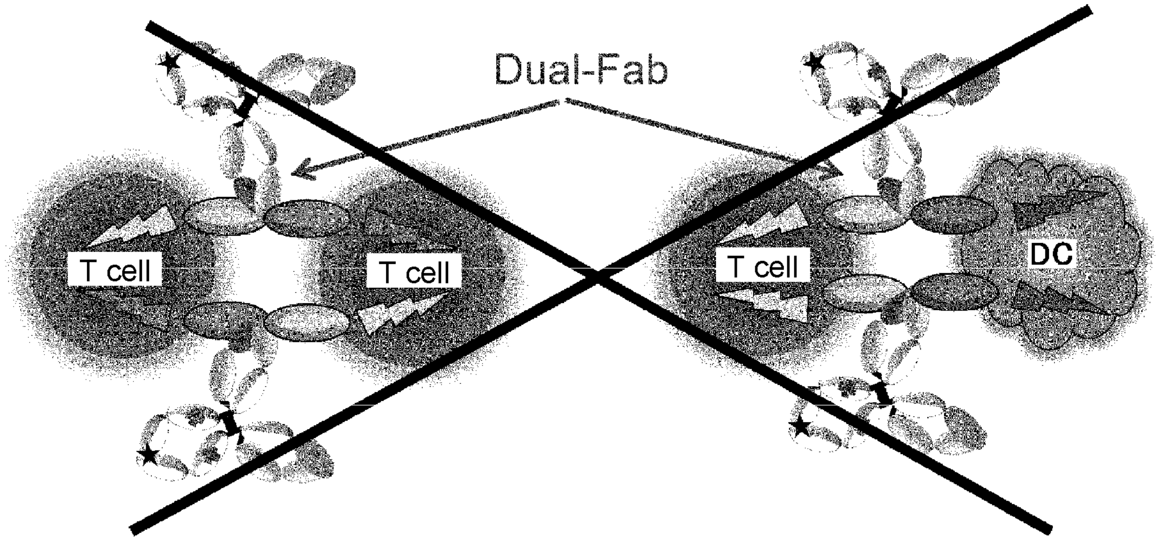
FIG. 3 is a conceptual diagram of an antibody that binds to two antigens at the same time, but does not link two cells at the same time.
Figure 4:
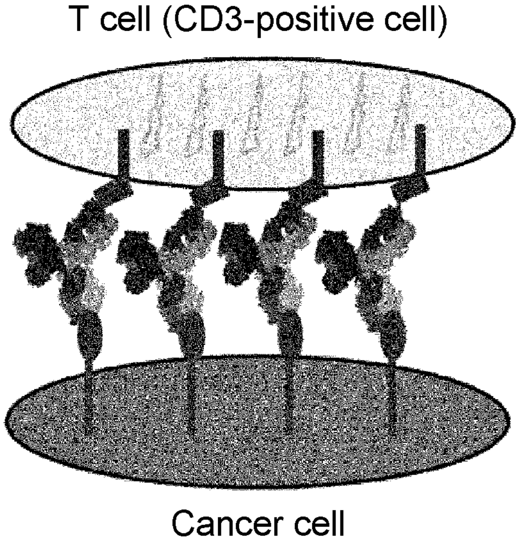
FIG. 4 is a conceptual diagram of an antibody that cross-links a cancer cell to a T cell expressing a first receptor.
Figure 5:
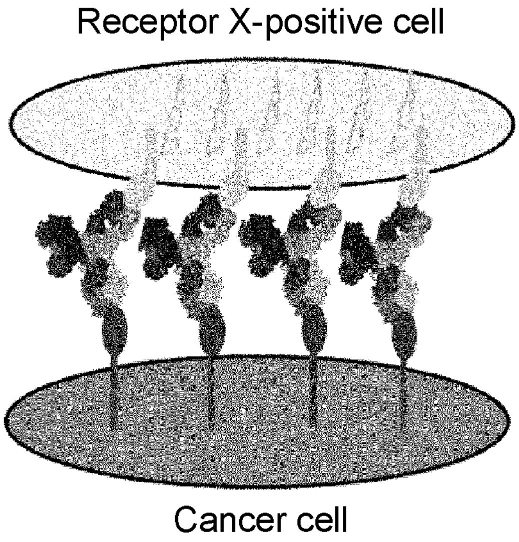
FIG. 5 is a conceptual diagram of an antibody that cross-links a cancer cell to a cell expressing a second receptor.

Accordingly, a possible method for controlling such unfavorable cross-linking reaction was dual binding Fab, which is one variable (Fab) region that binds to the first antigen through a portion thereof and binds to the second antigen through a different portion that does not participate in this binding to the first antigen (FIG. 1). Provided that two proximally positioned moieties in one variable (Fab) region are essential for the binding to their respective antigens, as shown in FIG. 1, the binding to the first antigen inhibits the binding to the second antigen while the binding to the second antigen also inhibits the binding to the first antigen. Thus, a modified antibody having the properties of such dual binding Fab cannot bind to the first antigen and the second antigen at the same time and therefore, presumably causes no cross-linking reaction between the first antigen and the second antigen (FIG. 2). Also, the dual binding Fab is considered to be capable of binding to both the first antigen and the second antigen at the same time when the first antigen and the second antigen are not expressed on cell membranes, as with soluble proteins, or both reside on the same cell, but to neither bind to these antigens each expressed on a different cell at the same time nor cross-link these two cells (FIG. 3). On the other hand, an antigen (third antigen) binding to another variable (Fab) region may undergo cross-linking reaction with the first antigen (FIG. 4) or may undergo cross-linking reaction with the second antigen (FIG. 5). For this antibody, an Fc region binding to FcγR may be used as a constant region, or an Fc region having reduced binding activity against FcγR may be used as a constant region.

By use of the properties of such dual binding Fab, for example, a technique of damaging cancer cells expressing a cancer antigen by the antibody-mediated redirection of T cells can be further provided with a function of targeting integrin in cancer tissues and thereby achieve higher cancer specificity.

Briefly, if a variable (Fab) region can be modified as dual binding Fab to confer the following properties, an antibody having the effects as shown in FIG. 1 can be developed:

1. having binding activity against the first antigen;
2. having binding activity against the second antigen; and
3. not binding to the first antigen and the second antigen at the same time.

The phrase "not bind to the first antigen and the second antigen at the same time" also includes not cross-linking a cell expressing the first antigen to a cell expressing the second antigen, or not binding to the first antigen and the second antigen each expressed on a different cell, at the same time. This phrase further includes the case where the variable region is capable of binding to both the first antigen and the second antigen at the same time when the first antigen and the second antigen are not expressed on cell membranes, as with soluble proteins, or both reside on the same cell, but cannot bind to the first antigen and the second antigen each expressed on a different cell, at the same time.

Figure 6:
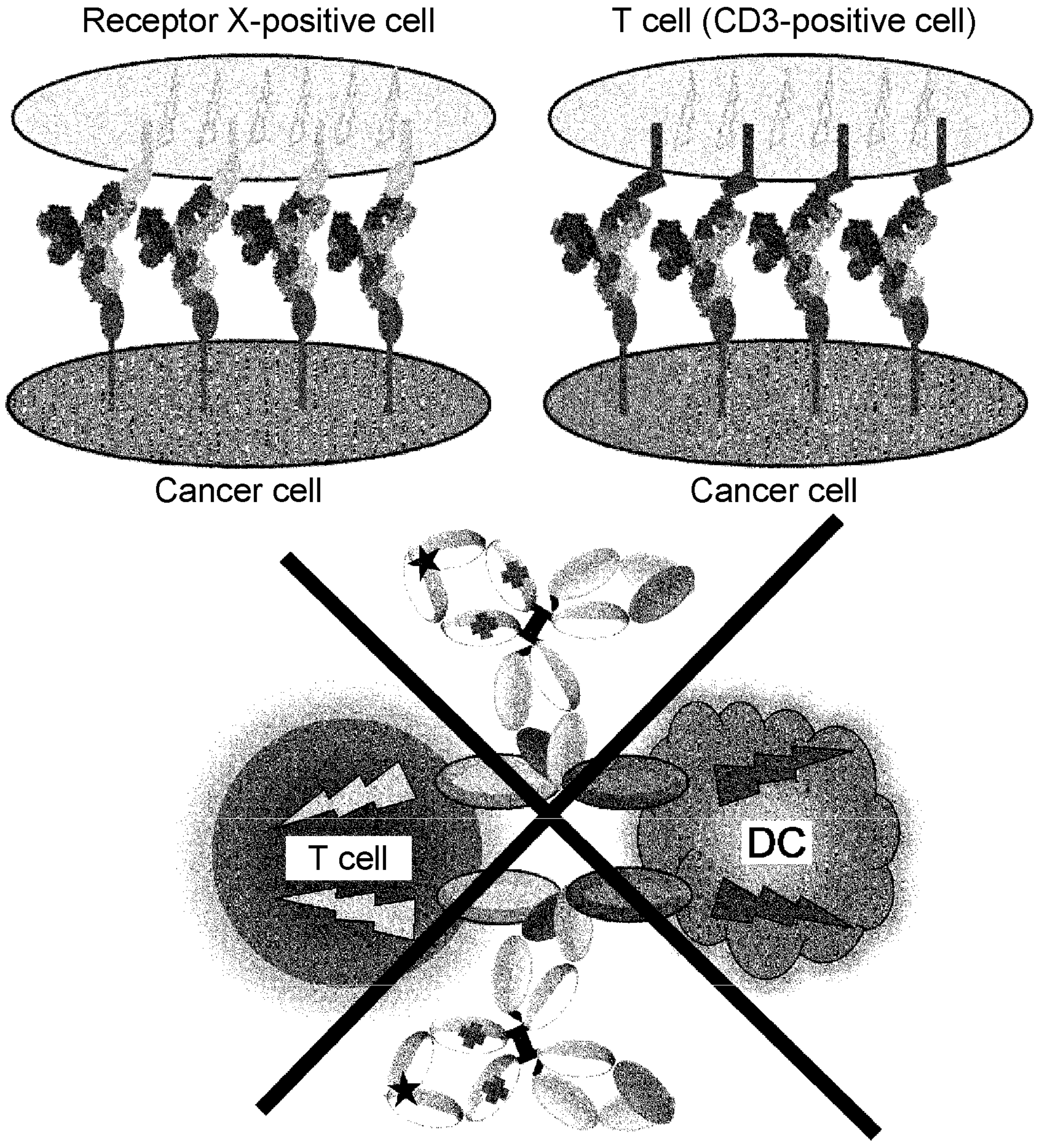
FIG. 6 is a conceptual diagram of an antibody that cross-links a cancer cell to an immunocyte, but does not cross-link immunocytes.

Likewise, if a variable (Fab) region can be modified as dual binding Fab to confer the following properties, an antibody having, for example, the effects as shown in FIG. 6 can be developed:

1. having binding activity against the first antigen on a T cell;
2. having binding activity against the second antigen on an antigen-presenting cell; and
3. not binding to the first antigen and the second antigen at the same time.

[Example 2] Preparation of Anti-Human and Anti-Cynomolgus Monkey CD3ε Antibody CE115

(2-1) Preparation of Hybridoma Using Rat Immunized with Cell Expressing Human CD3 and Cell Expressing Cynomolgus Monkey CD3

Each SD rat (female, 6 weeks old at the start of immunization, Charles River Laboratories Japan, Inc.) was immunized with Ba/F3 cells expressing human CD3εγ or cynomolgus monkey CD3εγ as follows: at day 0 (the priming date was defined as day 0), $5\times10^7$ Ba/F3 cells expressing human CD3εγ were intraperitoneally administered together with a Freund complete adjuvant (Difco Laboratories, Inc.) to the rat. At day 14, $5\times10^7$ Ba/F3 cells expressing cynomolgus monkey CD3εγ were intraperitoneally administered thereto together with a Freund incomplete adjuvant (Difco Laboratories, Inc.). Then, $5\times10^7$ Ba/F3 cells expressing human CD3εγ and Ba/F3 cells expressing cynomolgus monkey CD3εγ were intraperitoneally administered thereto a total of four times every other week in an alternate manner. One week after (at day 49) the final administration of CD3εγ, Ba/F3 cells expressing human CD3εγ were intravenously administered thereto as a booster. Three days thereafter, the spleen cells of the rat were fused with mouse myeloma cells SP2/0 according to a routine method using PEG1500 (Roche Diagnostics K.K.). Fusion cells, i.e., hybridomas, were cultured in an RPMI1640 medium containing 10% FBS (hereinafter, referred to as 10% FBS/RPMI1640).

On the day after the fusion, (1) the fusion cells were suspended in a semifluid medium (Stemcell Technologies, Inc.). The hybridomas were selectively cultured and also colonized.

Figure 7:
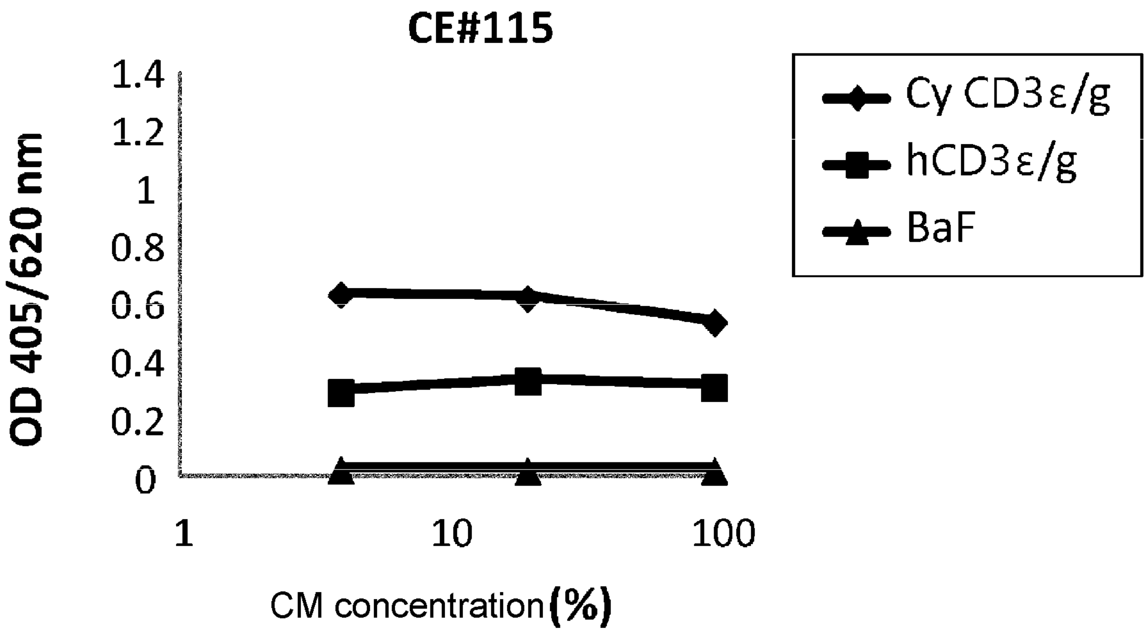
FIG. 7 is a graph showing results of cell-ELISA of CE115 for CD3ε.

Nine or ten days after the fusion, hybridoma colonies were picked up and inoculated at 1 colony/well to a 96-well plate containing a HAT selective medium (10% FBS/RPMI1640, 2 vol % HAT 50× concentrate (Sumitomo Dainippon Pharma Co., Ltd.), and 5 vol % BM-Condimed H1 (Roche Diagnostics K.K.)). After 3- to 4-day culture, the culture supernatant in each well was recovered, and the rat IgG concentration in the culture supernatant was measured. The culture supernatant confirmed to contain rat IgG was screened for a clone producing an antibody specifically binding to human CD3εγ by cell-ELISA using attached Ba/F3 cells expressing human CD3εγ or attached Ba/F3 cells expressing no human CD3εγ (FIG. 7). The clone was also evaluated for cross reactivity with monkey CD3εγ by cell-ELISA using attached Ba/F3 cells expressing cynomolgus monkey CD3εγ (FIG. 7).

(2-2) Preparation of Anti-Human and Anti-Monkey CD3c Chimeric Antibody

Total RNA was extracted from each hybridoma cell using RNeasy Mini Kits (Qiagen N.V.), and cDNA was synthesized using SMART RACE cDNA Amplification Kit (BD Biosciences). The prepared cDNA was used in PCR to insert the antibody variable region gene to a cloning vector. The nucleotide sequence of each DNA fragment was determined using BigDye Terminator Cycle Sequencing Kit (Applied Biosystems, Inc.) and a DNA sequencer ABI PRISM 3700 DNA Sequencer (Applied Biosystems, Inc.) according to the method described in the instruction manual included therein. CDRs and FRs of the CE115 H chain variable domain (SEQ ID NO: 13) and the CE115 L chain variable domain (SEQ ID NO: 14) were determined according to the Kabat numbering.

A gene encoding a chimeric antibody H chain containing the rat antibody H chain variable domain linked to a human antibody IgG1 chain constant domain, and a gene encoding a chimeric antibody L chain containing the rat antibody L chain variable domain linked to a human antibody kappa chain constant domain were integrated to expression vectors for animal cells. The prepared expression vectors were used for the expression and purification of the CE115 chimeric antibody (Reference Example 1).

(2-3) Preparation of EGFR_ERY22_CE115

Next, IgG against a cancer antigen (EGFR) was used as a backbone to prepare a molecule in a form with one Fab replaced with CD3ε-binding domains. In this operation, silent Fc having attenuated binding activity against FcgR (Fcγ receptor) was used, as in the case mentioned above, as Fc of the backbone IgG. Cetuximab-VH (SEQ ID NO: 15) and Cetuximab-VL (SEQ ID NO: 16) constituting the variable region of cetuximab were used as EGFR-binding domains. G1d derived from IgG1 by the deletion of C-terminal Gly and Lys, A5 derived from G1d by the introduction of D356K and H435R mutations, and B3 derived from G1d by the introduction of a K439E mutation were used as antibody H chain constant domains and each combined with Cetuximab-VH to prepare Cetuximab-VH-G1d (SEQ ID NO: 17), Cetuximab-VH-A5 (SEQ ID NO: 18), and Cetuximab-VH-B3 (SEQ ID NO: 19) according to the method of Reference Example 1. When the antibody H chain constant domain was designated as H1, the sequence corresponding to the antibody H chain having Cetuximab-VH as a variable domain was represented by Cetuximab-VH-H1.

In this context, the alteration of an amino acid is represented by, for example, D356K. The first alphabet (which corresponds to D in D356K) means an alphabet that represents the one-letter code of the amino acid residue before the alteration. The number (which corresponds to 356 in D356K) following the alphabet means the EU numbering position of this altered residue. The last alphabet (which corresponds to K in D356K) means an alphabet that represents the one-letter code of an amino acid residue after the alteration.

Figure 8:
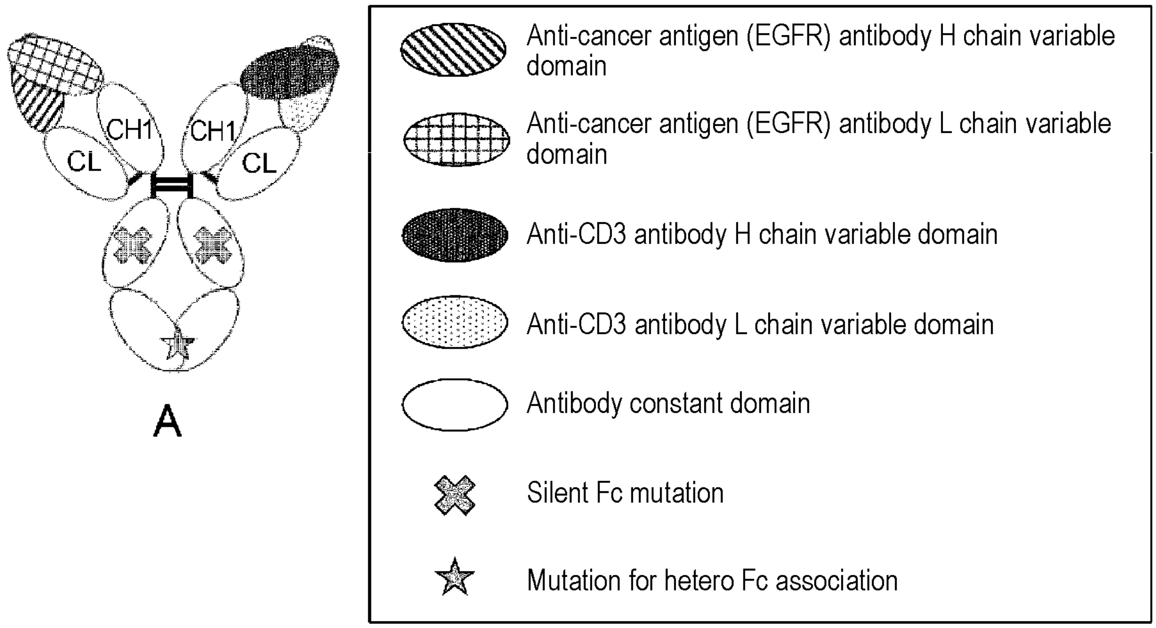
FIG. 8 is a diagram showing the molecular form of EGFR_ERY22_CE115.

EGFR_ERY22_CE115 (FIG. 8) was prepared by the exchange between the VH domain and the VL domain of Fab against EGFR. Specifically, a series of expression vectors having an insert of each polynucleotide encoding EGFR ERY22_Hk (SEQ ID NO: 20), EGFR ERY22_L (SEQ ID NO: 21), CE115_ERY22_Hh (SEQ ID NO: 22), or CE115_ERY22_L (SEQ ID NO: 23) was prepared by a method generally known to those skilled in the art, such as PCR, using primers with an appropriate sequence added in the same way as the aforementioned method.

The expression vectors were transferred in the following combination to FreeStyle 293-F cells where each molecule of interest was transiently expressed:

Molecule of interest: EGFR_ERY22_CE115

Polypeptides encoded by the polynucleotides inserted in the expression vectors: EGFR ERY22_Hk, EGFR ERY22_L, CE115_ERY22_Hh, and CE115_ERY22_L (2-4) Purification of EGFR_ERY22_CE115

The obtained culture supernatant was added to Anti FLAG M2 column (Sigma-Aldrich Corp.), and the column was washed, followed by elution with 0.1 mg/mL FLAG peptide (Sigma-Aldrich Corp.). The fraction containing the molecule of interest was added to HisTrap HP column (GE Healthcare Japan Corp.), and the column was washed, followed by elution with the concentration gradient of imidazole. The fraction containing the molecule of interest was concentrated by ultrafiltration. Then, this fraction was added to Superdex 200 column (GE Healthcare Japan Corp.). Only a monomer fraction was recovered from the eluate to obtain each purified molecule of interest.

(2-5) Measurement of Cytotoxic Activity Using Human Peripheral Blood Mononuclear Cell (2-5-1) Preparation of Human Peripheral Blood Mononuclear Cell (PBMC) Solution 50 mL of peripheral blood was collected from each healthy volunteer (adult) using a syringe pre-filled with 100 μL of 1,000 units/mL of a heparin solution (Novo-Heparin 5,000 units for Injection, Novo Nordisk A/S). The peripheral blood was diluted 2-fold with PBS(−) and then divided into four equal parts, which were then added to Leucosep lymphocyte separation tubes (Cat. No. 227290, Greiner Bio-One GmbH) pre-filled with 15 mL of Ficoll-Paque PLUS and centrifuged in advance. After centrifugation (2,150 rpm, 10 minutes, room temperature) of the separation tubes, a mononuclear cell fraction layer was separated. The cells in the mononuclear cell fraction were washed once with Dulbecco's Modified Eagle's Medium containing 10% FBS (Sigma-Aldrich Corp.; hereinafter, referred to as 10% FBS/D-MEM). Then, the cells were adjusted to a cell density of $4\times10^6$ cells/mL with 10% FBS/D-MEM. The cell solution thus prepared was used as a human PBMC solution in the subsequent test.

(2-5-2) Measurement of Cytotoxic Activity

The cytotoxic activity was evaluated on the basis of the rate of cell growth inhibition using xCELLigence real-time cell analyzer (Roche Diagnostics). The target cells used were an SK-pca13a cell line established by forcing an SK-HEP-1 cell line to express human EGFR. SK-pca13a was dissociated from the dish and inoculated at 1004/well ($1\times10^4$ cells/well) to an E-Plate 96 plate (Roche Diagnostics) to start the assay of live cells using the xCELLigence real-time cell analyzer. On the next day, the plate was taken out of the xCELLigence real-time cell analyzer, and 50 μL of each antibody adjusted to each concentration (0.004, 0.04, 0.4, and 4 nM) was added to the plate. After reaction at room temperature for 15 minutes, 50 μL ($2\times10^5$ cells/well) of the human PBMC solution prepared in the preceding paragraph (2-5-1) was added thereto. This plate was reloaded to the xCELLigence real-time cell analyzer to start the assay of live cells. The reaction was carried out under conditions of 5% $CO_2$ and 37° C. 72 hours after the addition of human PBMC. The rate of cell growth inhibition (%) was determined from the cell index value according to the expression given below. A numeric value after normalization against the cell index value immediately before the addition of the antibody defined as 1 was used as the cell index value in this calculation.

$$\text{Rate of cell growth inhibition (\%)}=(A-B)\times100/(A-1),\ \text{wherein}$$

A represents the average cell index value of wells non-supplemented with the antibody (only the target cells and human PBMC), and B represents the average cell index value of the wells supplemented with each antibody. The test was conducted in triplicate.

Figure 9:
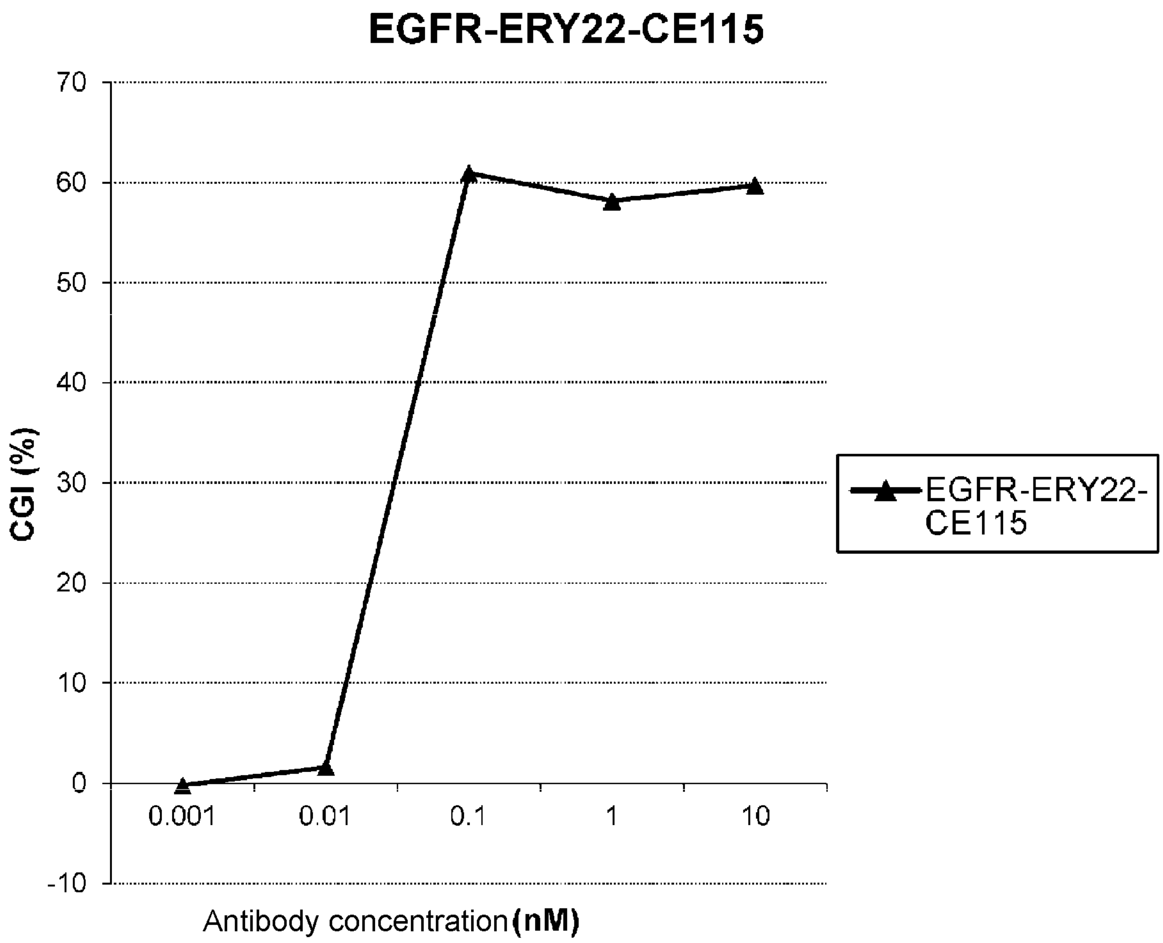
FIG. 9 is a graph showing results of TDCC (SK-pca13a) of EGFR_ERY22_CE115.
Figure 10:
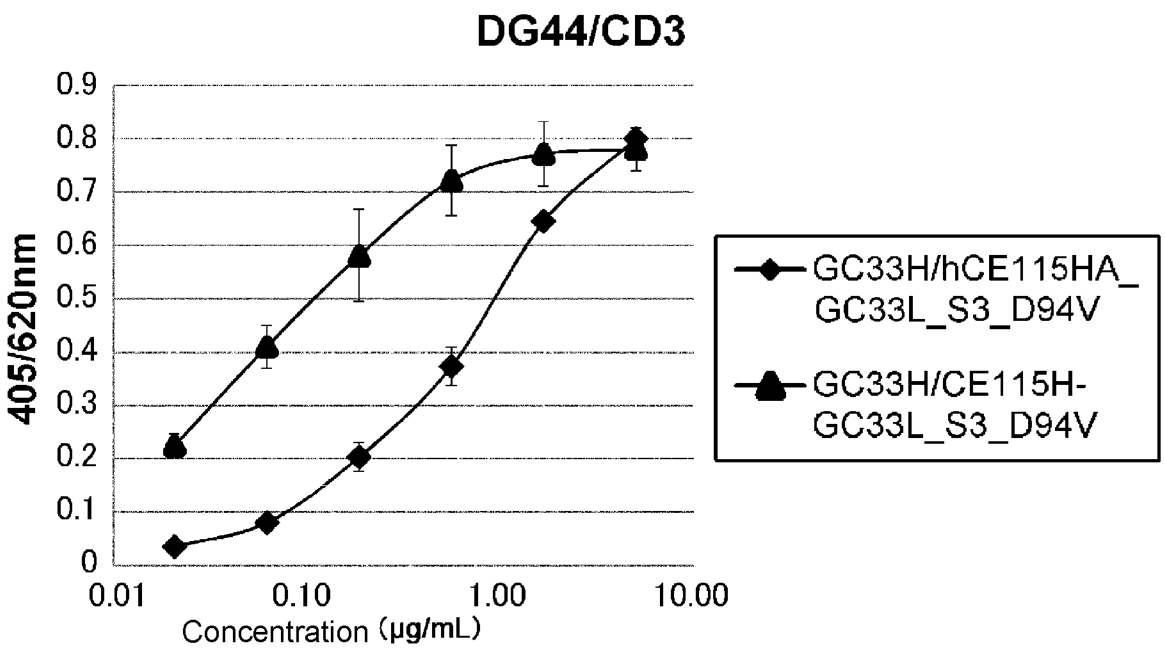
FIG. 10 is a graph showing the binding activity of humanized CE115 against CD3ε.

The cytotoxic activity of EGFR_ERY22_CE115 containing CE115 was measured with PBMC prepared from human blood as effector cells. As a result, very strong activity was confirmed (FIG. 9).

[Example 3] Preparation of Antibody that Binds to CD3 and Human Integrin αvβ3, but does not Bind to these Antigens at Same Time As shown in FIGS. 1 to 6, the dual binding Fab is a molecule that binds to CD3 (first antigen) and the antigen of interest (second antigen) through its variable (Fab) region, but does not bind to CD3 (first antigen) and the antigen of interest (second antigen) at the same time. In the case of introducing amino acid alteration for binding to the second antigen to a CD3 (first antigen)-binding antibody Fab region, the amino acid alteration is usually introduced to both of two H chains or L chains. As a result of introducing the alteration to both of the H chains or the L chains, the two antibody Fabs become capable of binding to two antigens, respectively. Thus, these two Fabs might bind to CD3 (first antigen) and the antigen of interest (second antigen) at the same time to cross-link them. Thus, one Fab of the antibody is prepared as Fab binding to a third antigen or nothing, and the other Fab is prepared as dual binding Fab to prevent the cross-linking reaction between CD3 (first antigen) and the antigen of interest (second antigen).

(3-1) Preparation of Antibody that Binds to CD3 and Human Integrin αvβ3, but does not Bind to these Antigens at Same Time Integrin αvβ3, known as an adhesion molecule, is expressed in many cancer cells and peritumoral blood vessels and as such, is useful as a target molecule in tumor targeting, whereas this molecule is also known to be expressed in various normal cells (Thromb Haemost. 1998 November; 80 (5): 726-34). Thus, binding to CD3 and integrin αvβ3 at the same time might damage normal cells due to potent cytotoxic activity mediated by T cells. Accordingly, it was assumed that an anti-EGFR antibody molecule can target tumor cells expressing integrin αvβ3 without damaging normal cells, if a molecule that does not bind to CD3 and integrin αvβ3 at the same time can be prepared. Thus, a study was conducted to obtain a dual binding Fab molecule capable of binding to EGFR through one variable region (Fab) and binding to the first antigen CD3 and the second antigen integrin αvβ3 through the other variable region, but not capable of binding to CD3 and integrin αvβ3 at the same time.

Given that a "molecule that binds to CD3 through one Fab region under integrin αvβ3-free conditions and binds to integrin αvβ3 through the other Fab region under CD3-free conditions" can be shown to be a "molecule that does not bind to integrin αvβ3 in a state bound with CD3 or does not bind to CD3 in a state bound with integrin αvβ3", it can be concluded that a dual binding Fab molecule having the properties of dual binding Fab of interest (i.e., the properties of being capable of binding to CD3 and the second antigen, but not binding to CD3 and the second antigen at the same time) has been developed successfully.

(3-2) Obtainment of Antibody Having Fab Region Binding to Integrin αvβ3

Possible methods for obtaining the dual binding Fab molecule were a method using libraries and a method using the insertion of a peptide known to have binding activity against a protein. An RGD (Arg-Gly-Asp) peptide is known as a peptide having binding activity against integrin αvβ3. Thus, the RGD peptide was inserted to the heavy chain loop of the CD3ε-binding antibody CE115 (heavy chain variable domain: SEQ ID NO: 13, light chain variable domain: SEQ ID NO: 14) to prepare each heterodimerized antibody having EGFR-binding domains in one Fab and a CD3-binding domain and an integrin αvβ3-binding domain in the other Fab according to Reference Example 1. Specifically, a series of expression vectors was prepared so as to have an insert of each polynucleotide encoding EGFR ERY22_Hk (SEQ ID NO: 20), EGFR ERY22_L (SEQ ID NO: 21), or CE115_ERY22_L (SEQ ID NO: 23) as well as a polynucleotide encoding any of the following fragments:

CE115_2 ERY22_Hh (SEQ ID NO: 24 with Kabat numbering positions 52b and 53 substituted by K and N, respectively), CE115_4_ERY22_Hh (SEQ ID NO: 25 with Kabat numbering positions 52b and 54 substituted by S and N, respectively), CE115_9_ERY22_Hh (SEQ ID NO: 26 with RGD inserted between Kabat numbering positions 52a and 52b), CE115_10_ERY22_Hh (SEQ ID NO: 27 with RGD inserted between Kabat numbering positions 52b and 52c), CE115_12 ERY22_Hh (SEQ ID NO: 28 with RGD inserted between Kabat numbering positions 72 and 73), CE115_17 ERY22_Hh (SEQ ID NO: 29 with Kabat numbering positions 52b and 52c substituted by K and S, respectively), CE115_47 ERY22_Hh (SEQ ID NO: 30 with RGD inserted between Kabat numbering positions 98 and 99), CE115_48 ERY22_Hh (SEQ ID NO: 31 with RGD inserted between Kabat numbering positions 99 and 100), and CE115_49 ERY22_Hh (SEQ ID NO: 32 with RGD inserted between Kabat numbering positions 100 and 100a).

Also, an antibody (EH240-Kn125/EH240-H1076/L73; SEQ ID NO: 33/34/35) with the RGD (Arg-Gly-Asp) peptide inserted in an antibody CH3 region reported in J. Biotech, 155, 193-202, 2011 was prepared as a control according to Reference Example 1. This molecule binding to integrin αvβ3 through its CH3 region is presumably capable of binding to CD3 and integrin αvβ3 at the same time.

(3-3) Confirmation of Binding of Antibody to Integrin αvβ3

Each molecule with the RGD (Arg-Gly-Asp) peptide inserted in the Fab region was evaluated for its binding to integrin αvβ3 by the electrochemiluminescence method (ECL method). Specifically, biotin-anti human IgG Ab (Southern Biotech) diluted with a TBS solution containing 0.1% BSA, 0.1 g/L calcium chloride, and 0.1 g/L magnesium chloride (referred to as a dilution(+) solution), each antibody solution adjusted to 5 μg/mL or 1 μg/mL, and integrin αvβ3 (R&D Systems, Inc.) tagged with sulfo-tag were each added at 25 μL/well to Nunc-Immuno™ MicroWell™ 96 well round plates (Nunc), and mixed, and the plate was then incubated overnight at 4° C. to form an antibody-antigen complex. A TBS solution containing 0.5% BSA, 0.1 g/L calcium chloride, and 0.1 g/L magnesium chloride (referred to as a blocking(+) solution) was added at 150 μL/well to streptavidin plate (MSD K.K.), and the plate was incubated overnight at 4° C. After removal of the blocking solution, each well was washed three times with 250 μL of a TBS solution containing 0.1 g/L calcium chloride and 0.1 g/L magnesium chloride (referred to as a TBS(+) solution). The antibody-antigen complex solution was added thereto at 75 μL/well, and the plate was incubated at room temperature for 2 hours so that the biotin-anti human IgG Ab bound to the streptavidin plate. After removal of the antibody-antigen complex solution, each well was washed three times with a TBS(+) solution, and READ buffer (MSD K.K.) was added thereto at 150 μL/well, followed by the detection of the luminescence signal of the sulfo-tag using Sector Imager 2400 (MSD K.K.).

Figure 11:
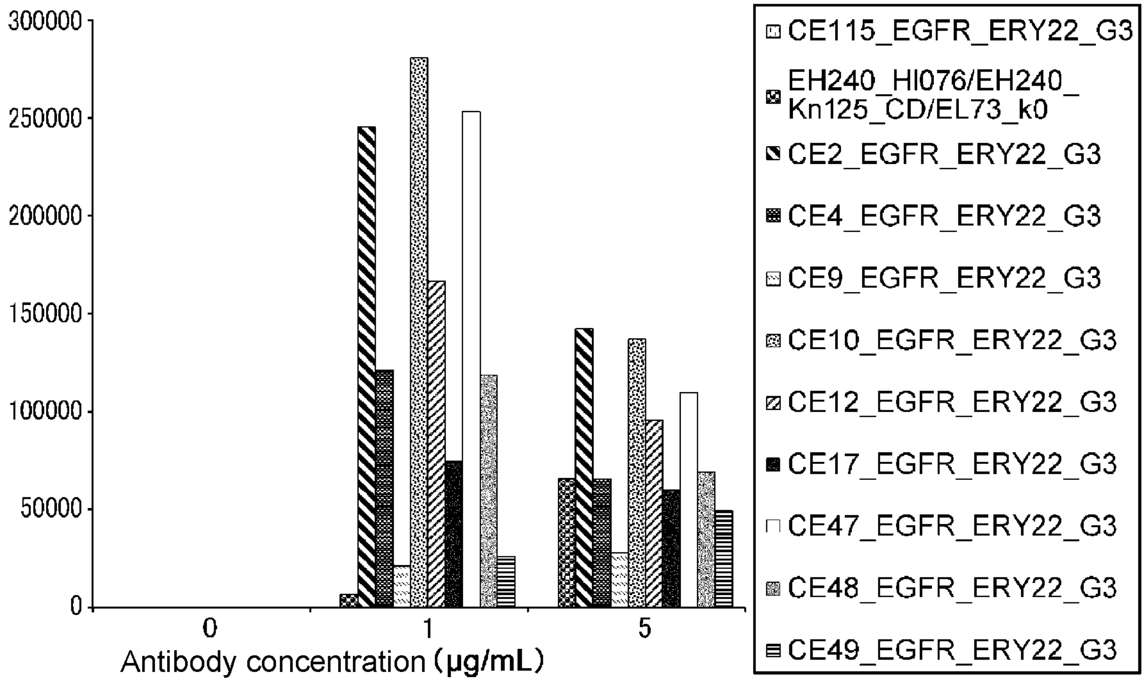
FIG. 11 is a graph showing results of ECL-ELISA for detecting the binding of RGD-inserted CE115 to integrin.

The results are shown in FIG. 11. The parent antibody EGFR ERY22_Hk/EGFR ERY22_L/CE115 ERY22_Hh/CE115_ERY22_L exhibited no binding activity against integrin αvβ3, whereas all of EGFR ERY22_Hk/EGFR ERY22_L/CE115_2 ERY22_Hh/CE115_ERY22_L, EGFR ERY22_Hk/EGFR ERY22_L/CE115_4 ERY22_Hh/CE115_ERY22_L, EGFR ERY22_Hk/EGFR ERY22_L/CE115_9 ERY22_Hh/CE115_ERY22_L, EGFR ERY22_Hk/EGFR ERY22_L/CE115_10 ERY22_Hh/CE115_ERY22_L, EGFR ERY22_Hk/EGFR ERY22_L/CE115_12 ERY22_Hh/CE115_ERY22_L, EGFR ERY22_Hk/EGFR ERY22_L/CE115_17 ERY22_Hh/CE115_ERY22_L, EGFR ERY22_Hk/EGFR ERY22_L/CE115_47 ERY22_Hh/CE115_ERY22_L, EGFR ERY22_Hk/EGFR ERY22_L/CE115_48 ERY22_Hh/CE115_ERY22_L, and EGFR ERY22_Hk/EGFR ERY22_L/CE115_49 ERY22_Hh/CE115_ERY22_L were observed to bind to integrin αvβ3.

(3-4) Confirmation of Binding of Antibody to CD3 (CD3ε)

Next, each antibody having an integrin αvβ3-binding Fab region prepared in the previous section was evaluated for whether to retain binding activity against CD3 by the ECL method. Specifically, biotin-anti human IgG Ab (Southern Biotech) diluted with a TBS solution containing 0.1% BSA (referred to as a dilution(−) solution), each antibody solution adjusted to 5 μg/mL or 1 μg/mL, and CD3ε homodimer protein tagged with sulfo-tag were each added at 25 μL/well to Nunc-Immuno™ MicroWell™ 96 well round plates (Nunc), and mixed, and the plate was then incubated overnight at 4° C. to form an antibody-antigen complex. A TBS solution containing 0.5% BSA (referred to as a blocking(−) solution) was added at 150 μL/well to streptavidin plate (MSD K.K.), and the plate was incubated overnight at 4° C. After removal of the blocking solution, each well was washed three times with 250 μL of a TBS(−) solution. The antibody-antigen complex solution was added thereto at 75 μL/well, and the plate was incubated at room temperature for 2 hours so that the biotin-anti human IgG Ab bound to the streptavidin plate. After removal of the antibody-antigen complex solution, each well was washed three times with a TBS(−) solution, and READ buffer (MSD K.K.) was added thereto at 150 μL/well, followed by the detection of the luminescence signal of the sulfo-tag using Sector Imager 2400 (MSD K.K.).

Figure 12:
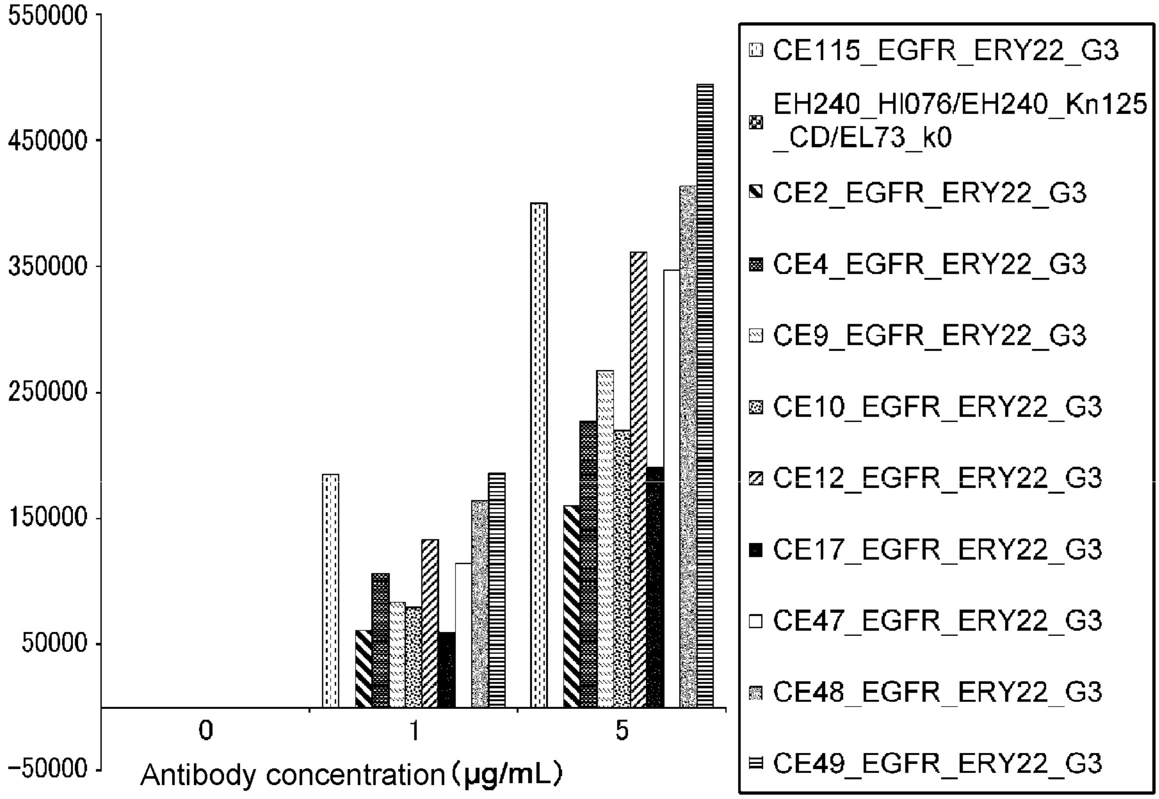
FIG. 12 is a graph showing results of ECL-ELISA for detecting the binding of RGD-inserted CE115 to CD3ε.

The results are shown in FIG. 12. All of the parent antibody EGFR ERY22_Hk/EGFR ERY22_L/CE115_ERY22_Hh/CE115_ERY22_L as well as EGFR ERY22_Hk/EGFR ERY22_L/CE115_2 ERY22_Hh/CE115_ERY22_L, EGFR ERY22_Hk/EGFR ERY22_L/CE115_4 ERY22_Hh/CE115_ERY22_L, EGFR ERY22_Hk/EGFR ERY22_L/CE115_9 ERY22_Hh/CE115_ERY22_L, EGFR ERY22_Hk/EGFR ERY22_L/CE115_10 ERY22_Hh/CE115_ERY22_L, EGFR ERY22_Hk/EGFR ERY22_L/CE115_12 ERY22_Hh/CE115_ERY22_L, EGFR ERY22_Hk/EGFR ERY22_L/CE115_17 ERY22_Hh/CE115_ERY22_L, EGFR ERY22_Hk/EGFR ERY22_L/CE115_47 ERY22_Hh/CE115_ERY22_L, EGFR ERY22_Hk/EGFR ERY22_L/CE115_48 ERY22_Hh/CE115_ERY22_L, and EGFR ERY22_Hk/EGFR ERY22_L/CE115_49 ERY22_Hh/CE115_ERY22_L were observed to bind to CD3.

(3-5) Confirmation that Fab Region does not Bind to Integrin αvβ3 and CD3 at Same Time by ECL Method As is evident from the results of the above paragraphs, the obtained molecules had binding activity against integrin αvβ3 and had binding activity against CD3. Next, each Fab region prepared in the above paragraphs was evaluated for whether to bind to CD3 (CD3ε) and integrin αvβ3 at the same time.

When a molecule with the RGD (Arg-Gly-Asp) peptide inserted in the Fab region binds to integrin αvβ3 and CD3 at the same time, its binding to both the antigens can be detected by the ECL method by adding integrin αvβ3 and biotinylated CD3 to the antibody solution. Specifically, biotinylated human CD3c homodimer protein diluted with a dilution(+) solution, each antibody solution adjusted to 10 μg/mL or 5 μg/mL, and integrin αvβ3 (R&D Systems, Inc.) tagged with sulfo-tag were each added at 254/well to Nunc-Immuno™ MicroWell™ 96 well round plates (Nunc), and mixed, and the plate was then incubated overnight at 4° C. to form an antibody-antigen complex. A blocking(+) solution was added at 150 μL/well to streptavidin plate (MSD K.K.), and the plate was incubated overnight at 4° C. After removal of the blocking solution, each well was washed three times with 250 μL of a TBS(+) solution containing 0.1 g/L calcium chloride and 0.1 g/L magnesium chloride. The antibody-antigen complex solution was added thereto at 75 μL/well, and the plate was incubated at room temperature for 2 hours so that the biotin-anti human IgG Ab bound to the streptavidin plate. After removal of the antibody-antigen complex solution, each well was washed three times with a TBS(+) solution, and READ buffer (MSD K.K.) was added thereto at 150 μL/well, followed by the detection of the luminescence signal of the sulfo-tag using Sector Imager 2400 (MSD K.K.).

Figure 13:
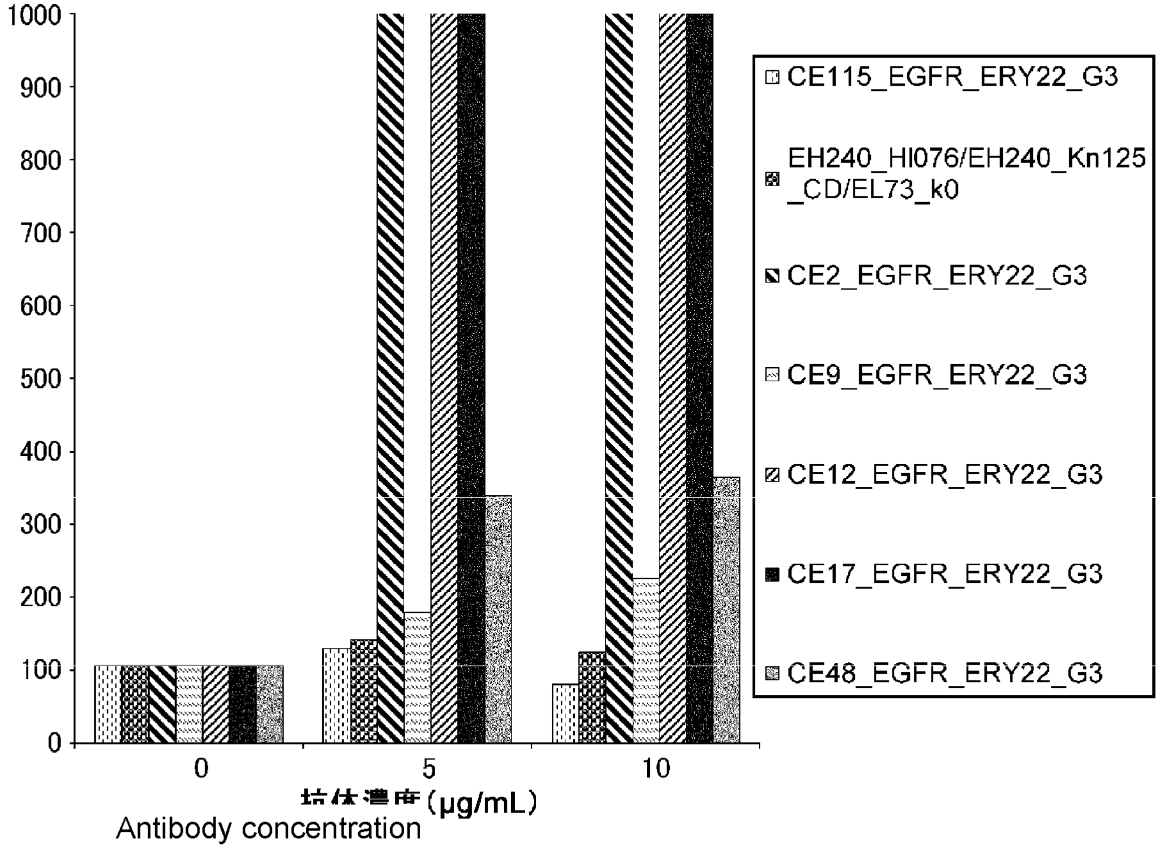
FIG. 13 is a graph showing results of ECL-ELISA for detecting the binding of RGD-inserted CE115 to integrin and CD3ε at the same time. The results about altered forms binding thereto at the same time are shown.
Figure 14:
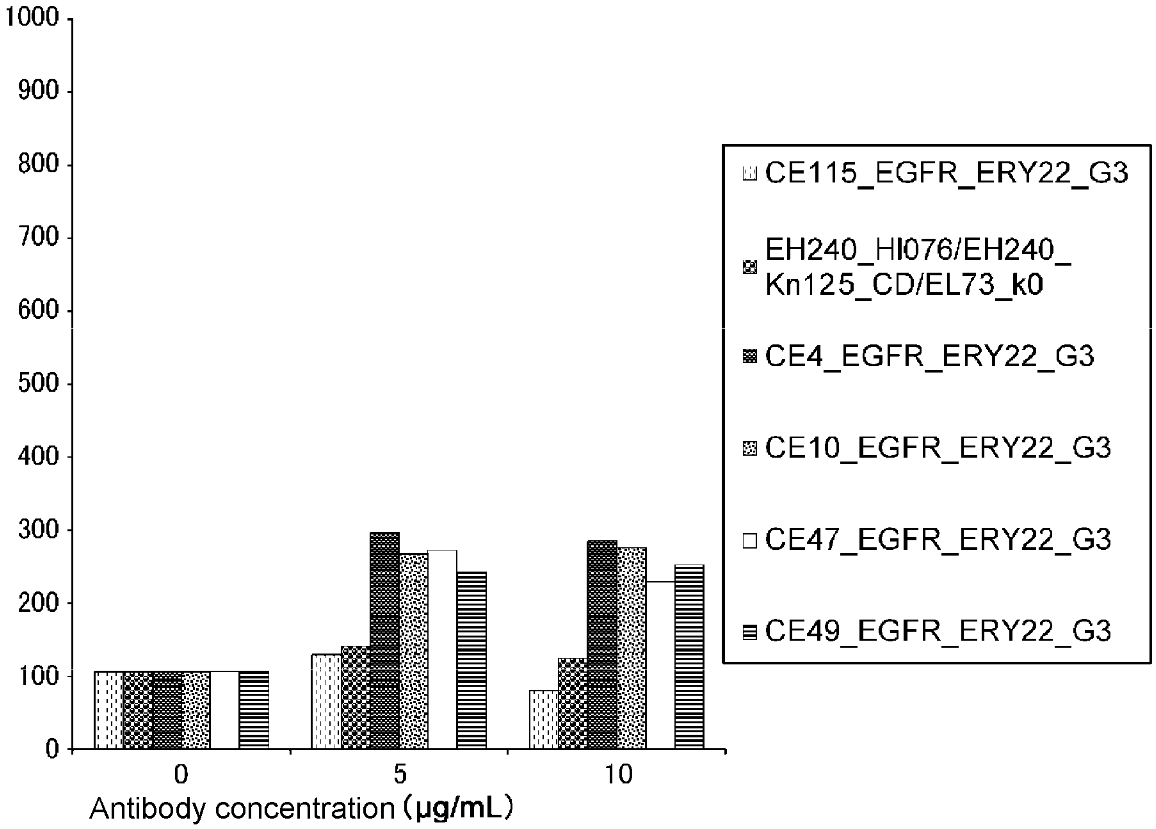
FIG. 14 is a graph showing results of ECL-ELISA for detecting the binding of RGD-inserted CE115 to the antigens at the same time. The results about altered forms that do not bind to the antigens at the same time are shown.

The results are shown in FIGS. 13 and 14. EGFR ERY22_Hk/EGFR ERY22_L/CE115_2 ERY22_Hh/CE115_ERY22_L, EGFR ERY22_Hk/EGFR ERY22_L/CE115_12 ERY22_Hh/CE115_ERY22_L, and EGFR ERY22_Hk/EGFR ERY22_L/CE115_17 ERY22_Hh/CE115_ERY22_L with the RGD (Arg-Gly-Asp) peptide inserted in the Fab region bound to integrin αvβ3 and CD3 at the same time, resulting in the strong signal detected in the ECL assay. By contrast, EGFR ERY22_Hk/EGFR ERY22_L/CE115_9 ERY22_Hh/CE115_ERY22_L and EGFR ERY22_Hk/EGFR ERY22_L/CE115_48 ERY22_Hh/CE115_ERY22_L produced only a weak signal in this assay (FIG. 13). All of EGFR ERY22_Hk/EGFR ERY22_L/CE115_4 ERY22_Hh/CE115_ERY22_L, EGFR ERY22_Hk/EGFR ERY22_L/CE115_10 ERY22_Hh/

CE115_ERY22_L, EGFR ERY22_Hk/EGFR ERY22_L/CE115_47 ERY22_Hh/CE115_ERY22_L, and EGFR ERY22_Hk/EGFR ERY22_L/CE115_49 ERY22_Hh/CE115_ERY22_L rarely produced a detectable signal in the ECL assay (FIG. 14). These results suggested that these antibodies do not bind to integrin αvβ3 in a state bound with CD3.

(3-6) Discussion on Results of ECL Method Showing that Fab Region does not Bind to Integrin αvβ3 and CD3 at Same Time As is evident from the results described above, the developed antibody had the properties of the dual binding Fab molecule binding to each of CD3 (CD3ε) and integrin αvβ3 through one Fab, but not binding to CD3 (CD3ε) and integrin αvβ3 at the same time. In this Example, the RGD peptide binding to the second antigen integrin αvβ3 was inserted to the variable region (Fab) of the antibody having this variable region binding to the first antigen CD3 to successfully obtain a molecule that was provided with the binding activity against the second antigen, but did not bind to CD3 and the second antigen at the same time. By similar methods, a peptide having binding activity against a protein as illustrated in WO2006036834 can be inserted to the Fab loop to obtain a dual binding Fab molecule having binding activity against an arbitrary second antigen. The peptide exhibiting binding activity against a protein can be obtained by preparing a peptide library by use of a method generally known to those skilled in the art and selecting a peptide having the desired activity from the library (Pasqualini R., Nature, 1996, 380 (6572): 364-6). Furthermore, a library of antigen-binding molecules prepared by alteration to a larger length (extension) of loops in Fab as described in Example 5 may be used to develop a dual binding Fab molecule having binding activity against an arbitrary second antigen. The variable regions against the first antigen can be obtained by various methods generally known to those skilled in the art. Hence, it can be concluded that such libraries can be used to develop dual binding Fab molecules that have binding activity against an arbitrary first antigen and an arbitrary second antigen, but cannot bind to the first antigen and the second antigen at the same time.

The results described above indicated that EGFR ERY22_Hk/EGFR ERY22_L/CE115_4 ERY22_Hh/CE115_ERY22_L, EGFR ERY22_Hk/EGFR ERY22_L/CE115_10 ERY22_Hh/CE115_ERY22_L, EGFR ERY22_Hk/EGFR ERY22_L/CE115_47 ERY22_Hh/CE115_ERY22_L, and EGFR ERY22_Hk/EGFR ERY22_L/CE115_49 ERY22_Hh/CE115_ERY22_L bind to CD3 and integrin αvβ3, but do not bind to CD3 and integrin αvβ3 at the same time. These results demonstrated that EGFR ERY22_Hk/EGFR ERY22_L/CE115_4 ERY22_Hh/CE115_ERY22_L, EGFR ERY22_Hk/EGFR ERY22_L/CE115_10 ERY22_Hh/CE115_ERY22_L, EGFR ERY22_Hk/EGFR ERY22_L/CE115_47 ERY22_Hh/CE115_ERY22_L, and EGFR ERY22_Hk/EGFR ERY22_L/CE115_49 ERY22_Hh/CE115_ERY22_L are molecules having dual binding Fab, and such molecules can be developed.

[Example 4] Preparation of Antibody that Binds to CD3 and Human Toll-Like Receptor 2 (TLR2), but does not Bind to these Antigens at Same Time (4-1) Preparation of Antibody that Binds to CD3 and Human TLR2, but does not Bind to these Antigens at Same Time TLR2, known as a pattern recognition receptor, is expressed mainly on immunocytes such as macrophages, dendritic cells, or B cells and is useful as a target molecule activating the immunocytes. TLR2 is also known to be expressed on normal cells other than immunocytes, such as epithelial cells or endothelial cells. The binding of a cancer antigen and CD3 at the same time recruits T cells expressing CD3 in a tumor environment so that the T cells damage the cancer cells. In this case, the binding of the cancer antigen and TLR2 at the same time can also recruit immunocytes expressing TLR2 in the tumor environment, presumably activating the immunocytes. The cancer cells damaged by the T cells are taken up by the immunocytes recruited by TLR2. The antigen can be processed and presented on HLA to activate the T cells. This might activate T cells more strongly and also induce acquired immunity. However, binding to CD3 and TLR2 at the same time might damage immunocytes and normal cells due to potent cytotoxic activity mediated by T cells. Accordingly, it was assumed that immunocytes and normal cells expressing TLR2 can be recruited without damaging these cells, if a molecule that does not bind to CD3 and TLR2 at the same time can be prepared. Thus, a study was conducted to obtain a dual binding Fab molecule capable of binding to EGFR through one variable region (Fab) and binding to the first antigen CD3 and the second antigen TLR2 through the other variable region, but not capable of binding to CD3 and TLR2 at the same time.

Given that a "molecule that binds to CD3 through one Fab region under TLR2-free conditions and binds to TLR2 through the other Fab region under CD3-free conditions" can be shown to be a "molecule that does not bind to TLR2 in a state bound with CD3 or does not bind to CD3 in a state bound with TLR2", it can be concluded that a dual binding Fab molecule having the properties of dual binding Fab of interest (i.e., the properties of binding to CD3 and the second antigen, but not binding to CD3 and the second antigen at the same time) has been developed successfully.

(4-2) Obtainment of Antibody Having Fab Region Binding to TLR2

An RWGYHLRDRKYKGVRSHKGVPR peptide (SEQ ID NO: 36) is known as a peptide having binding activity against human TLR2. Thus, the TRL2-binding peptide was inserted to the heavy chain loop of the CD3ε-binding antibody CE115 (heavy chain variable domain: SEQ ID NO: 13, light chain variable domain: SEQ ID NO: 14) to prepare each heterodimerized antibody having EGFR-binding domains in one Fab and a CD3-binding domain and a TLR2-binding domain in the other Fab according to Reference Example 1. Specifically, a series of expression vectors was prepared so as to have an insert of each polynucleotide encoding EGFR ERY22_Hk (SEQ ID NO: 20), EGFR ERY22_L (SEQ ID NO: 21), or CE115_ERY22_L (SEQ ID NO: 23) as well as a polynucleotide encoding any of the following fragments:

CE115_DU21 ERY22_Hh (SEQ ID NO: 37 with the TRL2-binding peptide inserted between Kabat numbering positions 52b and 52c), CE115_DU22 ERY22_Hh (SEQ ID NO: 38 with the TRL2-binding peptide inserted between Kabat numbering positions 52b and 52c), CE115_DU26 ERY22_Hh (SEQ ID NO: 39 with the TRL2-binding peptide inserted between Kabat numbering positions 72 and 73), and CE115_DU27 ERY22_Hh (SEQ ID NO: 40 with the TRL2-binding peptide inserted between Kabat numbering positions 72 and 73).

Also, an antibody (CE115_ERY22 DU42 Hh, SEQ ID NO: 41) with the TLR2-binding peptide added to the C terminus of the CH3 region, and an antibody (CE115_ERY22 DU43 Hh, SEQ ID NO: 42) in which a TLR2-binding peptide having Cys residues at both ends was added to the C terminus of the CH3 region were prepared as controls according to Reference Example 1. These molecules binding to TLR2 through their CH3 regions are presumably capable of binding to CD3 and TLR2 at the same time.

(4-3) Confirmation of Binding of Antibody to TLR2

Each molecule with the TLR2-binding peptide inserted in the Fab region was evaluated for its binding to TLR2 by the electrochemiluminescence method (ECL method). Specifically, biotin-anti human IgG Ab (Southern Biotech) diluted with a TBS solution containing 0.1% BSA (referred to as a dilution(−) solution), each antibody solution adjusted to 5 μg/mL or 1 μg/mL, and TLR2 (Abnova Corp.) tagged with sulfo-tag were each added at 25 μL/well to Nunc-Immuno™ MicroWell™ 96 well round plates (Nunc), and mixed, and the plate was then incubated overnight at 4° C. to form an antibody-antigen complex. A TBS solution containing 0.5% BSA (referred to as a blocking(−) solution) was added at 150 μL/well to streptavidin plate (MSD K.K.), and the plate was incubated overnight at 4° C. After removal of the blocking solution, each well was washed three times with 250 μL of a TBS(−) solution. The antibody-antigen complex solution was added thereto at 75 μL/well, and the plate was incubated at room temperature for 2 hours so that the biotin-anti human IgG Ab bound to the streptavidin plate. After removal of the antibody-antigen complex solution, each well was washed three times with a TBS(−) solution, and READ buffer (MSD K.K.) was added thereto at 150 μL/well, followed by the detection of the luminescence signal of the sulfo-tag using Sector Imager 2400 (MSD K.K.).

Figure 15:
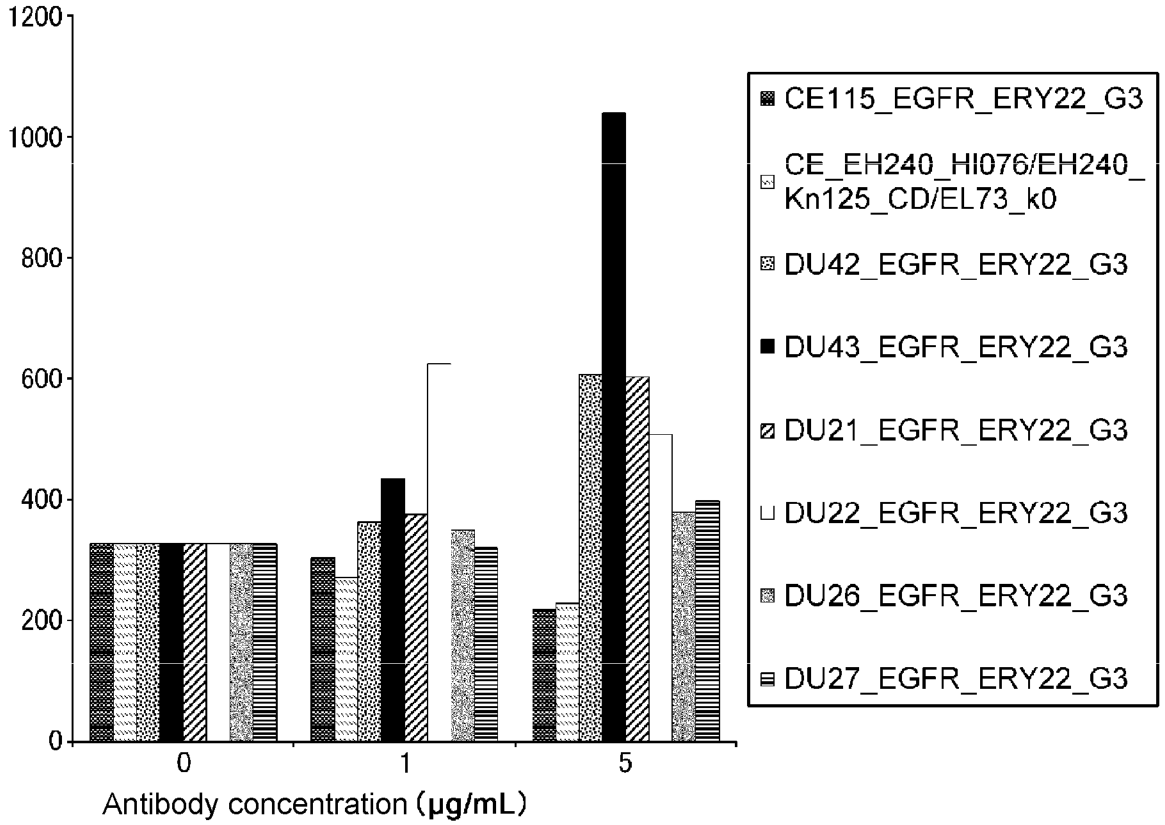
FIG. 15 is a graph showing results of ECL-ELISA for detecting the binding of TLR2-binding peptide-inserted CE115 to TLR2.

The results are shown in FIG. 15. The parent antibody EGFR ERY22_Hk/EGFR ERY22_L/CE115_ERY22_Hh/CE115_ERY22_L exhibited no binding activity against TLR2, whereas all of EGFR ERY22_Hk/EGFR ERY22_L/CE115_DU21 ERY22_Hh/CE115_ERY22_L, EGFR ERY22_Hk/EGFR ERY22_L/CE115_DU22 ERY22_Hh/CE115_ERY22_L, EGFR ERY22_Hk/EGFR ERY22_L/CE115_DU26 ERY22_Hh/CE115_ERY22_L, and EGFR ERY22_Hk/EGFR ERY22_L/CE115_DU27 ERY22_Hh/CE115_ERY22_L were observed to bind to TLR2.

(4-4) Confirmation of Binding of Antibody to CD3 (CD3ε)

Next, each antibody having a TLR2-binding Fab region prepared in the previous section was evaluated for whether to retain binding activity against CD3 (CD3ε) by the ECL method. Specifically, biotin-anti human IgG Ab (Southern Biotech) diluted with a TBS solution containing 0.1% BSA (referred to as a dilution(−) solution), each antibody solution adjusted to 5 μg/mL or 1 μg/mL, and CD3ε homodimer protein tagged with sulfo-tag were each added at 25 μL/well to Nunc-Immuno™ MicroWell™ 96 well round plates (Nunc), and mixed, and the plate was then incubated overnight at 4° C. to form an antibody-antigen complex. A TBS solution containing 0.5% BSA (referred to as a blocking(−) solution) was added at 150 μL/well to streptavidin plate (MSD K.K.), and the plate was incubated overnight at 4° C. After removal of the blocking solution, each well was washed three times with 250 μL of a TBS(−) solution. The antibody-antigen complex solution was added thereto at 75 μL/well, and the plate was incubated at room temperature for 2 hours so that the biotin-anti human IgG Ab bound to the streptavidin plate. After removal of the antibody-antigen complex solution, each well was washed three times with a TBS(−) solution, and READ buffer (MSD K.K.) was added thereto at 150 μL/well, followed by the detection of the luminescence signal of the sulfo-tag using Sector Imager 2400 (MSD K.K.).

Figure 16:
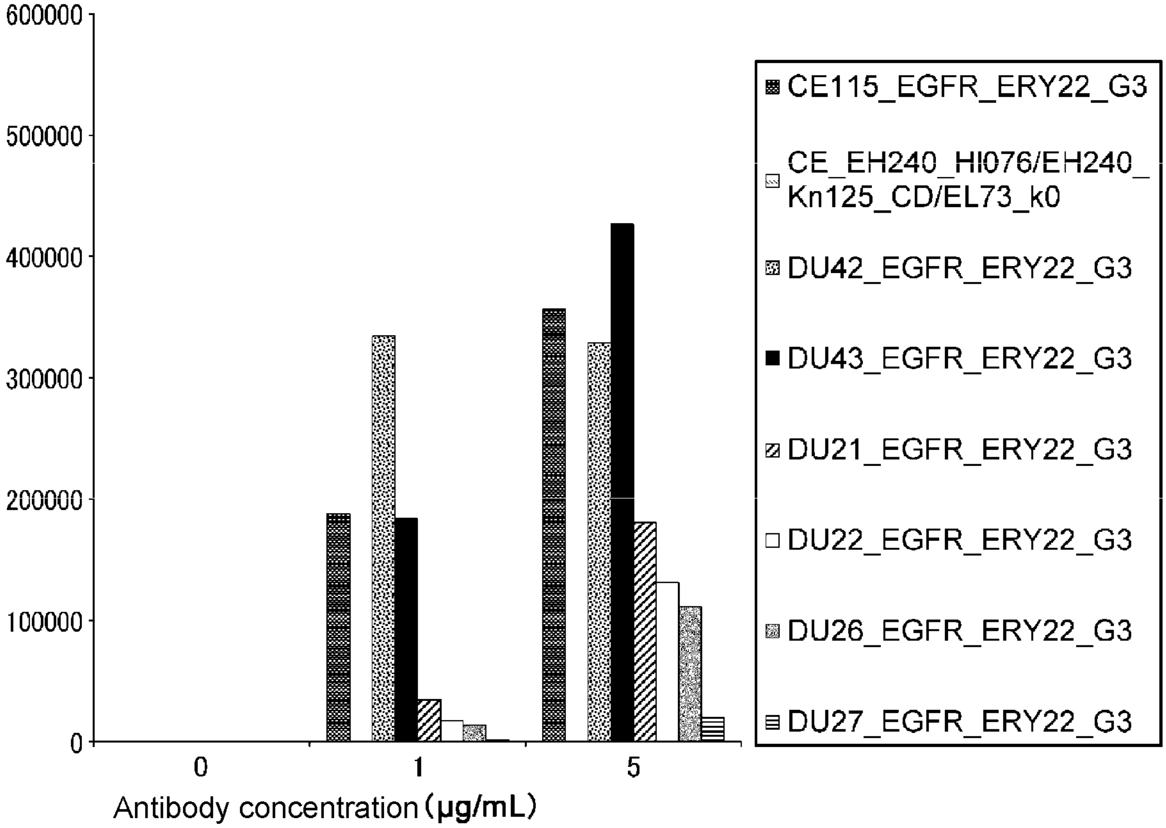
FIG. 16 is a graph showing results of ECL-ELISA for detecting the binding of TLR2-binding peptide-inserted CE115 to CD3ε.

The results are shown in FIG. 16. All of the parent antibody EGFR ERY22_Hk/EGFR ERY22_L/CE115_ERY22_Hh/CE115_ERY22_L as well as EGFR ERY22_Hk/EGFR ERY22_L/CE115_DU21 ERY22_Hh/CE115_ERY22_L, EGFR ERY22_Hk/EGFR ERY22_L/CE115_DU22 ERY22_Hh/CE115_ERY22_L, EGFR ERY22_Hk/EGFR ERY22_L/CE115_DU26 ERY22_Hh/CE115_ERY22_L, and EGFR ERY22_Hk/EGFR ERY22_L/CE115_DU27 ERY22_Hh/CE115_ERY22_L were observed to bind to CD3.

(4-5) Confirmation that Fab Region does not Bind to TLR2 and CD3 at Same Time by ECL Method As is evident from the results of the above paragraphs, the obtained molecules had binding activity against TLR2 and had binding activity against CD3. Next, each Fab region prepared in the above paragraphs was evaluated for whether to bind to CD3 and TLR2 at the same time.

When a molecule with the TLR2-binding peptide inserted in the Fab region binds to TLR2 and CD3 at the same time, its binding to both the antigens can be detected by the ECL method by adding TLR2 and biotinylated CD3 to the antibody solution. Specifically, biotinylated human CD3ε homodimer protein diluted with a dilution(−) solution, each antibody solution adjusted to 10 μg/mL or 5 μg/mL, and TLR2 (R&D Systems, Inc.) tagged with sulfo-tag were each added at 254/well to Nunc-Immuno™ MicroWell™ 96 well round plates (Nunc), and mixed, and the plate was then incubated overnight at 4° C. to form an antibody-antigen complex. A blocking(−) solution was added at 150 μL/well to streptavidin plate (MSD K.K.), and the plate was incubated overnight at 4° C. After removal of the blocking solution, each well was washed three times with 250 μL of a TBS(−) solution containing 0.1 g/L calcium chloride and 0.1 g/L magnesium chloride. The antibody-antigen complex solution was added thereto at 75 μL/well, and the plate was incubated at room temperature for 2 hours so that the biotin-anti human IgG Ab bound to the streptavidin plate. After removal of the antibody-antigen complex solution, each well was washed three times with a TBS(−) solution, and READ buffer (MSD K.K.) was added thereto at 150 μL/well, followed by the detection of the luminescence signal of the sulfo-tag using Sector Imager 2400 (MSD K.K.).

Figure 17:
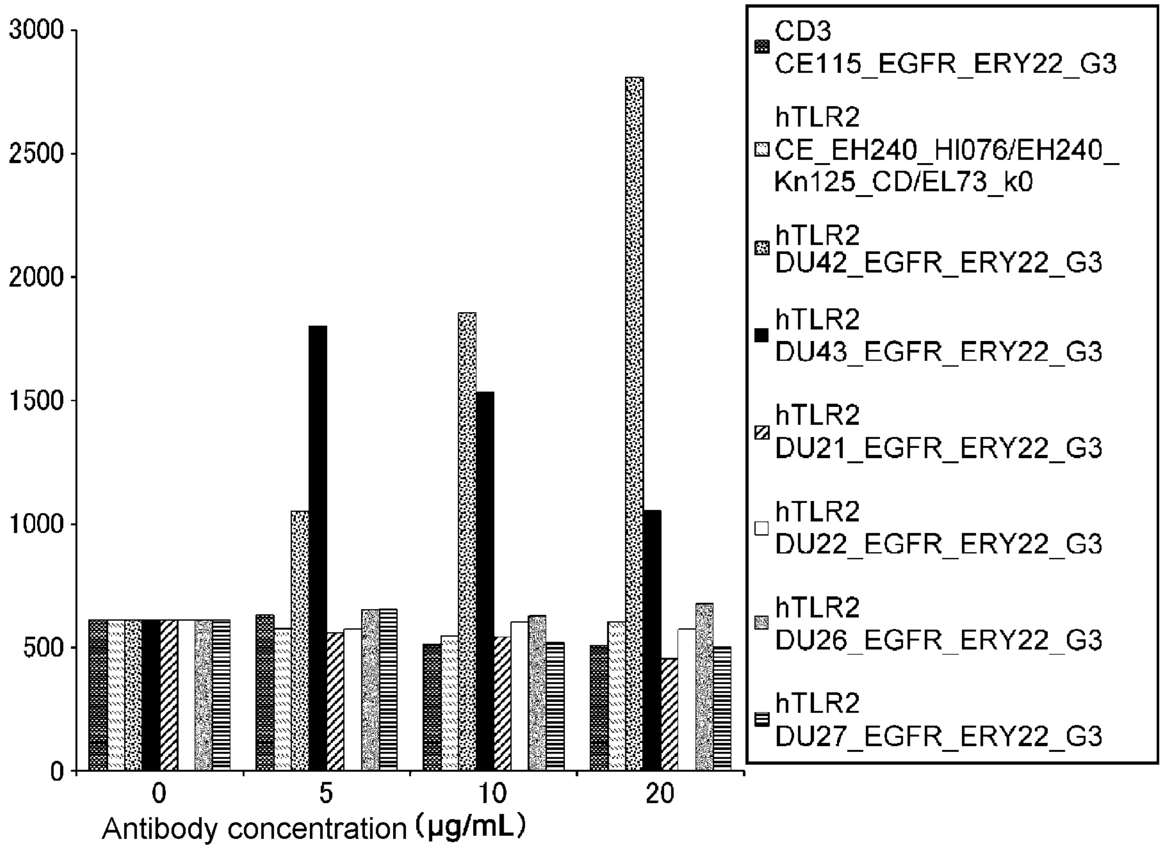
FIG. 17 is a graph showing results of ECL-ELISA for detecting the binding of TLR2-binding peptide-inserted CE115 to TLR2 and CD3 at the same time.

The results are shown in FIG. 17. EGFR ERY22_Hk/EGFR ERY22_L/CE115_DU42 ERY22_Hh/CE115_ERY22_L and EGFR ERY22_Hk/EGFR ERY22_L/CE115_DU43 ERY22_Hh/CE115_ERY22_L with the TLR2-binding peptide added to the CH3 region bound to TLR2 and CD3 at the same time, resulting in the strong signal detected in the ECL assay. By contrast, all of EGFR ERY22_Hk/EGFR ERY22_L/CE115_DU21 ERY22_Hh/CE115_ERY22_L, EGFR ERY22_Hk/EGFR ERY22_L/CE115_DU22 ERY22_Hh/CE115_ERY22_L, EGFR ERY22_Hk/EGFR ERY22_L/CE115_DU26 ERY22_Hh/CE115_ERY22_L, and EGFR ERY22_Hk/EGFR ERY22_L/CE115_DU27 ERY22_Hh/CE115_ERY22_L rarely produced a detectable signal in the ECL assay. These results suggested that these antibodies do not bind to TLR2 in a state bound with CD3.

(4-6) Discussion on Results of ECL Method Showing that Fab Region does not Bind to TLR2 and CD3 at Same Time As is evident from the results described above, the developed antibody had the properties of the dual binding Fab molecule binding to each of CD3 and TLR2 through one Fab, but not binding to CD3 and TLR2 at the same time. In this Example, the RWGYHLRDRKYKGVRSHKGVPR (SEQ ID NO:137) peptide binding to the second antigen TLR2 was inserted to the variable region (Fab) of the antibody having this variable region binding to the first antigen CD3 to successfully obtain a molecule that was provided with the binding activity against the second antigen, but did not bind to CD3 and the second antigen at the same time. By similar methods, a peptide having binding activity against a protein as illustrated in WO2006036834 can be inserted to the Fab loop to obtain a dual binding Fab molecule having binding activity against an arbitrary second antigen. The peptide exhibiting binding activity against a protein can be obtained by preparing a peptide library by use of a method generally known to those skilled in the art and selecting a peptide having the desired activity from the library (Pasqualini R., Nature, 1996, 380 (6572): 364-6). Furthermore, a library of antigen-binding molecules prepared by alteration to a larger length (extension) of loops in Fab as described in Example 5 may be used to develop a dual binding Fab molecule having binding activity against an arbitrary second antigen. The variable regions against the first antigen can be obtained by various methods generally known to those skilled in the art. Hence, it can be concluded that such libraries can be used to develop dual binding Fab molecules that have binding activity against an arbitrary first antigen and an arbitrary second antigen, but cannot bind to the first antigen and the second antigen at the same time.

The results described above indicated that EGFR ERY22_Hk/EGFR ERY22_L/CE115_DU21 ERY22_Hh/CE115_ERY22_L, EGFR ERY22_Hk/EGFR ERY22_L/CE115_DU22 ERY22_Hh/CE115_ERY22_L, EGFR ERY22_Hk/EGFR ERY22_L/CE115_DU26 ERY22_Hh/CE115_ERY22_L, and EGFR ERY22_Hk/EGFR ERY22_L/CE115_DU27 ERY22_Hh/CE115_ERY22_L bind to CD3 and TLR2, but do not bind to CD3 and TLR2 at the same time. These results demonstrated that EGFR ERY22_Hk/EGFR ERY22_L/CE115_DU21 ERY22_Hh/CE115_ERY22_L, EGFR ERY22_Hk/EGFR ERY22_L/CE115_DU22 ERY22_Hh/CE115_ERY22_L, EGFR ERY22_Hk/EGFR ERY22_L/CE115_DU26 ERY22_Hh/CE115_ERY22_L, and EGFR ERY22_Hk/EGFR ERY22_L/CE115_DU27 ERY22_Hh/CE115_ERY22_L are molecules having dual binding Fab, and such molecules can be developed.

[Example 5] Antibody Alteration for Preparation of Antibody Binding to CD3 and Second Antigen

(5-1) Study on Insertion Site and Length of Peptide Capable of Binding to Second Antigen A study was conducted to obtain a dual binding Fab molecule capable of binding to a cancer antigen through one variable region (Fab) and binding to the first antigen CD3 and the second antigen through the other variable region, but not capable of binding to CD3 and the second antigen at the same time. A GGS peptide was inserted to the heavy chain loop of the CD3ε-binding antibody CE115 to prepare each heterodimerized antibody having EGFR-binding domains in one Fab and CD3-binding domains in the other Fab according to Reference Example 1.

Specifically, EGFR ERY22_Hk/EGFR ERY22_L/CE115_CE31 ERY22_Hh/CE115_ERY22_L ((SEQ ID NO: 20/21/43/23) with GGS inserted between K52B and S52c in CDR2, EGFR ERY22_Hk/EGFR ERY22_L/CE115_CE32 ERY22_Hh/CE115_ERY22_L ((SEQ ID NO: 20/21/44/23) with a GGSGGS peptide (SEQ ID NO: 90) inserted at this position, and EGFR ERY22_Hk/EGFR ERY22_L/CE115_CE33 ERY22_Hh/CE115_ERY22_L ((SEQ ID NO: 20/21/45/23) with a GGSGGSGGS peptide (SEQ ID NO: 91) inserted at this position were prepared. Likewise, EGFR ERY22_Hk/EGFR ERY22_L/CE115_CE34 ERY22_Hh/CE115_ERY22_L ((SEQ ID NO: 20/21/46/23) with GGS inserted between D72 and D73 (loop) in FR3, EGFR ERY22_Hk/EGFR ERY22_L/CE115_CE35 ERY22_Hh/CE115_ERY22_L ((SEQ ID NO: 20/21/47/23) with a GGSGGS peptide (SEQ ID NO: 90) inserted at this position, and EGFR ERY22_Hk/EGFR ERY22_L/CE115_CE36 ERY22_Hh/CE115_ERY22_L ((SEQ ID NO: 20/21/48/23) with a GGSGGSGGS peptide (SEQ ID NO: 91) inserted at this position were prepared. In addition, EGFR ERY22_Hk/EGFR ERY22_L/CE115_CE37 ERY22_Hh/CE115_ERY22_L ((SEQ ID NO: 20/21/49/23) with GGS inserted between A99 and Y100 in CDR3, EGFR ERY22_Hk/EGFR ERY22_L/CE115_CE38 ERY22_Hh/CE115_ERY22_L ((SEQ ID NO: 20/21/50/23) with a GGSGGS peptide inserted at this position, and EGFR ERY22_Hk/EGFR ERY22_L/CE115_CE39 ERY22_Hh/CE115_ERY22_L ((SEQ ID NO: 20/21/51/23) with a GGSGGSGGS peptide inserted at this position were prepared.

(5-2) Confirmation of Binding of GGS Peptide-Inserted CE115 Antibody to CD3ε

The binding activity of each prepared antibody against CD3ε was confirmed using Biacore T100. A biotinylated CD3ε epitope peptide was immobilized to a CM5 chip via streptavidin, and the prepared antibody was injected thereto as an analyte and analyzed for its binding affinity.

The results are shown in Table 2. The binding affinity of CE35, CE36, CE37, CE38, and CE39 for CD3ε was equivalent to the parent antibody CE115. This indicated that a peptide binding to the second antigen can be inserted into their loops. The binding affinity was not reduced in GGSGGSGGS (SEQ ID NO:91)-inserted CE36 or CE39. This indicated that the insertion of a peptide up to at least 9 amino acids to these sites does not influence the binding activity against CD3ε.

TABLE 2

| Sample | ka | kd | KD | Insertion position | Linker |
|---|---|---|---|---|---|
| CE115_M | 1.5E+05 | 9.8E−03 | 6.7E−08 | | |
| CE31 | 2.3E+05 | 3.5E−02 | 1.5E−07 | K52b-S52c | GS3 |
| CE32 | 8.5E+04 | 1.8E−02 | 2.1E−07 | K52b-S52c | GS6 |
| CE33 | 4.9E+05 | 1.1E−01 | 2.3E−07 | K52b-S52c | 6S9 |
| CE34 | 1.1E+05 | 1.3E−02 | 1.2E−07 | D72-D73 | GS3 |
| CE35 | 1.3E+05 | 1.1E−02 | 8.7E−08 | D72-D73 | GS6 |
| CE36 | 1.2E+05 | 1.2E−02 | 9.9E−08 | D72-D73 | GS9 |
| CE37 | 2.2E+05 | 2.0E−02 | 9.4E−08 | A99-Y100 | GS3 |
| CE38 | 2.0E+05 | 1.7E−02 | 8.7E−08 | A99-Y100 | GS6 |
| CE39 | 1.6E+05 | 1.4E−02 | 9.1E−08 | A99-Y100 | GS9 |

These results indicated that the antibody capable of binding to CD3 and the second antigen, but does not bind to these antigens at the same time can be prepared by obtaining an antibody binding to the second antigen using such peptide-inserted CE115.

In this context, a library can be prepared by altering at random the amino acid sequence of the peptide for use in insertion or substitution according to a method known in the art such as site-directed mutagenesis (Kunkel et al., Proc. Natl. Acad. Sci. U.S.A. (1985) 82, 488-492) or overlap extension PCR, and comparing the binding activity, etc., of each altered form according to the aforementioned method to determine an insertion or substitution site that permits exertion of the activity of interest even after alteration of the amino acid sequence, and the types and length of amino acids of this site.

[Example 6] Library Design for Obtaining Antibody Binding to CD3 and Second Antigen (6-1) Antibody Library for Obtaining Antibody Binding to CD3 and Second Antigen (Also Referred to as Dual Fab Library)

In the case of selecting CD3 (CD3ε) as the first antigen, examples of a method for obtaining an antibody binding to CD3 (CD3ε) and an arbitrary second antigen include the following 6 methods:

1. a method which involves inserting a peptide or a polypeptide binding to the second antigen to a Fab domain binding to the first antigen (this method includes the peptide insertion shown in Example 3 or 4 as well as a G-CSF insertion method illustrated in Angew Chem Int Ed Engl. 2013 Aug. 5; 52 (32): 8295-8), wherein the binding peptide or polypeptide may be obtained from a peptide- or polypeptide-displaying library, or the whole or a portion of a naturally occurring protein may be used;

2. a method which involves preparing an antibody library such that various amino acids appear positions that permit alteration to a larger length (extension) of Fab loops as shown in Example 5, and obtaining Fab having binding activity against an arbitrary second antigen from the antibody library by using the binding activity against the antigen as an index;

3. a method which involves identifying amino acids that maintain binding activity against CD3 by use of an antibody prepared by site-directed mutagenesis from a Fab domain previously known to bind to CD3, and obtaining Fab having binding activity against an arbitrary second antigen from an antibody library in which the identified amino acids appear by using the binding activity against the antigen as an index;

4. the method 3 which further involves preparing an antibody library such that various amino acids appear positions that permit alteration to a larger length (extension) of Fab loops, and obtaining Fab having binding activity against an arbitrary second antigen from the antibody library by using the binding activity against the antigen as an index;

5. the method 1, 2, 3, or 4 which further involves altering the antibodies such that glycosylation sequences (e.g., NxS and NxT wherein x is an amino acid other than P) appear to add thereto sugar chains that are recognized by sugar chain receptors (e.g., high-mannose-type sugar chains are added thereto and thereby recognized by high-mannose receptors; it is known that the high-mannose-type sugar chains are obtained by the addition of kifunensine at the time of antibody expression (mAbs. 2012 July-August; 4 (4): 475-87)); and 6. the method 1, 2, 3, or 4 which further involves adding thereto domains (polypeptides, sugar chains, and nucleic acids typified by TLR agonists) each binding to the second antigen through a covalent bond by inserting Cys, Lys, or a non-natural amino acid to loops or sites found to be alterable to various amino acids or substituting these sites with Cys, Lys, or a non-natural amino acid (this method is typified by antibody drug conjugates and is a method for conjugation to Cys, Lys, or a non-natural amino acid through a covalent bond (described in mAbs 6: 1, 34-45; January/February 2014; WO2009/134891 A2; and Bioconjug Chem. 2014 Feb. 19; 25 (2): 351-61)).

The dual binding Fab that binds to the first antigen and the second antigen, but does not bind to these antigens at the same time is obtained by use of any of these methods, and can be combined with domains (referred to as the other variable region, which is described in Example 1) binding to an arbitrary third antigen by a method generally known to those skilled in the art, for example, common L chains, CrossMab, or Fab arm exchange.

(6-2) Preparation of One-Amino Acid Alteration Antibody of CD3 (CD3ε)-Binding Antibody Using Site-Directed Mutagenesis A VH domain CE115HA000 (SEQ ID NO: 52) and a VL domain GLS3000 (SEQ ID NO: 53) were selected as template sequences for a CD3 (CD3ε)-binding antibody. Each domain was subjected to amino acid alteration at a site presumed to participate in antigen binding according to Reference Example 1. Also, pE22Hh (sequence derived from natural IgG1 CH1 and subsequent sequences by the alteration of L234A, L235A, N297A, D356C, T366S, L368A, and Y407V, the deletion of a C-terminal GK sequence, and the addition of a DYKDDDDK sequence (SEQ ID NO: 89); SEQ ID NO: 54) was used as an H chain constant domain, and a kappa chain (SEQ ID NO: 55) was used as an L chain constant domain. The alteration sites are shown in Table 3. For CD3 (CD3ε)-binding activity evaluation, each one-amino acid alteration antibody was obtained as a one-arm antibody (naturally occurring IgG antibody lacking one of the Fab domains). Specifically, in the case of H chain alteration, the altered H chain linked to the constant domain pE22Hh, and Kn010G3 (naturally occurring IgG1 amino acid sequence from position 216 to the C terminus having C220S, Y349C, T366W, and H435R alterations; SEQ ID NO: 56) were used as H chains, and GLS3000 linked at the 3' side to the kappa chain was used as an L chain. In the case of L chain alteration, the altered L chain linked at the 3' side to the kappa chain was used as an L chain, and CE115HA000 linked at the 3' side to pE22Hh, and Kn010G3 were used as H chains. These sequences were expressed and purified in FreeStyle 293 cells (which employed the method of Reference Example 1).

TABLE 3

H chain alteration site (SEQ ID NO: 52)

| Domain | FR1 | | | | | CDR1 | | | | FR2 |
|---|---|---|---|---|---|---|---|---|---|---|
| Kabat numbering | 11 | 16 | 19 | 28 | 29 | 30 | 31 | 32 | 33 | 35 | 43 |
| Amino acid before substitution | V | R | R | T | F | S | N | A | W | H | K |

| Domain | CDR2 | | | | | | | | | | | | | | | | | |
|---|---|---|---|---|---|---|---|---|---|---|---|---|---|---|---|---|---|---|
| Kabat numbering | 50 | 51 | 52 | 52a | 52b | 52c | 53 | 54 | 55 | 56 | 57 | 58 | 59 | 60 | 61 | 62 | 64 | 65 |
| Amino acid before substitution | Q | I | K | A | K | S | N | N | Y | A | T | Y | Y | A | E | S | K | G |

TABLE 3-continued

| Domain | FR3 | | | | | | | | CDR3 | | | | | | | | FR4 | |
|---|---|---|---|---|---|---|---|---|---|---|---|---|---|---|---|---|---|---|
| Kabat numbering | 72 | 73 | 74 | 75 | 76 | 77 | 78 | 82a | 95 | 96 | 97 | 98 | 99 | 100 | 100a | 100b | 100c | 101 | 102 | 105 |
| Amino acid before substitution | D | D | S | K | N | S | L | N | V | H | Y | G | A | Y | Y | G | V | D | A | Q |

L chain alteration site (SEQ ID NO: 53)

| Domain | CDR1 | | | | | | | | | | | | | | | | FR2 |
|---|---|---|---|---|---|---|---|---|---|---|---|---|---|---|---|---|---|
| Kabat numbering | 24 | 25 | 26 | 27 | 272 | 27h | 27c | 27d | 27e | 28 | 29 | 30 | 31 | 32 | 33 | 34 | 45 |
| Amino acid before substitution | R | S | S | Q | S | L | V | H | S | N | R | N | T | Y | L | H | Q |

| Domain | CDR2 | | | | | | | FR3 | | | | CDR3 | | | | | | FR4 |
|---|---|---|---|---|---|---|---|---|---|---|---|---|---|---|---|---|---|---|
| Kabat numbering | 50 | 51 | 52 | 53 | 54 | 55 | 56 | 74 | 77 | 89 | 90 | 91 | 92 | 93 | 94 | 95 | 96 | 97 | 107 |
| Amino acid before substitution | K | V | S | N | R | F | S | K | R | G | Q | G | T | Q | V | P | Y | T | K |

(6-3) Evaluation of Binding of One-Amino Acid Alteration Antibody to CD3

Each one-amino acid altered form constructed, expressed, and purified in the paragraph (6-2) was evaluated using Biacore T200 (GE Healthcare Japan Corp.). An appropriate amount of CD3ε homodimer protein was immobilized onto Sensor chip CM4 (GE Healthcare Japan Corp.) by the amine coupling method. Then, the antibody having an appropriate concentration was injected thereto as an analyte and allowed to interact with the CD3ε homodimer protein on the sensor chip. Then, the sensor chip was regenerated by the injection of 10 mmol/L glycine-HCl (pH 1.5). The assay was conducted at 25° C., and HBS-EP+ (GE Healthcare Japan Corp.) was used as a running buffer. From the assay results, the dissociation constant KD (M) was calculated using single-cycle kinetics model (1:1 binding RI=0) for the amount bound and the sensorgram obtained in the assay. Each parameter was calculated using Biacore T200 Evaluation Software (GE Healthcare Japan Corp.).

(6-3-1) Alteration of H Chain

Figure 18:
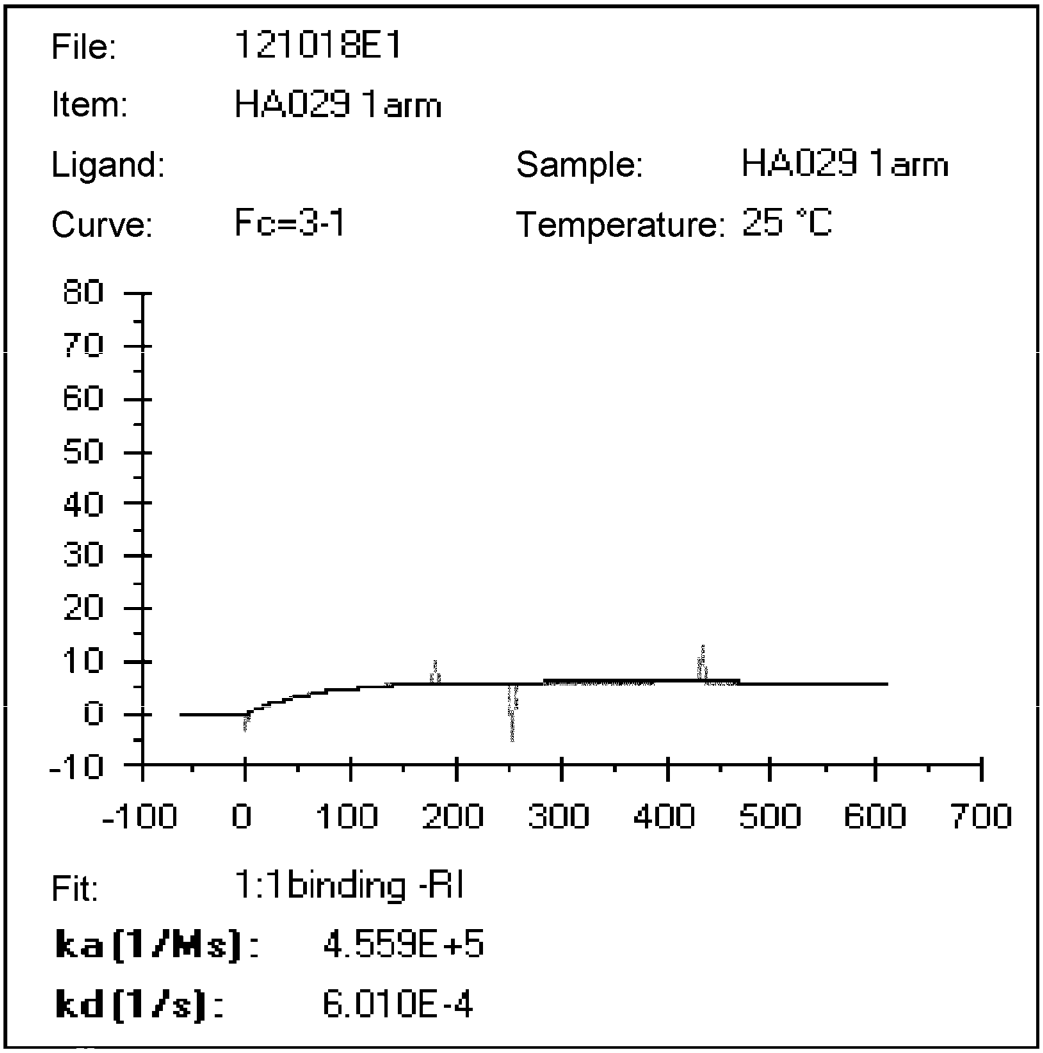
FIG. 18 is an exemplary sensorgram of an antibody having a ratio of the amounts bound of less than 0.8. The ordinate depicts an RU value (response). The abscissa depicts time.

Table 4 shows the results of the ratio of the amount of each H chain altered form bound to the amount of the corresponding unaltered antibody CE115HA000 bound. Specifically, when the amount of the antibody comprising CE115HA000 bound was defined as X and the amount of the H chain one-amino acid altered form bound was defined as Y, a value of Z (ratio of amounts bound)=Y/X was used. As shown in FIG. 18, a very small amount bound was observed in the sensorgram for Z of less than 0.8, suggesting the possibility that the dissociation constant KD (M) cannot be calculated correctly. Table 5 shows the dissociation constant KD (M) ratio of each H chain altered form to CE115HA000 (=KD value of CE115HA000/KD value of the altered form).

When Z shown in Table 4 is 0.8 or more, the altered form is considered to maintain the binding relative to the corresponding unaltered antibody CE115HA000. Therefore, an antibody library designed such that these amino acids appear can serve as a dual Fab library.

TABLE 4

SEQ ID NO: 138

| | Domain | | | | | | | | | | | | | | |
|---|---|---|---|---|---|---|---|---|---|---|---|---|---|---|---|
| | FR1 CDR1 | | | | | | | | | | FR2 | CDR2 | | | |
| | Kabat numbering | | | | | | | | | | | | | | |
| | 11 | 16 | 19 | 28 | 29 | 30 | 31 | 32 | 33 | 35 | 43 | 50 | 51 | 52 | 52a |
| | Amino acid before substitution | | | | | | | | | | | | | | |
| (wt) | V | R | R | T | F | S | N | A | W | H | K | Q | I | K | A |
| A | | | | | | | 0.5 | | 0.1 | 0.17 | | 0.24 | | | |
| D | | | | 0.56 | | 0.86 | 0.37 | | 0.1 | 0.2 | | 0.27 | 0.29 | 0.25 | 1.34 |
| E | | 0.88 | | | | | | | | 0.19 | 0.9 | 0.26 | 0.55 | 0.26 | 0.57 |
| F | | | | | | | 0.62 | | 0.65 | 0.21 | | | | 0.17 | |
| G | | | | | | 1.01 | 0.39 | | | 0.22 | | | | | 0.81 |
| H | | | | | | | 0.68 | | 0.13 | | | | | 0.22 | |
| I | | | | | | | 0.81 | | | 0.12 | | 0.4 | | 0.33 | |
| K | | | | | | | 1.01 | | | 0.15 | | 0.33 | | | |
| L | 1 | | | | | | | | 0.1 | 0.11 | | 0.23 | | | |
| M | | | | | | | | | | 0.29 | | | | | |
| N | | | | | | | | | | 0.35 | | 0.17 | | 0.34 | |
| P | | | | | | | | | | | | | | | 0.35 |
| Q | | 0.9 | | | | | 0.49 | | | 0.13 | 0.99 | | | | |
| R | | | | | | | 1.14 | | | 0.14 | | | | 0.91 | |
| S | | | | 0.91 | | | 0.81 | | | 0.23 | | 0.24 | | 0.28 | 1.05 |
| T | | | 0.8 | | | | | | | 0.26 | | | | | |
| V | | | | | 0.36 | | | | | 0.22 | | | | | 0.52 |

TABLE 4-continued

SEQ ID NO: 138

| | | | | | | | | | |
|---|---|---|---|---|---|---|---|---|---|
| W | 0.63 | | | 0.22 | | | | 0.22 | |
| Y | 0.64 | 0.33 | 0.66 | 0.16 | | 0.25 | | 0.18 | 0.31 |

| | Domain CDR2 Kabat numbering | | | | | | | | | | | | | |
|---|---|---|---|---|---|---|---|---|---|---|---|---|---|---|
| | 52b | 52c | 53 | 54 | 55 | 56 | 57 | 58 | 59 | 60 | 61 | 62 | 64 | 65 |
| | Amino acid before substitution | | | | | | | | | | | | | |
| (wt) | K | S | N | N | Y | A | T | Y | Y | A | E | S | K | G |
| A | 0.67 | 0.96 | 0.7 | 0.85 | | | 0.98 | 0.22 | 0.85 | | 1.09 | | 0.82 | |
| D | 0.27 | 0.6 | 0.39 | 0.62 | 0.45 | 0.51 | | 0.11 | 0.7 | 0.99 | 0.91 | 0.92 | 0.72 | 0.76 |
| E | | | | | | | | | 0.66 | 0.94 | | 0.92 | 0.74 | 0.78 |
| F | | 1.13 | | 1.12 | | | | | | | | | | |
| G | | 0.97 | 0.50 | 0.98 | 0.55 | 0.61 | | | | | | | | |
| H | | | 0.76 | | | | | | | | | | | |
| I | | | 0.68 | | | | 0.61 | | | | | | | |
| K | | 1.19 | 0.78 | 1.2 | | 1.35 | 1.32 | 0.3 | | | | 1.19 | | |
| L | 0.61 | 0.98 | | 0.94 | | 0.8 | | 0.27 | | | | | | |
| M | | | | | | | | | | | | | | |
| N | 0.27 | | | | | 0.87 | 0.97 | 0.23 | | | | | | |
| P | | | | | | | | | | | 1.07 | 1 | | |
| Q | 0.6 | 1.04 | 1.10 | 0.84 | | 0.76 | | 0.19 | | | 1.07 | | 0.89 | |
| R | 1.11 | | | | | | | | | | | | | |
| S | 0.68 | | 0.83 | 0.84 | 0.26 | | | 0.18 | 0.94 | | | | 0.84 | |
| T | | | | | | | | | | | | | | |
| V | | 0.93 | | | | | | | | | | | | |
| W | | | 0.88 | | | | | | | | | | | |
| Y | 0.74 | 1.11 | 0.63 | 1.09 | | 0.66 | | | | | | | | |

| | Domain | | | | | | | | | | |
|---|---|---|---|---|---|---|---|---|---|---|---|
| | FR3 | | | | | | | | CDR3 | | |
| | Kabat numbering | | | | | | | | | | |
| | 72 | 73 | 74 | 75 | 76 | 77 | 78 | 82a | 95 | 96 | 97 |
| | Amino acid before substitution | | | | | | | | | | |
| (wt ) | D | D | S | K | N | S | L | N | Y | H | Y |
| A | 1.41 | 0.83 | 1.05 | | | | | | 0.11 | 0.35 | 0.16 |
| D | | | | | | | | 0.73 | 0.24 | 0.09 | 0.24 |
| E | 1.05 | 0.73 | | | | | | | 0.24 | | |
| F | | | | | | | | | | | |
| G | | 1.07 | | | | | | | 0.19 | 0.43 | 0.18 |
| H | | | | | | | | | | | |
| I | | | | | | | 1.34 | | | | |
| K | | 0.87 | | | | | | | 0.64 | 025 | |
| L | | | | | | | | | | 0.14 | |
| M | | | | | | | | | | | |
| N | | 0.94 | | | | | | | | | |
| P | | | 0.91 | | | | | | | 0.12 | 0.11 |
| Q | | | | | | | | | | 0.42 | |
| R | | 1.04 | | 1.01 | | | | | | 0.46 | 0.27 |
| S | | | | | 0.92 | | | | 0.22 | 0.44 | 0.18 |
| T | | 0.63 | | 0.84 | | 0.9 | | | | | |
| V | 1.43 | | | | | | | | | | |
| W | | | | | | | | | | | |
| Y | | | | | | | | | | 0.17 | |

| | Domain | | | | | | | | |
|---|---|---|---|---|---|---|---|---|---|
| | CDR3 | | | | | | | | FR4 |
| | Kabat numbering | | | | | | | | |
| | 98 | 99 | 100 | 100a | 100b | 100c | 101 | 102 | 105 |
| | Amino acid before substitution | | | | | | | | |
| (wt ) | G | A | Y | Y | G | V | D | A | Q |
| A | 1.1 | | 0.9 | 0.62 | | | 1.26 | | |
| D | 0.26 | 0.28 | 0.52 | 0.31 | 0.27 | 0.44 | | | |
| E | | | | | 0.26 | 0.46 | | | 0.94 |
| F | | 1.43 | | 0.87 | 0.2 | | 0.75 | | |

TABLE 4-continued

| SEQ ID NO: 138 | | | | | | | | |
|---|---|---|---|---|---|---|---|---|
| G | | | 1.07 | 1.23 | | | 1.38 | |
| H | 1.58 | | | | | | 1.21 | |
| I | | | | | | | 1.18 | 1.48 |
| K | 2.83 | 1.48 | 1.07 | 0.9 | | | 0.63 | |
| L | | 1.13 | 0.7 | 0.48 | 0.27 | | 0.62 | |
| M | | | | | | | 1.2 | |
| N | | | | | | | 2.02 | |
| P | 1.02 | | 0.48 | | | 0.2 | 0.2 | 0.14 |
| Q | 1.22 | 0.91 | 0.8 | 0.56 | | | 2.35 | |
| R | 2.96 | | | | | | 0.24 | |
| S | 1.01 | 0.82 | 0.81 | 0.64 | 0.52 | | 1.16 | |
| T | 1.05 | 0.84 | | | | | 0.79 | |
| V | | | 0.6 | | | | 1.33 | 1.43 |
| W | | | 1.03 | | | | | |
| Y | 2.22 | 1.59 | | | 0.23 | | 0.49 | 0.91 |

TABLE 5

SEQ ID NO: 138

| | Domain | | | | | | | | | | | | | | |
|---|---|---|---|---|---|---|---|---|---|---|---|---|---|---|---|
| | FRI | | | | | | CDR1 | | | | FR2 | CDR2 | | | |
| | Kabat numbering | | | | | | | | | | | | | | |
| | 11 | 16 | 19 | 28 | 29 | 30 | 31 | 32 | 33 | 35 | 43 | 50 | 51 | 52 | 52a |
| | Amino acid before substitution | | | | | | | | | | | | | | |
| (wt) | V | R | R | T | F | S | N | A | W | H | R | Q | I | K | A |
| A | | | | | | | 0.96 | | 29.99 | 25.04 | | 22.63 | | | |
| D | | | | 0.93 | | 0.79 | 1.14 | | 1693.03 | 68.99 | | 75.37 | 6.37 | 166.47 | 1.35 |
| E | | 0.74 | | | | | | | | 70.35 | 0.88 | 16738.09 | 0.84 | 19.38 | 0.89 |
| F | | | | | | | 1.24 | | 0.66 | 53.59 | | | | 4.04 | |
| G | | | | | | 0.93 | 1.37 | | | 45.77 | | | | | 0.61 |
| H | | | | | | | 0.96 | | 4.96 | | | | | 2.65 | |
| I | | | | | | | 0.62 | | | 7.23 | | 1.21 | | 3.54 | |
| K | | | | | | | 0.97 | | | 14.45 | | 0.71 | | | |
| L | 0.83 | | | | | | | | 56573.23 | 4.8 | 0.89 | 1.41 | | | |
| M | | | | | | | | | | 3.98 | | | | | |
| N | | | | | | | | | | 2.88 | | 1.48 | | 3.29 | |
| P | | | | | | | | | | | | | | | 5 |
| Q | | 0.87 | | | | | 0.94 | | | 4.80 | | | | | |
| R | | | | | | | 0.98 | | | 15429.77 | | | | 0.8 | |
| S | | | | 0.79 | | | 0.67 | | | 293 | | 47.38 | | 92.1 | 0.82 |
| T | | | 0.81 | | | | | | | 4.4 | | | | | |
| V | | | | | 2.94 | | | | | 28.08 | | | | | 0.95 |
| W | | | | | | | 1.07 | | | 50.42 | | | | 2.69 | |
| Y | | | | | | | 1.1 | 2.11 | 0.69 | 119458.13 | | 49.09 | | 6.47 | 7.71 |

| | Domain CDR2 Kabat numbering | | | | | | | | | | | | | |
|---|---|---|---|---|---|---|---|---|---|---|---|---|---|---|
| | 52b | 52c | 53 | 54 | 55 | 56 | 57 | 58 | 59 | 60 | 61 | 62 | 64 | 65 |
| | Amino acid before substitution | | | | | | | | | | | | | |
| (wt) | K | S | N | N | Y | A | T | Y | Y | A | E | S | K | G |
| A | 0.58 | 0.67 | 0.55 | 0.58 | | | 0.87 | 1.06 | 0.74 | | 0.94 | | 0.81 | |
| D | 0.56 | 0.55 | 0.55 | 0.59 | 0.89 | 0.71 | | 4.81 | 0.66 | 0.94 | 0.9 | 0.87 | 0.76 | 0.61 |
| E | | | | | | | | | 0.61 | 0.88 | | 0.82 | 0.84 | 0.61 |
| F | | 0.93 | | 0.97 | | | | | | | | | | |
| G | | 0.81 | 0.95 | 0.84 | 0.99 | 0.59 | | | | | | | | |
| H | | | 0.55 | | | | | | | | | | | |
| I | | | 0.57 | | | | 0.81 | | | | | | | |
| K | | 0.88 | 0.79 | 0.82 | | 1.32 | 1.32 | 0.66 | | | | 0.99 | | |
| L | 0.61 | 0.94 | | 0.91 | | 0.77 | | 1.21 | | | | | | |
| M | | | | | | | | | | | | | | |
| N | 0.43 | | | | | 0.84 | 0.9 | 1.86 | | | | | | |
| P | | | | | | | | | | | 0.82 | 0.77 | | |
| Q | 0.62 | 0.97 | 1.05 | 0.8 | | 0.74 | | 1.24 | | | 0.85 | | 0.87 | |
| R | 0.91 | | | | | | | | | | | | | |
| S | 0.58 | | 0.59 | 0.57 | 5.65 | | | 1.22 | 0.79 | | | | 0.85 | |

TABLE 5-continued

| SEQ ID NO: 138 | | | | | | |
|---|---|---|---|---|---|---|
| T | | | | | | |
| V | | 0.82 | | | | |
| W | | | 0.69 | | | |
| Y | 0.61 | 0.87 | 0.94 | 1.03 | | 0.63 |

| | Domain | | | | | | | | | | |
|---|---|---|---|---|---|---|---|---|---|---|---|
| | FR3 | | | | | | | | CDR3 | | |
| | Kabat numbering | | | | | | | | | | |
| | 72 | 73 | 74 | 75 | 76 | 77 | 78 | 82a | 95 | 96 | 97 |
| | Amino acid before substitution | | | | | | | | | | |
| (wt) | D | D | S | R | N | S | L | N | V | H | Y |
| A | 1.19 | 0.73 | 0.77 | | | | | | 3.15 | 1 | 41309 |
| D | | | | | | | | 0.56 | 108.01 | 7.27 | 64.7 |
| E | 0.73 | 0.56 | | | | | | | 50.46 | | |
| F | | | | | | | | | | | |
| G | | 0.78 | | | | | | | 78256.33 | 0.8 | 47213 |
| H | | | | | | | | | | | |
| I | | | | | | | 1.08 | | | | |
| K | | 0.74 | | | | | | | 1.15 | 1.56 | |
| L | | | | | | | | | | 3.14 | |
| M | | | | | | | | | | | |
| N | | 0.7 | | | | | | | | | |
| P | | | 0.7 | | | | | | | 87044.4 | 12429 |
| Q | | | | | | | | | | 1.36 | |
| R | | 0.79 | | 0.88 | | | | | | 1.59 | 23180 |
| S | | | | | 0.84 | | | | 4.61 | 1.15 | 1178 |
| T | | 0.78 | | 0.75 | | 0.83 | | | | | |
| V | 1.17 | | | | | | | | | | |
| W | | | | | | | | | | | |
| Y | | | | | | | | | | 6.67 | |

| | Domain | | | | | | | | |
|---|---|---|---|---|---|---|---|---|---|
| | CDR3 | | | | | | | | FR4 |
| | Kabat numbering | | | | | | | | |
| | 98 | 99 | 100 | 100a | 100b | 100c | 101 | 102 | 105 |
| | Amino acid before substitution | | | | | | | | |
| (wt) | G | A | Y | Y | G | V | D | A | Q |
| A | 0.98 | | 0.92 | 0.66 | | | 0.86 | | |
| D | 2.36 | 1.03 | 0.63 | 1.1 | 6.25 | 1.54 | | | |
| E | | | | | 7.29 | 1.31 | | | 0.89 |
| F | | 1.15 | | 0.98 | 4.37 | | 0.73 | | |
| G | | | 0.97 | 1.01 | | | 3.16 | | |
| H | 1.14 | | | | | | 0.91 | | |
| I | | | | | | | 1.73 | 1.29 | |
| K | 4.85 | 1.4 | 0.93 | 0.79 | | | 4.37 | | |
| L | | 1 | 0.67 | 0.57 | 5.84 | | 0.71 | | |
| M | | | | | | | 1.94 | | |
| N | | | | | | | 2.28 | | |
| P | 0.88 | | 1.3 | | | 0.97 | 43.42 | 3.51 | |
| Q | 1.04 | 0.85 | 0.77 | 0.51 | | | 3.55 | | |
| R | 4.69 | | | | | | 5.66 | | |
| S | 0.98 | 0.76 | 0.7 | 0.59 | 1.25 | | 0.91 | | |
| T | 0.93 | 0.93 | | | | | 0.62 | | |
| V | | | 0.92 | | | | 1.18 | 1.27 | |
| W | | | 0.96 | | | | | | |
| Y | 2.75 | 1.25 | | | 51.41 | | 0.97 | 1 | |

(6-3-2) Alteration of L Chain

Table 6 shows the results of the ratio of the amount of each L chain altered form bound to the amount of the corresponding unaltered antibody GLS3000 bound. Specifically, when the amount of the GLS3000-containing antibody bound was defined as X and the amount of the L chain one-amino acid altered form bound was defined as Y, a value of Z (ratio of amounts bound)=Y/X was used. As shown in FIG. 18, a very small amount bound was observed in the sensorgram for Z of less than 0.8, suggesting the possibility that the dissociation constant KD (M) cannot be calculated correctly. Table 7 shows the dissociation constant KD (M) ratio of each L chain altered form to GLS3000.

When Z shown in Table 6 is 0.8 or more, the altered form is considered to maintain the binding relative to the corresponding unaltered antibody GLS3000. Therefore, an antibody library designed such that these amino acids appear can serve as a dual Fab library.

TABLE 6

SEQ ID NO: 139

| | Domain | | | | | | | | | | | | | | | | |
|---|---|---|---|---|---|---|---|---|---|---|---|---|---|---|---|---|---|
| | CDR1 | | | | | | | | | | | | | | | | FR2 |
| | Kabat numbering | | | | | | | | | | | | | | | | |
| | 24 | 25 | 26 | 27 | 27a | 27b | 27c | 27d | 27e | 28 | 29 | 30 | 31 | 32 | 33 | 34 | 45 |
| | Amino acid before substitution | | | | | | | | | | | | | | | | |
| | R | S | S | Q | S | L | V | H | S | N | R | N | T | Y | L | H | Q |
| A | 0.86 | 0.92 | | | | | | 0.48 | 1.03 | 0.25 | 0.63 | 0.5 | | 0.24 | 0.85 | 1.06 | |
| D | 0.75 | 0.18 | 0.86 | 0.85 | 0.79 | 0.17 | 0.32 | 0.22 | 0.69 | 0.19 | 0.41 | 0.34 | 0.23 | 0.23 | 0.17 | 0.22 | 0.77 |
| E | 0.83 | 0.21 | 0.74 | 0.88 | 0.81 | 0.17 | 0.61 | 0.23 | 0.76 | 0.4 | | 0.44 | 0.49 | | 0.72 | 0.23 | 0.75 |
| F | | | | | | 0.42 | | 0.63 | 1.32 | 0.46 | | 1.10 | | 0.29 | 0.78 | 0.27 | |
| G | 0.89 | | | | 1.03 | | | 0.3 | 1.04 | 0.46 | 0.67 | 0.47 | | | | 1.02 | |
| H | | | | | | | | | 1.23 | 0.42 | | 0.98 | | | | | |
| I | | 0.53 | | | 1 | 1.19 | 0.96 | 0.26 | 1.07 | 0.44 | 0.37 | 0.61 | 0.97 | | 0.83 | 0.65 | |
| K | | | | | | | | 0.29 | 1.59 | 0.44 | | 1.65 | 1.04 | | | 2.17 | |
| L | | 0.24 | | 0.92 | | | 0.84 | 0.3 | 1.17 | 0.39 | 0.56 | 0.7 | | | | 0.59 | |
| M | | 0.31 | | | | 0.71 | | 0.3 | 1.23 | 0.39 | | 0.8 | | | 0.93 | 0.35 | |
| N | | | | | 1.1 | | | 0.3 | 1.16 | | | | 0.32 | | | 0.65 | |
| P | 0.7 | 1.01 | 0.78 | 0.29 | 0.99 | 0.91 | 0.3 | 0.24 | 1.26 | 0.36 | 0.31 | 0.31 | 0.31 | 0.24 | 0.3 | 0.34 | |
| Q | 0.9 | | | | | | | 0.25 | 1.1 | 0.37 | | 0.87 | | | | 0.25 | 0.86 |
| R | | | | 1.19 | | | | 0.31 | 1.58 | | | 1.86 | | | | 0.2 | |
| S | 0.89 | | | | | 0.71 | 0.51 | 0.32 | | 0.32 | 0.68 | 0.29 | | | | 0.78 | |
| T | 0.88 | 0.83 | | | | | | 0.29 | 0.97 | 0.45 | 0.63 | 0.29 | | | | 0.89 | |
| V | | 0.73 | | | | 1.12 | | 0.3 | 1.08 | 0.36 | 0.34 | 0.61 | | | 1.05 | 0.85 | |
| W | | | | | | 0.26 | | 0.39 | 1.55 | 0.41 | | 0.99 | | | | 0.24 | |
| Y | 0.87 | | | | 1.1 | 0.25 | 0.77 | 0.64 | 1.2 | 0.26 | 0.69 | 1.04 | | | | 0.59 | |

| | Domain | | | | | | | | | | | | | | | | | | |
|---|---|---|---|---|---|---|---|---|---|---|---|---|---|---|---|---|---|---|---|
| | CDR2 | | | | | | | FR3 | | CDR3 | | | | | | | | | FR4 |
| | Kabat numbering | | | | | | | | | | | | | | | | | | |
| | 50 | 51 | 52 | 53 | 54 | 55 | 56 | 74 | 77 | 89 | 90 | 91 | 92 | 93 | 94 | 95 | 96 | 97 | 107 |
| | Amino acid before substitution | | | | | | | | | | | | | | | | | | |
| | K | V | S | N | R | F | S | K | R | G | Q | G | T | Q | V | P | Y | T | K |
| A | 0.23 | | 0.93 | 0.61 | 0.69 | 1.13 | 1.16 | | | 1.13 | 0.5 | 0.27 | 0.63 | 0.85 | 1.05 | 0.63 | | | |
| D | 0.22 | 0.33 | 0.63 | 0.34 | 0.36 | 0.65 | 0.77 | | | 0.33 | 0.19 | 0.16 | 0.18 | 0.72 | 0.89 | 0.24 | 0.17 | | |
| E | 0.24 | 0.64 | | 0.54 | 0.58 | 0.72 | 0.71 | | | 0.26 | 0.86 | 0.16 | 0.17 | 0.75 | 0.5 | 0.39 | 0.17 | | 0.94 |
| F | | | | 0.69 | | | 1.32 | | | 1.09 | | | | | 0.71 | | 1.17 | | |
| G | 0.16 | 0.84 | | 0.76 | 0.67 | 1.31 | 0.92 | | | | | | | | 0.48 | 0.37 | | | |
| H | | | | 1.18 | | 0.94 | 1.05 | | | 0.7 | | | | | 0.78 | | 0.23 | | |
| I | | 0.81 | | 0.5 | | 0.82 | 0.99 | | | 1.07 | | | 0.34 | | 0.66 | | | | |
| K | | | | 1.08 | | 1.33 | 1.46 | | | 0.4 | | | | | 0.57 | | | | |
| L | 0.24 | | | 0.56 | | 0.76 | 1.02 | | | 0.94 | | | 0.42 | | 0.44 | 0.24 | 0.32 | | |
| M | | | | 0.62 | | 0.8 | 1.05 | | | 0.52 | | | | | 0.44 | | | | |
| N | | | | | | 0.98 | 0.92 | | | 0.8 | | | | | 1.05 | | | | |
| P | 0.3 | 0.32 | 0.33 | 0.81 | 0.84 | 1.16 | 0.95 | | | 0.35 | 0.27 | 0.27 | 0.26 | 0.25 | 1.26 | | | 0.31 | |
| Q | 0.18 | | 1.05 | 0.77 | 0.68 | 0.91 | 1.04 | | | 0.38 | | | | | 0.76 | | | | |
| R | 0.5 | | | 1.58 | | 1.31 | 1.36 | | | 0.19 | | | | 1.13 | 0.66 | | | | |
| S | 0.23 | | | 0.69 | 0.79 | 0.69 | | | 0.92 | | 0.73 | 0.26 | 0.96 | 0.96 | 0.93 | 0.43 | | | |
| T | 0.19 | | | 0.56 | 0.65 | 0.41 | 0.97 | 0.84 | | 1.03 | | 0.26 | | | 0.93 | | | | |
| V | | | | 0.56 | | 0.71 | 0.95 | | | 1.63 | | | | | | | | | |
| W | | | | 0.81 | 0.78 | 0.69 | 1.38 | | | 0.5 | | | | | 0.58 | | | | |
| Y | 0.24 | | 1.12 | 0.67 | | 0.92 | 1.46 | | | 1.19 | 0.17 | 0.17 | 0.33 | 0.87 | 0.63 | | | | |

TABLE 7

| SEQ ID NO: 139 | | | | | | | | | |
|---|---|---|---|---|---|---|---|---|---|
| | Domain | | | | | | | | |
| | CDR1 Kabat numbering | | | | | | | | |
| | 24 | 25 | 26 | 27 | 27a | 27b | 27c | 27d | 27e |
| | Amino acid before substitution | | | | | | | | |
| | R | S | S | Q | S | L | V | H | S |
| Afinity up | 24 | 25 | 26 | 27 | 27a | 27b | 27c | 27d | 27e |
| A | 1 | 0.73 | | | | | | 2.57 | 1.01 |
| D | 0.83 | 8.86 | 1.06 | 0.89 | 0.94 | 25.07 | 3.21 | 13641 | 1.23 |
| E | 0.89 | 6.54 | 0.9 | 0.99 | 0.94 | 26.75 | 1.1 | 42.28 | 1.04 |
| F | | | | | | 2.67 | | 2.05 | 1.16 |
| G | 0.92 | | | | 0.8 | | | 3.51 | 1.03 |
| H | | | | | | | | | 1.09 |
| I | | 0.67 | | | 0.87 | 1.17 | 1.03 | 7.77 | 1.05 |
| R | | | | | | | | 3.8 | 1.32 |
| L | | 4.93 | | 0.86 | | | 0.81 | 3.37 | 1.06 |
| M | | 1.6 | | | | 1.31 | | 3.43 | 1.11 |
| N | | | | | 0.98 | | | 3.43 | 1.01 |
| P | 0.34 | 0.79 | 0.67 | 2.16 | 1.01 | 0.96 | 3.71 | 9.21 | 1.06 |
| Q | 0.87 | | | | | | | 7.48 | 1.08 |
| R | | | | 1.06 | | | | 2.35 | 1.35 |
| S | 0.97 | | | | | 0.9 | 3.04 | 3.05 | |
| T | 1.03 | 0.75 | | | | | | 12973 | 0.98 |
| V | | 0.74 | | | | 1.11 | | 353.86 | 0.95 |
| W | | | | | | 23.6 | | 1.86 | 1.32 |
| Y | 0.94 | | | | 0.93 | 22.2 | 1.25 | 1.98 | 1.1 |

| | Domain | | | | | | | |
|---|---|---|---|---|---|---|---|---|
| | CDR1 | | | | | | | FR2 |
| | Kabat numbering | | | | | | | |
| | 28 | 29 | 30 | 31 | 32 | 33 | 34 | 45 |
| | Amino acid before substitution | | | | | | | |
| | N | R | N | T | Y | L | H | Q |
| Afinity up | 28 | 29 | 30 | 31 | 32 | 33 | 34 | 45 |
| A | 4.18 | 1.15 | 1.16 | | 66.77 | 0.82 | 1.18 | |
| D | 4455.11 | 1.58 | 3.82 | 30.86 | 25.92 | 37.53 | 2100 | 0.86 |
| E | 5.47 | | 2.83 | 1.59 | | 0.83 | 8.03 | 1.01 |
| F | 2.59 | | f | | 4.51 | 0.65 | 3.5 | |
| G | 2.41 | 0.62 | 2.1 | | | | 1.08 | |
| H | 3 | | 1.08 | | | | | |
| I | 2.81 | 1.6 | 1.24 | 1.1 | | 0.86 | 0.89 | |
| R | 2.34 | | 1.35 | 0.88 | | | 4.1 | |
| L | 3.34 | 0.9 | 1.19 | | | | 1.03 | |
| M | 3.29 | | 1.2 | | | 0.9 | 3.16 | |
| N | | | | 4.46 | | | 2.84 | |
| P | 4.18 | 14.01 | 12.14 | 10.82 | 61.98 | 32.66 | 1.22 | |
| Q | 3.48 | | 1 | | | | 4.6 | 0.98 |
| R | | | 1.73 | | | | 85764 | |
| S | 4.3 | 1.05 | 10.64 | | | | 1.24 | |
| T | 2.67 | 1.02 | 12.72 | | | | 1.1 | |
| V | 3.73 | 2.25 | 2.62 | | | 1.26 | 1.04 | |
| W | 3.17 | | 0.97 | | | | 8.45 | |
| Y | 3.89 | 1.08 | 1.03 | | | | 2.44 | |

| | Domain | | | | | | | | | |
|---|---|---|---|---|---|---|---|---|---|---|
| | CDR2 | | | | | | | FR3 | | CDR3 |
| | Kabat numbering | | | | | | | | | |
| | 50 | 51 | 52 | 53 | 54 | 55 | 56 | 74 | 77 | 89 |
| | Amino acid before substitution | | | | | | | | | |
| | K | V | S | N | R | F | S | K | R | G |
| Affinity up | 50 | 51 | 52 | 53 | 54 | 55 | 56 | 74 | 77 | 89 |
| A | 59.5 | | 0.9 | 0.82 | 0.85 | 1.16 | 1.18 | | | 1.1 |

TABLE 7-continued

SEQ ID NO: 139

| | | | | | | | | | | |
|---|---|---|---|---|---|---|---|---|---|---|
| D | 114 | 1.5 | 0.94 | 2.8 | 1.8 | 1.02 | 1.11 | | | 1.96 |
| E | 57.2 | 0.88 | | 2.47 | 0.84 | 0.92 | 0.91 | | | 34.63 |
| F | | | | 0.96 | | | 1.12 | | | 3.34 |
| G | 42.4 | 0.83 | | 1.33 | 0.88 | 1.15 | 0.99 | | | |
| H | | | | 1.31 | | 1.02 | 0.96 | | | 1.44 |
| I | | 0.69 | | 2.69 | | 1.28 | 1.01 | | | 1.11 |
| K | | | | 1.05 | | 1.22 | 1.21 | | | 1.8 |
| L | 36.4 | | | 1.62 | | 1.43 | 1.03 | | | 2.38 |
| M | | | | 1.21 | | 1.29 | 0.93 | | | 1.96 |
| N | | | | | | 0.91 | 0.9 | | | 1.2 |
| P | 27.7 | 6 | 7.38 | 0.98 | 1.05 | 1.15 | 0.98 | | | 1.8 |
| Q | 8.13 | | 1.01 | 1.28 | 1.04 | 1.09 | 0.97 | | | 2.11 |
| R | 1.83 | | | 1.56 | | 1.27 | 1.15 | | | 4127.4 |
| S | 45.3 | | | 0.88 | 0.78 | 1.15 | | | 0.94 | |
| T | 25.1 | | | 2.68 | 0.89 | 2.42 | 1.01 | 0.85 | | 1.1 |
| V | | | | 2.14 | | 1.12 | 0.94 | | | 1.4 |
| W | | | | 1.01 | 0.65 | 1.72 | 1.12 | | | 23 |
| Y | 195 | | 1.02 | 0.99 | | 1.13 | 1.1 | | | 1.12 |

| | Domain | | | | | | | | |
|---|---|---|---|---|---|---|---|---|---|
| | CDR3 | | | | | | | | FR4 |
| | Kabat numbering | | | | | | | | |
| | 90 | 91 | 92 | 93 | 94 | 95 | 96 | 97 | 107 |
| | Amino acid before substitution | | | | | | | | |
| | Q | G | T | Q | V | P | Y | T | K |
| Affinity up | 90 | 91 | 92 | 93 | 94 | 95 | 96 | 97 | 107 |
| A | 0.89 | 28.14 | 1.35 | 0.65 | 1.05 | 0.87 | | | |
| D | 11.13 | 44.76 | 11.19 | 0.72 | 1.05 | 237 | 40.88 | | |
| E | 0.91 | 48.54 | 19.56 | 1.05 | 1.18 | 1.01 | 46.81 | | 0.95 |
| F | | | | | 1.75 | | 0.86 | | |
| G | | | | | 2.59 | 1.94 | | | |
| H | | | | | 1.16 | | 80.34 | | |
| I | | | 1.91 | | 1.46 | | | | |
| K | | | | | 0.91 | | | | |
| L | | | 1.61 | | 3.06 | 11.66 | 1.84 | | |
| M | | | | | 2.74 | | | | |
| N | | | | | 0.96 | | | | |
| P | 15.86 | 23.05 | 26.71 | 39.54 | 1.1 | | | 3.35 | |
| Q | | | | | 1.1 | | | | |
| R | | | | 0.79 | 1.11 | | | | |
| S | 0.96 | 72076 | 0.81 | 0.75 | 0.81 | 1.19 | | | |
| T | | 39.87 | | | 1.06 | | | | |
| V | | | | | | | | | |
| W | | | | | 1.81 | | | | |
| Y | 36.29 | 33.84 | 2.55 | 0.76 | 2.45 | | | | |

(6-4) Evaluation of Binding of One-Amino Acid Alteration Antibody to ECM (Extracellular Matrix)

ECM (extracellular matrix) is an extracellular constituent and resides at various sites in vivo. Therefore, an antibody strongly binding to ECM is known to have poorer kinetics in blood (shorter half-life) (WO2012093704 A1). Thus, amino acids that do not enhance ECM binding are preferably selected as the amino acids that appear in the antibody library.

Each antibody was obtained as an H chain or L chain altered form by the method described in the paragraph (6-2). Next, its ECM binding was evaluated according to the method of Reference Example 2. The ECM binding value (ECL reaction) of each altered form was divided by the ECM binding value of the antibody MRA (H chain: SEQ ID NO: 57, L chain: SEQ ID NO: 58) obtained in the same plate or at the same execution date, and the resulting value is shown in Tables 8 (H chain) and 9 (L chain). As shown in Tables 8 and 9, some alterations were confirmed to have tendency to enhance ECM binding.

Of the values shown in Tables 8 (H chain) and 9 (L chain), an effective value up to 10 times was adopted to the dual Fab library in consideration of the effect of enhancing ECM binding by a plurality of alterations.

TABLE 8

SEQ ID NO: 138

| | Domain | | | | | | | | | | | | | | |
|---|---|---|---|---|---|---|---|---|---|---|---|---|---|---|---|
| | FR1 | | | | | CDR1 | | | | FR2 | CDR2 | | | | |
| | Kabat numbering | | | | | | | | | | | | | | |
| | 11 | 16 | 19 | 28 | 29 | 30 | 31 | 32 | 33 | 35 | 43 | 50 | 51 | 52 | 52a |
| | Amino acid before substitution | | | | | | | | | | | | | | |
| | V | R | R | T | F | S | N | A | W | H | K | Q | I | K | A |
| A | | | | | | | | | | | | | | | |
| D | | | | 0.91 | | 1.11 | | | | 1.1 | | 1.06 | 4.75 | 1.07 | 1.66 |
| E | | 1.14 | | | | | | | | 1.04 | 1.8 | 1.08 | 4.55 | 1.18 | 1.19 |
| F | | | | | | | | | | 2.62 | | | | | |
| G | | | | | | 3.32 | | | | 8.82 | | | | | 4.72 |
| H | | | | | | | | | | | | | | | |
| I | | | | | | | 2.51 | | | | | | | | |
| K | | | | | | | 41.37 | | | | | | | | |
| L | 3.41 | | | | | | | | | | | | | | |
| M | | | | | | | | | | 4.69 | | | | | |
| N | | | | | | | | | | 3.06 | | | | | |
| P | | | | | | | | | | 51.18 | | | | | |
| Q | | 1.55 | | | | | | | | | 2 | | | | |
| R | | | | | | | 71.66 | | | | | | | 11.19 | |
| S | | | | 2.32 | | | 0.95 | | | | | | | | 3.34 |
| T | | | 1.17 | | | | | | | 3.49 | | | | | |
| V | | | | | 17.13 | | | | | 7.32 | | | | | |
| W | | | | | | | | | | 8.8 | | | | | |
| Y | | | | | | | | | | | | | | | |

| | Domain CDR2 Kabat numbering | | | | | | | | | | | | | |
|---|---|---|---|---|---|---|---|---|---|---|---|---|---|---|
| | 52b | 52c | 53 | 54 | 55 | 56 | 57 | 58 | 59 | 60 | 61 | 62 | 64 | 65 |
| | Amino acid before substitution | | | | | | | | | | | | | |
| | K | S | N | N | Y | A | T | Y | Y | A | E | S | K | G |
| A | | 2.95 | | 4.5 | | | 4.67 | | 5.82 | | 7.23 | | 2.08 | |
| D | | | | | | | | | 2.77 | 4.02 | 3.23 | 4.4 | 1.23 | 0.91 |
| E | | | | | | | | | 2.33 | 4.36 | | 2.75 | 1.33 | 2.13 |
| F | | 10.46 | | 15.16 | | | | | | | | | | |
| G | | 5.41 | | 4.43 | | | | | | | | | | |
| H | | | | | | | | | | | | | | |
| I | | | | | | | | | | | | | | |
| K | | 58.7 | | 85.86 | | 32.07 | 16.29 | | | | | 4.07 | | |
| L | | 4.07 | | 6.02 | | 3.56 | | | | | | | | |
| M | | | | | | | | | | | | | | |
| N | | | | | | 4.07 | 4.49 | | | | | | | |
| P | | | | | | | | | | | 9.99 | 3.83 | | |
| Q | | 4.99 | 3.18 | 3.23 | | | | | | | 9.29 | | 1.91 | |
| R | 7.28 | | | | | | | | | | | | | |
| S | | | 3.71 | 4.33 | | | | | 6.58 | | | | 1.89 | |
| T | | | | | | | | | | | | | | |
| V | | 3.23 | | | | | | | | | | | | |
| W | | | 23.56 | | | | | | | | | | | |
| Y | | 19.56 | | 17.47 | | | | | | | | | | |

| | Domain | | | | | | | | | | | | | | | | | | | |
|---|---|---|---|---|---|---|---|---|---|---|---|---|---|---|---|---|---|---|---|---|
| | FR3 | | | | | | | | CDR3 | | | | | | | | | | | FR4 |
| | Kabat numbering | | | | | | | | | | | | | | | | | | | |
| | 72 | 73 | 74 | 75 | 76 | 77 | 78 | 82a | 95 | 96 | 97 | 98 | 99 | 100 | 100a | 100b | 100c | 101 | 102 | 105 |
| | Amino acid before substitution | | | | | | | | | | | | | | | | | | | |
| | D | D | S | K | N | S | L | N | V | H | Y | G | A | Y | Y | G | V | D | A | Q |
| A | 22.3 | | | | | | | | | | | 2.7 | | 1.46 | | | | 66.85 | | |
| D | | | | | | | | 1.12 | 0.96 | | 0.65 | | | | | 0.98 | 1.18 | | | |
| E | | | | | | | | | 0.76 | | | | | | | 1.2 | 1.3 | | | 1.33 |
| F | | | | | | | | | | | | | 16.97 | | 2.81 | | | | | |
| G | | | | | | | | | | | | | | 1 | 2.61 | | | 56.66 | | |
| H | | | | | | | | | | | | 2.12 | | | | | | 16.16 | | |
| I | | | | | | | | | | | | | | | | | | 63.16 | 6.63 | |

TABLE 8-continued

SEQ ID NO: 138

| | | | | | | | | | | | | | | | | | | | |
|---|---|---|---|---|---|---|---|---|---|---|---|---|---|---|---|---|---|---|---|
| K | | | | | | | | | | | 32.29 | 57.13 | 8.2 | 10.3 | | | 38.94 | | |
| L | | | | | | | | | | | | 6.94 | | | | | | | |
| M | | | | | | | | | | | | | | | | | 123.87 | | |
| N | | | | | | | | | | | | | | | | | 90.66 | | |
| P | | | | | | | | | | | 3 | | | | | | | | |
| Q | | | | | | | | | | | 2.99 | 2.12 | 0.94 | | | | 130.29 | | |
| R | | | | 2.92 | | | | | | | 48.83 | | | | | | | | |
| S | | | | | 1.93 | | | | | | 2.41 | 3.34 | 1 | | | | 58.7 | | |
| T | | | | 1.2 | | 2.31 | | | | | 1.6 | 2.54 | | | | | | | |
| V | | | | | | | | | | | | | | | | | 48.47 | 6.29 | |
| W | | | | | | | | | | | | | 10.83 | | | | | | |
| Y | | | | | | | | | | | 27.01 | 30.37 | | | | | | 2.82 | |

TABLE 9

SEQ ID NO: 139

| | Domain | | | | | | | | | | | | | | | | |
|---|---|---|---|---|---|---|---|---|---|---|---|---|---|---|---|---|---|
| | CDR1 | | | | | | | | | | | | | | | | FR2 |
| | Kabat numbering | | | | | | | | | | | | | | | | |
| | 24 | 25 | 26 | 27 | 27a | 27b | 27c | 27d | 27e | 28 | 29 | 30 | 31 | 32 | 33 | 34 | 45 |
| | Amino acid before substitution | | | | | | | | | | | | | | | | |
| | R | S | S | Q | S | L | V | H | S | N | R | N | T | Y | L | H | Q |
| A | 2.62 | 2.28 | | | | | | | 3.25 | | 0.87 | | | 2.21 | 5.92 | 2.61 | |
| D | 1.86 | 1.01 | 1.31 | 1.3 | 1.03 | 1.16 | 0.76 | | | | 0.64 | | 0.66 | 0.98 | 0.6 | | 0.99 |
| E | 2.02 | 1.16 | 1.22 | 1.24 | 1.12 | 1.04 | 0.72 | | 1.19 | | | | 0.79 | | 1.45 | | 1.15 |
| F | | | | | | | | | 16.43 | | | 5.79 | | 1.55 | | | |
| G | 1.53 | | | | 10.04 | | | | 5.42 | | | | | | | 3.90 | |
| H | | | | | | | | | 13.64 | | | 8.6 | | | | | |
| I | | | | | 11.11 | 2.68 | 56.75 | | 4.28 | | | | 2.87 | | 4.74 | | |
| K | | | | | | | | | 34.74 | | | 31.93 | 59.62 | | | 84.66 | |
| L | | | | 11.8 | | | 3.16 | | 5.89 | | | | | | | | |
| M | | | | | | | | | 6.53 | | | 3.32 | | | 19.8 | | |
| N | | | | | 48.45 | | | | 4.63 | | | | | | | | |
| P | | 2.83 | | | 2.3 | 2.7 | | | 7.26 | | | | | | | | |
| Q | 1.26 | | | | | | | | 2.58 | | | 3.45 | | | | | 2.31 |
| R | | | | 18.19 | | | | | 74.03 | | | 69.62 | | | | | |
| S | 2.65 | | | | | 3.3 | | | | | | | | | | 2.17 | |
| T | 1.8 | 2.7 | | | | | | | 2.32 | | 0.63 | | | | | 4.51 | |
| V | | | | | | 2.82 | | | 2.31 | | | | | | 2.68 | 6.43 | |
| W | | | | | | | | | 46.73 | | | 11.21 | | | | | |
| Y | 1.89 | | | | 42.7 | | | | 30.66 | | | 3.08 | | | | | |

| | Domain | | | | | | | | | | | | | | | | | | |
|---|---|---|---|---|---|---|---|---|---|---|---|---|---|---|---|---|---|---|---|
| | CDR2 | | | | | | | FR3 | | CDR3 | | | | | | | | | FR4 |
| | Kabat numbering | | | | | | | | | | | | | | | | | | |
| | 50 | 51 | 52 | 53 | 54 | 55 | 56 | 74 | 77 | 89 | 90 | 91 | 92 | 93 | 94 | 95 | 96 | 97 | 107 |
| | Amino acid before substitution | | | | | | | | | | | | | | | | | | |
| | K | V | S | N | R | F | S | K | R | G | Q | G | T | Q | V | P | Y | T | K |
| A | 0.83 | | 3.65 | | 1.78 | 2.41 | 16.89 | | | 8.43 | 3.14 | | 3.11 | 3.34 | 3.22 | | | | |
| D | 0.64 | 1.01 | | | 1.44 | | | | | | 1.37 | 0.8 | 0.84 | | 0.88 | 4.38 | 0.66 | | |
| E | | 0.95 | | | 0.94 | | | | | | 2.55 | 1 | 0.67 | 0.85 | | 3.71 | 0.59 | | 2.96 |
| F | | | | | | | 10.25 | | | 31.93 | | | | | | | 3.44 | | |
| G | 0.67 | 3.5 | | | 1.19 | 6.49 | 3.26 | | | | | | | | | | | | |
| H | | | | 4.88 | | 7.39 | 6.83 | | | | | | | | | | | | |
| I | | 2.11 | | | | 23.25 | 5.1 | | | 14.58 | | | | | | | | | |
| K | | | | 19.31 | | 5.18 | 31.33 | | | | | | | | | | | | |
| L | | | | | | | 5.65 | | | 18.53 | | | | | | | | | |
| M | | | | | | 12.14 | 5.15 | | | | | | | | | | | | |
| N | | | | | | 7.83 | 3.96 | | | 4.96 | | | | | 3.01 | | | | |
| P | | | | 4.72 | 5.49 | 5.16 | 6 | | | | | | | | 10.7 | | | | |
| Q | 0.76 | | 2.37 | | 1.33 | 35.06 | 2.96 | | | | | | | | | | | | |
| R | | | | 34.13 | | 16.5 | 19.76 | | | | | | | 44.29 | | | | | |
| S | 0.84 | | | | | | | | 2.37 | | 4.37 | | 3.12 | 3.82 | 3.78 | | | | |
| T | 1.03 | | | | 1.39 | | 2.48 | 2.05 | | 6.79 | | | | | 2.63 | | | | |

TABLE 9-continued

| SEQ ID NO: 139 | | | | | | | | | | | | | | |
|---|---|---|---|---|---|---|---|---|---|---|---|---|---|---|
| V | | | | | | | 4 | | | 26.88 | | | | |
| W | | | | 2.19 | | | 26.63 | | | | | | | |
| Y | 0.88 | | 6.28 | | | 6.18 | 3.87 | | | 28.25 | 3.75 | 3.26 | 2.96 | 14.49 |

(6-5) Study on Insertion Site and Length of Peptide for Enhancing Diversity of Library Example 5 showed that a peptide can be inserted to each site using a GGS sequence without canceling binding to CD3 (CD3ε). If loop extension is possible for the dual Fab library, the resulting library might include more types of molecules (or have larger diversity) and permit obtainment of Fab domains binding to diverse second antigens. Thus, in view of presumed reduction in binding activity caused by peptide insertion, V11L/D72A/L78I/D101Q alteration to enhance binding activity against CD3ε was added to the CE115HA000 sequence, which was further linked to pE22Hh. A molecule was prepared by the insertion of the GGS linker to this sequence, as in Example 5, and evaluated for its CD3 binding. The GGS sequence was inserted between Kabat numbering positions 99 and 100. The antibody molecule was expressed as a one-arm antibody. Specifically, the GGS linker-containing H chain mentioned above and Kn010G3 (SEQ ID NO: 56) were used as H chains, and GLS3000 (SEQ ID NO: 53) linked to the kappa sequence (SEQ ID NO: 55) was adopted as an L chain. These sequences were expressed and purified according to Reference Example 1.

(6-6) Confirmation of Binding of GGS Peptide-Inserted CE115 Antibody to CD3

The binding of the GGS peptide-inserted altered antibody to CD3ε was confirmed using Biacore by the method described in Example 6. As shown in Table 10, the results demonstrated that the GGS linker can be inserted to loops. Particularly, the GGS linker was able to be inserted to the H chain CDR3 region, which is important for antigen binding, and the binding to CD3ε was maintained as a result of any of the 3-, 6-, and 9-amino acid insertions. Although this study was conducted using the GGS linker, an antibody library in which various amino acids other than GGS appear may be acceptable.

TABLE 10

| Inserted amino acid sequence (99-100) | CD3_KD[M] |
|---|---|
| GGS | 6.31E-08 |
| GGSGGS (SEQ ID NO: 90) | 3.46E-08 |
| GGSGGS (SEQ ID NO: 90) | 3.105E-08 |
| GGSGGGS (SEQ ID NO: 92) | 4.352E-08 |
| GGSGGGS (SEQ ID NO: 92) | 3.429E-08 |
| GGGSGGGS (SEQ ID NO: 93) | 4.129E-08 |
| GGGSGGGS (SEQ ID NO: 93) | 3.753E-08 |
| GGSGGSGGS (SEQ ID NO: 91) | 4.39E-08 |
| GGSGGSGGS (SEQ ID NO: 91) | 3.537E-08 |
| No insertion | 6.961E-09 |
| CE115HA000 | 1.097E-07 |

(6-7) Study on Insertion for Library to H Chain CDR3 Using NNS Nucleotide Sequence The paragraph (6-6) showed that the 3, 6, or 9 amino acids can be inserted using the GGS linker, and inferred that a library having the 3-, 6-, or 9-amino acid insertion can be prepared to obtain an antibody binding to the second antigen by use of a usual antibody obtainment method typified by the phage display method. Thus, a study was conducted on whether the 6-amino acid insertion to CDR3 could maintain binding to CD3 even if various amino acids appeared at the 6-amino acid insertion site using an NNS nucleotide sequence (which allows every type of amino acid to appear). In view of presumed reduction in binding activity, primers were designed using the NNS nucleotide sequence such that 6 amino acids were inserted between positions 99 and 100 (Kabat numbering) in CDR3 of a CE115HA340 sequence (SEQ ID NO: 59) having higher CD3ε-binding activity than that of CE115HA000. The antibody molecule was expressed as a one-arm antibody. Specifically, the altered H chain mentioned above and Kn010G3 (SEQ ID NO: 56) were used as H chains, and GLS3000 (SEQ ID NO: 53) linked to the kappa sequence (SEQ ID NO: 55) was adopted as an L chain. These sequences were expressed and purified according to Reference Example 1. The obtained altered antibody was evaluated for its binding by the method described in the paragraph (6-3). The results are shown in Table 11. The results demonstrated that the binding activity against CD3 (CD3ε) is maintained even if various amino acids appear at the site extended with the amino acids. Table 12 shows results of further evaluating the presence or absence of enhancement in nonspecific binding by the method described in Reference Example 2. As a result, the binding to ECM was enhanced if the extended loop of CDR3 was rich in amino acids having a positively charged side chain. Therefore, it was desired that three or more amino acids having a positively charged side chain should not appear in the loop.

TABLE 11

| SEQ ID NO: 140 | | |
|---|---|---|
| | CD3_ | CDR3 |
| VH1 | KD[M] | 9 1 0 |
| CD115HA340 | 2.0E-08 | 5 6 7 8 9 0 a b c d e f g h i k 1 1 2 |
| CE115HA340 | 2.7E-08 | V H Y A A X X X X X X Y Y G V • • D A |
| NNS6f17 | 7.4E-08 | • • • • • W G E G V V • • • • • • • • |
| NNS6f27 | 3.8E-08 | • • • • • V W G S V W • • • • • • • • |
| NNS6f29 | 9.0E-08 | • • • • • I Y Y P T N • • • • • • • • |
| NNS6f47 | 3.1E-08 | • • • • • H F M W W G • • • • • • • • |
| NNS6f50 | 7.1E-08 | • • • • • L T G G L G • • • • • • • • |
| NNS6f51 | 3.1E-08 | • • • • • G F L V L W • • • • • • • • |

TABLE 11-continued

| SEQ ID NO: 140 | | |
|---|---|---|
| | CD3_ | CDR3 |
| VH1 | KD[M] | 9 1 0 |
| NNS6f52 | 5.2E-08 | • • • • • Y M L G L G • • • • • • • • |
| NNS6f54 | 2.9E-08 | • • • • • F E W V G W • • • • • • • • |
| NNS6f55 | 3.1E-08 | • • • • • A G R W L A • • • • • • • • |
| NNS6f56 | 2.1E-08 | • • • • • R E A T R W • • • • • • • • |
| NNS6f58 | 4.4E-08 | • • • • • S W Q V S R • • • • • • • • |
| NNS6f59 | 2.0E-07 | • • • • • L L V Q E G • • • • • • • • |
| NNS6f62 | 6.1E-08 | • • • • • N G G T R H • • • • • • • • |
| NNS6f63 | 6.9E-08 | • • • • • G G G G W V • • • • • • • • |
| NNS6f64 | 7.8E-08 | • • • • • L V S L T V • • • • • • • • |
| NNS6f67 | 3.6E-08 | • • • • • G L L R A A • • • • • • • • |
| NNS6f68 | 4.5E-08 | • • • • • V E W G R W • • • • • • • • |
| NNS6f71 | 5.1E-08 | • • • • • G W V L G S • • • • • • • • |
| NNS6f72 | 1.5E-07 | • • • • • E G I W W G • • • • • • • • |
| NNS6f73 | 2.6E-08 | • • • • • W V V G V R • • • • • • • • |

TABLE 12

| SEQ ID NO: 140 | | | | |
|---|---|---|---|---|
| | | | Ratio | CDR3 |
| | ECL reaction | | ECM vs | 9 1 0 |
| H Chain | ECM 3µg/ml | MRA | MRA | 5 6 7 8 9 0 a b c d e f g h i k 1 1 2 |
| CE115HA340 | 394 | 448 | 0.9 | V H Y A A X X X X X X Y Y G V • • D A |
| NNS6f17 | 469 | 448 | 0.9 | • • • • • W G E G V V • • • • • • • • |
| NNS6f27 | 3441 | 448 | 7.7 | • • • • • V W G S V W • • • • • • • • |
| NNS6f29 | 481 | 448 | 1.1 | • • • • • I Y Y P T N • • • • • • • • |
| NNS6f47 | 94137 | 448 | 210.3 | • • • • • H F M W W G • • • • • • • • |
| NNS6f50 | 385 | 564 | 0.7 | • • • • • L T G G L G • • • • • • • • |
| NNS6f51 | 20148 | 564 | 35.7 | • • • • • G F L V L W • • • • • • • • |
| NNS6f52 | 790 | 564 | 1.4 | • • • • • Y M L G L G • • • • • • • • |
| NNS6f54 | 1824 | 564 | 3.2 | • • • • • F E W V G W • • • • • • • • |
| NNS6f55 | 14183 | 564 | 25.1 | • • • • • A G R W L A • • • • • • • • |
| NNS6f56 | 6534 | 564 | 11.0 | • • • • • R E A T R W • • • • • • • • |
| NNS6f58 | 2700 | 564 | 4.8 | • • • • • S W Q V S R • • • • • • • • |
| NNS6f59 | 388 | 564 | 0.7 | • • • • • L L V Q E G • • • • • • • • |
| NNS6f62 | 554 | 564 | 1.0 | • • • • • N G G T R H • • • • • • • • |
| NNS6f63 | 624 | 564 | 1.1 | • • • • • G G G G W V • • • • • • • • |
| NNS6f64 | 603 | 564 | 1.1 | • • • • • L V S L T V • • • • • • • • |
| NNS6f67 | 1292 | 564 | 2.3 | • • • • • G L L R A A • • • • • • • • |
| NNS6f68 | 2789 | 564 | 4.9 | • • • • • V E W G R W • • • • • • • • |
| NNS6f71 | 618 | 564 | 1.1 | • • • • • G W V L G S • • • • • • • • |
| NNS6f72 | 536 | 564 | 0.9 | • • • • • E G I W W G • • • • • • • • |
| NNS6f73 | 2193 | 564 | 3.9 | • • • • • W V V G V R • • • • • • • • |

(6-7) Design and Construction of Dual Fab Library

On the basis of the study described in Example 6, an antibody library (dual Fab library) for obtaining an antibody binding to CD3 and the second antigen was designed as follows:

step 1: selecting amino acids that maintain the ability to bind to CD3 (CD3ε) (to secure 80% or more of the amount of CE115HA000 bound to CD3);

step 2: selecting amino acids that keep ECM binding within 10 times that of MRA compared with before alteration; and step 3: inserting 6 amino acids to between positions 99 and 100 (Kabat numbering) in H chain CDR3.

The antigen-binding site of Fab can be diversified by merely performing the step 1. The resulting library can therefore be used for identifying an antigen-binding molecule binding to the second antigen. The antigen-binding site of Fab can be diversified by merely performing the steps 1 and 3. The resulting library can therefore be used for identifying an antigen-binding molecule binding to the second antigen. Even library design without the step 2 allows an obtained molecule to be assayed and evaluated for ECM binding.

Thus, for the dual Fab library, sequences derived from CE115HA000 by adding the V11L/L78I mutation to FR (framework) and further diversifying CDRs as shown in Table 13 were used as H chains, and sequences derived from GLS3000 by diversifying CDRs as shown in Table 14 were used as L chains. These antibody library fragments can be synthesized by a DNA synthesis method generally known to those skilled in the art. The dual Fab library may be prepared as (1) a library in which H chains are diversified as shown in Table 13 while L chains are fixed to the original sequence GLS3000 or the L chain having enhanced CD3ε binding described in Example 6, (2) a library in which H chains are fixed to the original sequence (CE115HA000) or the H chain having enhanced CD3ε binding described in Example 6 while L chains are diversified as shown in Table 14, and (3) a library in which H chains are diversified as shown in Table 13 while L chains are diversified as shown in Table 14. The H chain library sequences derived from CE115HA000 by adding the V11L/L78I mutation to FR (framework) and further diversifying CDRs as shown in Table 13 were entrusted to the DNA synthesizing company DNA2.0, Inc. to obtain antibody library fragments (DNA fragments). The obtained antibody library fragments were inserted to phagemids for phage display amplified by PCR. GLS3000 was selected as L chains. The constructed phagemids for phage display were transferred to *E. coli* by electroporation to prepare *E. coli* harboring the antibody library fragments.

TABLE 13

| | | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|
| SEQ ID: 141 | | | | | | | | | | | | | | | | | | | | | | | | | | | | | | | | | | | | | | | | | |
| | CDR1 | | | | | CDR2 | | | | | | | | | | | | | | | | | | | CDR3 | | | | | | | | | | | | | | | | |
| Kabat | 3 | | | | | 5 | | 5 | | | | | | | | | | | 6 | | | | | | 9 | | | | 1 | 0 | | | | | | | | | | | |
| numbering | 1 | 2 | 3 | 4 | 5 | 0 | 1 | 2 | a | b | c | 3 | 4 | 5 | 5 | 7 | 8 | 9 | 0 | 1 | 2 | 3 | 4 | 5 | 5 | 6 | 7 | 8 | 9 | 0 | a | b | c | d | e | f | g | h | i | 1 | 2 |
| Before substitution | N | A | W | M | H | Q | I | K | D | K | S | N | N | Y | A | T | Y | Y | A | E | S | V | K | G | V | H | Y | G | A | x | x | x | x | x | x | Y | Y | G | V | D | A |
| Library | I | A | W | M | H | Q | I | K | D | R | A | Q | A | Y | L | A | Y | Y | A | P | S | V | K | G | V | H | Y | A | A | A | A | G | A | L | P | A | Y | G | V | D | A |
| | N | | | | | | | | | K | G | S | G | | N | N | | | | E | | | | | | | | G | L | V | V | S | V | G | G | S | F | | | | |
| | S | | | | | | | | | | L | N | L | | A | T | | | | | | | | | | | | P | S | G | G | T | L | S | S | Q | G | | | | |
| | | | | | | | | | | | Q | | Q | | | | | | | | | | | | | | | S | Q | S | S | Y | G | Y | Y | K | | | | | |
| | | | | | | | | | | | V | | S | | | | | | | | | | | | | | | T | T | T | T | F | S | F | F | Y | | | | | |
| | | | | | | | | | | | S | | N | | | | | | | | | | | | | | | Q | | Y | Y | D | Y | | | G | | | | | |
| | | | | | | | | | | | | | | | | | | | | | | | | | | | | H | | F | F | | F | | | | | | | | |
| | | | | | | | | | | | | | | | | | | | | | | | | | | | | | | | D | | | | | | | | | | |

TABLE 14

| | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|
| SEQ ID NO: 139 | | | | | | | | | | | | | | | | | | | | | | | | | | | | | | | | | | | | |
| Domain | CDR1 | | | | | | | | | | | | | | | | FR2 | CDR2 | | | | | | | FR3 | | CDR3 | | | | | | | | | FR4 |
| Kabat | 2 | | | | | | | | | | | 3 | | | | | 4 | 5 | | | | | | | 7 | | | 9 | | | | | | | | 10 |
| numbering | 4 | 5 | 6 | 7 | a | b | c | d | e | 8 | 9 | 0 | 1 | 2 | 3 | 4 | 5 | 0 | 1 | 2 | 3 | 4 | 5 | 6 | 4 | 7 | 9 | 0 | 1 | 2 | 3 | 4 | 5 | 6 | 7 | 7 |
| Before substitution | R | S | S | Q | S | L | V | H | S | N | R | N | T | Y | L | H | Q | K | V | S | N | R | F | S | K | R | G | Q | G | T | Q | V | P | Y | T | K |
| Library | R | S | S | Q | S | L | V | H | S | N | R | N | T | Y | L | H | Q | K | V | S | N | R | F | S | K | R | G | Q | G | T | Q | V | P | Y | T | K |
| | A | A | D | D | E | I | L | | A | | | F | I | | A | A | | | G | A | P | P | A | G | T | S | A | E | | S | A | A | | F | | E |
| | E | P | | E | P | P | | | G | | | H | | | I | G | | | I | Q | W | | G | H | | | N | | | | S | D | | | | |
| | G | T | | | | V | | | I | | | M | | | V | T | | | | Y | | | H | I | | | T | | | | | N | | | | |
| | Q | | | | | | | | L | | | Q | | | | V | | | | | | | K | L | | | | | | | | S | | | | |
| | S | | | | | | | | M | | | Y | | | | | | | | | | | N | M | | | | | | | | T | | | | |
| | T | | | | | | | | N | | | | | | | | | | | | | | P | N | | | | | | | | | | | | |
| | Y | | | | | | | | P | | | | | | | | | | | | | | Y | P | | | | | | | | | | | | |
| | | | | | | | | | Q | | | | | | | | | | | | | | | Q | | | | | | | | | | | | |
| | | | | | | | | | T | | | | | | | | | | | | | | | T | | | | | | | | | | | | |
| | | | | | | | | | V | | | | | | | | | | | | | | | V | | | | | | | | | | | | |
| | | | | | | | | | | | | | | | | | | | | | | | | Y | | | | | | | | | | | | |

[Example 7] Obtainment of Fab Domain Binding to CD3 and Second Antigen (IL6R) from Dual Fab Library (7-1) Obtainment of Fab Domain Binding to Human IL6R Fab domains (antibody fragments) binding to human IL6R were identified from the dual Fab library designed and constructed in Example 6. Biotin-labeled human IL6R was used as an antigen, and antibody fragments having the ability to bind to human IL6R were enriched.

Phages were produced from the *E. coli* harboring the constructed phagemids for phage display. 2.5 M NaCl/10% PEG was added to the culture solution of the *E. coli* that had produced phages, and a pool of the phages thus precipitated was diluted with TBS to obtain a phage library solution. Next, BSA (final concentration: 4%) was added to the phage library solution. The panning method was performed with reference to a general panning method using antigens immobilized on magnetic beads (J. Immunol. Methods. (2008) 332 (1-2), 2-9; J. Immunol. Methods. (2001) 247 (1-2), 191-203; Biotechnol. Prog. (2002) 18 (2) 212-20; and Mol. Cell Proteomics (2003) 2 (2), 61-9). The magnetic beads used were NeutrAvidin coated beads (Sera-Mag SpeedBeads NeutrAvidin-coated) or Streptavidin coated beads (Dynabeads M-280 Streptavidin).

Specifically, 250 pmol of the biotin-labeled antigen was added to the prepared phage library solution and thereby contacted with the phage library solution at room temperature for 60 minutes. After addition of BSA-blocked magnetic beads, the antigen-phage complexes were attached to the magnetic beads at room temperature for 15 minutes. The beads were washed three times with TBST (TBS containing 0.1% Tween 20; TBS was available from Takara Bio Inc.) and then further washed twice with 1 mL of TBS. After addition of 0.5 mL of 1 mg/mL trypsin, the beads were suspended at room temperature for 15 minutes, immediately after which the beads were separated using a magnetic stand to recover a phage solution. The recovered phage solution was added to 10 mL of an *E. coli* strain ER2738 in a logarithmic growth phase (OD600: 0.4-0.5). The *E. coli* strain was infected by the phages through the gentle spinner culture of the strain at 37° C. for 1 hour. The infected *E. coli* was inoculated to a plate of 225 mm×225 mm. Next, phages were recovered from the culture solution of the inoculated *E. coli* to prepare a phage library solution. This cycle, called panning, was repeated several times. In the second and subsequent rounds of panning, 40 pmol of the biotin-labeled antigen was used. In the fourth round of panning, the phages were enriched with binding ability against CD3 as an index. Specifically, 250 pmol of biotin-labeled CD3c peptide antigen (amino acid sequence: SEQ ID NO: 60) was added to the prepared phage library solution and thereby contacted with the phage library solution at room temperature for 60 minutes. After addition of BSA-blocked magnetic beads, the antigen-phage complexes were attached to the magnetic beads at room temperature for 15 minutes. The beads were washed with 1 mL of TBS containing 0.1% Tween 20 and TBS. The beads supplemented with 0.5 mL of 1 mg/mL trypsin were suspended at room temperature for 15 minutes, immediately after which the beads were separated using a magnetic stand to recover a phage solution. The phages recovered from the trypsin-treated phage solution were added to 10 mL of an *E. coli* strain ER2738 in a logarithmic growth phase (OD600: 0.4-0.7). The *E. coli* strain was infected by the phages through the gentle spinner culture of the strain at 37° C. for 1 hour. The infected *E. coli* was inoculated to a plate of 225 mm×225 mm. Next, phages were recovered from the culture solution of the inoculated *E. coli* to recover a phage library solution.

In order to prevent a plurality of phages from infecting one *E. coli*, a phage library solution prepared from *E. coli* infected by phages recovered by the fifth round of panning was diluted again 100,000-fold, and *E. coli* was infected by the resulting phage solution to obtain single colonies.

(7-2) Binding of Fab Domain Displayed by Phage to CD3 or IL6R (Phage ELISA)

Figure 19:
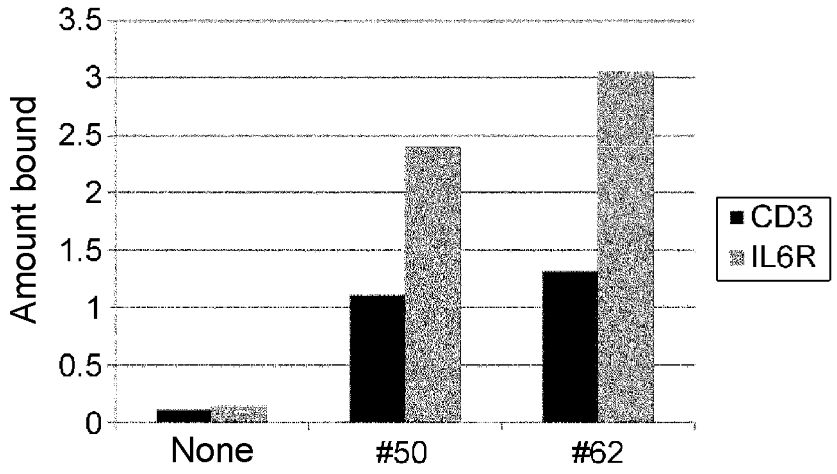
FIG. 19 is a diagram showing the binding of a Fab domain displayed by a phage to CD3ε and IL6R.

A phage-containing culture supernatant was recovered according to a routine method (Methods Mol. Biol. (2002) 178, 133-145) from each single colony of the *E. coli* obtained by the method described above. After addition of BSA (final concentration: 4%), the phage-containing culture supernatant was subjected to ELISA by the following procedures: StreptaWell 96 microtiter plate (F. Hoffmann-La Roche Ltd.) was coated overnight at 4° C. or at room temperature for 1 hour with 100 μL of PBS containing the biotin-labeled antigen (biotinylated CD3ε peptide or biotinylated human IL6R). Each well of the plate was washed with PBST to remove unbound antigens. Then, the well was blocked with 250 μL of 4% BSA-TBS for 1 hour or longer. After removal of 4% BSA-TBS, the prepared culture supernatant was added to each well, and the plate was left standing at room temperature for 1 hour so that the phage-displayed antibody bound to the antigen contained in each well. Each well was washed with TBST, and HRP-conjugated anti-M13 antibodies (Amersham Pharmacia Biotech Inc.) diluted with TBS containing BSA (final concentration: 4%) were then added to each well. The plate was incubated for 1 hour. After washing with TBST, TMB single solution (ZYMED Laboratories, Inc.) was added to the well. The chromogenic reaction of the solution in each well was terminated by the addition of sulfuric acid. Then, the developed color was assayed on the basis of absorbance at 450 nm. The results are shown in FIG. 19. Clones #50 and #62 were shown to have binding activity against CD3ε and human IL6R. In other words, clones exhibiting binding activity against the second antigen (in Example 7, human IL6R) were successfully selected by use of the dual Fab library. Clones exhibiting binding activity can be selected from a further increased number of library members to be evaluated, then converted to IgG (the VH and VL sequences of each clone are linked to human H chain and L chain constant domains, respectively), and evaluated for their binding activity against CD3ε and the second antigen (human IL6R). Furthermore, whether or not to bind to CD3ε and the second antigen (human IL6R) at the same time can be examined by the method described in Example 3 or 4 or the competition method. The competition method shows that the antibody does not bind to CD3ε and the second antigen at the same time, for example, when the level of its binding to CD3ε is reduced in the presence of the second antigen as compared with the antibody alone.

[Example 8] Obtainment of Fab Domain Binding to CD3 and Second Antigen (Human IgA) from Dual Fab Library (8-1) Obtainment of Fab Domain Binding to Human IgA IgA, which is an in vivo abundant antibody isotype, is known as a molecule involved in intestinal or mucosal biophylaxis and also known to bind to FcαR (Fc alpha receptor) (J. Pathol. 208: 270-282, 2006).

Fab domains (antibody fragments) binding to human IgA were identified from the dual Fab library designed and constructed in Example 6. Biotin-labeled human IgA (described in Reference Example 3) was used as an antigen, and antibody fragments having the ability to bind to human IgA were enriched.

Phages were produced from the *E. coli* harboring the constructed phagemids for phage display. 2.5 M NaCl/10% PEG was added to the culture solution of the *E. coli* that had produced phages, and a pool of the phages thus precipitated was diluted with TBS to obtain a phage library solution. Next, BSA (final concentration: 4%) was added to the phage library solution. The panning method was performed with reference to a general panning method using antigens immobilized on magnetic beads (J. Immunol. Methods. (2008) 332 (1-2), 2-9; J. Immunol. Methods. (2001) 247 (1-2), 191-203; Biotechnol. Prog. (2002) 18 (2) 212-20; and Mol. Cell Proteomics (2003) 2 (2), 61-9). The magnetic beads used were NeutrAvidin coated beads (Sera-Mag SpeedBeads NeutrAvidin-coated) or Streptavidin coated beads (Dynabeads M-280 Streptavidin).

Specifically, 250 pmol of the biotin-labeled antigen was added to the prepared phage library solution and thereby contacted with the phage library solution at room temperature for 60 minutes. After addition of BSA-blocked magnetic beads, the antigen-phage complexes were attached to the magnetic beads at room temperature for 15 minutes. The beads were washed three times with TBST (TBS containing 0.1% Tween 20; TBS was available from Takara Bio Inc.) and then further washed twice with 1 mL of TBS. After addition of 0.5 mL of 1 mg/mL trypsin, the beads were suspended at room temperature for 15 minutes, immediately after which the beads were separated using a magnetic stand to recover a phage solution. The recovered phage solution was added to 10 mL of an *E. coli* strain ER2738 in a logarithmic growth phase (OD600: 0.4-0.5). The *E. coli* strain was infected by the phages through the gentle spinner culture of the strain at 37° C. for 1 hour. The infected *E. coli* was inoculated to a plate of 225 mm×225 mm. Next, phages were recovered from the culture solution of the inoculated *E. coli* to prepare a phage library solution. This cycle, called panning, was repeated 4 times. In the second and subsequent rounds of panning, 40 pmol of human IgA was used.

(8-2) Binding of Fab Domain Displayed by Phage to CD3 or Human IgA

A phage-containing culture supernatant was recovered according to a routine method (Methods Mol. Biol. (2002) 178, 133-145) from each single colony of the *E. coli* obtained by the method described above. After addition of BSA (final concentration: 4%), the phage-containing culture supernatant was subjected to ELISA by the following procedures: StreptaWell 96 microtiter plate (F. Hoffmann-La Roche Ltd.) was coated overnight at 4° C. or at room temperature for 1 hour with 100 μL of PBS containing the biotin-labeled antigen (biotin-labeled CD3ε peptide or biotin-labeled human IgA; Reference Example 3). Each well of the plate was washed with PBST to remove unbound antigens. Then, the well was blocked with 250 μL of 0.1×TBS/150 mM NaCl/0.02% skim milk for 1 hour or longer. After removal of 0.1×TBS/150 mM NaCl/0.02% skim milk, the prepared culture supernatant was added to each well, and the plate was left standing at room temperature for 1 hour so that the phage-displayed antibody bound to the antigen contained in each well. Each well was washed with 0.1×TBS/150 mM NaCl/0.01% Tween 20, and HRP-conjugated anti-M13 antibodies (Amersham Pharmacia Biotech Inc.) diluted with 0.1×TBS/150 mM NaCl/0.01% Tween 20 were then added to each well. The plate was incubated for 1 hour. After washing with TBST, TMB single solution (ZYMED Laboratories, Inc.) was added to the well. The chromogenic reaction of the solution in each well was terminated by the addition of sulfuric acid. Then, the developed color was assayed on the basis of absorbance at 450 nm. The results are shown in FIG. 20. As shown in FIG. 20, some clones were shown to bind to CD3 and human IgA. Thus, clones exhibiting binding activity against the second antigen (in Example 8, human IgA) were successfully selected by use of the dual Fab library.

(8-3) Binding of IgG Having Obtained Fab Domain to CD3 or Human IgA

The VH fragment of each clone shown to bind to CD3 and human IgA in the paragraph (8-2) was amplified from *E. coli* having the sequence by PCR using primers specifically binding to the H chain in the dual Fab library. The amplified VH fragment was integrated to pE22Hh-containing plasmids for expression in animal cells by the method of Reference Example 1, and expressed and purified as a one-arm antibody, as in Example 6(6-2). The name of each clone and SEQ ID NO of its H chain sequence are shown in Table 15. Specifically, each H chain shown in Table 15 and Kn010G3 (SEQ ID NO: 56) were used as H chains, and GLS3000 (SEQ ID NO: 53) linked to the kappa sequence (SEQ ID NO: 55) was adopted as an L chain. These sequences were expressed and purified according to Reference Example 1.

TABLE 15

| Sample name | SEQ ID NO |
|---|---|
| IGAR4C09#1 | 61 |
| IGAR4C12#4 | 62 |
| IGAR6(2)B02#1 | 63 |

The antibody molecule having the obtained Fab region was evaluated for its binding to CD3ε and human IgA by the electrochemiluminescence method (ECL method). Specifically, biotin-labeled CD3ε peptide (described in Example 7) or biotin-labeled human IgA (Reference Example 3) diluted with a TBST solution (TBS (manufactured by Takara Bio Inc.) supplemented with 0.1% Tween 20), each antibody solution adjusted to 2 μg/mL, and anti-human IgG antibody (Invitrogen Corp., #628400) tagged with sulfo-tag were each added at 25 μL/well to Nunc-Immuno™ MicroWell™ 96 well round plates (Nunc), and mixed, and the plate was then incubated at room temperature for 1 hour or longer while shielded from light to form an antibody-antigen complex. A TBST solution containing 0.5% BSA (referred to as a blocking solution) was added at 150 μL/well to streptavidin plate (MSD K.K.), and the plate was incubated at room temperature for 1 hour or longer. After removal of the blocking solution, each well was washed three times with 250 μL of a TBS(−) solution. The antibody-antigen complex solution was added thereto at 50 μL/well, and the plate was incubated at room temperature for 1 hour so that the biotinylated antigen-antibody-detection sulfo-tag antibody complex solution bound via the biotinylated antigen to the streptavidin plate. After removal of the antibody-antigen complex solution, each well was washed three times with a TBST solution, and a solution of 4×READ buffer (MSD K.K.) diluted 2-fold with water was added thereto at 150 μL/well, followed by the detection of the luminescence signal of the sulfo-tag using Sector Imager 2400 (MSD K.K.).

Figure 21:
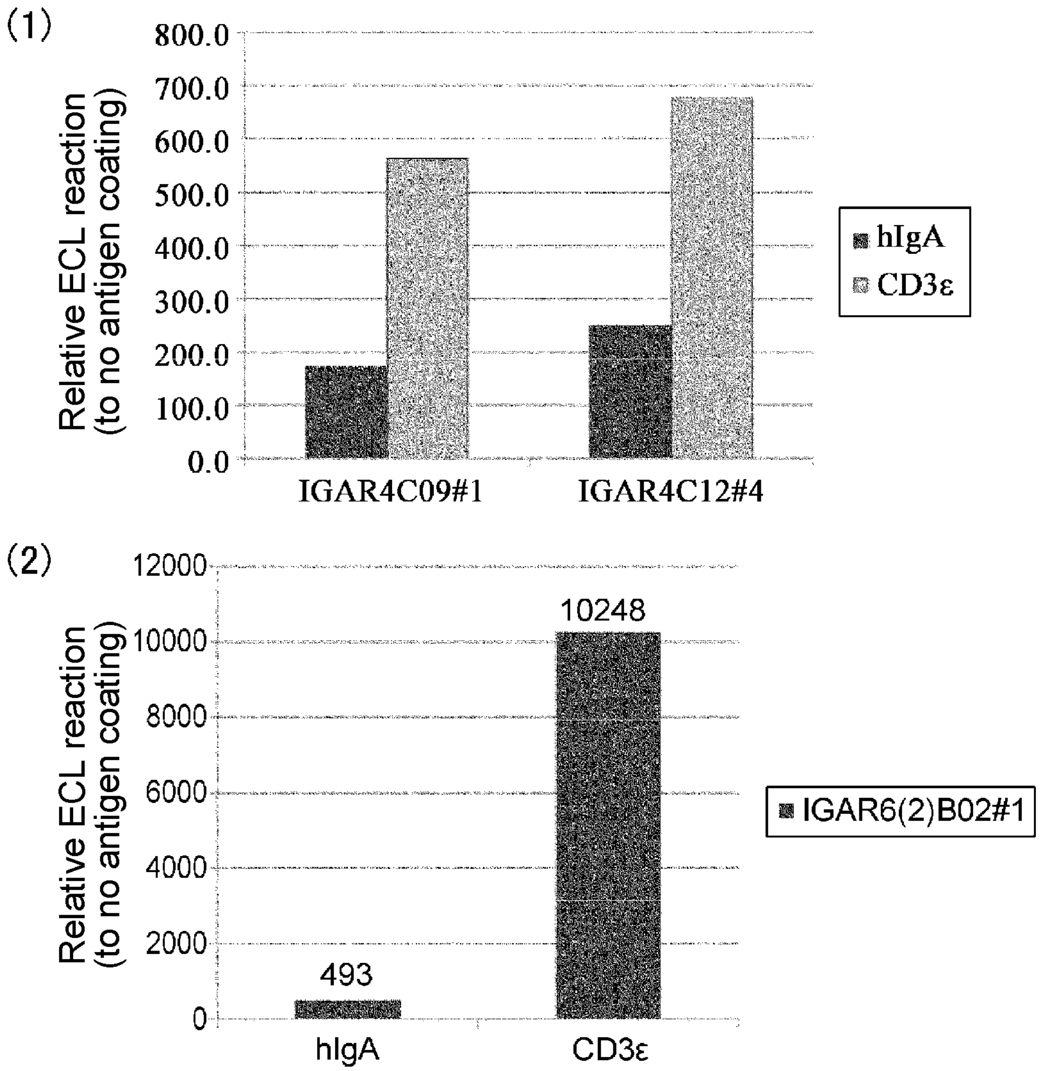
FIG. 21 is a diagram showing the binding of a clone converted to IgG to CD3ε and human IgA (hIgA).

The results are shown in FIG. 21. The clones confirmed to bind by phage ELISA were each converted to IgG, also including those containing some amino acid mutations. Consequently, these sequences confirmed to bind by phage ELISA were shown to bind to CD3ε and human IgA, even in the form of IgG.

These results demonstrated that: an antibody binding to the second antigen can be obtained from the dual Fab library; and clones confirmed to bind can be enriched even in the form of Fc region-containing IgG, though only Fab domains are enriched in usual panning using a phage library. Thus, it was concluded that the dual Fab library serves as a library that permits obtainment of a Fab domain having the ability to bind to the second antigen while maintaining the ability to bind to CD3.

(8-4) Evaluation of Binding of IgG Having Obtained Fab Domain to CD3 (CD3ε) and Human IgA at Same Time In the paragraph (8-3), the clones obtained from the dual Fab library were shown to have binding activity even in the form of IgG. Next, each obtained IgG was evaluated for its binding to CD3 (CD3ε) and human IgA at the same time by the competition method (electrochemiluminescence method (ECL method)). It can be expected that: when the IgG binds to CD3 (CD3ε) and human IgA at the same time, the addition of CD3 (CD3ε) to IgA-bound antibodies causes no change in ECL signal; and when the IgG cannot bind to these antigens at the same time, the addition of CD3 (CD3ε) decreases the ECL signal due to the binding of some antibodies to CD3 (CD3ε).

Specifically, 25 μL of biotinylated human IgA diluted with a TBST solution, 12.5 μL of each antibody solution adjusted to 1 μg/mL, 12.5 μL of TBST or CD3ε homodimer protein (9.4 pmol/μL) for competition, and 25 μL of anti-human IgG antibody (Invitrogen Corp., #628400) tagged with sulfo-tag were added to each well of Nunc-Immuno™ MicroWell™ 96 well round plates (Nunc), and mixed, and the plate was then incubated at room temperature for 1 hour or longer while shielded from light to form an antibody-antigen complex. A TBST solution containing 0.5% BSA (referred to as a blocking solution; the TBST solution was TBS (manufactured by Takara Bio Inc.) supplemented with 0.1% Tween 20) was added at 150 μL/well to streptavidin plate (MSD K.K.), and the plate was incubated at room temperature for 1 hour or longer. After removal of the blocking solution, each well was washed three times with 250 μL of a TBST solution. The antibody-antigen complex solution was added thereto at 50 μL/well, and the plate was incubated at room temperature for 1 hour so that the biotinylated antigen-antibody-detection sulfo-tag antibody complex solution bound via the biotinylated antigen to the streptavidin plate. After removal of the antibody-antigen complex solution, each well was washed three times with a TBST solution, and a solution of 4×READ buffer (MSD K.K.) diluted 2-fold with water was added thereto at 150 μL/well, followed by the detection of the luminescence signal of the sulfo-tag using Sector Imager 2400 (MSD K.K.).

Figure 22:
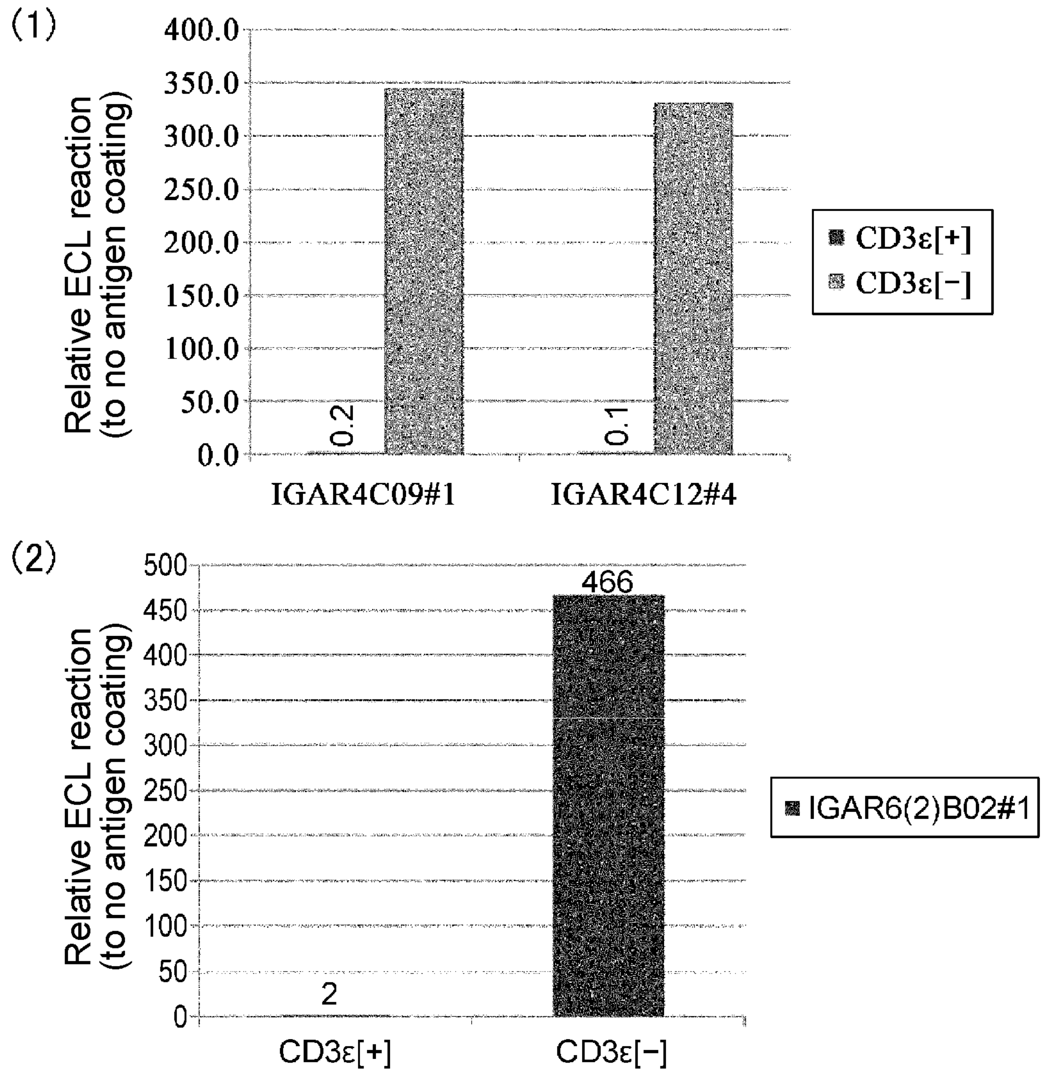
FIG. 22 is a diagram showing that the binding of a clone converted to IgG to human IgA is inhibited by CD3ε so that the clone cannot bind to human IgA (hIgA) and CD3ε at the same time.

The results are shown in FIG. 22. The addition of the CD3ε homodimer protein for competition was confirmed to decrease the ECL signal as compared with the addition of TBST. These results indicated that the molecule binding to CD3 and human IgA, found in this study, is a dual Fab molecule that cannot bind to human IgA in a state bound with CD3. There results demonstrated that an antibody having the ability to bind to the second antigen can be obtained from the dual Fab library and, among others, can be obtained as a dual Fab molecule that cannot bind to the second antigen in a state bound with CD3 (or cannot bind to CD3 in a state bound with the second antigen), i.e., cannot bind to plural types of antigens at the same time.

It is obvious to those skilled in the art that, provided that a binding molecule is found in the binding activity evaluation using phages in the paragraph (8-2), the sequence variety of the binding molecule can be increased by increasing the number of library members to be evaluated. Thus, it was concluded that the dual Fab library serves as a library that permits obtainment of a Fab domain having the ability to bind to the second antigen while maintaining the ability to bind to CD3. In this Example, the dual Fab library diversified by only H chains was used. A larger library size (also called diversity; which means that the library includes diverse sequences) usually allows more antigen-binding molecules to be obtained. Therefore, a dual Fab library diversified by both H and L chains can also be used for obtaining dual Fab molecules, as shown in this Example.

Provided that dual Fab molecules can be prepared as shown in Example 8, Fab or an antigen-binding domain binding to the third antigen can be identified by a method generally known to those skilled in the art, for example, a hybridoma method or a method for selecting binding antibodies (or binding domains) from antibody libraries. An antibody having the identified antigen-binding domain (e.g., Fab) binding to the third antigen and the Fab domain of the dual Fab molecule can be obtained as a multispecific antibody by a multispecific antibody preparation method generally known to those skilled in the art, for example, a method for preparing an antibody having common L chains and two different H chains (technique controlling the interface of each domain in the Fc region), CrossMab, or Fab arm exchange. In other words, provided that a dual Fab molecule can be identified, the desired multispecific antibody can be obtained according to a method generally known to those skilled in the art by combining Fab binding to the third antigen with the dual Fab binding to the first and second antigens as shown in Example 8.

(8-5) CD3/Human IgA Dual Fab Molecule

In Example 8, the obtained dual Fab molecule was shown to bind to CD3ε and human IgA, but not bind to CD3ε and human IgA at the same time. An antigen-binding domain binding to the third antigen can be further added thereto by a method generally known to those skilled in the art.

In recent years, an IgA molecule altered to bind to EGFR, a cancer antigen, has been found to induce the cell death of cancer cells expressing EGFR (J Immunol 2007; 179: 2936-2943). As this mechanism, the IgA receptor FcαR is expressed in polymorphonuclear cells and reportedly induces the autophagy of cancer cells (J Immunol 2011; 187: 726-732). This Example revealed that the dual Fab molecule binding to CD3 and IgA can be constructed. Anti-tumor effects mediated by FcαR can be expected by searching for a molecule binding to FcαR via IgA by a method generally known to those skilled in the art (e.g., ELISA or the ECL method). In other words, this dual Fab can induce both of T cell-mediated cytotoxic activity by binding to CD3ε and cytotoxic activity mediated by FcαR-expressing cells via binding to IgA against cells expressing an arbitrary third antigen and can be expected to produce strong cytotoxic activity.

[Example 9] Obtainment of Fab Domain Binding to CD3 and Second Antigen (Human CD154) from Dual Fab Library (9-1) Obtainment of Fab Domain Binding to Human CD154

Fab domains (antibody fragments) binding to human CD154 were identified from the dual Fab library designed and constructed in Example 6. Antibody fragments having the ability to bind to human CD154 were enriched using biotin-labeled human CD154 as an antigen.

Phages were produced from the *E. coli* harboring the constructed phagemids for phage display. 2.5 M NaCl/10% PEG was added to the culture solution of the *E. coli* that had produced phages, and a pool of the phages thus precipitated was diluted with TBS to obtain a phage library solution. Next, BSA (final concentration: 4%) was added to the phage library solution. The panning method was performed with reference to a general panning method using antigens immobilized on magnetic beads (J. Immunol. Methods. (2008) 332 (1-2), 2-9; J. Immunol. Methods. (2001) 247 (1-2), 191-203; Biotechnol. Prog. (2002) 18 (2) 212-20; and Mol. Cell Proteomics (2003) 2 (2), 61-9). The magnetic beads used were NeutrAvidin coated beads (Sera-Mag SpeedBeads NeutrAvidin-coated) or Streptavidin coated beads (Dynabeads M-280 Streptavidin).

Specifically, 250 pmol of the biotin-labeled antigen was added to the prepared phage library solution and thereby contacted with the phage library solution at room temperature for 60 minutes. After addition of BSA-blocked magnetic beads, the antigen-phage complexes were attached to the magnetic beads at room temperature for 15 minutes. The beads were washed three times with TBST (TBS containing 0.1% Tween 20; TBS was available from Takara Bio Inc.) and then further washed twice with 1 mL of TBS. After addition of 0.5 mL of 1 mg/mL trypsin, the beads were suspended at room temperature for 15 minutes, immediately after which the beads were separated using a magnetic stand to recover a phage solution. The recovered phage solution was added to 10 mL of an *E. coli* strain ER2738 in a logarithmic growth phase (OD600: 0.4-0.5). The *E. coli* strain was infected by the phages through the gentle spinner culture of the strain at 37° C. for 1 hour. The infected *E. coli* was inoculated to a plate of 225 mm×225 mm. Next, phages were recovered from the culture solution of the inoculated *E. coli* to prepare a phage library solution. This cycle, called panning, was repeated 5 times. In the second and subsequent rounds of panning, 40 pmol of human CD154 was used.

(9-2) Binding of Fab Domain Displayed by Phage to CD3 or Human CD154

A phage-containing culture supernatant was recovered according to a routine method (Methods Mol. Biol. (2002) 178, 133-145) from each single colony of the *E. coli* obtained by the method described above. After addition of BSA (final concentration: 4%), the phage-containing culture supernatant was subjected to ELISA by the following procedures: StreptaWell 96 microtiter plate (F. Hoffmann-La Roche Ltd.) was coated overnight at 4° C. or at room temperature for 1 hour with 100 μL of PBS containing the biotin-labeled antigen (biotin-labeled CD3ε peptide or biotin-labeled CD154). Each well of the plate was washed with PBST to remove unbound antigens. Then, the well was blocked with 250 μL of 0.1×TBS/150 mM NaCl/0.02% skim milk for 1 hour or longer. After removal of 0.1×TBS/150 mM NaCl/0.02% skim milk, the prepared culture supernatant was added to each well, and the plate was left standing at room temperature for 1 hour so that the phage-displayed antibody bound to the antigen contained in each well. Each well was washed with 0.1×TBS/150 mM NaCl/0.01% Tween 20, and HRP-conjugated anti-M13 antibodies (Amersham Pharmacia Biotech Inc.) diluted with 0.1×TBS/150 mM NaCl/0.01% Tween 20 were then added to each well. The plate was incubated for 1 hour. After washing with TBST, TMB single solution (ZYMED Laboratories, Inc.) was added to the well. The chromogenic reaction of the solution in each well was terminated by the addition of sulfuric acid. Then, the developed color was assayed on the basis of absorbance at 450 nm. The results are shown in FIG. 23. As shown in FIG. 23, some clones were shown to bind to CD3 and CD154. Thus, clones exhibiting binding activity against the second antigen (in Example 9, human CD154) were successfully selected by use of the dual Fab library. As shown in Examples 7, 8, and 9, binding Fab domains can be obtained for 3 different antigens, indicating that the dual Fab library functions as a library for obtaining a molecule binding to the second antigen.

(9-3) Binding of IgG Having Obtained Fab Domain to CD3 or Human CD154

The VH fragment of each clone shown to bind to CD3 and human CD154 in the paragraph (9-2) was amplified from *E. coli* having the sequence by PCR using primers specifically binding to the H chain in the dual Fab library. The amplified VH fragment was integrated to pE22Hh-containing plasmids for expression in animal cells by the method of Reference Example 1, and expressed and purified as a one-arm antibody, as in Example 6(6-2). The name of each obtained sequence and SEQ ID NO of its H chain sequence are shown in Table 16. Specifically, each H chain shown in Table 16 and Kn010G3 (SEQ ID NO: 56) were used as H chains, and GLS3000 (SEQ ID NO: 53) linked to the kappa sequence (SEQ ID NO: 55) was adopted as an L chain. These sequences were expressed and purified according to Reference Example 1.

TABLE 16

| Sample name | SEQ ID NO |
|---|---|
| 154R3A01#1 | 64 |
| 154R3A01#2 | 65 |
| 154R3A01#3 | 66 |
| 154R3A01#4 | 67 |
| 154R3B01#1 | 68 |
| 154R3F02#2 | 69 |
| 154R4B03#1 | 70 |
| 154R4B03#4 | 71 |
| 154R4B07#1 | 72 |
| 154R4F08#1 | 73 |
| 154R5A02#1 | 74 |
| 154R5A02#2 | 75 |
| 154R5F08#1 | 76 |
| 154R5F08#3 | 77 |
| 154R5E11#3 | 78 |

The antibody molecule having the Fab region shown to bind to CD3 and human CD154 by phage ELISA in the paragraph (9-2) was evaluated for its binding to CD3 and human CD154 by the electrochemiluminescence method (ECL method). Specifically, 25 μL of biotinylated CD3 or biotinylated human CD154 diluted with a TBST solution, 25 μL of each antibody solution adjusted to 2 μg/mL, and 25 μL of anti-human IgG antibody (Invitrogen Corp., #628400) tagged with sulfo-tag were added to each well of Nunc-Immuno™ MicroWell™ 96 well round plates (Nunc), and mixed, and the plate was then incubated at room temperature for 1 hour or longer while shielded from light to form an antibody-antigen complex. A TBST solution containing 0.5% BSA (referred to as a blocking solution; the TBST solution was TBS (manufactured by Takara Bio Inc.) supplemented with 0.1% Tween 20) was added at 150 μL/well to streptavidin plate (MSD K.K.), and the plate was incubated at room temperature for 1 hour or longer. After removal of the blocking solution, each well was washed three times with 250 μL of a TBST solution. The antibody-antigen complex solution was added thereto at 50 μL/well, and the plate was incubated at room temperature for 1 hour so that the biotinylated antigen-antibody-detection sulfo-tag antibody complex solution bound via the biotinylated antigen to the streptavidin plate. After removal of the antibody-antigen complex solution, each well was washed three times with a TBST solution, and a solution of 4×READ buffer (MSD K.K.) diluted 2-fold with water was added thereto at 150 μL/well, followed by the detection of the luminescence signal of the sulfo-tag using Sector Imager 2400 (MSD K.K.).

Figure 24:
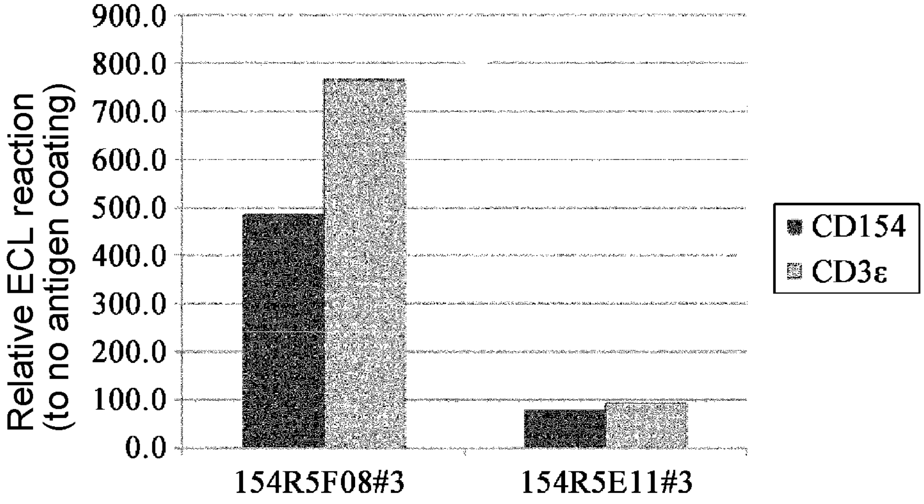
FIG. 24 is a diagram showing the binding of a clone converted to IgG to CD3ε and human CD154.

The results are shown in FIG. 24. The clones confirmed to bind by phage ELISA were each converted to IgG, also including those containing some amino acid mutations. Consequently, these sequences confirmed to bind by phage ELISA were shown to bind to CD3ε and human CD154, even in the form of IgG.

These results demonstrated that: an antibody binding to the second antigen can be obtained from the dual Fab library; and clones confirmed to bind can be enriched not only for human IgA but for human CD154 even in the form of Fc region-containing IgG, though only Fab domains are enriched in usual panning using a phage library. Thus, it was concluded that the dual Fab library serves as a library that permits obtainment of a Fab domain having the ability to bind to the second antigen while maintaining the ability to bind to CD3.

(9-4) Evaluation of Binding of IgG Having Obtained Fab Domain to CD3ε and Human CD154 at Same Time In the paragraph (9-3), the clones obtained from the dual Fab library were shown to have binding activity even in the form of IgG. Next, each obtained IgG was evaluated for its binding to CD3 and human CD154 at the same time by the competition method (electrochemiluminescence method (ECL method)). It can be expected that: when the IgG binds to CD3 and human CD154 at the same time, the addition of CD3 to CD154-bound antibodies causes no change in ECL signal; and when the IgG cannot bind to these antigens at the same time, the addition of CD3 decreases the ECL signal due to the binding of some antibodies to CD3.

Specifically, 25 μL of biotinylated human CD154 diluted with a TBST solution, 12.5 μL of each antibody solution adjusted to 1 μg/mL, 12.5 μL of TBST or CD3ε homodimer protein (9.4 pmol/μL) for competition, and 25 μL of anti-human IgG antibody (Invitrogen Corp., #628400) tagged with sulfo-tag were added to each well of Nunc-Immuno™ MicroWell™ 96 well round plates (Nunc), and mixed, and the plate was then incubated at room temperature for 1 hour or longer while shielded from light to form an antibody-antigen complex. A TBST solution containing 0.5% BSA (referred to as a blocking solution; the TBST solution was TBS (manufactured by Takara Bio Inc.) supplemented with 0.1% Tween 20) was added at 150 μL/well to streptavidin plate (MSD K.K.), and the plate was incubated at room temperature for 1 hour or longer. After removal of the blocking solution, each well was washed three times with 250 μL of a TBST solution. The antibody-antigen complex solution was added thereto at 50 μL/well, and the plate was incubated at room temperature for 1 hour so that the biotinylated antigen-antibody-detection sulfo-tag antibody complex solution bound via the biotinylated antigen to the streptavidin plate. After removal of the antibody-antigen complex solution, each well was washed three times with a TBST solution, and a solution of 4×READ buffer (MSD K.K.) diluted 2-fold with water was added thereto at 150 μL/well, followed by the detection of the luminescence signal of the sulfo-tag using Sector Imager 2400 (MSD K.K.).

Figure 25:
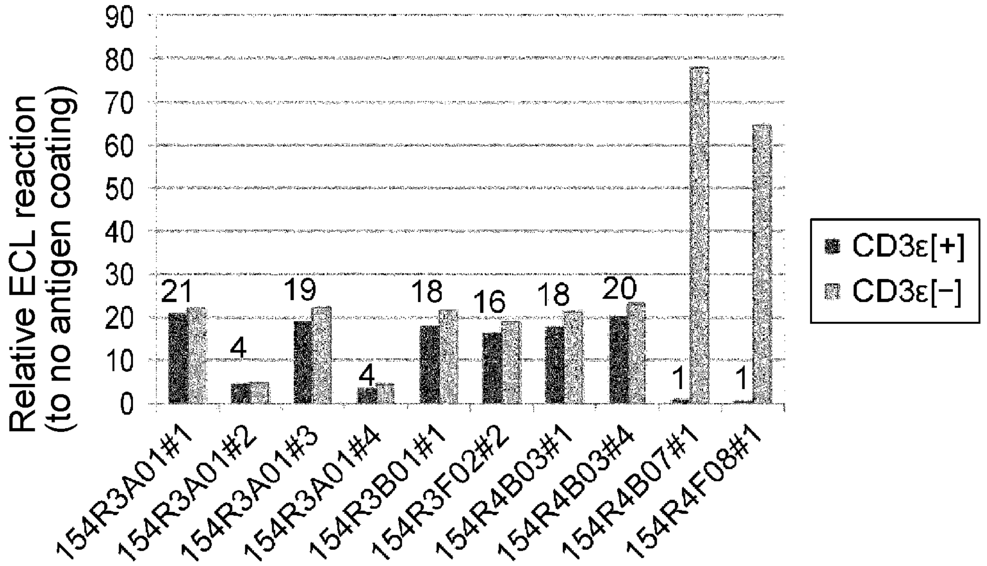
FIG. 25 is a diagram showing that the binding of a clone converted to IgG to human CD154 is inhibited by CD3ε so that the clone cannot bind to human CD154 and CD3ε at the same time.
Figure 25:
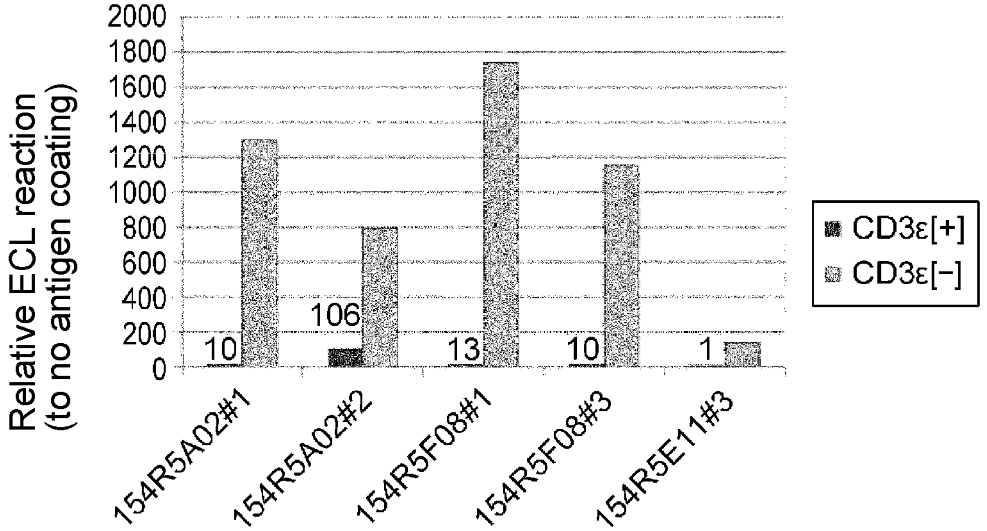

The results are shown in FIG. 25. The addition of the CD3ε homodimer protein for competition was confirmed to decrease the ECL signal as compared with the addition of TBST. These results indicated that the molecule binding to CD3ε and human CD154, found in this study, is a dual Fab molecule that cannot bind to human CD154 in a state bound with CD3. There results demonstrated that an antibody binding to the second antigen can be obtained from the dual Fab library and, among others, can be obtained as a dual Fab molecule that cannot bind to the second antigen in a state bound with CD3 (or cannot bind to CD3 in a state bound with the second antigen), i.e., cannot bind to plural types of antigens at the same time.

It is obvious to those skilled in the art that, provided that a binding molecule is found in the binding activity evaluation using phages in the paragraph (9-2), the sequence variety of the binding molecule can be increased by increasing the number of library members to be evaluated. Thus, it was concluded that the dual Fab library serves as a library that permits obtainment of a Fab domain having the ability to bind to the second antigen while maintaining the ability to bind to CD3. In this Example, the dual Fab library diversified by only H chains was used. A larger library size (also called diversity; which means that the library includes diverse sequences) usually allows more antigen-binding molecules to be obtained. Therefore, a dual Fab library diversified by both H and L chains can also be used for obtaining dual Fab molecules, as shown in this Example.

Provided that Dual Fab Molecules can be Prepared as Shown in Example 9, Fab or an antigen-binding domain binding to the third antigen can be identified by a method generally known to those skilled in the art, for example, a hybridoma method or a method for selecting binding antibodies or antigen binding domains from antibody libraries. An antibody having the identified antigen-binding domain (e.g., Fab) binding to the third antigen and the Fab domain of the dual Fab molecule can be obtained as a multispecific antibody by a multispecific antibody preparation method generally known to those skilled in the art, for example, a method for preparing an antibody having common L chains and two different H chains (technique controlling the interface of each domain in the Fc region), CrossMab, or Fab arm exchange. In other words, provided that a dual Fab molecule can be identified, the desired multispecific antibody can be obtained according to a method generally known to those skilled in the art by combining Fab binding to the third antigen with the dual Fab binding to the first and second antigens as shown in Example 9. These Examples showed that a molecule binding to CD3ε and the second antigen can be obtained by the adaptation of the dual Fab library to many types of antigens, and further demonstrated that the molecule that can be obtained as described in Example 8 or 9 binds to the first antigen (CD3ε) and the second antigen, but does not bind to the first antigen and the second antigen at the same time. As mentioned above, Fab binding to the third antigen can be identified by a method generally known to those skilled in the art. Therefore, the desired antibody described in Example 1 can be obtained using the dual Fab library.

(9-5) CD3/Human CD154 Dual Fab Molecule

In Example 9, the obtained dual Fab molecule was shown to bind to CD3ε and human CD154, but not bind to CD3ε and human CD154 at the same time. An antigen-binding domain binding to the third antigen can be further added thereto by a method generally known to those skilled in the art.

In recent years, an agonistic antibody of a CD154 receptor CD40 has been found to enhance antitumor activity in a method of transferring cancer antigen-responsive T cells (J Immunother. 2012 April; 35 (3): 276-82). This Example revealed that the dual Fab molecule binding to CD3 and CD154 can be constructed. Anti-tumor effects mediated by CD40 can be expected by selecting an antibody exhibiting agonist activity against CD40 via CD154. In other words, this dual Fab can be expected to have T cell-mediated cytotoxic activity by binding to CD3ε against cells expressing an arbitrary third antigen and to enhance antitumor effects mediated by CD40 agonist signals via binding to CD154.

[Example 10] Anti-Human CD3 Antibody-Derived Antibody Library

CD3 is a protein expressed on human T cells. In recent years, a bispecific antibody catumaxomab against CD3 and EpCAM has been found to exhibit a strong antitumor effect by cross-linking cancer cells to T cells.

If an antibody library that maintains CD3-binding activity can be constructed, the antibody library can be used, for example, in the following forms:

An immunoglobulin variable region (Fab) that binds to CD3 and another antigen and enhances the antitumor effect of CD3 can be obtained. One Fab has the ability to bind to two antigens.

An immunoglobulin variable region (Fab) that binds to CD3 and two other antigens and enhances the antitumor effect of CD3 can be obtained. One Fab has the ability to bind to three antigens.

The binding activity against CD3 is enhanced.

In the preparation of a bispecific antibody that recognizes both CD3 and a cancer antigen, an antigen-binding site that recognizes the cancer antigen is prepared.

[Example 11] Method for Enhancing Binding to CD3

(11-1) Method for Enhancing CD3 Binding

A possible method using the anti-CD3 antibody-derived antibody library described in Example 10 is a method for obtaining an antibody having increased binding to CD3. General examples of affinity maturation include a method which involves altering an amino acid in an obtained antibody sequence by site-directed mutagenesis and measuring affinity, and methods using in vitro display methods including phage display. In the in vitro display methods, plural types of antibody sequences mutated from an obtained sequence by error prone PCR or the like are used as a library to select a sequence having strong affinity.

Use of a dual-Fab library containing selected amino acids that maintain 80% or more of the CD3 binding of a conventional anti-CD3 antibody (e.g., a CD3-binding antibody having the template sequence mentioned above) may allow the efficient finding of a sequence having strong binding to CD3.

(11-2) Obtainment of Fab Domain Having Enhanced Binding to Human CD3

Fab domains (antibody fragments) binding to human CD3 were identified from the dual Fab library designed and constructed in Example 6. Biotin-labeled human CD3 was used as an antigen, and antibody fragments having the ability to bind to human CD3 were enriched.

Phages were produced from the *E. coli* harboring the constructed phagemids for phage display. 2.5 M NaCl/10% PEG was added to the culture solution of the *E. coli* that had produced phages, and a pool of the phages thus precipitated was diluted with TBS to obtain a phage library solution. Next, BSA (final concentration: 4%) was added to the phage library solution. The panning method was performed with reference to a general panning method using antigens immobilized on magnetic beads (J. Immunol. Methods. (2008) 332 (1-2), 2-9; J. Immunol. Methods. (2001) 247 (1-2), 191-203; Biotechnol. Prog. (2002) 18 (2) 212-20; and Mol. Cell Proteomics (2003) 2 (2), 61-9). The magnetic beads used were NeutrAvidin coated beads (Sera-Mag SpeedBeads NeutrAvidin-coated) or Streptavidin coated beads (Dynabeads M-280 Streptavidin).

Specifically, 250 pmol of the biotin-labeled antigen was added to the prepared phage library solution and thereby contacted with the phage library solution at room temperature for 60 minutes. After addition of BSA-blocked magnetic beads, the antigen-phage complexes were attached to the magnetic beads at room temperature for 15 minutes. The beads were washed three times with TBST (TBS containing 0.1% Tween 20; TBS was available from Takara Bio Inc.) and then further washed twice with 1 mL of TBS. After addition of 0.5 mL of 1 mg/mL trypsin, the beads were suspended at room temperature for 15 minutes, immediately after which the beads were separated using a magnetic stand to recover a phage solution. The recovered phage solution was added to 10 mL of an *E. coli* strain ER2738 in a logarithmic growth phase (OD600: 0.4-0.5). The *E. coli* strain was infected by the phages through the gentle spinner culture of the strain at 37° C. for 1 hour. The infected *E. coli* was inoculated to a plate of 225 mm×225 mm. Next, phages were recovered from the culture solution of the inoculated *E. coli* to prepare a phage library solution. This cycle, called panning, was repeated 7 times in total. In the second and subsequent rounds of panning, 40, 10, 10, 1, 1, and 0.1 pmol of the human CD3 were respectively used. In the fifth and subsequent rounds, a 1000-fold amount of a human CD3e homodimer was added each time the human CD3 was added.

(11-3) Preparation of IgG Having Obtained Fab Domain

A population of the antibody fragments having the ability to bind to CD3, obtained in the paragraph (11-2) are constituted by only Fab domains. Thus, these Fab domains were converted to IgG type (conjugate of Fab and Fc). The VH fragment was amplified from *E. coli* having each antibody fragment having the ability to bind to CD3 by PCR using primers specifically binding to the H chain in the dual Fab library. The amplified VH fragment was integrated to pE22Hh-containing plasmids for expression in animal cells by the method of Reference Example 1, and expressed and purified as a one-arm antibody, as in Example 6(6-2). The name of each obtained sequence and SEQ ID NO of its H chain sequence are shown in Table 17. Specifically, each H chain shown in Table 17 and Kn010G3 (SEQ ID NO: 56) were used as H chains, and GLS3000 (SEQ ID NO: 53) linked to the kappa sequence (SEQ ID NO: 55) was adopted as an L chain. These sequences were expressed and purified according to Reference Example 1.

TABLE 17

| Sample name | SEQ ID NO of H chain variable region | SEQ ID NO of H chain constant region |
|---|---|---|
| CE115_1 | 97 | 54 |
| C3D(2)_i099 | 106 | 54 |
| C3D(2)_i100 | 107 | 54 |
| C3D(2)_i101 | 108 | 54 |

TABLE 17-continued

| Sample name | SEQ ID NO of H chain variable region | SEQ ID NO of H chain constant region |
|---|---|---|
| C3D(2)_i102 | 109 | 54 |
| C3D(2)_i103 | 110 | 54 |
| C3D(2)_i104 | 111 | 54 |
| C3D(2)_i110 | 112 | 54 |
| C3D(2)_i112 | 113 | 54 |
| C3D(2)_i119 | 114 | 54 |
| C3D(2)_i121 | 115 | 54 |
| C3D(2)_i129 | 116 | 54 |
| C3D(2)_i136 | 117 | 54 |
| C3D(2)_i143 | 118 | 54 |
| C3D(2)_i144 | 119 | 54 |
| C3D(2)_i145 | 120 | 54 |
| C3D(2)_i150 | 121 | 54 |
| C3D(2)_i192 | 122 | 54 |
| C3D(2)_i197 | 123 | 54 |
| C3D(2)_i199 | 124 | 54 |
| C3D(2)_i233 | 125 | 54 |
| C3D(2)_i290 | 126 | 54 |
| C3D(2)_i291 | 127 | 54 |
| C3D(2)_i385 | 128 | 54 |
| C3D(2)_i387 | 129 | 54 |
| C3D(2)_i393 | 130 | 54 |
| C3D(2)_i395 | 131 | 54 |
| C3D(2)_i542 | 132 | 54 |
| C3D(2)_i669 | 133 | 54 |
| C3D(2)_i736 | 134 | 54 |
| C3D(2)_i863 | 135 | 54 |

(11-4) Evaluation of Binding of IgG Having Obtained Fab Domain

The binding of each IgG obtained in the paragraph (11-3) to human CD3 was confirmed using Biacore T200. Biotinylated CD3 was bound to a CM4 chip via streptavidin, and the prepared antibody was injected thereto as an analyte and analyzed for its binding affinity at 37° C. The results are shown in Table 18.

TABLE 18

| Sample name | ka (1/Ms) | kd (1/s) | KD (M) |
|---|---|---|---|
| CE115_1 | 1.09E+05 | 4.19E−02 | 3.83E−07 |
| C3D(2)_i099 | 9.55E+04 | 1.83E−03 | 1.92E−08 |
| C3D(2)_i100 | 4.91E+04 | 8.31E−04 | 1.69E−08 |
| C3D(2)_i101 | 9.61E+04 | 1.66E−03 | 1.73E−08 |
| C3D(2)_i102 | 9.21E+04 | 9.48E−04 | 1.03E−08 |
| C3D(2)_i103 | 6.77E+04 | 6.82E−04 | 1.01E−08 |
| C3D(2)_i104 | 6.01E+04 | 2.10E−03 | 3.49E−08 |
| C3D(2)_i110 | 8.84E+04 | 1.59E−03 | 1.79E−08 |
| C3D(2)_i112 | 9.49E+04 | 9.55E−04 | 1.01E−08 |
| C3D(2)_i119 | 6.28E+04 | 3.02E−04 | 4.82E−09 |
| C3D(2)_i121 | 1.00E+05 | 7.85E−04 | 7.82E−09 |
| C3D(2)_i129 | 6.89E+04 | 1.38E−03 | 2.00E−08 |
| C3D(2)_i136 | 1.79E+05 | 2.49E−03 | 1.39E−08 |
| C3D(2)_i143 | 2.08E+05 | 2.21E−03 | 1.06E−08 |
| C3D(2)_i144 | 1.08E+05 | 2.33E−03 | 2.15E−08 |
| C3D(2)_i145 | 8.67E+04 | 1.94E−03 | 2.24E−08 |
| C3D(2)_i150 | 1.09E+05 | 2.35E−03 | 2.16E−08 |
| C3D(2)_i192 | 1.22E+05 | 4.44E−03 | 3.65E−08 |
| C3D(2)_i197 | 1.68E+05 | 1.30E−03 | 7.74E−09 |
| C3D(2)_i199 | 3.47E+05 | 4.32E−02 | 1.25E−07 |
| C3D(2)_i233 | 6.47E+04 | 1.45E−03 | 2.24E−08 |
| C3D(2)_i290 | 6.76E+04 | 1.09E−03 | 1.62E−08 |
| C3D(2)_i291 | 9.26E+04 | 1.46E−03 | 1.57E−08 |
| C3D(2)_i385 | 8.60E+04 | 1.66E−03 | 1.93E−08 |
| C3D(2)_i387 | 6.37E+04 | 1.68E−03 | 2.63E−08 |
| C3D(2)_i393 | 6.27E+04 | 1.06E−03 | 1.69E−08 |
| C3D(2)_i395 | 1.46E+05 | 5.81E−03 | 3.97E−08 |
| C3D(2)_i542 | 1.54E+05 | 1.57E−03 | 1.02E−08 |
| C3D(2)_i669 | 1.56E+05 | 1.00E−03 | 6.43E−09 |
| C3D(2)_i736 | 1.87E+05 | 3.31E−03 | 1.77E−08 |
| C3D(2)_i863 | 1.27E+05 | 4.75E−03 | 3.74E−08 |

As shown in Table 18, antibodies having stronger affinity than that of CE115 were able to be obtained. These results demonstrated that the dual-Fab library of the present invention can be used in a method for obtaining a CD3-binding antibody having enhanced ability to bind to CD3.

[Example 12] Method for Obtaining Variable Region (Fab) that Recognizes Cancer Antigen (12-1) Variable Region (Fab) that Recognizes Cancer Antigen Examples of the method using the anti-CD3 antibody-derived antibody library described in Example 10 include a method for obtaining an antibody binding to a cancer antigen.

The light chain of a variable region that recognizes a cancer antigen is also used as the light chain of a variable region that recognizes CD3. Therefore, the light chain contained in the variable region that recognizes a cancer antigen is efficiently obtained from the dual-Fab library having binding activity against CD3.

(12-2) Obtainment of Fab Domain Binding to Human CD154

As described in Example 9, Fab domains (antibody fragments) binding to human CD154 were identified from the dual Fab library with the human CD154 as a model cancer antigen. Antibody fragments having the ability to bind to human CD154 were enriched using biotin-labeled human CD154 as an antigen.

Phages were produced from the *E. coli* harboring the phagemids for phage display constructed in Example 6. 2.5 M NaCl/10% PEG was added to the culture solution of the *E. coli* that had produced phages, and a pool of the phages thus precipitated was diluted with TBS to obtain a phage library solution. Next, BSA (final concentration: 4%) was added to the phage library solution. The panning method was performed with reference to a general panning method using antigens immobilized on magnetic beads (J. Immunol. Methods. (2008) 332 (1-2), 2-9; J. Immunol. Methods. (2001) 247 (1-2), 191-203; Biotechnol. Prog. (2002) 18 (2) 212-20; and Mol. Cell Proteomics (2003) 2 (2), 61-9). The magnetic beads used were NeutrAvidin coated beads (Sera-Mag SpeedBeads NeutrAvidin-coated) or Streptavidin coated beads (Dynabeads M-280 Streptavidin).

Specifically, 250 pmol of the biotin-labeled antigen was added to the prepared phage library solution and thereby contacted with the phage library solution at room temperature for 60 minutes. After addition of BSA-blocked magnetic beads, the antigen-phage complexes were attached to the magnetic beads at room temperature for 15 minutes. The beads were washed three times with TBST (TBS containing 0.1% Tween 20; TBS was available from Takara Bio Inc.) and then further washed twice with 1 mL of TBS. After addition of 0.5 mL of 1 mg/mL trypsin, the beads were suspended at room temperature for 15 minutes, immediately after which the beads were separated using a magnetic stand to recover a phage solution. The recovered phage solution was added to 10 mL of an *E. coli* strain ER2738 in a logarithmic growth phase (OD600: 0.4-0.5). The *E. coli* strain was infected by the phages through the gentle spinner culture of the strain at 37° C. for 1 hour. The infected *E. coli* was inoculated to a plate of 225 mm×225 mm. Next, phages were recovered from the culture solution of the inoculated *E. coli* to prepare a phage library solution. This cycle, called panning, was repeated 5 times. In the second and subsequent rounds of panning, 40 pmol of human CD154 was used.

(12-3) Binding of Fab Domain Displayed by Phage to CD3 or Human CD154

A phage-containing culture supernatant was recovered according to a general method (Methods Mol. Biol. (2002) 178, 133-145) from each single colony of the *E. coli* obtained by the method described above. After addition of BSA (final concentration: 4%), the phage-containing culture supernatant was subjected to ELISA by the following procedures: StreptaWell 96 microtiter plate (Roche.) was coated overnight at 4° C. or at room temperature for 1 hour with 100 μL of PBS containing the biotin-labeled antigen (biotin-labeled CD3ε peptide or biotin-labeled CD154). Each well of the plate was washed with PBST to remove unbound antigens. Then, the well was blocked with 250 μL of 0.1×TBS/150 mM NaCl/0.02% skim milk for 1 hour or longer. After removal of 0.1×TBS/150 mM NaCl/0.02% skim milk, the prepared culture supernatant was added to each well, and the plate was left standing at room temperature for 1 hour so that the phage-displayed antibody bound to the antigen contained in each well. Each well was washed with 0.1×TBS/150 mM NaCl/0.01% Tween 20, and HRP-conjugated anti-M13 antibodies (Amersham Pharmacia Biotech Inc.) diluted with 0.1×TBS/150 mM NaCl/0.01% Tween 20 were then added to each well. The plate was incubated for 1 hour. After washing with TBST, TMB single solution (ZYMED Laboratories, Inc.) was added to the well. The chromogenic reaction of the solution in each well was terminated by the addition of sulfuric acid. Then, the developed color was assayed on the basis of absorbance at 450 nm. The results are shown in FIG. 23. As shown in FIG. 23, some clones were shown to bind to CD3 and CD154. Thus, clones exhibiting binding activity against the second antigen (in Example 9, human CD154) were successfully selected by use of the dual Fab library. Among these clones, a clone that exhibits binding activity against CD154, but exhibits reduced binding activity against CD3 is a variable region (Fab) binding to only CD154 (cancer antigen). A CD154-binding antibody can be obtained using this Fab.

When a clone has binding activity against both CD154 and CD3, its CD3 binding can be attenuated by introducing thereto amino acid alteration that attenuates CD3 binding by site-directed mutagenesis, studied in Example 6, or an amino acid that was not studied in Example 6. The resulting variable region (Fab) can bind to only the cancer antigen.

In addition, a bispecific antibody can be produced by an approach generally known to those skilled in the art using the variable region (Fab) binding to only the cancer antigen, produced in this Example, and a variable region binding to only the first antigen (CD3) and comprising an L chain variable domain sequence in common with the variable region.

[Example 13] Variable Region (Multi-Fab) that Recognizes Three Different Antigens, but does not Bind to the Three Antigens at Same Time The variable region (dual-Fab) that recognized two different antigens such as CD3 and IgA or CD3 and CD154, but did not bind to these antigens at the same time was able to be prepared in Examples up to Example 12. If the variable region that recognizes the first and second antigens, but does not bind to these antigens at the same time can be modified to be capable of binding to a fourth antigen and is shown to not bind to the first, second, and fourth antigens at the same time, this variable region can serve as a multispecific antibody multi-Fab. However, such a variable region that is capable of binding to three or more different antigens, but does not bind to these antigens at the same time has been unknown so far.

(13-1) Obtainment of Variable Region (Fab) that Recognizes Three Antigens

Examples of the obtainment of the variable region that recognizes three antigens include, for the bispecific antibody dual-Fab disclosed in the present specification, 1. a method which involves altering an amino acid so as to bind to the antigen,
2. a method which involves searching for a peptide known to bind to the antigen or a peptide caused to bind thereto by a method generally known to those skilled in the art, and inserting the antigen-binding peptide, and
3. a method which involves using the antibody library disclosed in the present specification to select a variable region binding to an antigen different from that of the dual-Fab.

Alternatively, the antibody library disclosed in the present specification may be used to search for a molecule binding to a plurality of different antigens in advance. In the course of searching, an antigen-binding molecule that binds to the plurality of different antigens, but does not bind to these molecules at the same time can also be selected.

(13-2) Preparation of Variable Region (Multi-Fab) that Recognizes CD3, Human IgA, and Integrin αvβ3

A peptide known to bind to integrin αvβ3 was inserted to between position 72 (Kabat numbering) and position 73 (Kabat numbering) of the dual-Fab molecule IGAR6(2)B02 (heavy chain: SEQ ID NO: 63) that recognized CD3 and human IgA, obtained in Example 8 to prepare IGAR6(2)B02H1 (heavy chain: SEQ ID NO: 136) by PCR. The prepared DNA fragment was integrated to plasmids for expression in animal cells. As in Example 8, IGAR6(2)B02 or IGAR6(2)B02H1 was used as an H chain variable domain, and the H chain variable domain and Kn010G3 (SEQ ID NO: 56) were used as H chains. GLS3000 (SEQ ID NO: 53) linked to the kappa sequence (SEQ ID NO: 55) was adopted as an L chain. These sequences were expressed and purified according to Reference Example 1.

(13-3) Confirmation of CD3- or Human IgA-Binding Activity of Variable Region (Multi-Fab) that Recognizes CD3, Human IgA, and Integrin αvβ3

Next, a test antibody molecule having the obtained Fab region was evaluated for its binding to human IgA and CD3 and its binding to these antigens at the same time by the electrochemiluminescence method (ECL method). Specifically, 12.5 μL of biotinylated human IgA diluted with a TBST solution, 25 μL of each test antibody solution adjusted to 2 μg/mL, 12.5 μL of TBST or CD3ε homodimer protein (3.5 pmol/μL) for competition, and 25 μL of anti-human IgG antibody (Invitrogen Corp., #628400) tagged with sulfo-tag were added to each well of Nunc-Immuno™ MicroWell™ 96 well round plates (Nunc), and mixed, and the plate was then incubated overnight or longer at 4° C. while shielded from light to form an antibody-antigen complex. A TBST solution containing 0.5% BSA (referred to as a blocking solution; the TBST solution was TBS (manufactured by Takara Bio Inc.) supplemented with 0.1% Tween 20) was added at 150 μL/well to streptavidin plate (MSD K.K.), and the plate was incubated overnight or longer at 4° C. After removal of the blocking solution, the antibody-antigen complex solution was added thereto at 50 μL/well, and the plate was incubated at room temperature for 1 hour so that the biotinylated antigen-test antibody-detection sulfo-tag antibody complex solution bound via the biotinylated antigen to the streptavidin plate. After removal of the antibody-antigen complex solution, a solution of 4×READ buffer (MSD K.K.) diluted 2-fold with water was added thereto at 150 μL/well, followed by the detection of the luminescence signal (ECL signal) of the sulfo-tag using Sector Imager 2400 (MSD K.K.). The results are shown in Table 19.

TABLE 19

| Sample | ECL signal: hIgA | ECL signal: hIgA + CD3ε homodimer protein | ECL signal: CD3 peptide | ECL signal: No antigen | Value as compared with antigen-free well: hIgA | Value as compared with antigen-free well: hIgA + CD3ε homodimer protein | Value as compared with antigen-free well: CD3 peptide | Value as compared with antigen-free well: No antigen | Amount of binding to hIgA attenuated by CD3 |
|---|---|---|---|---|---|---|---|---|---|
| IGA6 (2) B02 | 20675 | 884 | 959436 | 1054 | 20 | 1 | 910 | 1 | 23.4 |
| IGAR6 (2) B02H1 | 5564 | 755 | 933057 | 663 | 8 | 1 | 1407 | 1 | 7.4 |
| TBST | 976 | 1144 | 1204 | 715 | 1 | 2 | 22 | 1 | 0.9 |

As shown in Table 19, IGAR6(2)B02H1 binds to hIgA (human IgA) or CD3. In the measurement of binding to human IgA, the binding signal was attenuated in the presence of the CD3ε homodimer protein, demonstrating that IGAR6(2)B02H1, as with IGAR6(2)B02 shown in Example 6, binds to IgA and CD3, but does not bind to these antigens at the same time.

(13-4) Confirmation of Integrin αvβ3-Binding Activity of Variable Region (Multi-Fab) that Recognizes CD3, Human IgA, and Integrin αvβ3

Next, a test antibody molecule having the Fab region obtained in the paragraph (13-2) was evaluated for its binding to integrin αvβ3 and its binding to integrin αvβ3 and CD3ε at the same time by the electrochemiluminescence method (ECL method). Specifically, integrin αvβ3 (R&D Systems, Inc.) was dissolved at 1 μg/mL in a 0.1 M $NaHCO_3$ solution (pH 9.6) and added at 50 μL/well to MULTI-ARRAY 96-well Plate (Meso Scale Diagnostics LLC). 50 μL of a 0.1 M $NaHCO_3$ solution (pH 9.6) was added to each integrin αvβ3-free well. The plate was left standing at 4° C. for 2 days. Next, a TBST solution (TBS (manufactured by Takara Bio Inc.) supplemented with 0.1% Tween 20) or a TBST-diluted CD3ε homodimer protein, each test antibody solution adjusted to 2 μg/mL, and anti-human IgG antibody (Invitrogen Corp., #628400) tagged with sulfo-tag were each added at 254/well to Nunc-Immuno™ MicroWell™ 96 well round plates (Nunc), and mixed, and the plate was then incubated at 4° C. for 2 days while shielded from light to form a complex of the test antibody and the anti-human IgG antibody. The antigen-immobilized MULTI-ARRAY 96-well Plate (Meso Scale Diagnostics LLC) was washed three times with TBST. Then, a TBST solution containing 0.5% BSA (referred to as a blocking solution) was added thereto at 150 μL/well, and the plate was incubated at room temperature for 1 hour or longer. After removal of the blocking solution, the solution of the complex of the test antibody and the anti-human IgG antibody (containing the CD3ε homodimer protein or TBST) was added thereto at 50 μL/well, and the plate was shaken at room temperature for 1 hour so that the antigen on the plate bound to the test antibody-detection sulfo-tag antibody complex. After removal of the antibody complex solution, a solution of 4×READ buffer (MSD K.K.) diluted 2-fold with water was added thereto at 150 μL/well, followed by the detection of the luminescence signal of the sulfo-tag using Sector Imager 2400 (MSD K.K.). The results are shown in Table 20.

TABLE 20

| Sample | ECL signal: Integrin αvβ3 | ECL signal: Integrin αvβp3 + CD3ε homodimer protein | ECL signal: No integrin αvβ3 | ECL signal: No integrin αvβ3 + CD3ε homodimer protein | Value as compared with integrin αvβ3-free well: Integrin αvβ3 | Value as compared with integrin αvβ3-free well: Integrin αvβ3 + CD3ε homodimer protein | Amount of binding to integrin αvβ3 attenuated by CD3 |
|---|---|---|---|---|---|---|---|
| IGA6 (2) B02 | 456 | 452 | 570 | 557 | 0.8 | 0.8 | 1.0 |
| IGAR6 (2) B02H1 | 549380 | 98552 | 1253 | 533 | 438.5 | 184.9 | 2.4 |
| TBST | 540 | 497 | 480 | 552 | 1.1 | 1.0 | 1.1 |

As shown in Table 20, the ECL signal derived from IGAR6(2)B02H1 was increased as compared with the integrin αvβ3-free or TBST sample, demonstrating that IGAR6 (2)B02H1 binds to integrin αvβ3. In addition, the signal was attenuated by the addition of the CD3ε homodimer, demonstrating that IGAR6(2)B02H1 binds to integrin αvβ3, but, in the presence of the CD3ε homodimer protein, binds to the CD3ε homodimer protein and does not bind to the integrin αvβ3.

(13-5) Confirmation of Binding Property of Variable Region (Multi-Fab) that Recognizes CD3, Human IgA, and Integrin αvβ3

The multi-Fab was shown to not bind to IgA and CD3 at the same time in the paragraph (13-3) and shown to not bind to integrin αvβ3 and CD3 at the same time in the paragraph (13-4). Next, the multi-Fab was evaluated for its binding to human IgA and integrin αvβ3 by the electrochemiluminescence method (ECL method). Specifically, 12.5 μL of biotinylated human IgA diluted with a TBST solution, 25 μL of each test antibody solution adjusted to 1 μg/mL, 12.5 μL of TBST or integrin αvβ3 (R&D Systems, Inc.) (250 pmol/μL) for competition, and 25 μL of anti-human IgG antibody (Invitrogen Corp., #628400) tagged with sulfo-tag were added to each well of Nunc-Immuno™ MicroWell™ 96 well round plates (Nunc), and mixed, and the plate was then incubated overnight or longer at 4° C. while shielded from light to form an antibody-antigen complex. A TBST solution containing 0.5% BSA (referred to as a blocking solution; the TBST solution was TBS (manufactured by Takara Bio Inc.) supplemented with 0.1% Tween 20) was added at 150 μL/well to streptavidin plate (MSD K.K.), and the plate was incubated at room temperature for 1 hour or longer. After removal of the blocking solution, the antibody-antigen complex solution was added thereto at 50 μL/well, and the plate was incubated at room temperature for 1 hour so that the biotinylated antigen-antibody-detection sulfo-tag antibody complex solution bound via the biotinylated antigen to the streptavidin plate. After removal of the antibody-antigen complex solution, a solution of 4×READ buffer (MSD K.K.) diluted 2-fold with water was added thereto at 150 μL/well, followed by the detection of the luminescence signal (ECL signal) of the sulfo-tag using Sector Imager 2400 (MSD K.K.). The results are shown in Table 21.

TABLE 21

| Sample | ECL signal | | | Value as compared with antigen-free well | | | Amount of binding to |
|---|---|---|---|---|---|---|---|
| | hIgA | hIgA + Integrin αvβ3 | No antigen | hIgA | hIgA + Integrin αvβ3 | No antigen | hIgA attenuated by integrin αvβ3 |
| IGA6 (2) B02 | 6356 | 6460 | 408 | 15.6 | 15.9 | 1.0 | 1.0 |
| IGAR6 (2) B02H1 | 2796 | 1121 | 718 | 3.9 | 1.6 | 1.0 | 2.5 |
| TBST | 582 | 567 | 624 | 0.9 | 0.9 | 1.0 | 1.0 |

As shown in Table 21, the binding signal for human IgA was attenuated by 2.5 times in the presence of integrin αvβ3, demonstrating that IGAR6(2)B02H1 does not bind to the human IgA and the integrin αvβ3 at the same time.

The results described above indicated that IGAR6(2) B02H1 is a molecule (multi-Fab) that binds to human IgA, CD3, and integrin αvβ3, but does not bind to these antigens at the same time.

Provided that a variable region (multi-Fab) that is capable of binding to three different antigens (first antigen, second antigen, and fourth antigen), but does not bind to the three antigens at the same time can be prepared as shown in this Example, Fab or an antigen-binding domain binding to the third antigen can be identified by a method generally known to those skilled in the art, for example, a hybridoma method or a method for selecting binding antibodies or antigen-binding domains from antibody libraries. An antibody having the identified antigen-binding domain (e.g., Fab) binding to the third antigen and the Fab domain of the multi-Fab molecule can be prepared by the aforementioned multispecific antibody preparation method generally known to those skilled in the art (e.g., technique controlling the interface of each domain in the Fc region, CrossMab, or Fab arm exchange). In other words, provided that the multi-Fab molecule binding to the three different antigens as shown in this Example can be identified, the desired multispecific antibody can be obtained according to a method generally known to those skilled in the art by combining Fab binding to the third antigen with the multi-Fab molecule.

REFERENCE EXAMPLES

[Reference Example 1] Preparation of Antibody Expression Vector and Expression and Purification of Antibody Amino acid substitution was carried out by a method generally known to those skilled in the art using QuikChange Site-Directed Mutagenesis Kit (Stratagene Corp.), PCR, or In fusion Advantage PCR cloning kit (Takara Bio Inc.), etc., to construct expression vectors. The obtained expression vectors were sequenced by a method generally known to those skilled in the art. The prepared plasmids were transiently transferred to human embryonic kidney cancer cell-derived HEK293H line (Invitrogen Corp.) or FreeStyle 293 cells (Invitrogen Corp.) to express antibodies. Each antibody was purified from the obtained culture supernatant by a method generally known to those skilled in the art using rProtein A Sepharose™ Fast Flow (GE Healthcare Japan Corp.). As for the concentration of the purified antibody, the absorbance was measured at 280 nm using a spectrophotometer, and the antibody concentration was calculated by use of an extinction coefficient calculated from the obtained value by PACE (Protein Science 1995; 4: 2411-2423).

[Reference Example 2] Evaluation of Binding of Antibody to ECM (Extracellular Matrix)

The binding of each antibody to ECM (extracellular matrix) was evaluated by the following procedures with reference to WO2012093704 A1: ECM Phenol red free (BD Matrigel #356237) was diluted to 2 mg/mL with TBS and added dropwise at 5 μL/well to the center of each well of a plate for ECL assay (L15XB-3, MSD K.K., high bind) cooled on ice. Then, the plate was capped with a plate seal and left standing overnight at 4° C. The ECM-immobilized plate was brought to room temperature. An ECL blocking buffer (PBS supplemented with 0.5% BSA and 0.05% Tween 20) was added thereto at 150 μL/well, and the plate was left standing at room temperature for 2 hours or longer or overnight at 4° C. Next, each antibody sample was diluted to 9 μg/mL with PBS-T (PBS supplemented with 0.05% Tween 20). A secondary antibody was diluted to 2 μg/mL with ECLDB (PBS supplemented with 0.1% BSA and 0.01% Tween 20). 20 μL of the antibody solution and 30 μL of the secondary antibody solution were added to each well of a round-bottomed plate containing ECLDB dispensed at 10 μL/well and stirred at room temperature for 1 hour while shielded from light. The ECL blocking buffer was removed by inverting the ECM plate containing the ECL blocking buffer. To this plate, a mixed solution of the aforementioned antibody and secondary antibody was added at 50 μL/well. Then, the plate was left standing at room temperature for 1 hour while shielded from light. The sample was removed by inverting the plate, and READ buffer (MSD K.K.) was then added thereto at 150 μL/well, followed by the detection of the luminescence signal of the sulfo-tag using Sector Imager 2400 (MSD K.K.).

[Reference Example 3] Preparation of Human IgA

An Fc region in a naturally occurring human IgA sequence was used as human IgA (human IgA-Fc). For the purpose of biotinylating the C terminus of the human IgA-Fc, a gene fragment encoding a specific sequence (AviTag sequence, SEQ ID NO: 79) for biotin ligase-mediated biotinylation was linked via a linker to a gene fragment encoding the human IgA-Fc. The gene fragment encoding a protein containing the human IgA-Fc and the AviTag sequence linked (SEQ ID NO: 80) was integrated to vectors for expression in animal cells, and the constructed plasmid vectors were transferred to FreeStyle 293 cells (Invitrogen Corp.) using 293Fectin (Invitrogen Corp.). In this operation, the cells were cotransfected with the expression vector and a gene encoding EBNA1 (SEQ ID NO: 81) and a gene encoding biotin ligase (BirA, SEQ ID NO: 82), and biotin was further added for the purpose of biotinylating the human IgA-Fc. The cells transfected according to the procedures mentioned above were cultured at 37° C. for 6 days in an 8% $CO_2$ environment so that the protein of interest was secreted into the culture supernatant.

The cell culture solution containing the human IgA-Fc of interest was filtered through a 0.22 μm bottle-top filter to obtain a culture supernatant. The culture supernatant diluted with 20 mM Tris-HCl (pH 7.4) was applied to HiTrap Q HP (GE Healthcare Japan Corp.) equilibrated with 20 mM Tris-HCl (pH 7.4), followed by the elution of the human IgA-Fc of interest with the concentration gradient of NaCl. Next, the HiTrap Q HP eluate diluted with 50 mM Tris-HCl (pH 8.0) was applied to SoftLink Avidin column (Promega Corp.) equilibrated with 50 mM Tris-HCl (pH 8.0), followed by the elution of the human IgA-Fc of interest with 5 mM biotin, 150 mM NaCl, and 50 mM Tris-HCl (pH 8.0). Then, associates were removed as undesired impurities by gel filtration chromatography using Superdex 200 (GE Healthcare Japan Corp.) to obtain purified human IgA-Fc with the buffer replaced with 20 mM histidine-HCl and 150 mM NaCl (pH 6.0).

INDUSTRIAL APPLICABILITY

The present invention can enhance activity brought about by antigen-binding molecules and provides a polypeptide that can circumvent the cross-linking between different cells resulting from binding to antigens expressed on the different cells, which is considered to be responsible for adverse reactions, and is suitable as a drug.

The invention claimed is:

1. A library comprising a plurality of antigen-binding polypeptide molecules that differ from each other in amino acid sequence, wherein each antigen-binding polypeptide molecule of the plurality comprises an antibody variable region that can bind to a first antigen and a second antigen, but not at the same time;

one of the antigens is CD3;

the other antigen is a molecule expressed on the surface of a naturally occurring immunocyte and is not CD3;

the antibody variable regions of the plurality of antigen-binding polypeptide molecules differ from each other in amino acid sequence;

each antibody variable region comprises a VH comprising the amino acid sequence of SEQ ID NO: 96 or an altered SEQ ID NO: 96, the alterations in SEQ ID NO: 96 being at one or more positions selected from Kabat numbering positions 31, 52b, 52c, 53, 54, 56, 57, 61, 98, 99, 100, 100a, 100b, 100c, 100d, 100e, 100f, and 100g; and each antibody variable region comprises a VL comprising the amino acid sequence of SEQ ID NO: 53 or an altered SEQ ID NO: 53, the alterations in SEQ ID NO: 53 being at one or more positions selected from Kabat numbering positions 24, 25, 26, 27, 27a, 27b, 27c, 27e, 30, 31, 33, 34, 51, 52, 53, 54, 55, 56, 74, 77, 89, 90, 92, 93, 94, and 96.

2. The library of claim 1, wherein the differences in sequence between at least some of the antibody variable regions include a peptide present in a VH loop, the loop being within or comprising part or all of VH CDR1, VH CDR2, VH CDR3, or VH FR3, wherein the peptide binds to one of the antigens.

3. The library of claim 2, wherein the peptide is present within the VH CDR3 of at least some of the antibody variable regions.

4. The library of claim 1, wherein the antigen that is not CD3 is selected from the group consisting of: an FcγR, a toll like receptor (TLR), a lectin, an immune checkpoint molecule, a tumor necrosis family receptor (TNFR) superfamily molecule, and a natural killer (NK) cell receptor molecule.

5. The library of claim 1, wherein the antigen-binding polypeptide molecules are fusion polypeptides, each comprising a portion of a viral coat protein.

6. A method for generating the library of claim 1, the method comprising:

(a) identifying a template sequence that is an amino acid sequence of a starting antibody variable region that binds to the first antigen;

(b) identifying a set of different amino acid alterations that can be made to the template sequence to produce a set of different variant sequences, each variant sequence having at least one amino acid alteration compared to the template sequence, wherein each alteration satisfies one or more of the following conditions (i)-(iii):

(i) the alteration does not substantially affect binding to the first antigen, (ii) the alteration does not substantially increase binding to extracellular matrix (ECM), and (iii) the alteration is an insertion of 1 to 25 contiguous amino acid residues into a VH CDR1, VH CDR2, VH CDR3, or VH FR3 of the template sequence;

(c) generating a nucleic acid library comprising nucleic acids that encode antigen-binding polypeptide molecules comprising antibody variable regions represented by the set of different variant sequences; and (d) expressing the nucleic acids, thereby producing the library of antigen-binding polypeptide molecules.

7. The method of claim 6, wherein the template sequence comprises one or both of SEQ ID NOs: 96 and 53.

8. The method of claim 6, wherein the antigen-binding polypeptide molecules encoded by the nucleic acids of (c) further comprise at least a portion of a viral coat protein.

9. A method of selecting an antigen-binding polypeptide molecule, the method comprising:

(a) contacting the antigen-binding polypeptide molecules of the library of claim 1 with the second antigen;

(b) recovering antigen-binding polypeptide molecules that bind to the second antigen;

(c) selecting, from the antigen-binding polypeptide molecules recovered in (b), an antigen-binding polypeptide molecule comprising a variable region that binds to the first and second antigens, but does not bind to both at the same time.

10. The method of claim 9, wherein the antigen that is not CD3 is selected from the group consisting of: an FcγR, a TLR, a lectin, an IgA, an immune checkpoint molecule, a TNF superfamily molecule, a TNFR superfamily molecule, and a NK cell receptor molecule.

11. A method for selecting an antibody variable region that binds more strongly to an antigen than does a control antigen-binding polypeptide molecule, the method comprising:

(a) contacting the antigen-binding polypeptide molecules of the library of claim 1 with the first antigen;

(b) recovering antigen-binding polypeptide molecules that bind to the first antigen;

(c) providing a control antigen-binding molecule that binds to the first antigen;

(d) of the antigen-binding polypeptide molecules recovered in (b), identifying an antigen-binding polypeptide molecule that binds more strongly to the first antigen than does the control antigen-binding polypeptide molecule; and (e) selecting the antigen-binding polypeptide molecule identified in (d).

* * * * *